(12) United States Patent
Tavazoie et al.

(10) Patent No.: US 9,493,841 B2
(45) Date of Patent: Nov. 15, 2016

(54) TREATMENT OF ANGIOGENESIS DISORDERS

(71) Applicants: Sohail Tavazoie, New York, NY (US); Nils Halberg, Brooklyn, NY (US); Kim Png, Singapore (SG)

(72) Inventors: Sohail Tavazoie, New York, NY (US); Nils Halberg, Brooklyn, NY (US); Kim Png, Singapore (SG)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 14/658,927

(22) Filed: Mar. 16, 2015

(65) Prior Publication Data

US 2015/0292031 A1    Oct. 15, 2015

Related U.S. Application Data

(62) Division of application No. 13/984,760, filed as application No. PCT/US2012/024697 on Feb. 10, 2012, now Pat. No. 8,980,261.

(60) Provisional application No. 61/441,738, filed on Feb. 11, 2011.

(51) Int. Cl.
| | | |
|---|---|---|
| *C12N 15/113* | (2010.01) | |
| *C12Q 1/68* | (2006.01) | |
| *C07K 16/18* | (2006.01) | |
| *A61K 38/17* | (2006.01) | |
| *A61K 39/395* | (2006.01) | |
| *A61K 39/00* | (2006.01) | |

(52) U.S. Cl.
CPC ......... *C12Q 1/6886* (2013.01); *A61K 38/1709* (2013.01); *A61K 39/3955* (2013.01); *C07K 16/18* (2013.01); *C12N 15/113* (2013.01); *C12N 15/1135* (2013.01); *A61K 2039/505* (2013.01); *C07K 2316/96* (2013.01); *C07K 2317/73* (2013.01); *C07K 2317/76* (2013.01); *C12N 2310/141* (2013.01); *C12N 2320/11* (2013.01); *C12N 2330/31* (2013.01); *C12Q 2600/136* (2013.01); *C12Q 2600/16* (2013.01); *C12Q 2600/178* (2013.01)

(58) Field of Classification Search
CPC .......................... C12N 15/113; C12Q 1/6886
See application file for complete search history.

(56) References Cited

U.S. PATENT DOCUMENTS

| | | |
|---|---|---|
| 8,715,660 B2 | 5/2014 | Tavazoie et al. |
| 2006/0178329 A1 | 8/2006 | Gleave et al. |
| 2008/0286287 A1 | 11/2008 | Russo et al. |

(Continued)

FOREIGN PATENT DOCUMENTS

| | | |
|---|---|---|
| WO | 2000069454 A1 | 11/2000 |
| WO | 2005059109 A2 | 6/2005 |
| WO | 20060102715 A1 | 10/2006 |

(Continued)

OTHER PUBLICATIONS

Information about Related Patents and Patent Applications, see Section 6 of the accompanying Information Disclosure Statement Letter, which concerns Related Patents and Patent Applications.

(Continued)

*Primary Examiner* — Jon E Angell
(74) *Attorney, Agent, or Firm* — Fox Rothschild LLP

(57) ABSTRACT

This invention concerns pathological angiogenesis and cancer, related treatment methods, and related compositions. Also disclosed are related diagnosis kits and methods.

7 Claims, 30 Drawing Sheets

(56) References Cited

U.S. PATENT DOCUMENTS

2013/0323241 A1 12/2013 Tavazoie et al.
2013/0330333 A1 12/2013 Tavazoie et al.

FOREIGN PATENT DOCUMENTS

| WO | 2008073660 A1 | 6/2008 |
|----|---------------|--------|
| WO | 2009082744 A2 | 7/2009 |
| WO | 2009126650 A2 | 10/2009 |
| WO | 2011011061 A2 | 1/2011 |

OTHER PUBLICATIONS

Bayes-Genis et al., "The insulin-like growth factor axis: a review of atherosclerosis and restenosis," Cir. Res. (2000): 86:125-130.

Busund et al, "Significant expression of IGFBP2 in breast cancer compared with benign lesions," J CLin Pathol, 2005, 58:361-366.

Chakrabarty et al., "Insulin-like growth factor binding protein-2 stimulates proliferation and activates multiple cascades of the mitogen-activated protein kinase pathways in NIH-OVCAR3 human epithelial ovarian cancer cells," Cancer Biology & Therapy (2006) 5(2):189-197.

Firth et al., "Cellular Actions of the Insulin-Like Growth Factor Binding Proteins," Endocrine Review (2002): 23 (6):824-854.

Forsyth et al., "growth inhibition of a human colon cancer cell line by antisense oligonucleotide to IGFBP-2," Gastroenterology (1995)108(4)A726.

Fukushima et al., "Roles of insulin-like growth factor binding protein-2 (IGFBP-2) in glioblastoma," Anticancer Research (2007): 27:3685-3692.

Halberg et al., "microRNA regulation of cancer-endothelial interactions vesicular microRNAs ont he move . . . ," The EMBO Journal (2012) 31(17)3509-3510.

Li et al., "Single-chain antibodies against human insulin-like growth factor I receptor: expression, purification, and effect on tumor growth," Cancer Immunol Immmunother (2000) 49:243-252.

Michell et al., "Insulin-like growth factor binding proteins asmediators of IGF-I effects on colon cancer cell proliferation," Growth Factors (1997)14(4)269-277.

Pereira et al., "Bimolecular Interaction of Insulin-Like Growth Factor (IGF) Binding Protein-2 with avB3 Negatively Modulates IGF-I-Mediated Migration and Tumor Growth." Cancer Research (2004) 64: 977-984.

Png et al., "A microRNA regulon that mediates endothelial recruitment and metastasis by cancer cells," Nature (Dec. 14, 2011): 481(7380):190-194.

Yu et al., "Role of the insulin-like growth factor family in cancer development and progression," Journal of the National Cancer Institute (2000) 92(18):1472-1489.

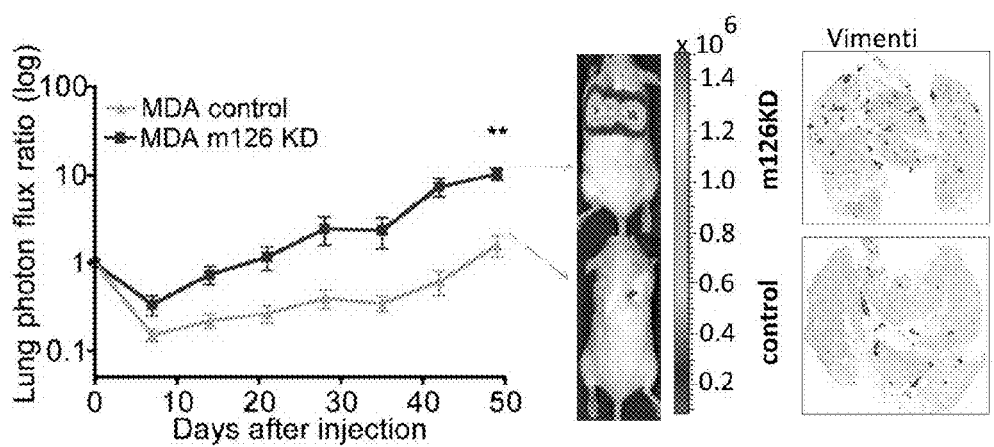
FIG. 1A
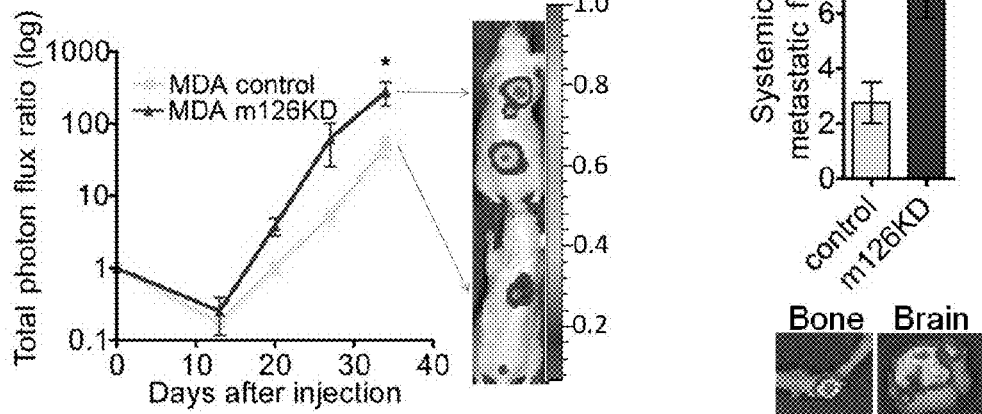 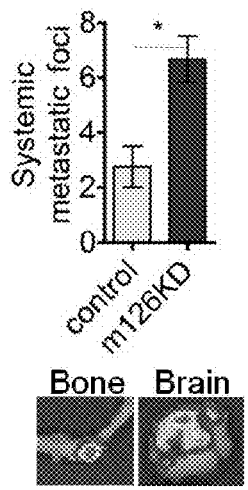
FIG. 1B
FIG. 1C

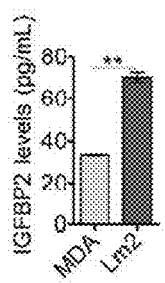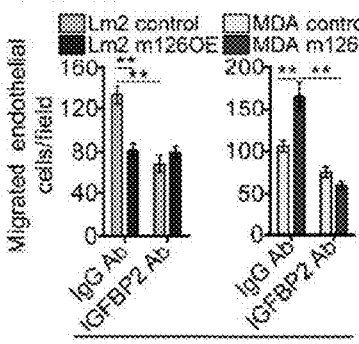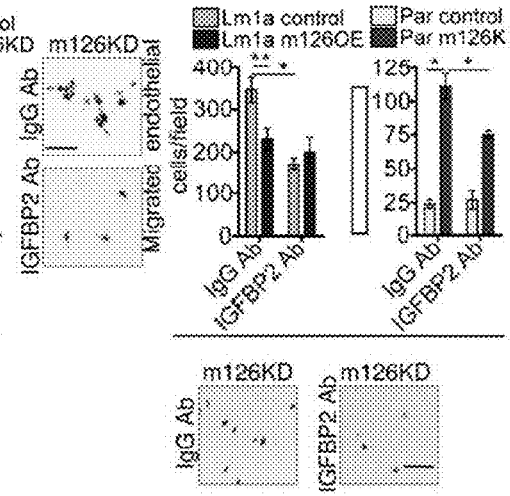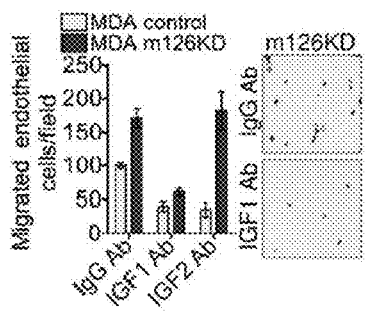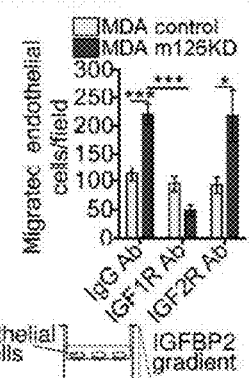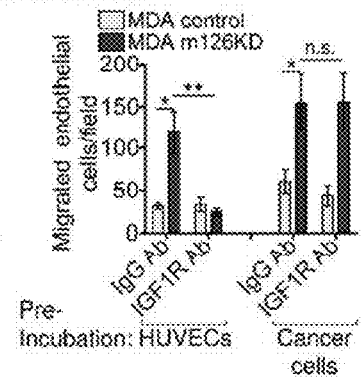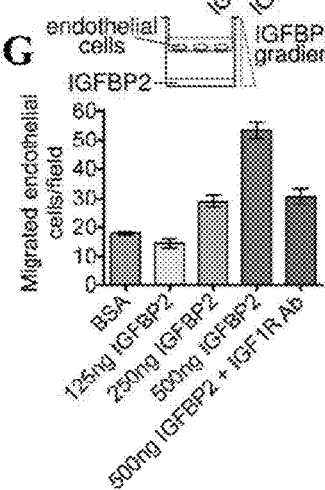

FIG. 22

TREATMENT OF ANGIOGENESIS DISORDERS

CROSS REFERENCE TO RELATED APPLICATION

This application is a Divisional of U.S. patent application Ser. No. 13/984,760, filed Aug. 9, 2013, which is a U.S. National Phase of International Application No. PCT/US12/24697, filed Feb. 10, 2012, which claims priority of U.S. Provisional Application No. 61/441,738, filed on Feb. 11, 2011. The contents of all the applications are incorporated herein by reference in their entirety.

GOVERNMENT CLAUSE

This invention was made with government support under W81WH-10-1-0535 awarded by DoD. The government has certain rights in the invention.

FIELD OF INVENTION

This invention relates to treatments for angiogenesis disorders.

BACKGROUND OF INVENTION

Angiogenesis is a process of growth of new blood vessels and remodeling of preexisting blood vessels. It is vital for normal growth and development, as well as other physiological processes, such as wound healing. On the other hand, angiogenesis is also important in various pathological processes. For example, pathological angiogenesis is a fundamental step in the transition of tumors from a dormant state to a malignant one, characterized by the properties of anaplasia, invasiveness, and metastasis.

Metastatic progression of cancer is a daunting clinical challenge. Technological advances have allowed for the detection and treatment of some early stage neoplasm, however, total death rates from epithelial malignancies have remained essentially unchanged over the last forty years (seer.cancer.gov/csr/1975_2007/, National Institute of Health, 2007). It generally is believed that this is due to several factors, including molecular heterogeneity within cancer types, chemotherapeutic regimens of modest efficacy that were historically empirically derived, and a long-standing focus on the molecular drivers of primary tumor growth rather than metastatic progression.

Effective prevention or treatment of metastasis calls for understanding of molecular and cellular events, including angiogenesis, underlying this complex process (Talmadge, J. E. et al., Cancer Res 70 (14), 5649 (2010); Sleeman, J. et al., Eur J Cancer 46 (7), 1177 (2010); and Hurst, D. R., et al., Cancer Res 69 (19), 7495 (2009)). VEGF has been discovered as a promoter of tumorigenesis in primary tumors (Kim, K. J. et al., Nature 362 (6423), 841 (1993)). Clinical trials have shown that VEGF inhibition can, in combination with chemotherapy, lengthen survival by 2-3 months in patients with stage IV colorectal or lung cancer (Hurwitz, H. et al., N Engl J Med 350 (23), 2335 (2004); Giantonio, B. J. et al., J Clin Oncol 25 (12), 1539 (2007); and Sandler, A. et al., N Engl J Med 355 (24), 2542 (2006)). However, VEGF inhibition has not proven beneficial for metastasis prevention in the adjuvant setting (Barugel, M. E., et al. Expert Rev Anticancer Ther 9 (12), 1829 (2009) and in recent preclinical metastasis models (Paez-Ribes, M. et al., Cancer Cell 15 (3), 220 (2009) and Ebos, J. M. et al., Cancer Cell 15 (3), 232 (2009)). While compensation by other unknown factors that promote metastatic angiogenesis has been proposed to underlie these outcomes, a number of investigators have sought to address metastasis via pathways other than angiogenesis. For example, WO 2009082744 described genes over-expressed in bone and lung metastases of breast cancer, where the genes were not related to angiogenesis. Others endeavored to identify factors that mediate metastatic angiogenesis. Yet, the success has been limited.

Thus, there is a need for agents and methods for regulating angiogenesis and for treating disorders characterized by pathological angiogenesis, including cancer.

SUMMARY OF INVENTION

This invention is based, at least in part, on an unexpected discovery of a new pathway that regulates endothelial recruitment and, in turn angiogenesis.

Accordingly, one aspect of this invention features a method for inhibiting endothelial recruitment, as well as angiogenesis, in a subject in need thereof. The method includes a step of administering to the subject a first agent that inhibits expression or activity of a first protein selected from the group consisting of IGFBP2, MERTK, and PITPNC1. In one embodiment, the subject has an angiogenesis disorder, i.e., a disorder characterized by pathological angiogenesis, such as cancer, an eye disorder, or an inflammatory disorder. Examples of the cancer include metastatic cancer. The above-mentioned method can further include a step of administering to the subject a second agent that inhibits expression or activity of a second protein selected from the group consisting of IGFBP2, IGF1, IGF1R, MERTK, PITPNC1, ABCB9, PSAT1, PYGB, SHMT2, and VIPR. The aforementioned first agent or second agent can be an antibody (or an antigen-binding portion thereof), a nucleic acid, a polypeptide, or a small molecule compound. In one example, the above antibody is an monoclonal that contains a heavy chain variable region comprising the amino acid sequence of SEQ ID NO: 9 and a light chain variable region comprising the amino acid sequence of SEQ ID NO: 10 shown below.

In a second aspect, this invention features a method for treating metastatic cancer in a subject in need thereof. The method includes a step of administering to the subject a first agent that inhibits expression or activity of a first protein selected from the group consisting of IGFBP2, MERTK, and PITPNC1, where the first agent inhibits angiogenesis. Examples of the cancer include breast cancer. The method can further include a step of administering to the subject a second agent that inhibits expression or activity of a second protein selected from the group consisting of IGFBP2, IGF1, IGF1R, MERTK, PITPNC1, ABCB9, PSAT1, PYGB, SHMT2, and VIPR. The first agent or second agent can be an antibody (or an antigen-binding portion thereof), a nucleic acid, a polypeptide, or a small molecule compound. In one example, the above antibody is an monoclonal that contains a heavy chain variable region comprising the amino acid sequence of SEQ ID NO: 9 and a light chain variable region comprising the amino acid sequence of SEQ ID NO: 10 shown below.

In a third aspect, this invention features an isolated nucleic acid having a sequence encoding an RNAi agent capable of inhibiting expression of a protein selected from the group consisting of IGFBP2, MERTK, and PITPNC1. In one embodiment, the RNAi agent has a double-stranded structure having a first strand and a second strand; each of the first and second strands is between 19 and 30 nucleotides long; and the first strand is encoded by any one of SEQ ID NOs: 1-6 as listed in Table 5 below.

In a fourth aspect, this invention provides a composition having an agent that inhibits expression or activity of a protein selected from the group consisting of IGFBP2, MERTK, and PITPNC1, where the agent can be an antibody (or an antigen-binding portion thereof), a nucleic acid, a polypeptide, or a small molecule compound. In one example, the agent is the above-mentioned isolated nucleic acid. In another, the agent is an antibody or an antigen-binding portion thereof.

In a fifth aspect, this invention features a method for diagnosing a metastatic potential of cancer in a subject. The method includes steps of obtaining a first expression level for a first gene of the subject selected from the group consisting of IGFBP2, MERTK, and PITPNC1, and comparing the first expression level with a first predetermined level for the selected first gene. The subject is determined to have or be prone to develop metastatic cancer if the first expression level is greater than the first predetermined level. The first predetermined level can be obtained from a control subject that is free of cancer. In one example, the method further includes steps of obtaining a second expression level for a second gene of the subject selected from the group consisting of IGFBP2, IGF1, IGF1R, MERTK, PITPNC1, ABCB9, PSAT1, PYGB, SHMT2, and VIPR; and comparing the second expression level with a second predetermined level for the selected second gene. The subject is determined to have or be prone to develop metastatic cancer if both the first expression level and the second expression level are greater than the first predetermined level and the second predetermined level, respectively. The second predetermined level can also be obtained from a control subject that is free of cancer.

The invention also features a method for inhibiting endothelial recruitment in a subject in need thereof. The method includes a step of administering to the subject a first agent that increases expression or activity of GAS6 (i.e. an activating agent of GAS6). The invention further features a composition having an agent that increases expression or activity of GAS6. In one example, the aforementioned agent has GAS6 activity. In another, the agent is an antibody (or an antigen-binding portion thereof), a nucleic acid, a polypeptide, or a small molecule compound. In one embodiment, the agent is a polypeptide having the sequence of GAS6.

In a yet another aspect, the invention features a kit for diagnosing a metastatic potential of cancer in a subject. The kit includes a first reagent that specifically binds to a first expression product (e.g., polypeptide or mRNA) of a first gene selected from the group consisting of IGFBP2, MERTK, and PITPNC1. The kit can further include a second reagent that specifically binds to a second expression product of a second gene selected from the group consisting of IGFBP2, IGF1, IGF1R, MERTK, PITPNC1, ABCB9, PSAT1, PYGB, SHMT2, and VIPR.

In a further aspect, the invention features a method for identifying genes and non-coding RNAs that regulate metastatic cancer colonization of any body tissue. The method includes a first step of generating a population of mammalian cancer cells with increased metastatic tissue colonization potential by performing serial rounds of a) transplantation of a population of labeled or unlabeled cancer cells into any living tissue of the body and then b) performing isolation of said labeled cancer cells from the tissue after metastatic colonization has occurred and then c) performing repeat transplantation of isolated labeled cancer cells into living tissue of the body. By performing serial rounds of transplantation, isolation, and repeat transplantation of labeled cancer cells as described above, a population of labeled or unlabeled cancer cells with high metastatic tissue colonization potential is generated. The second step of the method includes transducing, transfecting, or otherwise introducing a population of one or more shRNA molecules into the population of cancer cells with high metastatic tissue colonization potential to generate a population of engineered cancer cells with high metastatic potential that express one or more shRNA molecules that reduce expression of one or more genes or non-coding RNAs. This the population of engineered cancer cells with high metastatic potential that express one or more shRNA molecules is then a) transplanted into any living tissue and then b) isolated from the living tissue after metastatic colonization has occurred. The presence, absence, or abundance of one or more of the transfected, transduced, or otherwise introduced shRNAs in the population of isolated post-transplant engineered cancer cells is then assessed by either microarray analysis, DNA sequencing technology, deep sequencing technology, or cloning. The reduction in levels of any single shRNA in the population of isolated cells relative to its representation prior to injection indicates that the shRNA's target gene is required for metastatic colonization of the tissue. The increase in levels of any single shRNA in the population of isolated cells relative to its representation prior to injection indicates that the shRNA's target antagonizes metastatic colonization of the tissue. The second step of this method could also include transducing, transfecting, or otherwise introducing a population of one or more RNAi molecules, microRNAs, or non-coding RNAs. Additionally, the second step could also include transducing, transfecting, or otherwise introducing a population of one or more sequences encoding protein coding genes. The population of engineered cancer cells with high metastatic potential that express one or more protein coding genes is then a) transplanted into any living tissue and then b) isolated from the living tissue after metastatic colonization has occurred. The presence, absence, or abundance of one or more of the transfected, transduced, or otherwise introduced coding genes in the population of isolated post-transplant engineered cancer cells is then assessed by either microarray analysis, DNA sequencing technology, deep sequencing technology, or cloning. The increase in the levels of any single gene in the population of isolated cells relative to its representation prior to injection indicates that the gene represents a target gene required for metastatic colonization of the tissue. The decrease in the levels of any single gene in the population of isolated cells relative to its representation prior to injection indicates that the gene represents a target gene that antagonizes metastatic colonization of the tissue.

In a further aspect, the invention features a monoclonal antibody (e.g., a humanized or human monoclonal antibody) or an antigen-binding portion thereof that neutralizes IGFBP2 function by inhibiting IGFBP2 binding to IGF1. This antibody is capable of inhibiting endothelial recruitment by cancer cells, such as metastatic breast cancer cells or inhibiting pathological angiogenesis. This antibody is also capable of inhibiting tumor progression or tumor metastasis of cancer cells, such as human breast cancer, in vivo. In one example, the monoclonal antibody contains a heavy chain variable region comprising the amino acid sequence of SEQ ID NO: 9 and a light chain variable region comprising the amino acid sequence of SEQ ID NO: 10 shown below.

The details of one or more embodiments of the invention are set forth in the description below. Other features, objects, and advantages of the invention will be apparent from the description and from the claims.

DESCRIPTION OF DRAWINGS

FIGS. 1a-1f are diagrams and photographs showing that endogenous miR-126 suppresses metastatic colonization. FIG. 1a, Bioluminescence imaging of lung metastasis by poorly metastatic breast cancer cells upon miR-126 inhibition. $4 \times 10^4$ MDA-MB-231 cells expressing a short hairpin (miR-Zip) targeting miR-126 or the control hairpin were injected intravenously into immunodeficient NOD-SCID mice. Representative mice shown correspond to the MDA-MB-231/miR-126KD set (top) and MDA-MB-231/scrambled set (bottom) at day 49. Lung colonization was quantified through bioluminescence imaging. n=5; error bars represent s.e.m.; p-value based on a one-sided student's t-test at day 49. Lungs were extracted at day 49 and immuno-histochemically stained for human vimentin (right). FIG. 1b, Bioluminescence imaging of systemic metastasis by poorly metastatic breast cancer cells with inhibited miR-126 expression. $4 \times 10^4$ MDA-MB-231 cells expressing a short hairpin targeting miR-126 or the control hairpin were injected via intracardiac route into athymic nude mice. Representative mice shown correspond to the MDA-MB-231/miR-126KD set (top) and MDA-MB-231/scrambled set (bottom) at day 34. Whole body colonization was measured by bioluminescence and quantified. n=4; error bars represent s.e.m.; p-value based on a one-sided student's t-test at day 34. FIG. 1c, The total number of metastatic foci were counted in mice injected intracardiac with MDA-MB-231/miR-126KD and MDA-MB-231/scrambled cells (top). Representative images of bone and brain metastatic nodules are shown (bottom). FIG. 1d, $5 \times 10^5$ MDA-MB-231 cells expressing a short hairpin targeting miR-126 or the control hairpin were injected into the mammary fat pads of immunodeficient mice. Tumor volumes were measured over time. n=15; error bars indicate s.e.m.; p-values based on a one-sided student's t-test at day 35. FIG. 1e, Extracted lungs from (a) were stained for human-vimentin and the size of each metastatic nodule was measured through image analysis using ImageJ. FIG. 1f, $4 \times 10^4$ Lm2 cells expressing a doxycycline inducible pre-miR-126 cassette were injected via the tail vein into NOD-SCID mice at day 0. At day 3, doxycycline (2 mg/ml) and sucrose (5%) were added to the drinking water in one group of mice and only 5% sucrose in the other. At day 48, the lungs were removed and immuno-histochemically stained for human vimentin (right). Total number of nodules in each lung is shown to the left.

FIG. 2a, Lung sections from FIG. 1a were histologically double-stained for human vimentin and MECA-32 or FIG. 2b, for vimentin and intravenously injected lectin. The border of each nodule was demarcated based on vimentin staining and the lectin/MECA-32 staining inside the metastatic nodule highlighted in black (lower panels). The area positive for lectin/MECA-32 staining within each nodule was then determined by using ImageJ software and presented as the area covered by lectin/MECA-32 stain per area of the given nodule (% vessel density). The distribution of % vessel density between the injected MDA-MB-231 control and miR-126 KD cells are shown in a cumulative fraction plot. n=8/group (resulting in a total 18 metastatic nodules in the control, and 68 in the miR-126 KD cells), p-value based on the Kolmogorov-Smirnov test. FIG. 2c, $5 \times 10^4$ LM2 cells expressing miR-126 or a control hairpin were seeded onto a HUVEC monolayer and adhesion was quantified. Images of cells that had adhered to the HUVEC monolayer were obtained and analyzed using ImageJ software. n=4; error bars represent s.e.m. FIG. 2d, Conditioned media from $5 \times 10^5$ LM2 cells expressing miR-126 or a control hairpin was obtained by incubating the cells with EGM-2 media for 24 h. $2.5 \times 10^4$ HUVEC cells were seeded in triplicate, grown in the conditioned media and viable cells were counted at 5 days post seeding. n=3; error bars represent s.e.m. FIG. 2e, $2 \times 10^4$ HUVEC cells were mixed with $1 \times 10^4$ LM2 cells that were transduced with miR-126 or a control hairpin, and tube formation by the HUVEC cells was assayed. Images of each well were obtained and the number of branch points in each image was quantified using MetaMorph software. n=3; error bars represent s.e.m. Scale bar represents 250 µm. FIG. 2f, $2.5 \times 10^4$ MDA-MB-231 cells and LM2 cells were seeded in quadruplicate. Trans-well migration of $5 \times 10^4$ HUVEC cells towards the cancer cells was then assessed by counting the number of cells that had migrated to the basal side of the trans-well inserts in images obtained using ImageJ. n=4; error bars represent s.e.m., p-values were obtained using student's t-test. FIG. 2g, LM2 cells expressing miR-126 or the control hairpin, as well as MDA-MB-231 cells expressing a short hairpin targeting miR-126 or the control hairpin were subjected to the HUVEC recruitment assay. Images of the basal side of the inserts were obtained and cells counted using ImageJ software. n=4; error bars represent s.e.m., p-values were obtained using student's t-test. Representative images shown correspond to the LM2/miR-126OE or control set (top) and MDA-MB-231/miR-126KD or control set (bottom). Scale bar represents 100 µm. FIG. 2h, CN34 Parental cells and CN34 LM1a cells were subjected to the HUVEC recruitment assay. n=4; error bars represent s.e.m., p-values obtained using student's t-test. FIG. 2i, CN34 LM1a cells expressing miR-126 or the control hairpin, as well as CN34 Parental cells expressing a short hairpin targeting miR-126 or the control hairpin, were subjected to the HUVEC recruitment assay. n=4; error bars represent s.e.m., p-values obtained using student's t-test. Representative images are shown. Scale bar represents 100 µm. FIG. 2j, $5 \times 10^5$ Lm2 cells over-expressing miR-126 or the control hairpin, as well as $5 \times 10^5$ MDA-MB-231 cells expressing a short hairpin targeting miR-126 or the control hairpin were mixed 1:1 with matrigel and injected into the mammary fat pad. Size-matched tumors were analyzed for blood vessel density by immuno-histochemical staining for MECA-32. 5 individual fields were taken for each tumor and the percentage of each field covered by a thresholded MECA-32 staining are given as % vessel density. Quantification is shown on top and representative images shown below. n=4; error bars represent s.e.m., p-values obtained using student's t-test.

FIG. 3a, The miR-126 metastasis signature is comprised of genes overexpressed in metastatic cells, down-regulated by miR-126 OE, and induced by miR-126 KD. The heatmap represents variance-normalized expression levels based on microarray and qPCR analyses. Colourmap corresponds to standard deviations change from the mean. FIG. 3b, FIG. 3c and FIG. 3d, Kaplan-Meier curves for the (b) UCSF breast cancer cohort (117 tumors), (c) NKI cohort (295 tumors), and (d) the combined NKI/MSK/UCSF cohort (494 tumors) depicting metastasis-free-survival of those patients whose primary cancers over-expressed the miR-126 eight gene signature (positive) and those that did not (negative). P-values based on the Mantel-Cox log-rank test. FIG. 3e, Luciferase reporter assays of miR-126 metastasis genes in MDA-MB-231 cells expressing a short hairpin targeting miR-126 or the control KD hairpin. Reporter constructs containing the luciferase gene upstream of the 3'UTR or coding sequences (CDS) of each miR-126 regulated gene were transfected into the various cell lines and luciferase activity was assayed at 30 hours post transfection. n=4; error bars represent s.e.m.; p-values were obtained using student's t-test. FIG. 3f, The miR-126 complementary regions of the 3'UTR/CDS constructs were mutated and the luciferase reporter assay was repeated with these constructs in MDA-MB-231 cells expressing a short hairpin targeting miR-126 or the control hairpin (right). n=4; error bars represent s.e.m.; p-values were obtained using student's t-test.

FIG. 4a, $2.5 \times 10^4$ LM2 cells expressing hairpins targeting IGFBP2, MERTK, PITPNC1, SHMT2 or the control hairpin were seeded in quadruplicate. Trans-well migration of $5 \times 10^4$ HUVEC cells towards the cancer cells was then assessed. Images of cells that migrated through the trans-well inserts were obtained and analyzed using ImageJ software. n=4; error bars represent s.e.m., p-values obtained using a student's t-test. Representative images are shown. Scale bar represents 100 µm. FIG. 4b, The relative expression levels of IGFBP2, MERTK or PITPNC1 in human breast tumor samples from stage I/II (n=53) as compared to stage III (n=29) or stage IV (n=9) patients were quantified from the OriGene TissueScan Breast Cancer arrays using qPCR. Error bars represent s.e.m., p-values obtained using student's t-test. FIG. 4c, FIG. 4d and FIG. 4e, Bioluminescence imaging of lung metastasis by lung metastatic breast cancer cells with inhibited expression of the various miR-126 regulated genes. $4 \times 10^4$ LM2 cells expressing the control hairpin or independent short hairpins targeting IGFBP2 (c), PITPNC1 (d) and MERTK (e) were injected intravenously into immunodeficient NOD-SCID mice. Lung colonization was measured by bioluminescence imaging and quantified. n=5; error bars represent s.e.m.; p-value based on a one-sided student's t-test.

FIGS. 5a-5g are diagrams and photographs showing that IGFBP2 mediated endothelial recruitment by activating IGF1/IGF1R signaling in endothelial cells. FIG. 5a, IGFBP2 levels in conditioned media from HUVEC recruitment assays using MDA-MB-231 cells and LM2 cells (FIG. 2f) were quantified by ELISA. n=4; error bars represent s.e.m., p-values obtained using student's t-test. FIG. 5b, $2.5 \times 10^4$ MDA-MB-231 cells expressing a short hairpin targeting miR-126 or the control hairpin, as well as LM2 cells expressing miR-126 or the control hairpin, were seeded in quadruplicate. Trans-well recruitment of $5 \times 10^4$ HUVEC cells in the presence of 50 ng/ml IGFBP2 Ab or 50 ng/ml control IgG Ab towards the cancer cells was then assessed. Images of the basal side of the trans-well inserts were obtained and the number of cells that had migrated was quantified using ImageJ. n=4; error bars represent s.e.m., p-values obtained using student's t-test. Scale bar represents 100 µm. FIG. 5c, $2.5 \times 10^4$ CN34 Par cells expressing a short hairpin targeting miR-126 or the control hairpin, as well as CN34 Lm1a cells expressing miR-126 or the control hairpin, were seeded in quadruplicate. Trans-well migration of $5 \times 10^4$ HUVEC cells in the presence of 50 ng/ml IGFBP2 Ab or 50 ng/ml control IgG Ab towards the cancer cells was assessed. n=4; error bars represent s.e.m., p-values obtained using student's t-test. FIG. 5d, FIG. 5e, Trans-well recruitment of HUVEC cells incubated with 20 µg/ml IGF-1 blocking Ab (d), 40 µg/ml IGF-2 blocking Ab (d), 20 µg/ml IGF1R blocking Ab (e), 5 µg/ml IGF2R blocking Ab (e), or control IgG (d,e) towards MDA-MB-231 cells expressing a short hairpin targeting miR-126 or control hairpin was assayed. n=4; error bars represent s.e.m., p-values obtained using student's t-test. FIG. 5f, HUVEC and cancer cells were pretreated with 20 µg/ml IGF1R blocking Ab or control IgG Ab for 1 hour before trans-well recruitment of HUVEC cells towards cancer cells were assessed. n=4; error bars represent s.e.m., p-values obtained using student's t-test FIG. 5g, IGFBP2 gradient was simulated by mixing the given amounts of recombinant IGFBP2 protein with matrigel (1:1) in the bottom of a well. Chemotaxis of $1.5 \times 10^5$ HUVEC cells along the IGFBP2 gradient was then assessed by counting the number of cells that had migrated to the basal side of trans-well inserts after 20 h using ImageJ software. n=4; error bars represent s.e.m., p-values obtained using student's t-test.

FIG. 6a, IGFBP2 levels in conditioned media from Lm2 cells expressing control hairpin or 2 independent hairpins against PITPNC1 as determined by ELISA. FIG. 6b, $2.5 \times 10^4$ MDA-MB-231 cells expressing a control hairpin or a hairpin targeting miR-126 were seeded in quadruplicate. Trans-well migration of $5 \times 10^4$ HUVEC cells towards the cancer cells in the presence of 1 ng/ml GAS6 and/or 10 µg/ml MerFc was then assessed by counting the number of cells that had migrated to the basal side of porous inserts in images obtained using ImageJ. n=4; error bars represent s.e.m., p-values were obtained using student's t-test. FIG. 6c, IGFBP2 gradient in the presence of Gas6 and secreted MERTK was simulated by mixing rhIGFBP2 (520 ng), Gas6 (5 ng) and MerFc (10 ug) protein with matrigel (1:1) in the bottom of a well. Chemotaxis of $1.5 \times 10^5$ HUVEC cells along the gradient was then assessed by counting the number of cells that had migrated to the basal side of trans-well inserts after 20 h using ImageJ software. n=4; error bars represent s.e.m., p-values obtained using student's t-test. FIG. 6d, Lung sections were double stained for vimentin and MECA-32. The border of each nodule was drawn based on human-vimentin staining and MECA-32 staining inside the metastatic nodule highlighted in black (lower panels). The area positive for MECA-32 staining within each nodule was then determined by using ImageJ and presented as the area covered by MECA-32 staining per area of the given nodule (% vessel density). The distribution of % vessel density between the injected LM2 cells expressing hairpins targeting IGFBP2, PITPNC1, MERTK or a control hairpin are shown in a cumulative fraction plot. n=4, p-value based on the Kolmogorov-Smirnov Test. FIG. 6e, Schematic of miR-126 regulation of endothelial recruitment and metastatic colonization through interaction with IGFBP2, PITPNC1 and MERTK.

FIG. 9a, $5\times10^4$ MDA cells expressing miR-126 KD or control KD vector were seeded onto a HUVEC monolayer and adhesion was assessed. Images of cells that had adhered to the HUVEC monolayer were obtained and analyzed using ImageJ software. n=4; error bars represent s.e.m. FIG. 9b, Conditioned media from $5\times10^5$ MDA miR-126 KD or MDA control KD cells was obtained by incubating the cells with EGM-2 media for 24 h. $2.5\times10^4$ HUVEC cells were seeded in triplicate, grown in the conditioned media and viable cells were counted at 5 days after seeding. n=3; error bars represent s.e.m.

FIG. 10a, FIG. 10b and FIG. 10c, $5\times10^5$ MDA cells expressing control hairpin or hairpin targeting miR-126 were mixed in 1:1 ratio with Matrigel and injected in the mammary fat pad. 5 min prior to sacrifice, biotinlyated lectin was injected in the tail vein. Size matched tumors were excised and functional blood vessels were detected by staining of the injected lectin (FIG. 10a), CD45$^+$ lymphocyte detected by anti-CD45 (FIG. 10b) and Mac-2$^+$ macrophages detected by anti-Mac-2 (FIG. 10c).

FIG. 12a, FIG. 12b, Luciferase reporter assays of the miR-126 metastasis gene set in MDA-MB-231 cells expressing a short hairpin targeting miR-126 as well as the control KD hairpin. Reporter constructs containing the luciferase gene upstream of the 3'UTR (FIG. 12a) or CDS (FIG. 12b) of ABCB9, IGFBP2, MERTK, PITPNC1, PSAT1, PYBG, SHMT2 and VIPR1 were transfected into the various cell lines and luciferase activity was assayed at 30 hours post transfection. n=4; error bars represent s.e.m.; p-values were obtained using student's t-test.

FIG. 22 is a set of diagrams showing data from antibody capture ELISA assays used to characterize binding properties of IGFBP2 neutralizing monoclonal antibodies recovered from single hybridoma clones isolated from hybridoma library wo6663-1. Several of the IGFBP2 neutralizing monoclonal antibodies, including M1, M4, M6, M9, M13, M14, M15, and M16, were able to bind IGFBP2 with high affinity and neutralize its binding to IGF1.

DETAILED DESCRIPTION OF THE INVENTION

Figure 1D:
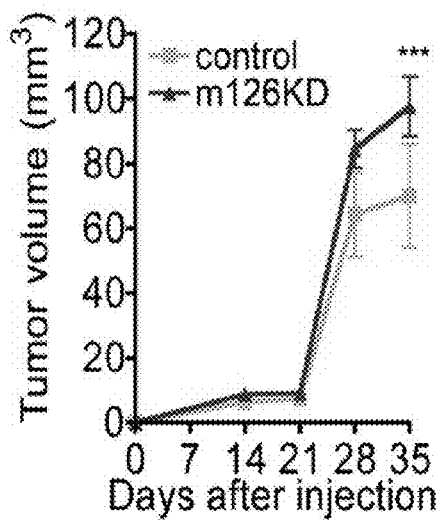

The described invention provides reagents and methods for treating disorders characterized by pathological angiogenesis, such as metastasis.

As disclosed herein, a systematic analysis and focus on metastasis and metastatic angiogenesis led to the identification of a number of molecules, including secreted IGFBP2, the transferase PITPNC1, the kinase MERTK, and miR-126, as targets for therapeutic inhibition with the potential for treating metastatic cancer. A newly discovered pathway coordinates IGFBP2, PITPNC1, and MERTK-pro-angiogenic genes that correlate in expression with human metastasis. These genes represent regulators of metastatic endothelial recruitment and angiogenesis. For example, IGFBP2, a protein secreted by metastatic cells, recruits endothelia by modulating IGF1-mediated activation of the IGF type-I Receptor on endothelial cells.

Endothelial recruitment is a process where endothelial cells or their progenitors are mobilized and homing to a site or region in a subject for generating new blood vessels or remodeling of preexisting blood vessels, i.e., angiogenesis. Inhibiting this process via the above-mentioned new pathway can be used to inhibit pathological angiogenesis, and thereby to treat disorders characterized by pathological angiogenesis, such as metastasis.

To inhibit endothelial recruitment and resulting angiogenesis in a subject in need thereof, one can administer to the subject an agent that inhibits expression or activity of a protein selected from IGFBP2, IGF1, IGF1R, MERTK, PITPNC1, ABCB9, PSAT1, PYGB, SHMT2, and VIPR. Listed below are the amino acid sequences of these proteins. The agent can be a nucleic acid, a polypeptide, an antibody, or a small molecule compound.

```
IGFBP2
MLPRVGCPALPLPPPPLLPLLPLLLLLLGASGGGGGARAEVLFRCPPCTPERLAACGPPP

VAPPAAVAAVAGGARMPCAELVREPGCGCCSVCARLEGEACGVYTPRCGQGLRCYPHPGS

ELPLQALVMGEGTCEKRRDAEYGASPEQVADNGDDHSEGGLVENHVDSTMNMLGGGGSAG

RKPLKSGMKELAVFREKVTEQHRQMGKGGKHHLGLEEPKKLRPPPARTPCQQELDQVLER

ISTMRLPDERGPLEHLYSLHIPNCDKHGLYNLKQCKMSLNGQRGECWCVNPNTGKLIQGA

PTIRGDPECHLFYNEQQEARGVHTQRMQ

IGF1 (isoform 1)
MGKISSLPTQLFKCCFCDFLKVKMHTMSSSHLFYLALCLLTFTSSATAGPETLCGAELVD

ALQFVCGDRGFYFNKPTGYGSSSRRAPQTGIVDECCFRSCDLRRLEMYCAPLKPAKSARS

VRAQRHTDMPKTQKYQPPSTNKNTKSQRRKGSTFEERK

IGF1 (isoform 2)
MITPTVKMHTMSSSHLFYLALCLLTFTSSATAGPETLCGAELVDALQFVCGDRGFYFNKP

TGYGSSSRRAPQTGIVDECCFRSCDLRRLEMYCAPLKPAKSARSVRAQRHTDMPKTQKEV

HLKNASRGSAGNKNYRM

IGF1 (isoform 3)
MGKISSLPTQLFKCCFCDFLKVKMHTMSSSHLFYLALCLLTFTSSATAGPETLCGAELVD

ALQFVCGDRGFYFNKPTGYGSSSRRAPQTGIVDECCFRSCDLRRLEMYCAPLKPAKSARS

VRAQRHTDMPKTQKYQPPSTNKNTKSQRRKGWPKTHPGGEQKEGTEASLQIRGKKKEQRR

EIGSRNAECRGKKGK
```

-continued

IGF1 (isoform 4)
MGKISSLPTQLFKCCFCDFLKVKMHTMSSSHLFYLALCLLTFTSSATAGPETLCGAELVD

ALQFVCGDRGFYFNKPTGYGSSSRRAPQTGIVDECCFRSCDLRRLEMYCAPLKPAKSARS

VRAQRHTDMPKTQKEVHLKNASRGSAGNKNYRM

IGF1R
MKSGSGGGSPTSLWGLLFLSAALSLWPTSGEICGPGIDIRNDYQQLKRLENCTVIEGYLH

ILLISKAEDYRSYRFPKLTVITEYLLLFRVAGLESLGDLFPNLTVIRGWKLFYNYALVIF

EMTNLKDIGLYNLRNITRGAIRIEKNADLCYLSTVDWSLILDAVSNNYIVGNKPPKECGD

LCPGTMEEKPMCEKTTINNEYNYRCWTTNRCQKMCPSTCGKRACTENNECCHPECLGSCS

APDNDTACVACRHYYYAGVCVPACPPNTYRFEGWRCVDRDFCANILSAESSDSEGFVIHD

GECMQECPSGFIRNGSQSMYCIPCEGPCPKVCEEEKKTKTIDSVTSAQMLQGCTIFKGNL

LINIRRGNNIASELENFMGLIEVVTGYVKIRHSHALVSLSFLKNLRLILGEEQLEGNYSF

YVLDNQNLQQLWDWDHRNLTIKAGKMYFAFNPKLCVSEIYRMEEVTGTKGRQSKGDINTR

NNGERASCESDVLHFTSTTTSKNRIIITWHRYRPPDYRDLISFTVYYKEAPFKNVTEYDG

QDACGSNSWNMVDVDLPPNKDVEPGILLHGLKPWTQYAVYVKAVTLTMVENDHIRGAKSE

ILYIRTNASVPSIPLDVLSASNSSSQLIVKWNPPSLPNGNLSYYIVRWQRQPQDGYLYRH

NYCSKDKIPIRKYADGTIDIEEVTENPKTEVCGGEKGPCCACPKTEAEKQAEKEEAEYRK

VFENFLHNSIFVPRPERKRRDVMQVANTTMSSRSRNTTAADTYNITDPEELETEYPFFES

RVDNKERTVISNLRPFTLYRIDIHSCNHEAEKLGCSASNFVFARTMPAEGADDIPGPVTW

EPRPENSIFLKWPEPENPNGLILMYEIKYGSQVEDQRECVSRQEYRKYGGAKLNRLNPGN

YTARIQATSLSGNGSWTDPVFFYVQAKTGYENFIHLIIALPVAVLLIVGGLVIMLYVFHR

KRNNSRLGNGVLYASVNPEYFSAADVYVPDEWEVAREKITMSRELGQGSFGMVYEGVAKG

VVKDEPETRVAIKTVNEAASMRERIEFLNEASVMKEFNCHHVVRLLGVVSQGQPTLVIME

LMTRGDLKSYLRSLRPEMENNPVLAPPSLSKMIQMAGEIADGMAYLNANKFVHRDLAARN

CMVAEDFTVKIGDFGMTRDIYETDYYRKGGKGLLPVRWMSPESLKDGVFTTYSDVWSFGV

VLWEIATLAEQPYQGLSNEQVLRFVMEGGLLDKPDNCPDMLFELMRMCWQYNPKMRPSFL

EIISSIKEEMEPGFREVSFYYSEENKLPEPEELDLEPENMESVPLDPSASSSSLPLPDRH

SGHKAENGPGPGVLVLRASFDERQPYAHMNGGRKNERALPLPQSSTC

MERTK
MGPAPLPLLLGLFLPALWRRAITEAREEAKPYPLFPGPFPGSLQTDHTPLLSLPHASGYQ

PALMFSPTQPGRPHTGNVAIPQVTSVESKPLPPLAFKHTVGHIILSEHKGVKFNCSISVP

NIYQDTTISWWKDGKELLGAHHAITQFYPDDEVTAIIASFSITSVQRSDNGSYICKMKIN

NEEIVSDPIYIEVQGLPHFTKQPESMNVTRNTAFNLTCQAVGPPEPVNIFWVQNSSRVNE

QPEKSPSVLTVPGLTEMAVFSCEAHNDKGLTVSKGVQINIKAIPSPPTEVSIRNSTAHSI

LISWVPGFDGYSPFRNCSIQVKEADPLSNGSVMIFNTSALPHLYQIKQLQALANYSIGVS

CMNEIGWSAVSPWILASTTEGAPSVAPLNVTVFLNESSDNVDIRWMKPPTKQQDGELVGY

RISHVWQSAGISKELLEEVGQNGSRARISVQVHNATCTVRIAAVTRGGVGPFSDPVKIFI

PAHGWVDYAPSSTPAPGNADPVLIIFGCFCGFILIGLILYISLAIRKRVQETKFGNAFTE

EDSELVVNYIAKKSFCRRAIELTLHSLGVSEELQNKLEDVVIDRNLLILGKILGEGEFGS

VMEGNLKQEDGTSLKVAVKTMKLDNSSQREIEEFLSEAACMKDFSHPNVIRLLGVCIEMS

SQGIPKPMVILPFMKYGDLHTYLLYSRLETGPKHIPLQTLLKFMVDIALGMEYLSNRNFL

HRDLAARNCMLRDDMTVCVADFGLSKKIYSGDYYRQGRIAKMPVKWIAIESLADRVYTSK

-continued

SDVWAFGVTMWEIATRGMTPYPGVQNHEMYDYLLHGHRLKQPEDCLDELYEIMYSCWRTD

PLDRPTFSVLRLQLEKLLESLPDVRNQADVIYVNTQLLESSEGLAQGSTLAPLDLNIDPD

SIIASCTPRAAISVVTAEVHDSKPHEGRYILNGGSEEWEDLTSAPSAAVTAEKNSVLPGE

RLVRNGVSWSHSSMLPLGSSLPDELLFADDSSEGSEVLM

PITPNC1 (isoform a)
MLLKEYRICMPLTVDEYKIGQLYMISKHSHEQSDRGEGVEVVQNEPFEDPHHGNGQFTEK

RVYLNSKLPSWARAVVPKIFYVTEKAWNYYPYTITEYTCSFLPKFSIHIETKYEDNKGSN

DTIFDNEAKDVEREVCFIDIACDEIPERYYKESEDPKHFKSEKTGRGQLREGWRDSHQPI

MCSYKLVTVKFEVWGLQTRVEQFVHKVVRDILLIGHRQAFAWVDEWYDMTMDEVREFERA

TQEATNKKIGIFPPAISISSIPLLPSSVRSAPSSAPSTPLSTDAPEFLSVPKDRPRKKSA

PETLTLPDPEKKATLNLPGMHSSDKPCRPKSE

PITPNC1 (isoform b)
MLLKEYRICMPLTVDEYKIGQLYMISKHSHEQSDRGEGVEVVQNEPFEDPHHGNGQFTEK

RVYLNSKLPSWARAVVPKIFYVTEKAWNYYPYTITEYTCSFLPKFSIHIETKYEDNKGSN

DTIFDNEAKDVEREVCFIDIACDEIPERYYKESEDPKHFKSEKTGRGQLREGWRDSHQPI

MCSYKLVTVKFEVWGLQTRVEQFVHKVVRDILLIGHRQAFAWVDEWYDMTMDDVREYEKN

MHEQTNIKVCNQHSSPVDDIESHAQTST

ABCB9
MRLWKAVVVTLAFMSVDICVTTAIYVFSHLDRSLLEDIRHFNIFDSVLDLWAACLYRSCL

LLGATIGVAKNSALGPRRLRASWLVITLVCLFVGIYAMVKLLLFSEVRRPIRDPWFWALF

VWTYISLGASFLLWWLLSTVRPGTQALEPGAATEAEGFPGSGRPPPEQASGATLQKLLSY

TKPDVAFLVAASFFLIVAALGETFLPYYTGRAIDGIVIQKSMDQFSTAVVIVCLLAIGSS

FAAGIRGGIFTLIFARLNIRLRNCLFRSLVSQETSFFDENRTGDLISRLTSDTTMVSDLV

SQNINVFLRNTVKVTGVVVFMFSLSWQLSLVTFMGFPIIMMVSNIYGKYYKRLSKEVQNA

LARASNTAEETISAMKTVRSFANEEEEAEVYLRKLQQVYKLNRKEAAAYMYYVWGSGLTL

LVVQVSILYYGGHLVISGQMTSGNLIAFIIYEFVLGDCMESVGSVYSGLMQGVGAAEKVF

EFIDRQPTMVHDGSLAPDHLEGRVDFENVTFTYRTRPHTQVLQNVSFSLSPGKVTALVGP

SGSGKSSCVNILENFYPLEGGRVLLDGKPISAYDHKYLHRVISLVSQEPVLFARSITDNI

SYGLPTVPFEMVVEAAQKANAHGFIMELQDGYSTETGEKGAQLSGGQKQRVAMARALVRN

PPVLILDEATSALDAESEYLIQQAIHGNLQKHTVLIIAHRLSTVEHAHLIVVLDKGRVVQ

QGTHQQLLAQGGLYAKLVQRQMLGLQPAADFTAGHNEPVANGSHKA

PSAT1 (isoform 1)
MDAPRQVVNFGPGPAKLPHSVLLEIQKELLDYKGVGISVLEMSHRSSDFAKIINNTENLV

RELLAVPDNYKVIFLQGGGCGQFSAVPLNLIGLKAGRCADYVVTGAWSAKAAEEAKKFGT

INIVHPKLGSYTKIPDPSTWNLNPDASYVYYCANETVHGVEFDFIPDVKGAVLVCDMSSN

FLSKPVDVSKFGVIFAGAQKNVGSAGVTVVIVRDDLLGFALRECPSVLEYKVQAGNSSLY

NTPPCFSIYVMGLVLEWIKNNGGAAAMEKLSSIKSQTIYEIIDNSQGFYVCPVEPQNRSK

MNIPFRIGNAKGDDALEKRFLDKALELNMLSLKGHRSVGGIRASLYNAVTIEDVQKLAAF

MKKFLEMHQL

PSAT1 (isoform 2)
MDAPRQVVNFGPGPAKLPHSVLLEIQKELLDYKGVGISVLEMSHRSSDFAKIINNTENLV

RELLAVPDNYKVIFLQGGGCGQFSAVPLNLIGLKAGRCADYVVTGAWSAKAAEEAKKFGT

INIVHPKLGSYTKIPDPSTWNLNPDASYVYYCANETVHGVEFDFIPDVKGAVLVCDMSSN

-continued

FLSKPVDVSKFGVIFAGAQKNVGSAGVTVVIVRDDLLGFALRECPSVLEYKVQAGNSSLY

NTPPCFSIYVMGLVLEWIKNNGGAAAMEKLSSIKSQTIYEIIDNSQGFYVSVGGIRASLY

NAVTIEDVQKLAAFMKKFLEMHQL

PYGB
MAKPLTDSEKRKQISVRGLAGLGDVAEVRKSFNRHLHFTLVKDRNVATPRDYFFALAHTV

RDHLVGRWIRTQQHYYERDPKRIYYLSLEFYMGRTLQNTMVNLGLQNACDEAIYQLGLDL

EELEEIEEDAGLGNGGLGRLAACFLDSMATLGLAAYGYGIRYEFGIFNQKIVNGWQVEEA

DDWLRYGNPWEKARPEYMLPVHFYGRVEHTPDGVKWLDTQVVLAMPYDTPVPGYKNNTVN

TMRLWSAKAPNDFKLQDFNVGDYIEAVLDRNLAENISRVLYPNDNFFEGKELRLKQEYFV

VAATLQDIIRRFKSSKFGCRDPVRTCFETFPDKVAIQLNDTHPALSIPELMRILVDVEKV

DWDKAWEITKKTCAYTNHTVLPEALERWPVSMFEKLLPRHLEIIYAINQRHLDHVAALFP

GDVDRLRRMSVIEEGDCKRINMAHLCVIGSHAVNGVARIHSEIVKQSVFKDFYELEPEKF

QNKTNGITPRRWLLLCNPGLADTIVEKIGEEFLTDLSQLKKLLPLVSDEVFIRDVAKVKQ

ENKLKFSAFLEKEYKVKINPSSMFDVHVKRIHEYKRQLLNCLHVVTLYNRIKRDPAKAFV

PRTVMIGGKAAPGYHMAKLIIKLVTSIGDVVNHDPVVGDRLKVIFLENYRVSLAEKVIPA

ADLSQQISTAGTEASGTGNMKFMLNGALTIGTMDGANVEMAEEAGAENLFIFGLRVEDVE

ALDRKGYNAREYYDHLPELKQAVDQISSGFFSPKEPDCFKDIVNMLMHHDRFKVFADYEA

YMQCQAQVDQLYRNPKEWTKKVIRNIACSGKFSSDRTITEYAREIWGVEPSDLQIPPPNI

PRD

SHMT2 (isoform 1)
MLYFSLFWAARPLQRCGQLVRMAIRAQHSNAAQTQTGEANRGWTGQESLSDSDPEMWELL

QREKDRQCRGLELIASENFCSRAALEALGSCLNNKYSEGYPGKRYYGGAEVVDEIELLCQ

RRALEAFDLDPAQWGVNVQPYSGSPANLAVYTALLQPHDRIMGLDLPDGGHLTHGYMSDV

KRISATSIFFESMPYKLNPKTGLIDYNQLALTARLFRPRLIIAGTSAYARLIDYARMREV

CDEVKAHLLADMAHISGLVAAKVIPSPFKHADIVTTTHKTLRGARSGLIFYRKGVKAVD

PKTGREIPYTFEDRINFAVFPSLQGGPHNHAIAAVAVALKQACTPMFREYSLQVLKNARA

MADALLERGYSLVSGGTDNHLVLVDLRPKGLDGARAERVLELVSITANKNTCPGDRSAIT

PGGLRLGAPALTSRQFREDDFRRVVDFIDEGVNIGLEVKSKTAKLQDFKSFLLKDSETSQ

RLANLRQRVEQFARAFPMPGFDEH

SHMT2 (isoform 2)
MLYFSLFWAARPLQRCGQLVRMAIRAQHSNAAQTQTGEANRGWTGQESLSDSDPEMWELL

QREKDRQCRGLELIASENFCSRAALEALGSCLNNKYSEGYPGKRYYGGAEVVDEIELLCQ

RRALEAFDLDPAQWGVNVQPYSGSPANLAVYTALLQPHDRIMGLDLPDGGHLTHGYMSDV

KRISATSIFFESMPYKLNLALTARLFRPRLIIAGTSAYARLIDYARMREVCDEVKAHLLA

DMAHISGLVAAKVIPSPFKHADIVTTTTHKTLRGARSGLIFYRKGVKAVDPKTGREIPYT

FEDRINFAVFPSLQGGPHNHAIAAVAVALKQACTPMFREYSLQVLKNARAMADALLERGY

SLVSGGTDNHLVLVDLRPKGLDGARAERVLELVSITANKNTCPGDRSAITPGGLRLGAPA

LTSRQFREDDFRRVVDFIDEGVNIGLEVKSKTAKLQDFKSFLLKDSETSQRLANLRQRVE

QFARAFPMPGFDEH

SHMT2 (isoform 3)
MAIRAQHSNAAQTQTGEANRGWTGQESLSDSDPEMWELLQREKDRQCRGLELIASENFCS

RAALEALGSCLNNKYSEGYPGKRYYGGAEVVDEIELLCQRRALEAFDLDPAQWGVNVQPY

SGSPANLAVYTALLQPHDRIMGLDLPDGGHLTHGYMSDVKRISATSIFFESMPYKLNPKT

-continued

```
GLIDYNQLALTARLFRPRLIIAGTSAYARLIDYARMREVCDEVKAHLLADMAHISGLVAA

KVIPSPFKHADIVTTTTHKTLRGARSGLIFYRKGVKAVDPKTGREIPYTFEDRINFAVFP

SLQGGPHNHAIAAVAVALKQACTPMFREYSLQVLKNARAMADALLERGYSLVSGGTDNHL

VLVDLRPKGLDGARAERVLELVSITANKNTCPGDRSAITPGGLRLGAPALTSRQFREDDF

RRVVDFIDEGVNIGLEVKSKTAKLQDFKSFLLKDSETSQRLANLRQRVEQFARAFPMPGF

DEH

VIPR1
MRPPSPLPARWLCVLAGALAWALGPAGGQAARLQEECDYVQMIEVQHKQCLEEAQLENET

IGCSKMWDNLTCWPATPRGQVVVLACPLIFKLFSSIQGRNVSRSCTDEGWTHLEPGPYPI

ACGLDDKAASLDEQQTMFYGSVKTGYTIGYGLSLATLLVATAILSLFRKLHCTRNYIHMH

LFISFILRAAAVFIKDLALFDSGESDQCSEGSVGCKAAMVFFQYCVMANFFWLLVEGLYL

YTLLAVSFFSERKYFWGYILIGWGVPSTFTMVWTIARIHFEDYGCWDTINSSLWWIIKGP

ILTSILVNFILFICIIRILLQKLRPPDIRKSDSSPYSRLARSTLLLIPLFGVHYIMFAFF

PDNFKPEVKMVFELVVGSFQGFVVAILYCFLNGEVQAELRRKWRRWHLQGVLGWNPKYRH

PSGGSNGATCSTQVSMLTRVSPGARRSSSFQAEVSLV
```

An inhibitory agent (i.e., inhibitor) or an activating agent (i.e., activator) can be a nucleic acid, a polypeptide, an antibody, or a small molecule compound. Preferably, it is an isolated agent, but not an endogenous molecule (a micro RNA) in a cell of the subject. In one example, it excludes a micro RNA that is endogenous in human cells, e.g., miR-126, miR206, or/and miR-335. In another example, the inhibitory or activating agent functions at a level of transcription, mRNA stability, translation, protein stability/degradation, protein modification, and protein binding.

A nucleic acid refers to a DNA molecule (for example, but not limited to, a cDNA or genomic DNA), an RNA molecule (for example, but not limited to, an mRNA), or a DNA or RNA analog. A DNA or RNA analog can be synthesized from nucleotide analogs. The nucleic acid molecule can be single-stranded or double-stranded. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The terms "RNA," "RNA molecule," and "ribonucleic acid molecule" are used interchangeably herein, and refer to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA also can be chemically synthesized. DNA and RNA can be single-stranded (i.e., ssRNA and ssDNA, respectively) or multi-stranded (e.g., double-stranded, i.e., dsRNA and dsDNA, respectively).

The nucleic acid sequence can encode a small interference RNA (e.g., an RNAi agent) that targets one or more of the above-mentioned genes and inhibits its expression or activity. The term "RNAi agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("iRNA") is a double stranded short-interfering RNA (siRNA), short hairpin RNA (shRNA), or single-stranded micro-RNA (miRNA) that results in catalytic degradation of specific mRNAs, and also can be used to lower or inhibit gene expression.

The term "short interfering RNA" or "siRNA" (also known as "small interfering RNAs") refers to an RNA agent, preferably a double-stranded agent, of about 10-50 nucleotides in length, preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The term "miRNA" or "microRNA" refers to an RNA agent, preferably a single-stranded agent, of about 10-50 nucleotides in length, preferably between about 15-25 nucleotides in length, more preferably about 17, 18, 19, 20, 21, 22, 23, 24, or 25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer orthologue or homologue capable of processing dsRNA structures into siRNAs, miRNAs, siRNA-like or miRNA-like molecules. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

Thus, also within the scope of this invention is utilization of RNAi featuring degradation of RNA molecules (e.g., within a cell). Degradation is catalyzed by an enzymatic, RNA-induced silencing complex (RISC). A RNA agent having a sequence sufficiently complementary to a target RNA sequence (e.g., one or more of the above-mentioned genes) to direct RNAi means that the RNA agent has a homology of at least 50%, (e.g., 50%, 60%, 70%, 80%, 90%, 95%, 98%, 99%, or 100% homology) to the target RNA sequence so that the two are sufficiently complementary to each other to hybridize and trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent also can have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence.

The above-mentioned polynucleotides can be delivered using polymeric, biodegradable microparticle or microcapsule delivery devices known in the art. Another way to achieve uptake of the polynucleotides is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of naked DNA (i.e., without a delivery vehicle) to an intramuscular, intradermal, or subcutaneous site is another means to achieve in vivo expression.

siRNA, miRNA, and asRNA (antisense RNA) molecules can be designed by methods well known in the art. siRNA, miRNA, and asRNA molecules with homology sufficient to provide sequence specificity required to uniquely degrade any RNA can be designed using programs known in the art, including, but not limited to, those maintained on websites for AMBION, Inc. and DHARMACON, Inc. Systematic testing of several designed species for optimization of the siRNA, miRNA, and asRNA sequence can be routinely performed by those skilled in the art. Considerations when designing short interfering nucleic acid molecules include, but are not limited to, biophysical, thermodynamic, and structural considerations, base preferences at specific positions in the sense strand, and homology. These considerations are well known in the art and provide guidelines for designing the above-mentioned RNA molecules.

In one example, the polypeptide is an antibody. The term "antibody" refers to an immunoglobulin molecule or immunologically active portion thereof, i.e., an antigen-binding portion. Examples include, but are not limited to, a protein having at least one or two, heavy (H) chain variable regions ($V_H$), and at least one or two light (L) chain variable regions ($V_L$). The $V_H$ and $V_L$ regions can be further subdivided into regions of hypervariability, termed "complementarity determining regions" ("CDR"), interspersed with regions that are more conserved, termed "framework regions" (FR). As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, and IgG4), delta, epsilon and mu constant region genes, as well as the myriad immunoglobulin variable region genes.

The term "antigen-binding portion" of an antibody (or "antibody portion") refers to one or more fragments of an antibody that retain the ability to specifically bind to an antigen (e.g., IGFBP2, IGF1, IGF1R, MERTK, PITPNC1, ABCB9, PSAT1, PYGB, SHMT2, or VIPR). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Antibodies that specifically bind to one of the above-mentioned target protein can be made using methods known in the art. This antibody can be a polyclonal or a monoclonal antibody. Examples of such antibodies include those described in the working examples below. In one embodiment, the antibody can be recombinantly produced, e.g., produced by phage display or by combinatorial methods. In another embodiment, the antibody is a fully human antibody (e.g., an antibody made in a mouse which has been genetically engineered to produce an antibody from a human immunoglobulin sequence), a humanized antibody, or a non-human antibody, for example, but not limited to, a rodent (mouse or rat), goat, primate (for example, but not limited to, monkey), rabbit, or camel antibody. Examples of methods to generate humanized version of antibodies include, but are not limited to, CDR grafting (Queen et al., U.S. Pat. No. 5,585,089; Riechmann et al., Nature 332:323

(1988)), chain shuffling (U.S. Pat. No. 5,565,332); and veneering or resurfacing (EP 592,106; EP 519,596); Padlan, Molecular Immunology 28(415):489-498 (1991); Studnicka et al., Protein Engineering 7(6):805-814 (1994); Roguska. et al., PNAS 91:969-973 (1994)). Examples of methods to generate fully human antibodies include, but are not limited to, generation of antibodies from mice that can express human immunoglobulin genes and use of phage-display technology to generate and screen human immunoglobulin gene libraries.

An "isolated antibody" is intended to refer to an antibody that is substantially free of other antibodies having different antigenic specificities (e.g., an isolated antibody that specifically binds IGFBP2, IGF1, IGF1R, MERTK, PITPNC1, ABCB9, PSAT1, PYGB, SHMT2, or VIPR is substantially free of antibodies that specifically bind antigens other than such an antigen). An isolated antibody that specifically binds the antigen may, however, have cross-reactivity to other antigens, such as IGFBP2, IGF1, IGF1R, MERTK, PITPNC1, ABCB9, PSAT1, PYGB, SHMT2, or VIPR molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, the term "high affinity" for an IgG antibody refers to an antibody having a $K_D$ of $10^{-7}$ M or less, preferably $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

In one example, a composition comprising a monoclonal antibody that neutralizes IGFBP2 function by inhibiting IGFBP2 binding to IGF1 is described. In one embodiment, this antibody can be a fully human antibody, a humanized antibody, or a non-human antibody, for example, but not limited to, a rodent (mouse or rat), goat, primate (for example, but not limited to, monkey), rabbit, or camel antibody. In one embodiment, one or more amino-acids of this monoclonal monoclonal antibody may be substituted in order to alter its physical properties. These properties include, but are not limited to, binding specificity, binding affinity, immunogenicity, and antibody isotype. Pharmaceutical compositions containing fully human or humanized versions of the above described antibodies can be used to treat disorders of pathological angiogenesis.

In one example, a composition comprising an IGFBP2 neutralizing antibody that inhibits IGF1 from binding to IGFBP2 inhibits breast cancer tumor progression and tumor burden in vivo. In this example, administration of the above described antibody reduced tumor burden of human breast cancer in vivo in a mouse model of human cancer.

Pharmaceutical compositions containing fully human or humanized versions of the above described antibodies can be used to inhibit breast cancer metastasis in human patients by inhibiting endothelial recruitment by metastatic cells. In another embodiment, pharmaceutical compositions containing fully human or humanized versions of these antibodies can be used to treat other types of vascular tumors. Typical vascularized tumors that can be treated with this composition include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

In another embodiment, the polypeptide is a mutant form of the above-mentioned protein, which interferes with the above-mentioned pathway and therefore inhibits endothelial recruitment and angiogenesis. The term "mutant" encompasses naturally occurring mutants and mutants created chemically and/or using recombinant DNA techniques. A mutant of one of the above-mentioned wild type polypeptide can be due to alteration, e.g., truncation, elongation, substitution, deletion, or insertion, of one or more amino acids. The alteration also can have a modified amino acid, such as one comprising a post-translational modification. The pro-angiogenic activity of a mutant, if any, is substantially lower than the activity of the wild type polypeptide by at least about 20% (e.g., 30%, 40%, 50%, 60%, 70%, 80%, 90%, or 100%) as measured using an assay described herein or known in the art. One example is a polypeptide having the extracellular domain of IGF1-R, but lacking the intra-cellular domain. By competing for IGF-1, this mutant can inhibit the above-mentioned pathway and pro-angiogenic activity in a dominant-negative manner.

The amino acid compositions of the above-mentioned antibodies or polypeptides may vary with or without disrupting the ability (e.g., affinity) to bind to the respective antigens or targets, and trigger or inhibit the respective cellular response. For example, they can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in, e.g., SEQ ID NO: 9 or 10 can be replaced with another amino acid residue from the same side chain family. Alternatively, mutations can be introduced randomly along all or part of the sequences, such as by saturation mutagenesis, and the resultant mutants can be screened for the ability to bind to the respective antigen and trigger the respective cellular response to identify mutants that retain the activity.

Compositions

Within the scope of this invention is a composition that contains a suitable carrier and one or more of the agents described above. The composition can be a pharmaceutical composition that contains a pharmaceutically acceptable carrier, a dietary composition that contains a dietarily acceptable suitable carrier, or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, sodium lauryl sulfate, and D&C Yellow #10.

The above-described composition, in any of the forms described above, can be used for treating disorders characterized by pathological angiogenesis. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas. The topical composition is useful for treating disorders in the skin, such as melanoma and certain inflammatory disorders.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, allergic response, and the like. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition.

Treatment Methods

The described invention provides methods for treating in a subject an angiogenic disorder or a disorder of angiogenesis.

The terms "angiogenic disorder," "disorder of angiogenesis," and "angiogenesis disorder" are used interchangeably herein, and refer to a disorder characterized by pathological angiogenesis. A disorder characterized by pathological angiogenesis refers to a disorder where abnormal or aberrant angiogenesis, alone or in combination with others, contributes to causation, origination, or symptom of the disorder. Examples of this disorder include various cancers (e.g., vascularized tumors), eye disorders, inflammatory disorders, and others.

Typical vascularized tumors that can be treated with the method include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

A number of disorders or conditions, other than cancer, also can be treated with the above-described method. Examples include arthritis, rheumatoid arthritis, psoriasis, atherosclerosis, diabetic retinopathy, age-related macular degeneration, Grave's disease, vascular restenosis (including restenosis following angioplasty), arteriovenous malformations (AVM), meningioma, hemangioma, neovascular glaucoma, chronic kidney disease, diabetic nephropathy, polycystic kidney disease, interstitial lung disease, pulmonary hypertension, chronic obstructive pulmonary disease (COPD), emphysema, autoimmune hepatitis, chronic inflammatory liver disease, hepatic cirrhosis, cutaneous T-cell lymphoma, rosacea, and basal cell carcinoma.

Other treatment targets include those described in, e.g., US Applications 2009004297, 20090175791, and 20070161553, such as angiofibroma, atherosclerotic plaques, corneal graft neovascularization, hemophilic joints, hypertrophic scars, Osler-Weber syndrome, pyogenic granuloma retrolental fibroplasia, scleroderma, trachoma, vascular adhesions, synovitis, dermatitis, various other inflammatory diseases and disorders, and endometriosis.

A "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model. A subject to be treated for a disorder can be identified by standard diagnosing techniques for the disorder.

Optionally, the subject can be examined for mutation, expression level, or activity level of one or more of the genes or proteins mentioned above by methods known in the art or described above before treatment. If the subject has a particular mutation in the gene, or if the gene expression or activity level is, for example, greater in a sample from the subject than that in a sample from a normal person, the subject is a candidate for treatment.

To confirm the inhibition or treatment, one can evaluate and/or verify the inhibition of endothelial recruitment or resulting angiogenesis using technology known in the art before and/or after the administering step. Exemplary technologies include angiography or arteriography, a medical imaging technique used to visualize the inside, or lumen, of blood vessels and organs of the body, can generally be done by injecting a radio-opaque contrast agent into the blood vessel and imaging using X-ray based techniques such as fluoroscopy.

"Treating" or "treatment" refers to administration of a compound or agent to a subject who has a disorder with the purpose to cure, alleviate, relieve, remedy, delay the onset of, prevent, or ameliorate the disorder, the symptom of the disorder, the disease state secondary to the disorder, or the predisposition toward the disorder.

An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The agent can be administered in vivo or ex vivo, alone or co-administered in conjunction with other drugs or therapy, i.e., a cocktail therapy. As used herein, the term "co-administration" or "co-administered" refers to the administration of at least two agent(s) or therapies to a subject. For example, in the treatment of tumors, particularly vascularized, malignant tumors, the agents can be used alone or in combination with, e.g., chemotherapeutic, radiotherapeutic, apoptopic, anti-angiogenic agents and/or immunotoxins or coaguligands.

In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, a compound or agent is administered to a subject. Generally, the compound is suspended in a pharmaceutically-acceptable carrier (such as, for example, but not limited to, physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

Diagnosis

The described invention also provides diagnosis kits and methods. A subject having cancer cells or a cells prone to tumorigenesis can be diagnosed based on the expression or activity of one or more of the above-described genes or polypeptides in a test sample from the subject. The polypeptide and nucleic acids can be used as markers to indicate the presence or absence of a cancer cell or cell prone to tumorigenesis. Diagnostic and prognostic assays of the described invention include methods for assessing the expression level of the polypeptide or nucleic acid.

The presence, level, or absence of the polypeptide or nucleic acid in a test sample can be evaluated by obtaining a test sample from a test subject and contacting the test sample with a compound or an agent capable of detecting the polypeptide or nucleic acid (e.g., mRNA probe, genomic cDNA probe, or cDNA probe). The "test sample" can include tissues, cells and biological fluids isolated from a subject, as well as tissues, cells and fluids present within a subject. The level of expression of the gene can be measured in a number of ways, including, but not limited to, measuring the mRNA encoded by the gene; measuring the amount of polypeptide encoded by the gene; or measuring the activity of polypeptide encoded by the gene.

The level of mRNA corresponding to the gene in a cell can be determined both by in situ and by in vitro formats. Messenger RNA isolated from a test sample can be used in hybridization or amplification assays that include, but are not limited to, Southern or Northern analyses, PCR analyses, and probe arrays. For example, one diagnostic method for the detection of mRNA levels involves contacting the isolated mRNA with a nucleic acid probe that can hybridize to the mRNA encoded by the gene. The probe can be a full-length nucleic acid, or a portion thereof, such as an oligonucleotide of at least 10 nucleotides in length and sufficient to specifically hybridize under stringent conditions to mRNA or genomic DNA.

In one format, mRNA (or cDNA prepared from it) is immobilized on a surface and contacted with the probes, for example, by running the isolated mRNA on an agarose gel and transferring the mRNA from the gel to a membrane, such as nitrocellulose. In another format, the probes are immobilized on a surface and the mRNA (or cDNA) is contacted with the probes, for example, in a gene chip array. A skilled artisan can adapt known mRNA detection methods for detecting the level of mRNA.

The level of mRNA (or cDNA prepared from it) in a sample encoded by one or more of the above-mentioned genes can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art. As used herein, "amplification primers" are defined as being a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers.

For in situ methods, a cell or tissue sample can be prepared and immobilized on a support, such as, but not limited to, a glass slide, and then contacted with a probe that can hybridize to genomic DNA on chromosomes or mRNA that encodes the corresponding polypeptide.

In another embodiment, the methods of the described invention further include contacting a control sample with a compound or agent capable of detecting mRNA, or genomic DNA, and comparing the presence of mRNA or genomic DNA in the control sample with the presence of mRNA or genomic DNA in the test sample.

The above-described nucleic acid-based diagnostic methods can provide qualitative and quantitative information to determine whether a subject has or is predisposed to a disease associated with aberrant gene expression and aberrant angiogenesis, e.g., cancers.

A variety of methods can be used to determine the level of one or more of the above-mentioned polypeptide. In general, these methods include contacting an agent that selectively binds to the polypeptide, such as an antibody, to evaluate the level of polypeptide in a sample. Antibodies can be polyclonal, or monoclonal. An intact antibody, or a fragment thereof (e.g., Fab or F(ab')$_2$) also can be used. In another embodiment, the antibody bears a detectable label. The term "labeled", with regard to the probe or antibody, is intended to encompass direct labeling of the probe or antibody by physically linking a detectable substance to the probe or antibody, as well as indirect labeling of the probe or antibody by reactivity with a detectable substance. For example, an antibody with a rabbit Fc region can be indirectly labeled using a second antibody directed against the rabbit Fc region, wherein the second antibody is coupled to a detectable substance. Examples of detectable substances are provided herein. Appropriate detectable substance or labels include, but are not limited to, radio isotopes (for example, but not limited to $^{125}$I, $^{131}$I, $^{35}$S, $^{3}$H, or $^{32}$P), enzymes (for example, but not limited to alkaline phosphatase, horseradish peroxidase, luciferase, or β-glactosidase), fluorescent moieties or proteins (for example, but not limited to, fluorescein, rhodamine, phycoerythrin, GFP, or BFP), or luminescent moieties (for example, but not limited to, Qdot™ nanoparticles by the Quantum Dot Corporation, Palo Alto, Calif.).

The detection methods can be used to detect one or more of the above-mentioned polypeptide in a biological sample in vitro as well as in vivo. In vitro techniques for detection of the polypeptide include ELISAs, immuno-precipitations, immunofluorescence, EIA, RIA, and Western blotting analysis. In vivo techniques for detection of the polypeptide include introducing into a subject a labeled antibody. For example, the antibody can be labeled with a detectable substance as described above. The presence and location of the detectable substance in a subject can be detected by standard imaging techniques.

The diagnostic methods described herein can identify subjects having, or at risk of developing, a disease or disorder associated with aberrant expression or activity of one or more of the above-mentioned polypeptides. As described herein, examples of such a disease or disorder include those described above.

The prognostic assays described herein can be used to determine whether a subject is suitable to be administered with an agent (e.g., an agonist, antagonist, peptidomimetic, protein, peptide, nucleic acid, small molecule, or other drug candidate) to treat a disorder, such as cancer. For example, such assays can be used to determine whether a subject can be administered with a cytotoxic drug to treat the disorder.

Information obtained from practice of the above assays is useful in prognostication, identifying progression of, and clinical management of diseases and other deleterious conditions affecting an individual's health status. In some embodiments, the foregoing diagnostic assays provide information useful in prognostication, identifying progression of and management of malignancies (cancers) that are characterized by abnormal, pathological angiogenesis. The information more specifically assists the clinician in designing chemotherapeutic or other treatment regimes to eradicate such malignancies from the body of an afflicted mammal, e.g., a human.

EXAMPLE 1

Methods and Materials

This example describes general methods and materials used in Examples 2-8.

Cell Culture

All cell lines were propagated as described in Tavazoie, S. F. et al., Nature 451 (7175), 147 (2008). 293T cells were cultured with DMEM media supplemented with 10% FBS; H29 cells were cultured with DMEM media supplemented with 10% FBS, 20 ng/mL doxycycline, 2 µg/mL puromycin, and 0.3 mg/mL G418; and HUVEC cells were cultured with EGM-2 media (CC-3162, Lonza, Basel, Switzerland). The MDA-MB-231 and CN34 breast cancer cell line and its metastatic derivatives LM2, BoM2 and Lm1a are described in Minn, A. J. et al., Nature 436 (7050), 518 (2005).

Animal Studies

All animal work was conducted in accordance with a protocol approved by the Institutional Animal Care and Use Committee (IACUC) at The Rockefeller University. Age-matched female NOD/SCID mice (6-8 week old) were used for both orthotopic mammary fat pad tumor initiation assays (Minn, A. J. et al., Nature 436 (7050), 518 (2005) and for lung metastasis assays (Tavazoie, S. F. et al., Nature 451 (7175), 147 (2008)). Eight-week old age-matched female athymic mice were used for systemic metastasis assays (Kang, Y. et al., Cancer Cell 3 (6), 537 (2003) and Yin, J. J. et al., J Clin Invest 103 (2), 197 (1999)).

Inducible miR-126 expression was obtained by cloning pre-miR-126 into the tet-ON containing pTripz vector (Thermo Scientific, Huntsville, Ala.). At day 3, 2 mg/ml doxycycline (Sigma Aldrich) was added to the drinking water containing 5% sucrose. Control mice were given drinking water with 5% sucrose.

Generation of Lentivirus, Retrovirus, Knockdown and Over-Expressing Cells

For generation of lentivirus, $1 \times 10^6$ 293 T cells were seeded onto a 10 cm plate and incubated for 24 h. Twelve micrograms of vector K (Gag/Pol), 6 µg of vector A (Env) and 12 µg of the appropriate shRNA plasmid were then co-transfected into the 293T cells using 40 µL of TRAN-SIT®-293 transfection reagent (MIR 2700, MIRUS BIO LLC, Madison, Wis.). After 16 h, the media was replaced with fresh antibiotic-free DMEM supplemented with 10% FBS. After another 24 h, the virus was harvested by spinning for 5 min at 1,500 g before being filtered through a 0.45 µm filter. For generation of retrovirus, H29 cells were seeded onto a 10-cm plate and allowed to grow to 90% confluence. Ten micrograms of the appropriate plasmid was then transfected into H29 cells using 60 µl of LIPOFECTAMINE™ 2000 transfection reagent (11668-019, INVITROGEN by LIFE TECHNOLOGIES, Carlsbad, Calif.). After 16 h, the media were replaced with fresh antibiotic-free DMEM supplemented with 10% FBS. After another 48 h, the virus was harvested by spinning for 5 min at 1,500 g and filtered through a 0.45 µm filter. Two milliliters of the appropriate virus was used to transduce 50K cancer cells in the presence of 10 µg/mL of polybrene (TR-1003-G, MILLIPORE, Billerica, A). After 24 h, the media was changed to DMEM supplemented with 10% FBS and 2 µg/mL puromycin (lentivirus) or 10 µg/mL blasticidin for selection. After another 72 h, the cells were washed and allowed to grow in D10F and tested for knock down of the gene of interest by qPCR.

Endothelial Recruitment

Cancer cells (25,000) were seeded into 24-well plates approximately 24 h before the start of the recruitment assay. HUVEC cells were serum starved in EGM-2 media supplemented with 0.2% FBS for 24 hours. The HUVEC cells were then labeled with CELLTRACKER Red CMTPX dye (C34552, INVITROGEN) for 45 min and rescued in EGM-2 media supplemented with 2% FBS for 30 min. Meanwhile, cancer cells were washed with PBS and 1 mL 0.2% FBS EGM-2 media was added to each well. Each well was then fitted with a 3.0 µm HTS FLUROBLOCK Insert (351151, BD FALCON, San Jose, Calif.). For antibody experiments, the appropriate concentration of each antibody was then added to each well: 50 ng/mL anti-IGFBP2 (AF674, R&D SYSTEMS, Minneapolis, Minn.), 20 µg/mL anti-IGF-1 (AF-291-NA, R&D SYSTEMS), 40 µg/mL anti-IGF-2 (MAB292, R&D SYSTEMS), 20 µg/mL anti-IGF1R (MAB391, R&D SYSTEMS), 5 µg/mL anti-IGF2R (AF2447, R&D Systems) and anti-IgG (AB-108-C, R&D SYSTEMS). For endothelial recruitment assays that require pre-incubation with antibodies, either HUVEC cells or cancer cells were then incubated with 20 µg/mL anti-IGF1R or control IgG antibody for 1 h and washed once with PBS. The HUVEC cells were then serum starved for 1 h before being resuspended 0.2% FBS EGM-2 at 100K HUVECs per mL. The resuspension (0.5 mL) was then added into each FLUO-ROBLOCK insert and the recruitment assay was allowed to proceed for 16 h. After completion of the assay, FLUORO-BLOCK inserts were fixed with 4% paraformaldehyde for 15 min and mounted onto slides with VECTASHIELD mounting media (H-1000, VECTOR LABORATORIES, Burlingame, Calif.). Three images of each insert were taken and the images were analyzed using IMAGEJ (NIH).

Chemotaxis Assay

Matrigel (250 µl, BD BIOSCIENCES, #356231) containing given amounts of bovine serum albumin (A2153, Sigma Aldrich), rhIGFBP2 (674-B2, R&D Systems), rhGas6 (885-GS, R&D Systems), anti-IGF1R (MAB391, R&D Systems) and MerFc (891-MR-100, R&D Systems) were allowed to solidify at the bottom of a 24 well plate for 30 min before 250 µl HUVEC media containing 0.2% FBS were added. A 3.0-µm HTS Fluroblock Insert (351151, BD Falcon) was then placed in each well. HUVEC cells were labeled with CellTracker Red CMTPX dye (C34552, Invitrogen) before resuspending 300K HUVECs per mL of 0.2% FBS EGM-2. 0.5 mL of the resuspension was then added into each Fluoroblock insert and the assay allowed proceeding for 20 h. The inserts were then fixed for 15 min in 4% paraformaldehyde and mounted onto slides with VectaShield mounting media (H-1000, Vector Laboratories). 5 fields of the basal side of each insert were then imaged and the images were analyzed using ImageJ (NIH).

Migration Assay

HUVEC cells were grown to 90% confluence and stimulated in the given concentrations of bovine serum albumin (Sigma Aldrich, #A2153), rhIGFBP2 (674-B2, R&D Systems) and anti-IGF1R (MAB391, R&D Systems) in HUVEC media containing 0.2% FBS for 40 min at 37° C. The cells were then trypsinized and 50K cells were added into HTS Fluroblock Inserts (351151, BD Falcon). After 24 hours in 37° C. with 5% $CO_2$, the inserts were removed, the membrane excised and fixed in 4% paraformaldehyde. HUVEC cells that had migrated to the basal side of the membrane were visualized with DAPI and counted in 5 fields per membrane using Image J (NIH).

Endothelial Adhesion

HUVEC cells were seeded on a 6-cm plate and allowed to grow to confluence. Cancer cells were serum starved in DMEM media supplemented with 0.2% FBS for 30 min, labeled with CELLTRACKER Green CMFDA dye (C7025, Invitrogen) for 45 min and incubated in DMEM media supplemented with 10% FBS for 30 min. Cancer cells were then trypsinized and resuspended in 10% FBS/DMEM to 10K cells/mL. Five milliliters of the resuspension was then added to each plate of HUVECs and the plate was incubated at 37° C. for 10 min. The plates were then washed gently with PBS and fixed with 4% paraformaldehyde for 15 min. Each plate was then treated with 1 mL of PBS and 6 images were taken from each plate. The number of cancer cells adherent to the HUVEC cells were then quantified using IMAGEJ.

Endothelial Proliferation

Cancer cells ($1 \times 10^6$) were seeded to a 10-cm plate and allowed to grow for 24 h. The cancer cells were then washed gently with PBS and EGM-2 media supplemented with 2% FBS was added to each plate. The conditioned EGM-2 media was collected after 24 h. HUVEC cells (25K) were seeded in triplicate in a 6-well plate and allowed to grow for 16 h. The HUVEC cells were then washed gently with PBS and 3 mL conditioned EGM-2 media was added to each well. After 48 h, the conditioned media was replaced with another 3 mL of conditioned media. After another 48 h, the cells were trypsinized and counted using a haemocytometer.

Tube Formation Assay

Tube formation assay was performed according to manufacturer's protocol (354149, BD BIOCOAT™ ANGIOGENESIS SYSTEM—Endothelial Cell Tube Formation). Briefly, HUVEC cells were serum starved in EGM-2 media supplemented with 0.2% FBS for 24 hours. The HUVEC cells were then labeled with CELLTRACKER Red CMTPX dye (C34552, INVITROGEN) for 45 min and subsequently treated in EGM-2 media supplemented with 2% FBS for 30 min. Meanwhile, the tube formation assay plate, which was in 96-well format, was incubated at 37° C. for 30 min. The cancer cells and HUVEC cells were trypsinized and resuspended at 400 K/mL and 800 K/mL respectively in EGM-2 media supplemented with 2% FBS. The cancer cell and HUVEC cell suspensions were then mixed at a 1:1 ratio and 50 μl of each mixture was seeded into each well of the tube formation assay plate. The assay plate was incubated at 37° C. for 16 h. Images of each well were taken and the images were processed using METAMORPH analysis software (MOLECULAR DEVICES, Inc.) to obtain the number of branch points per image.

Analysis of miRNA and mRNA Expression

Total RNA was extracted from various cell lines using the MIRVANA kit (AM1560, APPLIED BIOSYSTEMS, Austin, Tex.). TAQMAN microRNA assay (4427975-0002228, APPLIED BIOSYSTEMS) was used to quantify expression levels of mature miRNA as described in Tavazoie, S. F. et al., Nature 451 (7175), 147 (2008). For quantification of mRNA, 400 ng of total RNA were reverse transcribed using the cDNA First-Strand Synthesis Kit (18080-051, INVITROGEN). Approximately 4 ng of the resulting cDNA was then mixed with SYBR green PCR MASTER MIX (4309155, APPLIED BIOSYSTEMS) and appropriate primers (Table 1). Quantitative mRNA expression data was obtained using an ABI PRISM 7900HT Real-Time PCR System (APPLIED BIOSYSTEMS). Smad4 was used as an endogenous control for normalization. Expression analysis of human breast cancers at various disease stages was performed using the TISSUESCAN qPCR Array Breast Cancer Panels 2 and 3 (BCRT102 & BCRT103, ORIGENE, Rockville, Md.).

TABLE 1

SYBR green qPCR primers

| Gene | Forward | Reverse |
|---|---|---|
| ABCB9 | GACCTTCACCTACC GCACTC | CACAGGAGCTC TTCCCACTG |
| BEX2 | GCCCCGAAAGTAGG AAGC | CTCCATTACTC CTGGGCCTAT |
| BGLAP | GGCGCTACCTGTAT CAATGG | TCAGCCAACTC GTCACAGTC |
| CA12 | CCAAGGCTACAATC TGTCTGC | GGGCAGGTTCA GCTTCACT |
| GDF15 | CCGGATACTCACGC CAGA | AGAGATACGCA GGTGCAGGT |
| GEM | GACAGCATGGACAG CGACT | AACCATCAGGG TTCGTTCAT |
| IGFBP2 | CCAAGAAGCTGCGA CCAC | GGGATGTGCAG GGAGTAGAG |
| ITGB4 | TCAGCCTCTCTGGG ACCTT | TATCCACACGG ACACACTCC |
| KIAA0746 | GTTGTCTGTGCAGA TGTACGC | TAGCAGGGCCA GGTTAAAAA |
| KLF4 | GCCGCTCCATTACC AAGA | TCTTCCCCTCT TTGGCTTG |
| MARS | AACAACCTGGGCAA CTTCAT | ACCATCTCAGG CACATAGCC |
| MERTK | GGAGACAGGACCAA AGC | GGGCAATATCC ACCATGAAC |
| PADI4 | AAGTGCAAGCTGAC CATCTG | GCCGATCTCCA TTTCATCC |
| PHGDH | TGGTGGAAAAGCAG AACCTT | AACAATAAGGC CTTCACAGTCC |
| PITPNC1 | GCGCTACTACAAAG AATCTGAGG | GAGCACATGAT AGGCTGATGAC |
| PSAT1 | TCTTGTGCGGGAAT TGCTA | AAGGGGACAGC ACTGAACTG |
| PYGB | TCCAGGGTCCTGTA TCCAAA | CCACGAAGTAC TCCTGCTTCA |

TABLE 1-continued

SYBR green qPCR primers

| Gene | Forward | Reverse |
|---|---|---|
| RGC32 | TGCTGATCTTGACAAAACTTTAGC | GCAGGTCCTCGGAACTTTCT |
| SHMT2 | GAGGGAGAAGGACAGGCAGT | CTCGGCTGCAGAAGTTCTCT |
| SMAD4 | TGGCCCAGGATCAGTAGGT | CATCAACACCAATTCCAGCA |
| THBD | AATTGGGAGCTTGGGAATG | TGAGGACCTGATTAAGGCTAGG |
| TNFSF4 | GTATCCTCGAATTCAAAGTATCAAAGT | CTGAGTTGTTCTGCACCTTCA |
| VIPR1 | CTGTCCCCTCATCTTCAAGC | CAGCTGCGGCTTACATTG | miR-126 Target Prediction

Potential miR-126 targets were identified by using 3 sets of microarray profiles: LM2 control cells relative to LM2 cells over-expressing miR-126 (GSE No. 23905) and 2 replicate arrays of MDA and LM2 cells (GSE No. 23904 and Minn, A. J. et al., Nature 436 (7050), 518 (2005). With these arrays, the following criteria were used to identify possible miR-126 targets genes: (1) Genes down-regulated more than 1.6 fold upon miR-126 over-expression in LM2 cells and (2) Genes up-regulated by more than 1.4 fold in one of the two LM2 versus MDA arrays. All potential targets were subsequently verified by qPCR.

Luciferase Reporter Assay

Luciferase reporter assay was performed as described in Tavazoie, S. F. et al., Nature 451 (7175), 147 (2008). Briefly the full-length 3'UTR's and CDS's of ABCB9, IGFBP2, MERTK, PITPNC1, PSAT1, PYGB, SHMT2 and VIPR1 were cloned into the psiCheck2 dual luciferase reporter vector (C8021, PROMEGA, Madison, Wis.). Listed below are the sequences of the CDS's and 3'UTR's.

```
ABCB9 CDS
ATGCGGCTGTGGAAGGCGGTGGTGGTGACTTTGGCCTTCATGAGTGTGGACATCTGCGTGACCACGGCCAT

CTATGTCTTCAGCCACCTGGACCGCAGCCTCCTGGAGGACATCCGCCACTTCAACATCTTTGACTCGGTGC

TGGATCTCTGGGCAGCCTGCCTGTACCGCAGCTGCCTGCTGCTGGGAGCCACCATTGGTGTGGCCAAGAAC

AGTGCGCTGGGGCCCCGGCGGCTGCGGGCCTCGTGGCTGGTCATCACCCTCGTGTGCCTCTTCGTGGGCAT

CTATGCCATGGTGAAGCTGCTGCTCTTCTCAGAGGTGCGCAGGCCCATCCGGGACCCCTGGTTTTGGGCCC

TGTTCGTGTGGACGTACATTTCACTCGGCGCATCCTTCCTGCTCTGGTGGCTGCTGTCCACCGTGCGGCCA

GGCACCCAGGCCCTGGAGCCAGGGGCGGCCACCGAGGCTGAGGGCTTCCCTGGGAGCGGCCGGCCACCGCC

CGAGCAGGCGTCTGGGGCCACGCTGCAGAAGCTGCTCTCCTACACCAAGCCCGACGTGGCCTTCCTCGTGG

CCGCCTCCTTCTTCCTCATCGTGGCAGCTCTGGGAGAGACCTTCCTGCCCTACTACACGGGCCGCGCCATT

GATGGCATCGTCATCCAGAAAAGCATGGATCAGTTCAGCACGGCTGTCGTCATCGTGTGCCTGCTGGCCAT

TGGCAGCTCATTTGCCGCAGGTATTCGGGGCGGCATTTTTACCCTCATATTTGCCAGACTGAACATTCGCC

TTCGAAACTGTCTCTTCCGCTCACTGGTGTCCCAGGAGACAAGCTTCTTTGATGAGAACCGCACAGGGGAC

CTCATCTCCCGCCTGACCTCGGACACCACCATGGTCAGCGACCTGGTCTCCCAGAACATCAATGTCTTCCT

GCGGAACACAGTCAAGGTCACGGGCGTGGTGGTCTTCATGTTCAGCCTCTCATGGCAGCTCTCCTTGGTCA

CCTTCATGGGCTTCCCCATCATCATGATGGTGTCCAACATCTACGGCAAGTACTACAAGAGGCTCTCCAAA

GAGGTCCAGAATGCCCTGGCCAGAGCGAGCAACACGGCGGAGGAGACCATCAGTGCCATGAAGACTGTCCG

GAGCTTCGCCAATGAGGAGGAGGAGGCAGAGGTGTACCTGCGGAAGCTGCAGCAGGTGTACAAGCTGAACA

GGAAGGAGGCAGCTGCCTACATGTACTACGTCTGGGGCAGCGGGCTCACACTGCTGGTGGTCCAGGTCAGC

ATCCTCTACTACGGGGGCCACCTTGTCATCTCAGGCCAGATGACCAGCGGCAACCTCATCGCCTTCATCAT

CTACGAGTTTGTCCTGGGAGATTGTATGGAGTCCGTGGGCTCCGTCTACAGTGGCCTGATGCAGGGAGTGG

GGGCTGCTGAGAAGGTGTTCGAGTTCATCGACCGGCAGCCGACCATGGTGCACGATGGCAGCTTGGCCCCC

GACCACCTGGAGGGCCGGGTGGACTTTGAGAATGTGACCTTCACCTACCGCACTCGGCCCCACACCCAGGT

CCTGCAGAATGTCTCCTTCAGCCTGTCCCCGGCAAGGTGACGGCCCTGGTGGGCCCTCGGGCAGTGGGA

AGAGCTCCTGTGTCAACATCCTGGAGAACTTCTACCCCCTGGAGGGGGGCCGGGTGCTGCTGGACGGCAAG

CCCATCAGCGCCTACGACCACAAGTACTTGCACCGTGTGATCTCCCTGGTGAGCCAGGAGCCCGTGCTGTT

CGCCCGCTCCATCACGGATAACATCTCCTACGGCCTGCCCACTGTGCCTTTCGAGATGGTGGTGGAGGCCG

CACAGAAGGCCAATGCCCACGGCTTCATCATGGAACTCCAGGACGGCTACAGCACAGAGACAGGGGAGAAG
```

-continued

GGCGCCCAGCTGTCAGGTGGCCAGAAGCAGCGGGTGGCCATGGCCCGGGCTCTGGTGCGGAACCCCCCAGT

CCTCATCCTGGATGAAGCCACCAGCGCTTTGGATGCCGAGAGCGAGTATCTGATCCAGCAGGCCATCCATG

GCAACCTGCAGAAGCACACGGTACTCATCATCGCGCACCGGCTGAGCACCGTGGAGCACGCGCACCTCATT

GTGGTGCTGGACAAGGGCCGCGTAGTGCAGCAGGGCACCCACCAGCAGCTGCTGGCCCAGGGCGGCCTCTA

CGCCAAGCTGGTGCAGCGGCAGATGCTGGGGCTTCAGCCCGCCGCAGACTTCACAGCTGGCCACAACGAGC

CTGTAGCCAACGGCAGTCACAAGGCCTGA

ABCB9 3'UTR
TGGGGGGCCCCTGCTTCTCCCGGTGGGGCAGAGGACCCGGTGCCTGCCTGGCAGATGTGCCCACGGAGGCC

CCCAGCTGCCCTCCGAGCCCAGGCCTGCAGCACTGAAAGACGACCTGCCATGTCCCATGGATCACCGCTTC

CTGCATCTTGCCCCTGGTCCCTGCCCCATTCCCAGGGCACTCCTTACCCCTGCTGCCCTGAGCCAACGCCT

TCACGGACCTCCCTAGCCTCCTAAGCAAAGGTAGAGCTGCCTTTTTAAACCTAGGTCTTACCAGGGTTTTT

ACTGTTTGGTTTGAGGCACCCCAGTCAACTCCTAGATTTCAAAAACCTTTTTCTAATTGGGAGTAATGGCG

GGCACTTTCACCAAGATGTTCTAGAAACTTCTGAGCCAGGAGTGAATGGCCCTTCCTTAGTAGCCTGGGGG

ATGTCCAGAGACTAGGCCTCTCCCCTTTACCCCTCCAGAGAAGGGGCTTCCCTGTCCCGAGGGAGACACG

GGGAACGGGATTTTCCGTCTCTCCCTCTTGCCAGCTCTGTGAGTCTGGCCAGGGCGGGTAGGGAGCGTGGA

GGGCATCTGTCTGCCATCGCCCGCTGCCAATCTAAGCCAGTCTCACTGTGAACCACACGAAACCTCAACTG

GGGGAGTGAGGGGCTGGCCAGGTCTGGAGGGGCCTCAGGGGTGCCCCAGCCCGGCACCCAGCGCTTTCGC

CCCTCGTCCACCCACCCCTGGCTGGCAGCCTCCCTCCCCACACCCGCCCCTGTGCTCTGCTGTCTGGAGGC

CACGTGGATGTTCATGAGATGCATTCTCTTCTGTCTTTGGTGGATGGGATGGTGGCAAAGCCCAGGATCTG

GCTTTGCCAGAGGTTGCAACATGTTGAGAGAACCCGGTCAATAAAGTGTACTACCTCTTACCCCTAA

IGFBP2 CDS
ATGCTGCCGAGAGTGGGCTGCCCCGCGCTGCCGCTGCCGCCGCCGCCGCTGCTGCCGCTGCTGCTGCTGCT

ACTGGGCGCGAGTGGCGGCGGCGGCGGGGCGCGCGCGGAGGTGCTGTTCCGCTGCCCGCCCTGCACACCCG

AGCGCCTGGCCGCCTGCGGGCCCCCGCCGGTTGCGCCGCCCGCCGCGGTGGCCGCAGTGGCCGGAGGCGCC

CGCATGCCATGCGCGGAGCTCGTCCGGGAGCCGGGCTGCGGCTGCTGCTCGGTGTGCGCCCGGCTGGAGGG

CGAGGCGTGCGGCGTCTACACCCCGCGCTGCGGCCAGGGGCTGCGCTGCTATCCCCACCCGGGCTCCGAGC

TGCCCCTGCAGGCGCTGGTCATGGGCGAGGGCACTTGTGAGAAGCGCCGGGACGCCGAGTATGGCGCCAGC

CCGGAGCAGGTTGCAGACAATGGCGATGACCACTCAGAAGGAGGCCTGGTGGAGAACCACGTGGACAGCAC

CATGAACATGTTGGGCGGGGAGGCAGTGCTGGCCGGAAGCCCCTCAAGTCGGGTATGAAGGAGCTGGCCG

TGTTCCGGGAGAAGGTCACTGAGCAGCACCGGCAGATGGGCAAGGGTGGCAAGCATCACCTTGGCCTGGAG

GAGCCCAAGAAGCTGCGACCACCCCCTGCCAGGACTCCCTGCCAACAGGAACTGGACCAGGTCCTGGAGCG

GATCTCCACCATGCGCCTTCCGGATGAGCGGGGCCCTCTGGAGCACCTCTACTCCCTGCACATCCCCAACT

GTGACAAGCATGGCCTGTACAACCTCAAACAGTGCAAGATGTCTCTGAACGGGCAGCGTGGGGAGTGCTGG

TGTGTGAACCCCAACACCGGGAAGCTGATCCAGGGAGCCCCCACCATCCGGGGGGACCCCGAGTGTCATCT

CTTCTACAATGAGCAGCAGGAGGCTCGCGGGGTGCACACCCAGCGGATGCAGTAG

IGFBP2 3'UTR
ACCGCAGCCAGCCGGTGCCTGGCGCCCCTGCCCCCCGCCCCTCTCCAAACACCGGCAGAAAACGGAGAGTG

CTTGGGTGGTGGGTGCTGGAGGATTTTCCAGTTCTGACACACGTATTTATATTTGGAAAGAGACCAGCACC

GAGCTCGGCACCTCCCCGGCCTCTCTCTTCCCAGCTGCAGATGCCACACCTGCTCCTTCTTGCTTTCCCCG

GGGGAGGAAGGGGGTTGTGGTCGGGGAGCTGGGGTACAGGTTTGGGGAGGGGGAAGAGAAATTTTTATTTT

TGAACCCCTGTGTCCCTTTTGCATAAGATTAAAGGAAGGAAAAGTAA

MERTK CDS
ATGGGGCCGGCCCCGCTGCCGCTGCTGCTGGGCCTCTTCCTCCCCGCGCTCTGGCGTAGAGCTATCACTGA

GGCAAGGGAAGAAGCCAAGCCTTACCCGCTATTCCCGGGACCTTTTCCAGGGAGCCTGCAAACTGACCACA

CACCGCTGTTATCCCTTCCTCACGCCAGTGGGTACCAGCCTGCCTTGATGTTTTCACCAACCCAGCCTGGA

AGACCACATACAGGAAACGTAGCCATTCCCCAGGTGACCTCTGTCGAATCAAAGCCCCTACCGCCTCTTGC

CTTCAAACACACAGTTGGACACATAATACTTTCTGAACATAAAGGTGTCAAATTTAATTGCTCAATCAGTG

TACCTAATATATACCAGGACACCACAATTTCTTGGTGGAAAGATGGGAAGGAATTGCTTGGGGCACATCAT

GCAATTACACAGTTTTATCCAGATGATGAAGTTACAGCAATAATCGCTTCCTTCAGCATAACCAGTGTGCA

GCGTTCAGACAATGGGTCGTATATCTGTAAGATGAAAATAAACAATGAAGAGATCGTGTCTGATCCCATCT

ACATCGAAGTACAAGGACTTCCTCACTTTACTAAGCAGCCTGAGAGCATGAATGTCACCAGAAACACAGCC

TTCAACCTCACCTGTCAGGCTGTGGGCCCGCCTGAGCCCGTCAACATTTTCTGGGTTCAAAACAGTAGCCG

TGTTAACGAACAGCCTGAAAAATCCCCCTCCGTGCTAACTGTTCCAGGCCTGACGGAGATGGCGGTCTTCA

GTTGTGAGGCCCACAATGACAAAGGGCTGACCGTGTCCAAGGGAGTGCAGATCAACATCAAAGCAATTCCC

TCCCCACCAACTGAAGTCAGCATCCGTAACAGCACTGCACACAGCATTCTGATCTCCTGGGTTCCTGGTTT

TGATGGATACTCCCCGTTCAGGAATTGCAGCATTCAGGTCAAGGAAGCTGATCCGCTGAGTAATGGCTCAG

TCATGATTTTTAACACCTCTGCCTTACCACATCTGTACCAAATCAAGCAGCTGCAAGCCCTGGCTAATTAC

AGCATTGGTGTTTCCTGCATGAATGAAATAGGCTGGTCTGCAGTGAGCCCTTGGATTCTAGCCAGCACGAC

TGAAGGAGCCCCATCAGTAGCACCTTTAAATGTCACTGTGTTTCTGAATGAATCTAGTGATAATGTGGACA

TCAGATGGATGAAGCCTCCGACTAAGCAGCAGGATGGAGAACTGGTGGGCTACCGGATATCCCACGTGTGG

CAGAGTGCAGGGATTTCCAAAGAGCTCTTGGAGGAAGTTGGCCAGAATGGCAGCCGAGCTCGGATCTCTGT

TCAAGTCCACAATGCTACGTGCACAGTGAGGATTGCAGCCGTCACCAGAGGGGGAGTTGGGCCCTTCAGTG

ATCCAGTGAAAATATTTATCCCTGCACACGGTTGGGTAGATTATGCCCCCTCTTCAACTCCGGCGCCTGGC

AACGCAGATCCTGTGCTCATCATCTTTGGCTGCTTTTGTGGATTATTTTGATTGGGTTGATTTTATACAT

CTCCTTGGCCATCAGAAAAAGAGTCCAGGAGACAAAGTTTGGGAATGCATTCACAGAGGAGGATTCTGAAT

TAGTGGTGAATTATATAGCAAAGAAATCCTTCTGTCGGCGAGCCATTGAACTTACCTTACATAGCTTGGGA

GTCAGTGAGGAACTACAAAATAAACTAGAAGATGTTGTGATTGACAGGAATCTTCTAATTCTTGGAAAAAT

TCTGGGTGAAGGAGAGTTTGGGTCTGTAATGGAAGGAAATCTTAAGCAGGAAGATGGGACCTCTCTGAAAG

TGGCAGTGAAGACCATGAAGTTGGACAACTCTTCACAGCGGGAGATCGAGGAGTTTCTCAGTGAGGCAGCG

TGCATGAAAGACTTCAGCCACCCAAATGTCATTCGACTTCTAGGTGTGTGTATAGAAATGAGCTCTCAAGG

CATCCCAAAGCCCATGGTAATTTTACCCTTCATGAAATACGGGGACCTGCATACTTACTTACTTTATTCCC

GATTGGAGACAGGACCAAAGCATATTCCTCTGCAGACACTATTGAAGTTCATGGTGGATATTGCCCTGGGA

ATGGAGTATCTGAGCAACAGGAATTTTCTTCATCGAGATTTAGCTGCTCGAAACTGCATGTTGCGAGATGA

CATGACTGTCTGTGTTGCGGACTTCGGCCTCTCTAAGAAGATTTACAGTGGCGATTATTACCGCCAAGGCC

GCATTGCTAAGATGCCTGTTAAATGGATCGCCATAGAAAGTCTTGCAGACCGAGTCTACACAAGTAAAAGT

GATGTGTGGGCATTTGGCGTGACCATGTGGGAAATAGCTACGCGGGGAATGACTCCCTATCCTGGGGTCCA

GAACCATGAGATGTATGACTATCTTCTCCATGGCCACAGGTTGAAGCAGCCCGAAGACTGCCTGGATGAAC

TGTATGAAATAATGTACTCTTGCTGGAGAACCGATCCCTTAGACCGCCCCACCTTTTCAGTATTGAGGCTG

CAGCTAGAAAAACTCTTAGAAAGTTTGCCTGACGTTCGGAACCAAGCAGACGTTATTTACGTCAATACACA

GTTGCTGGAGAGCTCTGAGGGCCTGGCCCAGGGCTCCACCCTTGCTCCACTGGACTTGAACATCGACCCTG

ACTCTATAATTGCCTCCTGCACTCCCCGCGCTGCCATCAGTGTGGTCACAGCAGAAGTTCATGACAGCAAA

CCTCATGAAGGACGGTACATCCTGAATGGGGGCAGTGAGGAATGGGAAGATCTGACTTCTGCCCCCTCTGC

```
TGCAGTCACAGCTGAAAAGAACAGTGTTTTACCGGGGGAGAGACTTGTTAGGAATGGGGTCTCCTGGTCCC

ATTCGAGCATGCTGCCCTTGGGAAGCTCATTGCCCGATGAACTTTTGTTTGCTGACGACTCCTCAGAAGGC

TCAGAAGTCCTGATGTGA

MERTK 3'UTR
GGAGAGGTGCGGGGAGACATTCCAAAAATCAAGCCAATTCTTCTGCTGTAGGAGAATCCAATTGTACCTGA

TGTTTTTGGTATTTGTCTTCCTTACCAAGTGAACTCCATGGCCCCAAAGCACCAGATGAATGTTGTTAAGT

AAGCTGTCATTAAAAATACATAATATATATTTATTTAAAGAGAAAAAATATGTGTATATCATGGAAAAGA

CAAGGATATTTTAATAAAACATTACTTATTTCATTTCACTTATCTTGCATATCTTAAAATTAAGCTTCAGC

TGCTCCTTGATATTAACATTTGTACAGAGTTGAAGTTGTTTTTTCAAGTTCTTTTCTTTTTCATGACTATT

AAATGTAAAAATATTTGTAAAATGAAATGCCATATTTGACTTGGCTTCTGGTCTTGATGTATTTGATAAGA

ATGATTCATTCAATGTTTAAAGTTGTATAACTGATTAATTTTCTGATATGGCTTCCTAATAAAATATGAAT

AAGGAAG

PITPNC1 isoform A CDS
ATGCTGCTGA AAGAGTACCG GATCTGCATG CCGCTCACCG TAGACGAGTA CAAAATTGGA

CAGCTGTACA TGATCAGCAA ACACAGCCAT GAACAGAGTG ACCGGGGAGA AGGGGTGGAG

GTCGTCCAGA ATGAGCCCTT TGAGGACCCT CACCATGGCA ATGGGCAGTT CACCGAGAAG

CGGGTGTATC TCAACAGCAA ACTGCCTAGT TGGGCTAGAG CTGTTGTCCC CAAAATATTT

TATGTGACAG AGAAGGCTTG GAACTATTAT CCCTACACAA TTACAGAATA CACATGTTCC

TTTCTGCCGA AATTCTCCAT TCATATAGAA ACCAAGTATG AGGACAACAA AGGAAGCAAT

GACACCATTT TCGACAATGA AGCCAAAGAC GTGGAGAGAG AAGTTTGCTT TATTGATATT

GCCTGCGATG AAATTCCAGA GCGCTACTAC AAAGAATCTG AGGATCCTAA GCACTTCAAG

TCAGAGAAGA CAGGACGGGG ACAGTTGAGG GAAGGCTGGA GAGATAGTCA TCAGCCTATC

ATGTGCTCCT ACAAGCTGGT GACTGTGAAG TTTGAGGTCT GGGGGCTTCA GACCAGAGTG

GAACAATTTG TACACAAGGT GGTCCGAGAC ATTCTGCTGA TTGGACATAG ACAGGCTTTT

GCATGGGTTG ATGAGTGGTA TGACATGACA ATGGATGAAG TCCGAGAATT TGAACGAGCC

ACTCAGGAAG CCACCAACAA GAAAATCGGC ATTTTCCCAC TGCAATTTC TATCTCCAGC

ATCCCCCTGC TGCCTTCTTC CGTCCGCAGT GCGCCTTCTA GTGCTCCATC CACCCCTCTC

TCCACAGACG CACCCGAATT TCTGTCCGTT CCCAAAGATC GGCCCCGGAA AAAGTCTGCC

CCAGAAACTC TCACACTTCC AGACCCTGAG AAAAAAGCCA CCCTGAATTT ACCCGGCATG

CACTCTTCAG ATAAGCCATG TCGGCCCAAA TCTGAGTAA

PITPNC1 isoform B CDS
ATGCTGCTGAAAGAGTACCGGATCTGCATGCCGCTCACCGTAGACGAGTACAAAATTGGACAGCTGTACAT

GATCAGCAAACACAGCCATGAACAGAGTGACCGGGGAGAAGGGGTGGAGGTCGTCCAGAATGAGCCCTTTG

AGGACCCTCACCATGGCAATGGGCAGTTCACCGAGAAGCGGGTGTATCTCAACAGCAAACTGCCTAGTTGG

GCTAGAGCTGTTGTCCCCAAAATATTTTATGTGACAGAGAAGGCTTGGAACTATTATCCCTACACAATTAC

AGAATACACATGTTCCTTTCTGCCGAAATTCTCCATTCATATAGAAACCAAGTATGAGGACAACAAAGGAA

GCAATGACACCATTTTCGACAATGAAGCCAAAGACGTGGAGAGAGAAGTTTGCTTTATTGATATTGCCTGC

GATGAAATTCCAGAGCGCTACTACAAAGAATCTGAGGATCCTAAGCACTTCAAGTCAGAGAAGACAGGACG

GGGACAGTTGAGGGAAGGCTGGAGAGATAGTCATCAGCCTATCATGTGCTCCTACAAGCTGGTGACTGTGA

AGTTTGAGGTCTGGGGGCTTCAGACCAGAGTGGAACAATTTGTACACAAGGTGGTCCGAGACATTCTGCTG

ATTGGACATAGACAGGCTTTTGCATGGGTTGATGAGTGGTATGATATGACAATGGATGATGTTCGGGAATA
```

-continued

CGAGAAAAACATGCATGAACAAACCAACATAAAAGTTTGCAATCAGCATTCCTCCCCTGTGGATGACATAG

AGAGTCATGCCCAAACAAGTACATGA

PITPNC1 3'UTR
CAATGGATGAAGTCCGAGAATTTGAACGAGCCACTCAGGAAGCCACCAACAAGAAAATCGGCATTTTCCCA

CCTGCAATTTCTATCTCCAGCATCCCCCTGCTGCCTTCTTCCGTCCGCAGTGCGCCTTCTAGTGCTCCATC

CACCCCTCTCTCCACAGACGCACCCGAATTTCTGTCCGTTCCCAAAGATCGGCCCCGGAAAAAGTCTGCCC

CAGAAACTCTCACACTTCCAGACCCTGAGAAAAAAGCCACCCTGAATTTACCCGGCATGCACTCTTCAGAT

AAGCCATGTCGGCCCAAATCTGAGTAACTTTATATAAATATCTCATGGGGTTTTATATTTTCATTTGTTGT

TGTTGTTTTTTTTAAGAATCTTCTGATAGAGAAAAAGACTGCTTTGTCACTCAAACATGTTCCTTCGACC

TTTCAGTGTGCATGTGACTCAGTAACTTCACATAGAATATGATTCCCTAAGTATGCTACACAGCATCATAT

TAGATGTAAGATGTAAGACTTGCAAAGGACAGAAGGAATCTTCTGTAACCACATAGCTGTATGCCAGAGAG

GAAGCCTTGTTATTGGGCATTTGATGAGGTTTGGCATGGACTTCAAGGATAAATGAATGAAAACTTTGCAC

CACTTTTGTTACAAGGTACGGTAGAAAATAGTGAAGTCAGTTTCCTCTCATCAAATCTAAAATTCTCCAAA

ATACTCTCAGGCATAACATACTTAGCTGTTAAATTTTGAACTGCTAATTACTAATACTTGAATACCAATAG

TTACTGAGATTCCTATTTTGTGGTTAGTCTGACTCAGGATTTGGAGCCTAATTAACTCTAAACTTTTGAAA

ATTTTAATCATCAAGCTATAGAGGCTCCAAGTGCAATTAATAATAACTCATTTATACCTTCCACAGAATTT

AATAAAGATTCTACTTGTTTCTGTCTTTTAA

PSAT1 CDS
ATGGACGCCCCCAGGCAGGTGGTCAACTTTGGGCCTGGTCCCGCCAAGCTGCCGCACTCAGTGTTGTTAGA

GATACAAAAGGAATTATTAGACTACAAAGGAGTTGGCATTAGTGTTCTTGAAATGAGTCACAGGTCATCAG

ATTTTGCCAAGATTATTAACAATACAGAGAATCTTGTGCGGGAATTGCTAGCTGTTCCAGACAACTATAAG

GTGATTTTTCTGCAAGGAGGTGGGTGCGGCCAGTTCAGTGCTGTCCCCTTAAACCTCATTGGCTTGAAAGC

AGGAAGGTGTGCTGACTATGTGGTGACAGGAGCTTGGTCAGCTAAGGCCGCAGAAGAAGCCAAGAAGTTTG

GGACTATAAATATCGTTCACCCTAAACTTGGGAGTTATACAAAAATTCCAGATCCAAGCACCTGGAACCTC

AACCCAGATGCCTCCTACGTGTATTATTGCGCAAATGAGACGGTGCATGGTGTGGAGTTTGACTTTATACC

CGATGTCAAGGGAGCAGTACTGGTTTGTGACATGTCCTCAAACTTCCTGTCCAAGCCAGTGGATGTTTCCA

AGTTTGGTGTGATTTTTGCTGGTGCCCAGAAGAATGTTGGCTCTGCTGGGGTCACCGTGGTGATTGTCCGT

GATGACCTGCTGGGGTTTGCCCTCCGAGAGTGCCCCTCGGTCCTGGAATACAAGGTGCAGGCTGGAAACAG

CTCCTTGTACAACACGCCTCCATGTTTCAGCATCTACGTCATGGGCTTGGTTCTGGAGTGGATTAAAAACA

ATGGAGGTGCCGCGGCCATGGAGAAGCTTAGCTCCATCAAATCTCAAACAATTTATGAGATTATTGATAAT

TCTCAAGGATTCTACGTTTGTCCAGTGGAGCCCCAAAATAGAAGCAAGATGAATATTCCATTCCGCATTGG

CAATGCCAAAGGAGATGATGCTTTAGAAAAAAGATTTCTTGATAAAGCTCTTGAACTCAATATGTTGTCCT

TGAAAGGGCATAGGTCTGTGGGAGGCATCCGGGCCTCTCTGTATAATGCTGTCACAATTGAAGACGTTCAG

AAGCTGGCCGCCTTCATGAAAAAATTTTTGGAGATGCATCAGCTATGA

PSAT1 3'UTR
ACACATCCTAACCAGGATATACTCTGTTCTTGAACAACATACAAAGTTTAAAGTAACTTGGGGATGGCTAC

AAAAAGTTAACACAGTATTTTTCTCAAATGAACATGTTTATTGCAGATTCTTCTTTTTTGAAAGAACAACA

GCAAAACATCCACAACTCTGTAAAGCTGGTGGGACCTAATGTCACCTTAATTCTGACTTGAACTGGAAGCA

TTTTAAGAAATCTTGTTGCTTTTCTAACAAATTCCCGCGTATTTTGCCTTTGCTGCTACTTTTTCTAGTTA

GATTTCAAACTTGCCTGTGGACTTAATAATGCAAGTTGCGATTAATTATTTCTGGAGTCATGGGAACACAC

AGCACAGAGGGTAGGGGGGCCCTCTAGGTGCTGAATCTACACATCTGTGGGGTCTCCTGGGTTCAGCGGCT

GTTGATTCAAGGTCAACATTGACCATTGGAGGAGTGGTTTAAGAGTGCCAGGCGAAGGGCAAACTGTAGAT

-continued
CGATCTTTATGCTGTTATTACAGGAGAAGTGACATACTTTATATATGTTTATATTAGCAAGGTCTGTTTTT
AATACCATATACTTTATATTTCTATACATTTATATTTCTAATAATACAGTTATCACTGATATATGTAGACA
CTTTTAGAATTTATTAAATCCTTGACCTTGTGCATTATAGCATTCCATTAGCAAGAGTTGTACCCCTCCC
CAGTCTTCGCCTTCCTCTTTTTAAGCTGTTTTATGAAAAAGACCTAGAAGTTCTTGATTCATTTTTACCAT
TCTTTCCATAGGTAGAAGAGAAAGTTGATTGGTTGGTTGTTTTCAATTATGCCATTAAACTAAACATTTC
TGTTAAATTACCCTATCCTTTGTTCTCTACTGTTTTCTTTGTAATGTATGACTACGAGAGTGATACTTTGC
TGAAAAGTCTTTCCCCTATTGTTTATCTATTGTCAGTATTTTATGTTGAATATGTAAAGAACATTAAAGTC
CTAAAACATCTAA PYGB CDS
ATGGCGAAGCCGCTGACGGACAGCGAGAAGCGGAAGCAGATCAGCGTGCGCGGCCTGGCGGGGCTAGGCGA
CGTGGCCGAGGTGCGGAAGAGCTTCAACCGGCACTTGCACTTCACGCTGGTCAAGGACCGCAATGTGGCCA
CGCCCCGCGACTACTTCTTCGCGCTGGCGCACACGGTGCGCGACCACCTCGTGGGCCGCTGGATCCGCACG
CAGCAGCACTACTACGAGCGCGACCCCAAGCGCATTTATTATCTTTCCCTGGAATTCTACATGGGTCGCAC
GCTGCAGAACACGATGGTGAACCTGGGCCTTCAGAATGCCTGCGATGAAGCCATCTATCAGTTGGGGTTAG
ACTTGGAGGAACTCGAGGAGATAGAAGAAGATGCTGGCCTTGGGAATGGAGGCCTGGGGAGGCTGGCAGCG
TGTTTCCTTGACTCAATGGCTACCTTGGGCCTGGCAGCATACGGCTATGGAATCCGCTATGAATTTGGGAT
TTTTAACCAGAAGATTGTCAATGGCTGGCAGGTAGAGGAGGCCGATGACTGGCTGCGCTACGGCAACCCCT
GGGAGAAAGCGCGGCCTGAGTATATGCTTCCCGTGCACTTCTACGGACGCGTGGAGCACACCCCCGACGGC
GTGAAGTGGCTGGACACACAGGTGGTGCTGGCCATGCCCTACGACACCCCAGTGCCCGGCTACAAGAACAA
CACCGTCAACACCATGCGGCTGTGGTCCGCCAAGGCTCCCAACGACTTCAAGCTGCAGGACTTCAACGTGG
GAGACTACATCGAGGCGGTCCTGGACCGGAACTTGGCTGAGAACATCTCCAGGGTCCTGTATCCAAATGAT
AACTTCTTTGAGGGGAAGGAGCTGCGGCTGAAGCAGGAGTACTTCGTGGTGGCCGCCACGCTCCAGGACAT
CATCCGCCGCTTCAAGTCGTCCAAGTTCGGCTGCCGGGACCCTGTGAGAACCTGTTTCGAGACGTTCCCAG
ACAAGGTGGCCATCCAGCTGAACGACACCCACCCCGCCCTCTCCATCCCTGAGCTCATGCGGATCCTGGTG
GACGTGGAGAAGGTGGACTGGGACAAGGCCTGGGAAATCACGAAGAAGACCTGTGCATACACCAACCACAC
TGTGCTGCCTGAGGCCTTGGAGCGCTGGCCCGTGTCCATGTTTGAGAAGCTGCTGCCGCGGCACCTGGAGA
TAATCTATGCCATCAACCAGCGGCACCTGGACCACGTGGCCGCGCTGTTTCCCGGCGATGTGGACCGCCTG
CGCAGGATGTCTGTGATCGAGGAGGGGGACTGCAAGCGGATCAACATGGCCCACCTGTGTGTGATTGGGTC
CCATGCTGTCAATGGTGTGGCGAGGATCCACTCGGAGATCGTGAAACAGTCGGTCTTTAAGGATTTTTATG
AACTGGAGCCAGAGAAGTTCCAGAATAAGACCAATGGCATCACCCCCCGCCGGTGGCTGCTGCTGTGCAAC
CCGGGGCTGGCCGATACCATCGTGGAGAAAATTGGGGAGGAGTTCCTGACTGACCTGAGCCAGCTGAAGAA
GCTGCTGCCGCTGGTCAGTGACGAGGTGTTCATCAGGGACGTGGCCAAGGTCAAACAGGAGAACAAGCTCA
AGTTCTCGGCCTTCCTGGAGAAGGAGTACAAGGTGAAGATCAACCCCTCCTCCATGTTCGATGTGCATGTG
AAGAGGATCCACGAGTACAAGCGGCAGCTGCTCAACTGCCTGCACGTCGTCACCCTGTACAATCGAATCAA
GAGAGACCCGGCCAAGGCTTTTGTGCCCAGGACTGTTATGATTGGGGGCAAGGCAGCGCCCGGTTACCACA
TGGCCAAGCTGATCATCAAGTTGGTCACCTCCATCGGCGACGTCGTCAATCATGACCCAGTTGTGGGTGAC
AGGTTGAAAGTGATCTTCCTGGAGAACTACCGTGTGTCCTTGGCTGAGAAAGTGATCCCGGCCGCTGATCT
GTCGCAGCAGATCTCCACTGCAGGCACCGAGGCCTCAGGCACAGGCAACATGAAGTTCATGCTCAACGGGG
CCCTCACCATCGGCACCATGGACGGCGCCAACGTGGAGATGGCCGAGGAGGCCGGGGCCGAGAACCTCTTC
ATCTTCGGCCTGCGGGTGGAGGATGTCGAGGCCTTGGACCGGAAAGGGTACAATGCCAGGGAGTACTACGA
CCACCTGCCCGAGCTGAAGCAGGCCGTGGACCAGATCAGCAGTGGCTTTTTTTCTCCCAAGGAGCCAGACT -continued

GCTTCAAGGACATCGTGAACATGCTGATGCACCATGACAGGTTCAAGGTGTTTGCAGACTATGAAGCCTAC

ATGCAGTGCCAGGCACAGGTGGACCAGCTGTACCGGAACCCCAAGGAGTGGACCAAGAAGGTCATCAGGAA

CATCGCCTGCTCGGGCAAGTTCTCCAGTGACCGGACCATCACGGAGTATGCACGGGAGATCTGGGGTGTGG

AGCCCTCCGACCTGCAGATCCCGCCCCCCAACATCCCCCGGGACTAG

PYGB 3'UTR
GCACACCCTGCCTTGGCGGGACCAGCGGGCATTTGTTTTCTTGCTGACTTTGCACCTCCTTTTTTCCCCAA

ACACTTTGCCAGCCACTGGTGGTCCCTGCTTTTCTGAGTACCATGTTTCCAGGAGGGGCCATGGGGGTCAG

GGTGGTTTTGAGAGAGCAGGGTAAGGAAGGAATGTGCTAGAAGTGCTCCTAGTTTCTTGTAAAGGAAGCCA

GAGTTGACAGTACAAAGGGTCGTGGCCAGCCCTGCAGCTTCAGCACCTGCCCCACCCAGAGTGGGAGTCAG

GTGGAGCCACCTGCTGGGCTCCCCCAGAACTTTGCACACATCTTGCTATGTATTAGCCGATGTCTTTAGTG

TTGAGCCTCTGGATTCTGGGGTCTGGGCCAGTGGCCATAGTGAAGCCTGGGAATGAGTGTTACTGCAGCAT

CTGGGCTGCCAGCCACAGGGAAGGGCCAAGCCCCATGTAGCCCCAGTCATCCTGCCCAGCCCTGCCTCCTG

GCCATGCCGGGAGGGGTCGGATCCTCTAGGCATCGCCTTCACAGCCCCCTGCCCCCTGCCCTCTGTCCTGG

CTCTGCACCTGGTATATGGGTCATGGACCCAGATGGGCTTTCCCTTTGTAGCCATCCAATGGGCATTGTG

TGGGTGCTTGGAACCCGGGATGACTGAGGGGGACACTGGAGTGGGTGCTTGTGTCTGCTGTCTCAGAGGCC

TTGGTCAGGATGAAGTTGGCTGACACAGCTTAGCTTGGTTTTGCTTATTCAAAAGAGAAAATAACTACACA

TGGAAATGAAACTAGCTGAAGCCTTTTCTTGTTTTAGCAACTGAAAATTGTACTTGGTCACTTTTGTGCTT

GAGGAGGCCCATTTTCTGCCTGGCAGGGGGCAGGTCTGTGCCCTCCCGCTGACTCCTGCTGTGTCCTGAGG

TGCATTTCCTGTTGTACACACAAGGGCCAGGCTCCATTCTCCCTCCCTTTCCACCAGTGCCACAGCCTCGT

CTGGAAAAAGGACCAGGGGTCCCGGAGGAACCCATTTGTGCTCTGCTTGGACAGCAGGCCTGGCACTGGGA

GGTGGGGGTGAGCCCCTCACAGCCTTGCCCCTCCCCAAGGCTGGCAACCTGCCTCCCATTGCCCAAGAGAG

AGGGCAGGGAACAGGCTACTGTCCTTCCCTGTGGAATTGCCGAGAAATCTAGCACCTTGCATGCTGGATCT

GGGCTGCGGGGAGGCTCTTTTTCTCCCTGGCCTCCAGTGCCCACCAGGAGGATCTGCGCACGGTGCACAGC

CCACCAGAGCACTACAGCCTTTTATTGAGTGGGGCAAGTGCTGGGCTGTGGTCGTGCCCTGACAGCATCTT

CCCCAGGCAGCGGCTCTGTGGAGGAGGCCATACTCCCCTAGTTGGCCACTGGGGCCACCACCCTGACCACC

ACTGTGCCCCTCATTGTTACTGCCTTGTGAGATAAAAACTGATTAAACCTTTGTGGCTGTGGTTGGCTGA

SHMT2 CDS
ATGCTGTACTTCTCTTTGTTTTGGGCGGCTCGGCCTCTGCAGAGATGTGGGCAGCTGGTCAGGATGGCCAT

TCGGGCTCAGCACAGCAACGCAGCCCAGACTCAGACTGGGGAAGCAAACAGGGGCTGGACAGGCCAGGAGA

GCCTGTCGGACAGTGATCCTGAGATGTGGGAGTTGCTGCAGAGGGAGAAGGACAGGCAGTGTCGTGGCCTG

GAGCTCATTGCCTCAGAGAACTTCTGCAGCCGAGCTGCGCTGGAGGCCCTGGGGTCCTGTCTGAACAACAA

GTACTCGGAGGGTTATCCTGGCAAGAGATACTATGGGGGAGCAGAGGTGGTGGATGAAATTGAGCTGCTGT

GCCAGCGCCGGGCCTTGGAAGCCTTTGACCTGGATCCTGCACAGTGGGGAGTCAATGTCCAGCCCTACTCC

GGGTCCCCAGCCAACCTGGCCGTCTACACAGCCCTTCTGCAACCTCACGACCGGATCATGGGGCTGGACCT

GCCCGATGGGGCCATCTCACCCACGGCTACATGTCTGACGTCAAGCGGATATCAGCCACGTCCATCTTCT

TCGAGTCTATGCCCTATAAGCTCAACCCCAAAACTGGCCTCATTGACTACAACCAGCTGGCACTGACTGCT

CGACTTTTCCGGCCACGGCTCATCATAGCTGGCACCAGCGCCTATGCTCGCCTCATTGACTACGCCCGCAT

GAGAGAGGTGTGTGATGAAGTCAAAGCACACCTGCTGGCAGACATGGCCCACATCAGTGGCCTGGTGGCTG

CCAAGGTGATTCCCTCGCCTTTCAAGCACGCGGACATCGTCACCACCACTACTCACAAGACTCTTCGAGGG

GCCAGGTCAGGGCTCATCTTCTACCGGAAAGGGGTGAAGGCTGTGGACCCCAAGACTGGCCGGGAGATCCC

TTACACATTTGAGGACCGAATCAACTTTGCCGTGTTCCCATCCCTGCAGGGGGGCCCCCACAATCATGCCA

TTGCTGCAGTAGCTGTGGCCCTAAAGCAGGCCTGCACCCCCATGTTCCGGGAGTACTCCCTGCAGGTTCTG

```
AAGAATGCTCGGGCCATGGCAGATGCCCTGCTAGAGCGAGGCTACTCACTGGTATCAGGTGGTACTGACAA

CCACCTGGTGCTGGTGGACCTGCGGCCCAAGGGCCTGGATGGAGCTCGGGCTGAGCGGGTGCTAGAGCTTG

TATCCATCACTGCCAACAAGAACACCTGTCCTGGAGACCGAAGTGCCATCACACCGGGCGGCCTGCGGCTT

GGGGCCCCAGCCTTAACTTCTCGACAGTTCCGTGAGGATGACTTCCGGAGAGTTGTGGACTTTATAGATGA

AGGGGTCAACATTGGCTTAGAGGTGAAGAGCAAGACTGCCAAGCTCCAGGATTTCAAATCCTTCCTGCTTA

AGGACTCAGAAACAAGTCAGCGTCTGGCCAACCTCAGGCAACGGGTGGAGCAGTTTGCCAGGGCCTTCCCC

ATGCCTGGTTTTGATGAGCATTGA

SHMT2 3'UTR
AGGCACCTGGGAAATGAGGCCCACAGACTCAAAGTTACTCTCCTTCCCCCTACCTGGGCCAGTGAAATAGA

AAGCCTTTCTATTTTTTGGTGCGGGAGGGAAGACCTCTCACTTAGGGCAAGAGCCAGGTATAGTCTCCCTT

CCCAGAATTTGTAACTGAGAAGATCTTTTCTTTTTCCTTTTTTTGGTAACAAGACTTAGAAGGAGGGCCCA

GGCACTTTCTGTTTGAACCCCTGTCATGATCACAGTGTCAGAGACGCGTCCTCTTTCTTGGGGAAGTTGAG

GAGTGCCCTTCAGAGCCAGTAGCAGGCAGGGGTGGGTAGGCACCCTCCTTCCTGTTTTTATCTAATAAAAT

GCTAACCTGCCCTGAGTTTCCATTACTGTGGGTGGGGTTCCCCTGGGCCAAACAGTGATTTGTCTCCCTCA

ATGTGTACACCGCTCCGCTCCCACCACCGCTACCACAAGGACCCCCGGGGCTGCAGCCTCCTCTTTCTGTC

TCTGATCAGAGCCGACACCAGACGTGATTAGCAGGCGCAGCAAATTCAATTTGTTAAATGAAATTGTATTT

TG

VIPR1 CDS
ATGCGCCCGCCAAGTCCGCTGCCCGCCCGCTGGCTATGCGTGCTGGCAGGCGCCCTCGCCTGGGCCCTTGG

GCCGGCGGGCGGCCAGGCGGCCAGGCTGCAGGAGGAGTGTGACTATGTGCAGATGATCGAGGTGCAGCACA

AGCAGTGCCTGGAGGAGGCCCAGCTGGAGAATGAGACAATAGGCTGCAGCAAGATGTGGGACAACCTCACC

TGCTGGCCAGCCACCCCTCGGGGCCAGGTAGTTGTCTTGGCCTGTCCCCTCATCTTCAAGCTCTTCTCCTC

CATTCAAGGCCGCAATGTAAGCCGCAGCTGCACCGACGAAGGCTGGACGCACCTGGAGCCTGGCCCGTACC

CCATTGCCTGTGGTTTGGATGACAAGGCAGCGAGTTTGGATGAGCAGCAGACCATGTTCTACGGTTCTGTG

AAGACCGGCTACACCATTGGCTACGGCCTGTCCCTCGCCACCCTTCTGGTCGCCACAGCTATCCTGAGCCT

GTTCAGGAAGCTCCACTGCACGCGGAACTACATCCACATGCACCTCTTCATATCCTTCATCCTGAGGGCTG

CCGCTGTCTTCATCAAAGACTTGGCCCTCTTCGACAGCGGGGAGTCGGACCAGTGCTCCGAGGGCTCGGTG

GGCTGTAAGGCAGCCATGGTCTTTTTCCAATATTGTGTCATGGCTAACTTCTTCTGGCTGCTGGTGGAGGG

CCTCTACCTGTACACCCTGCTTGCCGTCTCCTTCTTCTCTGAGCGGAAGTACTTCTGGGGGTACATACTCA

TCGGCTGGGGGGTACCCAGCACATTCACCATGGTGTGGACCATCGCCAGGATCCATTTTGAGGATTATGGG

TGCTGGGACACCATCAACTCCTCACTGTGGTGGATCATAAAGGGCCCCATCCTCACCTCCATCTTGGTAAA

CTTCATCCTGTTTATTTGCATCATCCGAATCCTGCTTCAGAAACTGCGGCCCCCAGATATCAGGAAGAGTG

ACAGCAGTCCATACTCAAGGCTAGCCAGGTCCACACTCCTGCTGATCCCCCTGTTTGGAGTACACTACATC

ATGTTCGCCTTCTTTCCGGACAATTTTAAGCCTGAAGTGAAGATGGTCTTTGAGCTCGTCGTGGGGTCTTT

CCAGGGTTTTGTGGTGGCTATCCTCTACTGCTTCCTCAATGGTGAGGTGCAGGCGGAGCTGAGGCGGAAGT

GGCGGCGCTGGCACCTGCAGGGCGTCCTGGGCTGGAACCCCAAATACCGGCACCCGTCGGGAGGCAGCAAC

GGCGCCACGTGCAGCACGCAGGTTTCCATGCTGACCCGCGTCAGCCCAGGTGCCCGCCGCTCCTCCAGCTT

CCAAGCCGAAGTCTCCCTGGTCTGA

VIPR1 3'UTR
CCACCAGGATCCCAGGGGCCCAAGGCGGCCCCTCCCGCCCCTTCCCACTCACCCCGGCAGACGCCGGGGAC

AGAGGCCTGCCCGGGCGCGGCCAGCCCCGGCCCTGGGCTCGGAGGCTGCCCCCGGCCCCCTGGTCTCTGGT

CCGGACACTCCTAGAGAACGCAGCCCTAGAGCCTGCCTGGAGCGTTTCTAGCAAGTGAGAGAGATGGGAGC
```

-continued

```
TCCTCTCCTGGAGGATTGCAGGTGGAACTCAGTCATTAGACTCCTCCTCCAAAGGCCCCCTACGCCAATCA

AGGGCAAAAAGTCTACATACTTTCATCCTGACTCTGCCCCCTGCTGGCTCTTCTGCCCAATTGGAGGAAAG

CAACCGGTGGATCCTCAAACAACACTGGTGTGACCTGAGGGCAGAAAGGTTCTGCCCGGGAAGGTCACCAG

CACCAACACCACGGTAGTGCCTGAAATTTCACCATTGCTGTCAAGTTCCTTTGGGTTAAGCATTACCACTC

AGGCATTTGACTGAAGATGCAGCTCACTACCCTATTCTCTCTTTACGCTTAGTTATCAGCTTTTTAAAGTG

GGTTATTCTGGAGTTTTTGTTTGGAGAGCACACCTATCTTAGTGGTTCCCCACCGAAGTGGACTGGCCCCT

GGGTCAGTCTGGTGGGAGGACGGTGCAACCCAAGGACTGAGGGACTCTGAAGCCTCTGGGAAATGAGAAGG

CAGCCACCAGCGAATGCTAGGTCTCGGACTAAGCCTACCTGCTCTCCAAGTCTCAGTGGCTTCATCTGTCA

AGTGGGATCTGTCACACCAGCCATACTTATCTCTCTGTGCTGTGGAAGCAACAGGAATCAAGAGCTGCCCT

CCTTGTCCACCCACCTATGTGCCAACTGTTGTAACTAGGCTCAGAGATGTGCACCCATGGGCTCTGACAGA

AAGCAGATACCTCACCCTGCTACACATACAGGATTTGAACTCAGATCTGTCTGATAGGAATGTGAAAGCAC

GGACTCTTACTGCTAACTTTTGTGTATCGTAACCAGCCAGATCCTCTTGGTTATTTGTTTACCACTTGTAT

TATTAATGCCATTATCCCTGAATCCCCCTTGCCACCCCACCCTCCCTGGAGTGTGGCTGAGGAGGCCTCCA

TCTCATGTATCATCTGGATAGGAGCCTGCTGGTCACAGCCTCCTCTGTCTGCCCTTCACCCCAGTGGCCAC

TCAGCTTCCTACCCACACCTCTGCCAGAAGATCCCCTCAGGACTGCAACAGGCTTGTGCAACAATAAATGT

TGGCTTGGA
```

MDA-MB-231 cells expressing either a control hairpin or a hairpin targeting miR-126 were transfected with the respective specific reporter construct. Thirty hours after transfection, the cells were lysed and the ratio of renilla to firefly luciferase expression was determined using the dual luciferase assay (E1910, PROMEGA). Cloning primer sequences are shown in Table 2 below.

TABLE 2

Cloning Primers

| Gene | Forward | Reverse |
|---|---|---|
| ABCB9 3'UTR | CCGGCCCTCGAGTGGGG GGCCCCTGCTTCTCC | CCGGCCGCGGCCGCTTA GGGGTAAGAGGTAGTAC |
| ABCB9 CDS | CCGGCCCTCGAGATGCG GCTGTGGAAGGCGGT | CCGGCCGCGGCCGCTCA GGCCTTGTGACTGCCGT |
| IGFBP2 3'UTR | CCGGCCCTCGAGACCGC AGCCAGCCGGTGCCT | CCGGCCGCGGCCGCTTA CTTTTCCTTCCTTTAAT |
| IGFBP2 CDS | CCGGCCCTCGAGATGCT GCCGAGAGTGGGCTG | CCGGCCGCGGCCGCCTA CTGCATCCGCTGGGTGT |
| MERTK 3'UTR | CCGGCCCTCGAGGGAGA GGTGCGGGGAGACAT | CCGGCCGCGGCCGCCTT CCTTATTCATATTTTAT |
| MERTK CDS | CCGGCCCTCGAGATGGG GCCGGCCCCGCTGCC | CCGGCCGCGGCCGCTCA CATCAGGACTTCTGAGC |
| PITPNC1 3'UTR | CCGGCCCTCGAGCAATG GATGAAGTCCGAGAA | CCGGCCGCGGCCGCTTA AAAGACAGAAACAAGTA |
| PITPNC1 CDS | CCGGCCCTCGAGATGCT GCTGAAAGAGTACCG | CCGGCCGCGGCCGCTCA TGTACTTGTTTGGGCAT |
| PSAT1 3'UTR | CCGGCCCTCGAGACACA TCCTAACCAGGATAT | CCGGCCGCGGCCGCTTA GATGTTTTAGGACTTTA |
| PSAT1 CDS | CCGGCCGCGGCCGCTCA TAGCTGATGCATCTCCA | CCGGCCCTCGAGATGGA CGCCCCCAGGCAGGT |
| PYGB 3'UTR | CCGGCCCTCGAGGCACA CCCTGCCTTGGCGGG | CCGGCCGCGGCCGCTCA GCCAACCACAGCCACAA |
| PYGB CDS | CCGGCCGTTTAAACATG GCGAAGCCGCTGACGGA | CCGGCCGCGGCCGCCTA GTCCCGGGGATGTTGG |
| SHMT2 3'UTR | CCGGCCCTCGAGAGGCA CCTGGGAAATGAGGC | CCGGCCGCGGCCGCCAA AATACAATTTCATTTAA |
| SHMT2 CDS | CCGGCCCTCGAGATGCT GTACTTCTCTTTGTT | CCGGCCGCGGCCGCTCA ATGCTCATCAAAACCAG |
| VIPR CDS | CCGGCCGTTTAAACTCA GACCAGGGAGACTTCGG | CCGGCCCTCGAGATGCG CCCGCCAAGTCCGCT |
| VIPR1 3'UTR | CCGGCCCTCGAGCCACC AGGATCCCAGGGGCC | CCGGCCGCGGCCGCTCC AAGCCAACATTTATTGT |

Potential miR-126 sites in genes were identified by alignment to the complementary miR-126 sequence 5-TTACT-CACGGTACGA-3, and mutagenesis was performed using the QUICKCHANGE Multi Site-Directed Mutagenesis Kit (200514, AGILENT TECHNOLOGIES, Santa Clara, Calif.). Based on the UCSC genome browser the 3'UTR of MERTK was mutated at position 5 (GTT to CAC), the 3'UTR of IGFBP2 was mutated at position 246 (GGT to CAC), the CDS of PITPNC1 was mutated at position 709 (TAC to GTA) from the start codon and the CDS of SHMT2 was mutated at position 1126 (GGT to CAC). Mutagenesis primers are in shown in Table 3 below.

TABLE 3

Mutagenesis Primers

| Gene | |
|---|---|
| | Forward |
| IGFBP2 3'UTR | AAGGGGGTTGTGGTCGGGGAGCTGGCA CACAGGTTTGGGGAGGGGAAGAGAA |
| MERTK 3'UTR | ATTCTAGGCGATCGCTCGAGGGAGACA CGCGGGGAGACATTCCAAAAATCAAG |
| PITPNC1 CDS | TATGACAATGGATGATGTTCGGGAAGT AGAGAAAAACATGCATGAACAAACCA |
| SHMT2 CDS | GCGAGGCTACTCACTGGTATCAGGTCA CACTGACAACCACCTGGTGCTGGTGG |
| | Reverse |
| IGFBP2 3'UTR | TTCTCTTCCCCCTCCCCAAACCTGTGT GCCAGCTCCCCGACCACAACCCCCTT |
| MERTK 3'UTR | CTTGATTTTTGGAATGTCTCCCCGCGT GTCTCCCTCGAGCGATCGCCTAGAAT |
| PITPNC1 CDS | TGGTTTGTTCATGCATGTTTTTCTCTA CTTCCCGAACATCATCCATTGTCATA |
| SHMT2 CDS | CCACCAGCACCAGGTGGTTGTCAGTGT GACCTGATACCAGTGAGTAGCCTCGC |

Cancer Cell Proliferation

LM2 cells ($2.5 \times 10^4$) expressing a control hairpin or short hairpins targeting IGFBP2, PITPNC1 or MERTK were seeded in triplicate in 6 well plates and viable cells were counted at 5 days after seeding.

Histology

Lungs were prepared by perfusion fixation with 4% paraformaldehyde infused through the vascular system and through the trachea. After excision, the lungs were placed in 4% paraformaldehyde overnight and embedded in paraffin. Five minutes prior to fixation, 100 mg biotinylated lectin (B-1175, VECTOR LABORATORIES) was injected into the circulation via the tail vein. Five-micrometer thick paraffin sections were stained with primary antibodies against MECA-32 (Developmental Studies Hybridoma Bank, The University of Iowa, Iowa), Vimentin (VP-V684, VECTOR LABORATORIES) and with FITC labeled Avidin (B-1175, VECTOR LABORATORIES) for the detection of injected biotinylated lectin. Primary antibodies were detected using various Alexa Flour dye-conjugated secondary antibodies. Fluorescence was obtained using a ZEISS laser scanning confocal microscope (LSM 510). To determine the vascularisation of metastatic nodules, the MECA-32 and lectin signals were quantified using IMAGEJ while the metastatic nodules' extents were determined through co-staining with human vimentin. The collective area covered by vessels was determined by subtracting background (rolling ball radius of 1 pixel) and by using a pre-determined threshold as cut-off. Vessel density is given as the percentage of area covered by the blood vessels compared to the total area of the metastatic nodule. A metastatic nodule was defined by an area positive for vimentin staining with a total area above 2000 $\mu m^2$.

Mammary fat pad tumors were excised and submerged into 4% paraformaldehyde for 24 hours. The fixed tissue was embedded in paraffin and sectioned in 5 µm thick slices. Immuno-detection were performed using antibodies directed towards MECA-32 (Developmental Studies Hybridoma Bank), Mac-2 (CL8942AP, Cederlane, Burlington) and CD45 (550539, BD Biosciences). Detection of primary antibodies was performed using various biotinylated secondary antibodies (Vector Laboratories). The signal was subsequently amplified using the ABC kit (Vector Laboratories), and detected using DAB (3,3'-diaminodbenzidine). Before mounting the slides were counterstained with hematoxilin.

Dextran permeability was determined as described in Arnold et al., 2010 Dis Model Mech 3 (1-2), 57 (2010) with slight modifications. Briefly, an intravenous bolus of 10 mg/ml rhodamine B labeled low molecular weight Dextran ($1 \times 10^4$ kDa: D1824, INVITROGEN) in sterile PBS was infused. Fifteen minutes later, the mice were anaesthetized and the lungs were perfused with OCT, removed and frozen on dry ice. Ten-micrometer section was cut and the dextran permeability inside metastatic nodules—as determined by vimentin staining—was measured by fluorescence microscopy. Using IMAGEJ, a preset threshold was used to determine the levels of dextran permeability. The results are presented as the mean percentage of the thresholded area inside the metastatic nodule.

ELISA

IGBFP2 levels in conditioned media were determined using an IGFBP2 ELISA (AAHBLG-1-2, RAYBIOTECH, Norgross, Ga.).

Western Blotting

Cellular lysates from MDA-MB-231 cells were prepared by lysing cells in 1 ml ice-cold RIPA buffer containing protease inhibitors (ROCHE, Mannheim, Germany). Conditioned media were prepared by incubating MDA-MB-231 cells in serum free media for 24 hours. The media was then concentrated twenty times by spin filtering. 40 µg protein was subsequently separated on a 4-12% SDS-PAGE, and transferred to a PVDF membrane. A monoclonal antibody against human MERTK (CVO-311, CAVEO THERAPEUTICS, Aurora, Colo.) was used to detect MERTK.

Metastasis Free Survival Analysis

Upon identifying the eight miR-126 regulated genes through an integrative analysis, it was determined whether the expression of these genes in aggregate correlates with human clinical metastasis. Published microarray data of series from UCSF46, NKI47, and MSKCC13 were used to obtain probe-level expression values. For genes that were represented by multiple probes, probes that displayed sufficient signal intensity as well as the highest coefficient of variation (most informative) in an independent dataset were used. Each breast cancer was classified as miR-126 signature positive if the sum of the Zscores for the expression values of the 8 genes was greater than the mean of the population. Kaplan-Meier metastasis-free survival curves were generated using GRAPHPAD PRISM 5 software (GRAPHPAD Software, Inc., LA Jolla, Calif.). Statistical significance for differences between survival curves of patients was determined using the Mantel-Cox log-rank test using GRAPHPAD Prism 5 software.

Vessel Density Analysis

The Kolmogorov-Smirnov test was used to determine the significance of difference in the blood vessel density for both MECA-32 and lectin staining using the publicly available software at physics.csbsju.edu/stats/KS-test.html.

EXAMPLE 2

Endogenous Mir-126 Suppressed Systemic Metastatic Colonization

In this example, assays were carried out to analyze metastatic progression in the setting of miR-126 loss-offunction. This enabled one to compare in vivo metastatic events between control and miR-126 knockdown (KD) cells and to reveal the influence of endogenous miR-126 on metastatic colonization.

Figure 7:
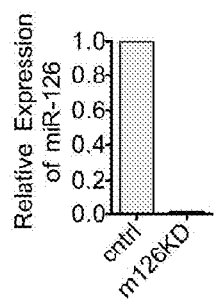
FIG. 7 is a diagram showing that miR-Zip miRNA-antisense shRNA system stably inhibited miR-126 expression in MDA-MB-231 cells. MDA-MB-231 cells were transduced with lentivirus expressing either a miR-Zip construct that targets miR-126 or a scrambled version of the construct that does not target any known microRNA (SYSTEM BIOSCIENCES, Mountain View, Calif.). The expression levels of mature miR-126 were then tested using qPCR.

A MDA-231 breast cancer cell line was generated in which miR-126 was stably knocked down (94% knock down; FIG. 7) using the miR-Zip anti-sense hairpin microRNA inhibition system. miR-126 KD and control KD cells were injected into immunodeficient mice and evaluated for metastatic colonization capacity in tail-vein colonization assays. miR-126 silencing in poorly metastatic cells increased lung metastatic colonization by 4.2 fold (P=0.0073) as assessed by quantitative bioluminescence imaging (FIG. 1a) and dramatically increased metastatic colonization on gross histology (FIG. 1a). Intracardiac injection of MDA miR-126 KD and control KD cells further revealed endogenous miR-126 to suppress systemic metastasis as evidenced by enhanced colonization of multiple organs such as brain and bone in the setting of miR-126 knockdown (FIG. 1b-c; P=0.0232(b), P=0.0119(c)).

Next, assays were carried out to examine to what extent the dramatic increase in metastatic colonization observed with miR-126 inhibition was due to the effect of miR-126 on tumor growth. To this end, miR-126 KD and control KD cells were injected into the mammary fat pads of immunodeficient mice and monitored tumor volume. miR-126 inhibition led to a modest increase (39.4%) in tumor volume (FIG. 1d) that was an order of magnitude smaller than the effect of miR-126 inhibition on metastasis enhancement—indicating that the effect of miR-126 on metastasis is not simply a result of its effect on tumor growth suppression.

Figure 1E:
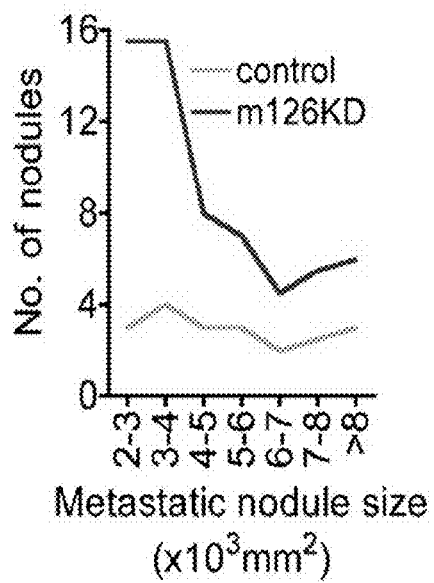
Figure 1F:
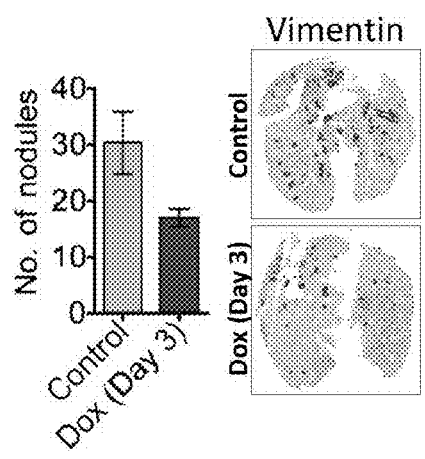

To better understand the role of this miRNA on metastatic colonization, the numbers and sizes of all metastases were quantified through image analysis of lungs from control and miR-126 KD mice (FIG. 1e). This revealed a substantial increase in the total number of metastatic nodules in miR-126 KD lungs relative to control lungs (13.6±3.2 versus 4.9±1.8; P=0.03). This increase was noted for both small and large nodules (FIG. 1e) and mirrored the increase in the number of metastases to other organs (FIG. 1c). Importantly, the increase in nodule number was more pronounced for smaller nodule sizes relative to larger ones, consistent with primarily an increase in the initiation of metastases rather than an increase in the growth of established metastases. Without being bound by theory, if miR-126 silencing provides a metastatic initiation advantage for cells as they initiate metastases in the metastatic niche, its induction in the initial phase of metastasis formation should reduce the number of metastatic nodules. To test this, miR-126 expression was induced in metastatic breast cancer cells (LM2) displaying silencing of this miRNA using a conditional tet-on system. Consistent with this, restoring miR-126 expression to LM2 cells after they have extravasated in the lung (Day 3) significantly reduced metastatic colonization (FIG. 1f). Thus, restoring miR-126 expression at this early phase of metastasis initiation in the niche significantly reduced the number of metastasis nodules visualized at day 49.

The above findings demonstrated that miR-126 silencing enhances the efficiency of metastasis formation leading to a larger number of metastases. The findings thus revealed endogenous miR-126 to be a suppressor of metastatic initiation and metastatic colonization.

EXAMPLE 3 miR-126 Suppresses Metastatic Endothelial Recruitment by Breast Cancer Cells

Figure 2A:
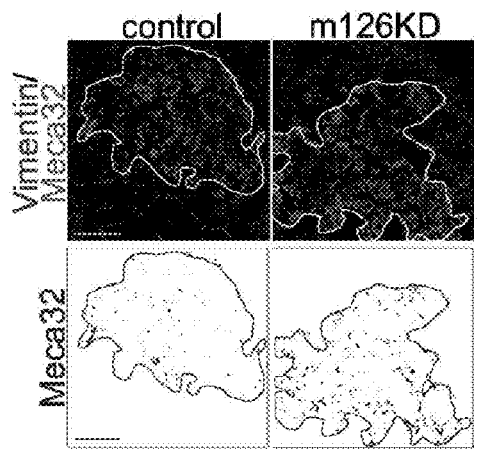
FIGS. 2a-2J are diagrams and photographs showing that endogenous miR-126 non-cell autonomously suppressed metastatic angiogenesis by metastatic breast cancer cells.

The above findings suggest that miR-126 silencing can provide metastatic cells and incipient metastases an advantage during metastatic colonization. While considering the basis of this advantage, it was noted that miR-126 knockdown metastases displayed higher vessel densities on microscopic visualization of lung H&E tissue sections. To quantify this, co-immunostaining was performed for human vimentin, which labels MDA-231 breast cancer cells, and the endothelial marker MECA-32, which allowed one to quantify the endothelial density within metastatic nodules in lungs of mice injected with either control or miR-126 KD breast cancer cells. Image analysis and quantification revealed metastases derived from miR-126 KD cells to have a significantly higher endothelial density (FIG. 2a; 35% increase; P=0.02).

Figure 2B:
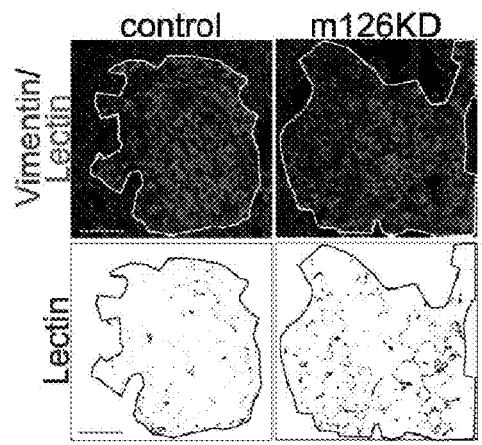

To determine if the enhanced endothelial density in miR-126 KD metastases represents functional vessels, sugar-binding lectin was injected into the circulation of mice prior to lung extractions, and subsequently stained for the injected lectin. Lectin cytochemistry revealed that miR-126 knockdown metastases displayed increased density of functional blood vessels (FIG. 2b; 33% increase; P=0.001).

Figure 8:
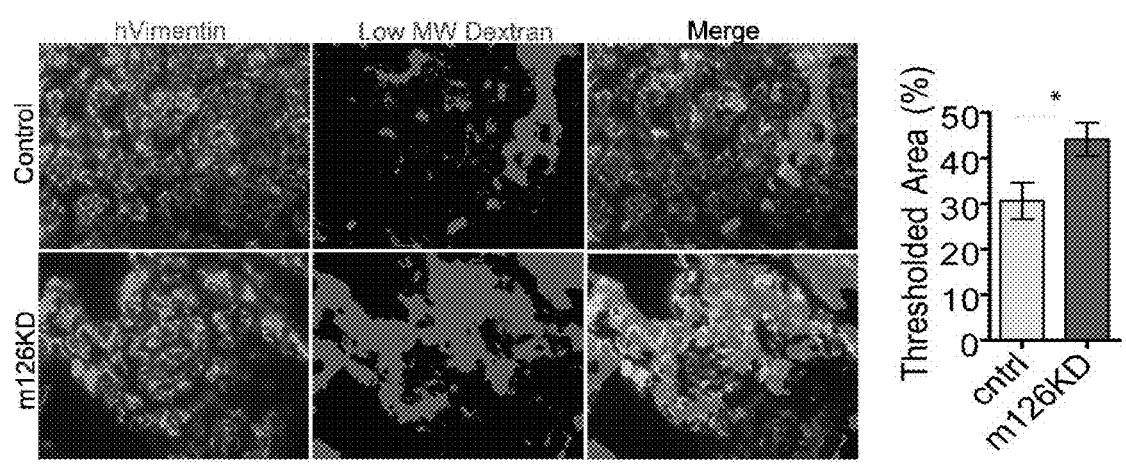
FIG. 8 is a set of photographs and a diagram showing that breast cancer cell-expressed miR-126 regulates perfusion in metastatic nodules. $4 \times 10^4$ MDA-MB-231 cells expressing a short hairpin targeting miR-126 or the control hairpin were injected intravenously into immunodeficient NOD-SCID mice. At day 59, FITC labeled low molecular weight dextran (10.000 MW) solution was injected intravenously. The dextran molecules were allowed to circulate for 15 min before mice were euthanized and the lungs excised. Frozen section were prepared, and stained for human Vimentin in order to localize metastatic nodules, and the FITC signal inside the nodules was quantified with a constant threshold using ImageJ. n=5; error bars represent s.e.m., p-values obtained using student's t-test.

Finally, it was sought to determine if miR-126 regulates hemodynamic perfusion to metastases through intravenous perfusion and subsequent visualization of low-molecular weight dextran ($1\times10^4$ kDa). Indeed, miR-126 KD metastases displayed significantly increased perfusion relative to control metastases (FIG. 8; P=0.02).

Thus, these independent and complementary methods reveal that miR-126 suppresses in vivo functional metastatic angiogenesis and perfusion. These findings are consistent with miR-126 silencing providing metastases a selective advantage in angiogenic progression.

EXAMPLE 4

Mir-126 Suppresses Cancer Endothelial Recruitment In Vitro

In this example, it was sought to determine the cellular basis for the miR-126 dependent angiogenesis phenotype observed.

Figure 2C:
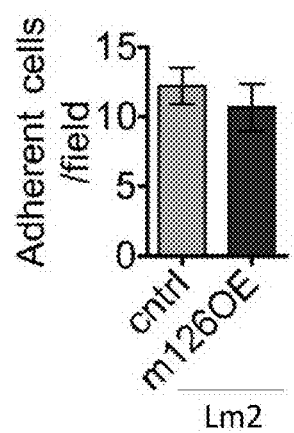
Figure 2D:
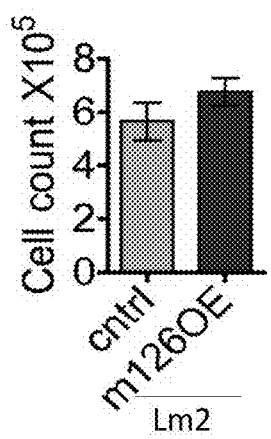
Figure 2E:
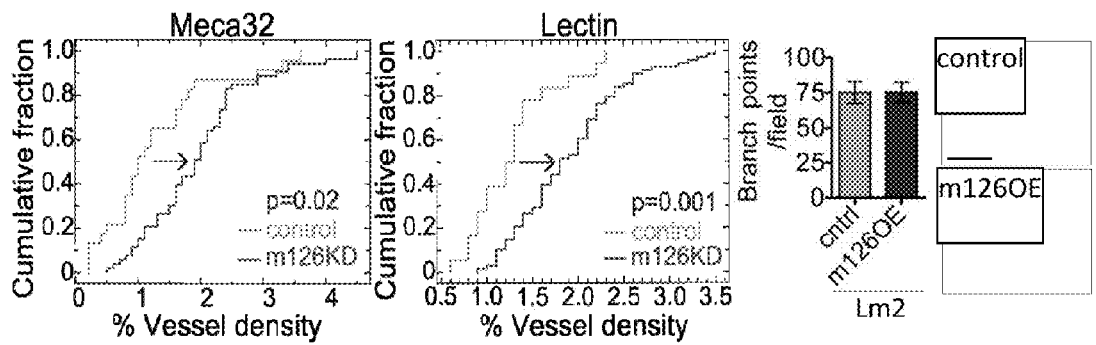
Figures 9A, 9B, 9C:
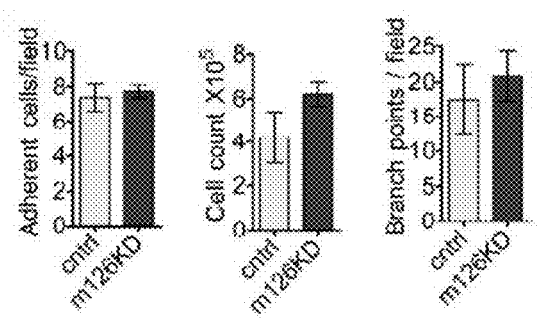
FIGS. 9a-9b are a set of diagrams showing that endogenous miR-126 did not suppress endothelial adhesion, proliferation, or tube formation.
FIG. 9c, $2\times10^4$ HUVEC cells were mixed with $1\times10^4$ MDA miR-126 KD or MDA control KD cells, and tube formation by HUVEC cells was assayed. Images of each well were obtained and the number of branch points in each image was analyzed using MetaMorph software. n=3; error bars represent s.e.m.

The ability of miR-126 to regulate various cancer-endothelial interactions such as endothelial adhesion, endothelial proliferation, and tube-formation was analyzed in LM2 metastatic cells (originally derived from the poorly metastatic MDA-231 population, Minn, A. J. et al., Nature 436 (7050), 518 (2005)) in co-culture with human umbilical vein endothelial cells (HUVECs). Restoring miR-126 expression to LM2 cells, which display silencing of miR-126, did not suppress adhesion of metastatic cells to endothelial cells (FIG. 2c), proliferation of endothelial cells (FIG. 2d), or tube formation as assessed by automated quantification of branch points (FIG. 2e). Consistent with this, inhibition of miR-126 in MDA-231 cells did not enhance these angiogenic phenotypes either (FIGS. 9a-c).

Figures 2F, 2G:
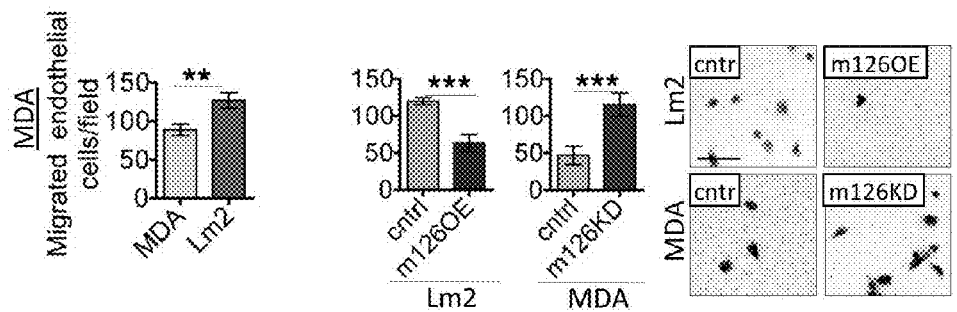
Figures 2H, 2I:
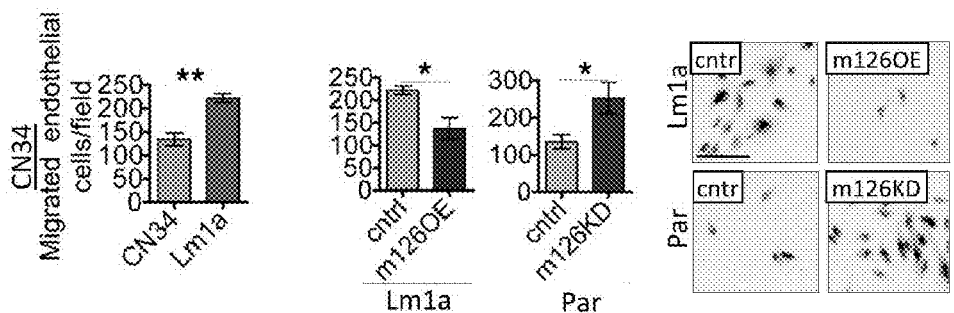

The role of miR-126 in regulation of recruitment of endothelial cells to metastatic cells was investigated. Metastatic LM2 cells placed in the bottom of a Boyden chamber strongly recruited HUVECS through a porous trans-well insert and displayed a significantly enhanced ability to recruit endothelia compared to their poorly metastatic parental line (FIG. 20. Endothelial recruitment by metastatic cells was strongly inhibited (47% reduction) by miR-126 overexpression (FIG. 2g). Conversely, knockdown of miR-126 in the poorly metastatic parental MDA-231 population significantly increased endothelial recruitment (146% increase; FIG. 2g). The CN34LM1a line, a highly lung metastatic derivative that was previously obtained through in-vivo selection of the CN34 primary malignant population (Tavazoie et al., *Nature* 451 (7175), 147 (2008)) (an independent primary malignant population obtained from the pleural fluid of a patient with metastatic breast cancer Gupta et al., *Nature* 446 (7137), 765 (2007)), also displayed significantly enhanced endothelial recruitment capacity compared to its poorly metastatic parental line (FIG. 2h). Both gain- and loss-of-function experiments revealed miR-126 to significantly suppress endothelial recruitment by the CN34 population as well (FIG. 2i). The findings reveal enhanced endothelial recruitment capacity to be a key feature of metastatic breast cancer populations and identify endogenous miR-126 as a major regulator of this process.

Figure 2J:
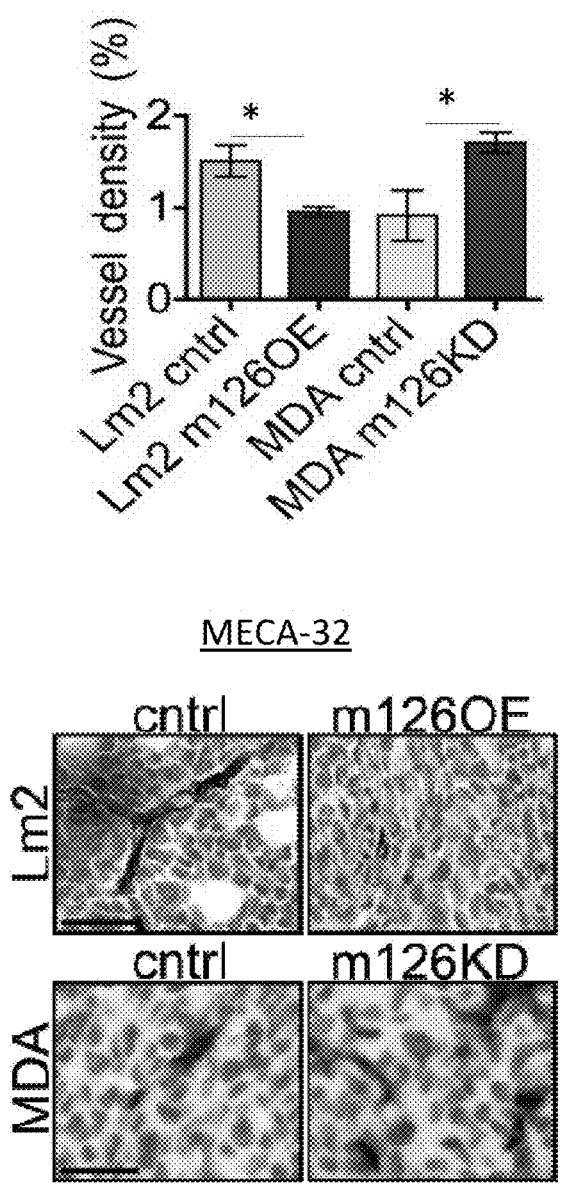
Figure 10A:
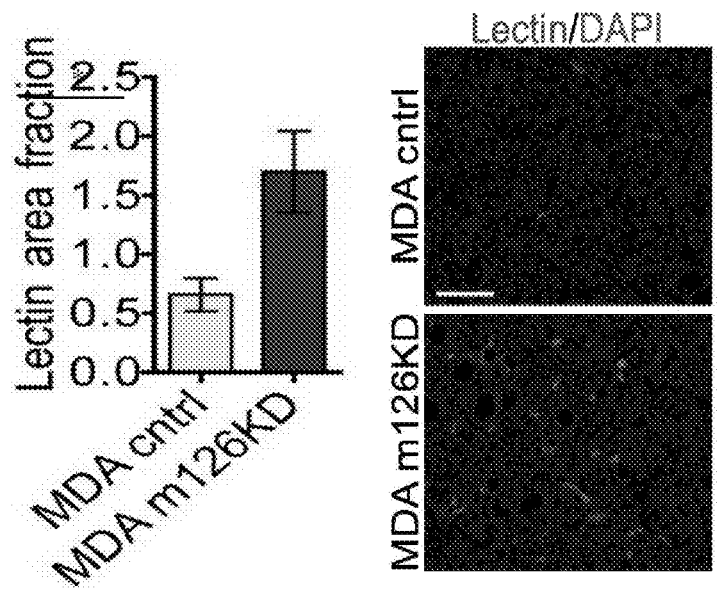
FIGS. 10a-10c are a set of diagrams and diagrams showing that endogenous miR-126 regulated angiogenesis, but not CD45 positive lymphocyte and Mac-2 positive macrophage recruitment.
Figure 10B:
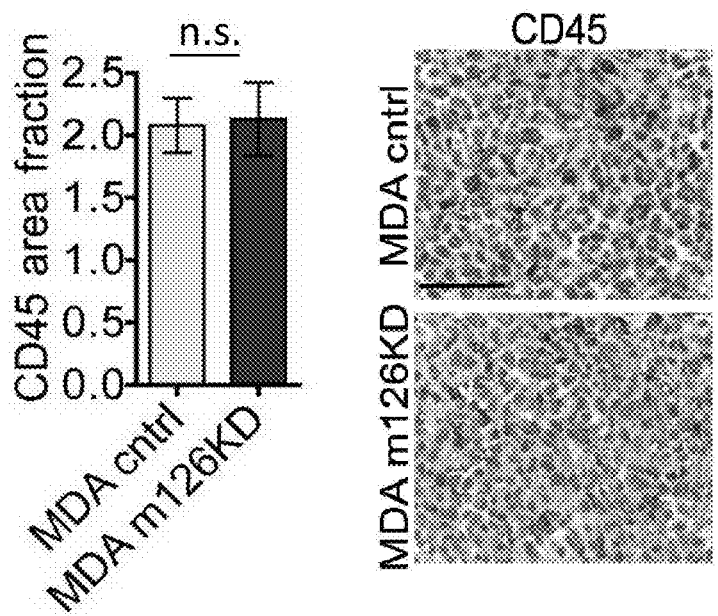
Figure 10C:
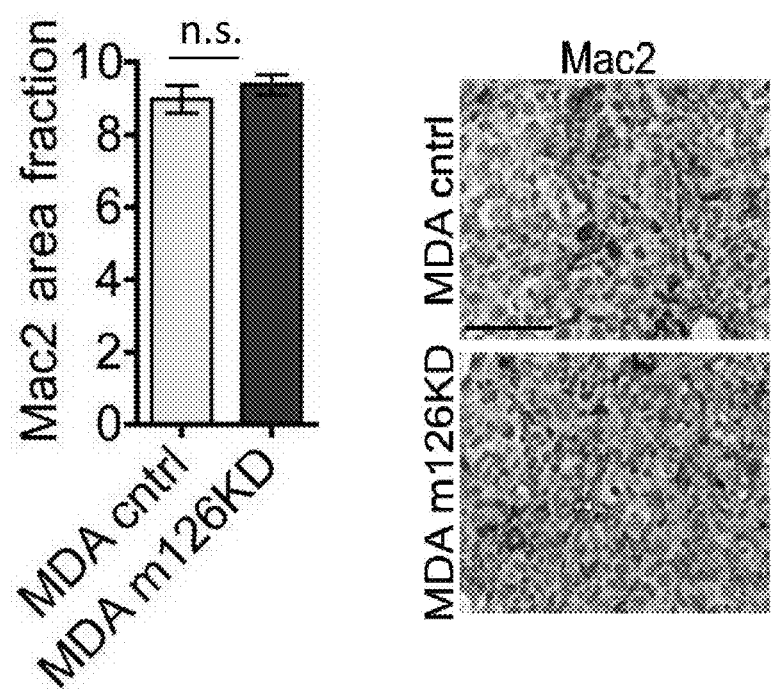

Next, it was sought to determine if endogenous miR-126 can selectively regulate endothelial recruitment to breast cancer cells independent of their location. Metastatic breast cancer cells expressing a control hairpin or over-expressing miR-126 were thus implanted into the mammary fat pads of mice. Metastatic cells, which display silenced miR-126 expression, displayed higher vessel density in the mammary gland relative to poorly metastatic cells. Endothelial recruitment to metastatic cells in the mammary fat pad was inhibited by miR-126 expression (FIG. 2j), while miR-126 knockdown in poorly metastatic cells significantly increased endothelial recruitment to and functional vessel content of breast tumors growing in mammary fat pads as determined by meca-32 staining (FIG. 2j) and lectin staining (FIG. 10a) respectively. This recruitment effect was selective to endothelial cells as miR-126 silencing did not increase leukocyte density (FIG. 10b) or macrophage density (FIG. 16c) in mammary tumors.

The above findings revealed that miR-126 selectively regulates endothelial recruitment to breast cancer cells independent of their anatomic location.

EXAMPLE 5

Mir-126 Regulon Promotes Endothelial Recruitment

In this example, a systematic search was conducted to identify the molecular targets of miR-126 that mediate endothelial recruitment and metastatic colonization. Specifically, transcriptomic analysis of LM2 cells over-expressing miR-126 was performed and global transcript alterations to poorly metastatic MDA-231 cells and highly metastatic LM2 cells were compared.

Figure 11:
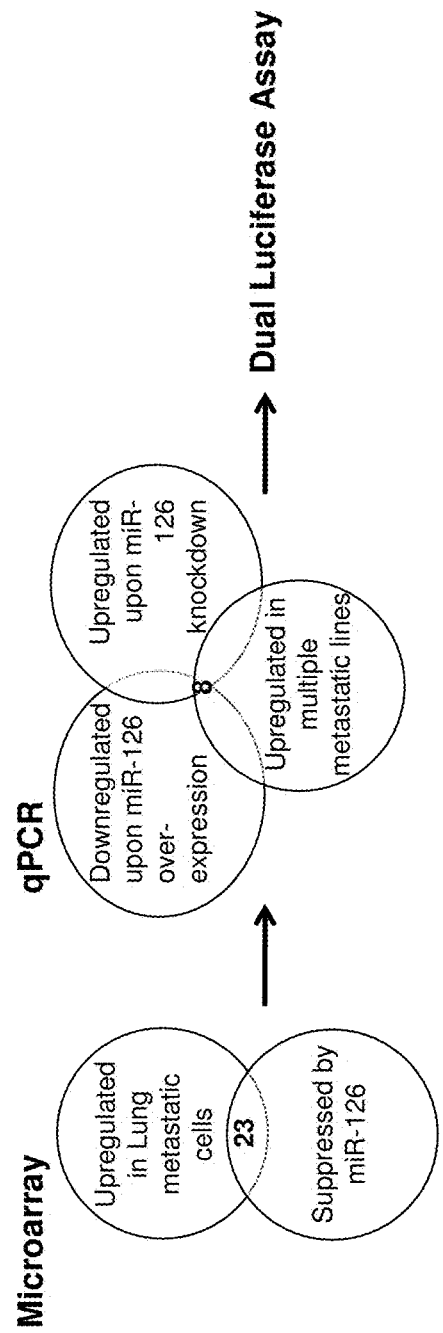
FIG. 11 is a Venn diagram showing the integrative experimental path that resulted in the identification of putative miR-126 target genes. Transcriptomic profiling of genes down-regulated by greater than 1.6 fold upon miR-126 over-expression were overlapped with genes up-regulated by more than 1.4 fold in metastatic LM2 cells as compared to the parental MDA cells. This led to the identification of 23 potential miR-126 target genes. By qPCR, 8 of these 23 genes were modulated by miR-126 in both the MDA-MB-231 breast cancer cell line and the primary CN34 cell line. These 8 genes were functionally tested for direct regulation by miR-126 through luciferase reporter assays.

Without being bound by theory, it was hypothesized that, given the role of miR-126 in inhibiting metastasis, the biological mediators of miR-126 display increased expression in metastatic cells and that they would be suppressed by this miRNA. A set of 23 genes were identified as they were suppressed upon miR-126 over-expression (>1.6-fold; FIG. 11; Table 4), and up-regulated (>1.4-fold) in metastatic cells relative to the parental MDA-231 line (FIG. 11).

Figure 3A:
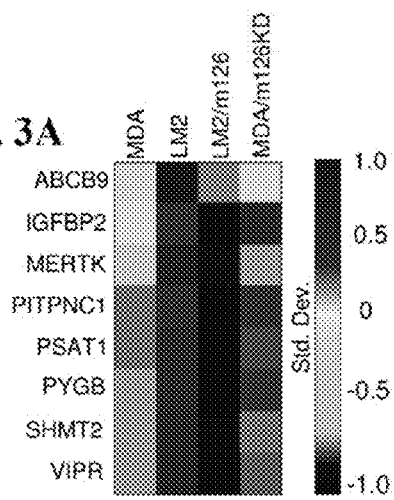
FIGS. 3a-3f are diagrams and photographs showing systematic identification of a miR-126 regulatory network that mediates metastatic endothelial recruitment.

Of these genes, 14 were validated to be significantly changed by quantitative real-time PCR (qPCR) of MDA-231 control and miR-126KD cells as well as LM2 control and miR-126 over-expressing cells. To further increase the confidence of this list, the expression of these genes in the metastatic derivatives of the independent CN34 line was tested, and 8 genes were identified as displaying significantly increased expression in multiple metastatic CN34 derivatives relative to their parental line (FIG. 3a).

Figure 3B:
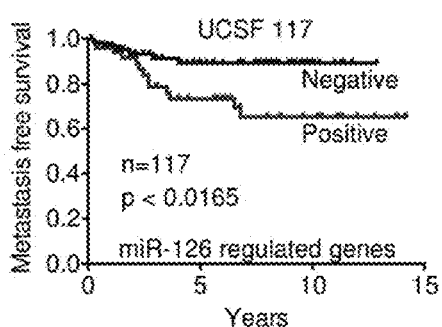
Figure 3C:
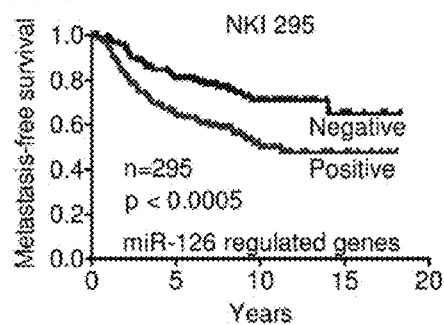
Figure 3D:
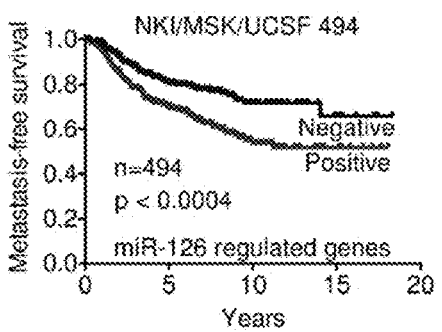

The contribution of these 8 genes to human metastasis was ascertained by determining whether their over-expression in primary human breast cancers correlates with distal metastasis-free survival. Patients whose primary breast cancers displayed their over-expression were significantly more likely to develop distal metastases and experienced shorter metastasis-free survival than those whose cancers did not over-express these genes (FIG. 3b-d). This association displayed significance in the UCSF (n=117; P<0.0165), NKI (n=295; P<0.0005), and the combined MSK/NKI/UCSF cohorts (n=494; P<0.0004). Thus, miR-126 suppressed the expression of a set of eight genes that are positively and strongly correlated with human metastatic relapse.

Figure 3E:
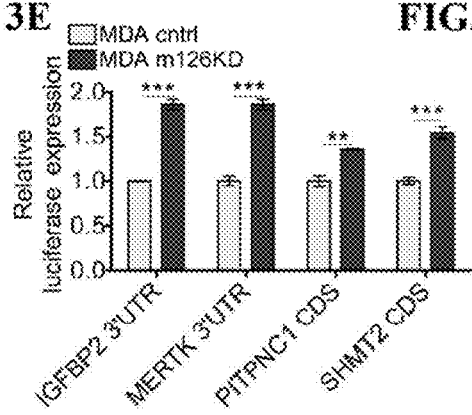
Figure 3F:
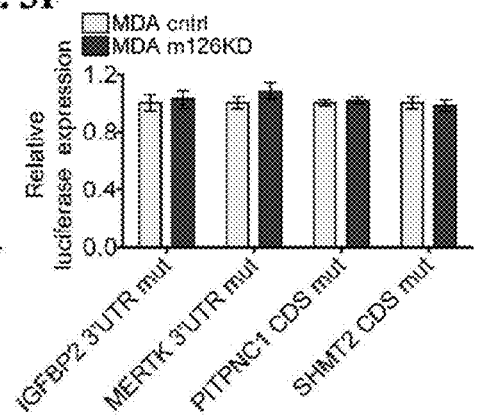
Figure 12A:
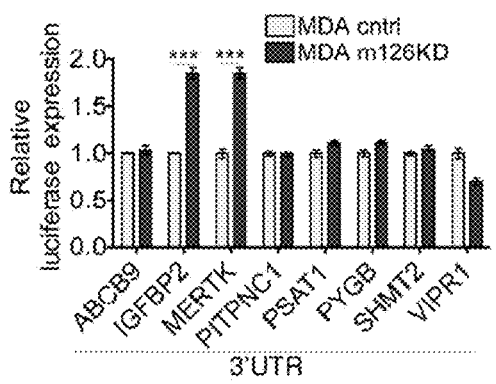
FIGS. 12a-12b are diagrams showing that miR-126 regulated IGFBP2 and MERTK through 3'UTR interactions and PITPNC1 and SHMT2 through CDS interactions.
Figure 12B:
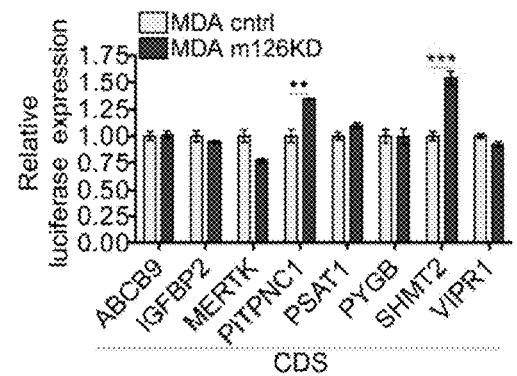
Figure 13A:
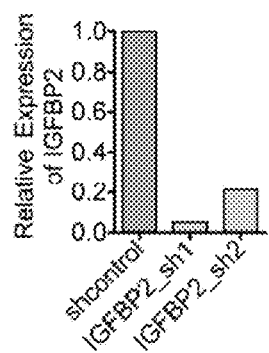
FIGS. 13a, 13b, 13c and 13d are a set of diagrams showing that independent hairpins down-regulated the expression levels of IGFBP2, PITPNC1 and MERTK in LM2 cells. LM2 cells were transduced with lentivirus expressing a control hairpin or a short hairpin construct targeting IGFBP2, PITPNC1 or MERTK. The expression levels of the target genes were analyzed through qPCR.
Figure 13B:
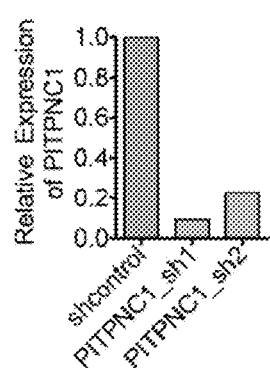
Figure 13C:
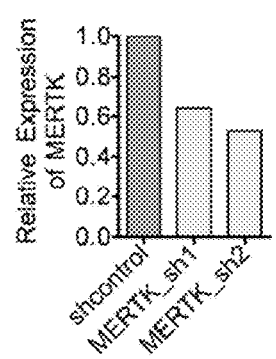
Figure 13D:
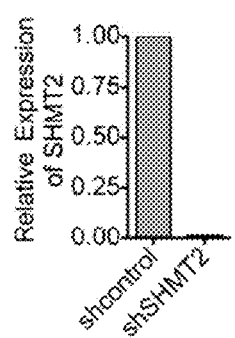

Next, assays were carried out to identify the direct targets of miR-126. To this end, the 3'-untranslated regions (3'-UTR's) and coding sequences (CDS's) of all eight miR-126 regulated genes were cloned and used to generate luciferase fusion constructs. Luciferase reporter assays with this entire set revealed miR-126 to regulate the expression of IGFBP2 and MERTK through interactions with their 3'-UTR's and PITPNC1 and SHMT2 through interactions with their coding regions as knockdown of endogenous miR-126 in MDA-231 cells enhanced expression of these luciferase fusion genes (FIG. 3e and FIG. 12). Mutation of miR-126 complementary sequences in the 3'-UTR's of IGFBP2 and MERTK abolished miR-126 mediated regulation of luciferase expression (FIG. 30, while mutation of the CDS's of PIPNC1 and SHMT2 abolished miRNA mediated targeting (FIG. 30.

TABLE 4

| Fold reduction by miR-126 in LM2 cells | | | | | | | |
|---|---|---|---|---|---|---|---|
| Gene Name | Fold | Gene Name | Fold | Gene Name | Fold | Gene Name | Fold |
| GDF15 | −4.15 | CTAGE5 | −1.93 | PRKAR1A | −1.80 | KIAA0746 | −1.71 |
| RARA | −3.53 | CDA | −1.93 | CHAC1 | −1.80 | PADI4 | −1.71 |
| P8 | −2.98 | FLJ46385 | −1.92 | SCD | −1.80 | BEX2 | −1.71 |
| RPS6KA2 | −2.54 | RALGPS2 | −1.92 | PCK2 | −1.80 | TAF13 | −1.70 |
| C20orf100 | −2.47 | BDNFOS | −1.91 | CDC42BPB | −1.79 | KLF4 | −1.70 |
| C12orG9 | −2.38 | MBNL1 | −1.91 | DSCR1 | −1.79 | DLG1 | −1.70 |
| HERPUD1 | −2.37 | MKX | −1.91 | TCF7L2 | −1.79 | DDEFL1 | −1.70 |
| CTH | −2.36 | LPIN1 | −1.90 | TNRC6C | −1.79 | MID1IP1 | −1.70 |
| LOC23117 | −2.35 | DNAJB9 | −1.90 | TncRNA | −1.78 | LOC124220 | −1.70 |
| LOC23117 | −2.35 | TncRNA | −1.90 | CLDN23 | −1.78 | C10orf58 | −1.70 |
| ASNS | −2.35 | BCL2L1 | −1.90 | GPR153 | −1.78 | CDKN1C | −1.70 |
| RGC32 | −2.33 | DNAJB9 | −1.90 | KRTHA4 | −1.78 | DTX3 | −1.70 |
| CTH | −2.33 | ENTH | −1.89 | SCD | −1.78 | SETD5 | −1.70 |
| NRP1 | −2.28 | S100A5 | −1.89 | VIPR1 | −1.78 | SLC7A11 | −1.69 |
| RIT1 | −2.26 | CST4 | −1.89 | SLC1A4 | −1.77 | WSB1 | −1.69 |
| HMGA1 | −2.24 | TRIB3 | −1.89 | PNPLA3 | −1.77 | KIAA1618 | −1.69 |

TABLE 4-continued

Fold reduction by miR-126 in LM2 cells

| Gene Name | Fold | Gene Name | Fold | Gene Name | Fold | Gene Name | Fold |
|---|---|---|---|---|---|---|---|
| DDIT3 | −2.20 | PHLDA1 | −1.89 | PPP1R11 | −1.77 | PYGB | −1.69 |
| MBNL1 | −2.20 | RGNEF | −1.89 | CFLAR | −1.77 | CSNK1A1 | −1.69 |
| SUPT6H | −2.16 | GFPT1 | −1.88 | NSF | −1.77 | THBD | −1.68 |
| LPIN1 | −2.15 | TMTC2 | −1.88 | ABHD4 | −1.77 | CG012 | −1.68 |
| ZNF451 | −2.12 | TPARL | −1.87 | SOCS2 | −1.77 | DDX17 | −1.68 |
| THBD | −2.10 | INHBB | −1.87 | TACSTD2 | −1.76 | BGLAP | −1.68 |
| ITGB4 | −2.10 | FASN | −1.87 | SESN2 | −1.76 | MAGI1 | −1.68 |
| BHLHB8 | −2.09 | CALB2 | −1.86 | CTNNB1 | −1.76 | WARS | −1.68 |
| SLCO4C1 | −2.09 | IGFBP2 | −1.86 | MAP1LC3B | −1.76 | LOC283050 | −1.68 |
| AFF4 | −2.07 | SLC6A9 | −1.86 | LOC165186 | −1.76 | AQP3 | −1.68 |
| ATP6V0D2 | −2.05 | PLAT | −1.86 | FLJ20054 | −1.75 | LOC400581 | −1.68 |
| KRT19 | −2.05 | SIN3B | −1.86 | ZNF69 | −1.74 | CYLN2 | −1.68 |
| SMAD3 | −2.04 | S100A6 | −1.85 | TNFSF4 | −1.74 | CD97 | −1.68 |
| ARHGAP5 | −2.04 | WSB1 | −1.85 | LOC441453 | −1.74 | CNTNAP3 | −1.67 |
| DNAJB9 | −2.04 | C20orf18 | −1.85 | MARS | −1.74 | PDE2A | −1.67 |
| ATF3 | −2.03 | HMGCS1 | −1.85 | LOC647135 | −1.74 | AOF1 | −1.67 |
| LOC440092 | −2.03 | MBNL1 | −1.85 | ACSL3 | −1.74 | IDS | −1.67 |
| RIT1 | −2.03 | MBNL1 | −1.85 | SCD | −1.74 | SCD | −1.67 |
| ZNF499 | −2.02 | WHSC1L1 | −1.85 | SERINC2 | −1.73 | SHMT2 | −1.67 |
| ATXN1 | −2.02 | NCF2 | −1.85 | ZCCHC7 | −1.73 | RNF10 | −1.67 |
| CST6 | −2.01 | MERTK | −1.84 | ETNK1 | −1.73 | CRLF3 | −1.67 |
| WBP2 | −2.00 | PFAAP5 | −1.84 | CHRM3 | −1.73 | PSAT1 | −1.67 |
| ZFAND3 | −2.00 | RTN4 | −1.83 | DCAMKL1 | −1.73 | FNBP1 | −1.67 |
| FLJ38717 | −1.99 | LARP6 | −1.83 | C20orf119 | −1.73 | LOC554203 | −1.66 |
| LOC158160 | −1.99 | TRIB3 | −1.83 | CDKN1C | −1.73 | MYADM | −1.66 |
| PITPNC1 | −1.99 | RAB37 | −1.83 | CXorG3 | −1.72 | ATXN1 | −1.66 |
| JMJD1C | −1.99 | LOC399959 | −1.83 | LPIN1 | −1.72 | CA12 | −1.66 |
| PRO2852 | −1.98 | SYTL1 | −1.82 | GEM | −1.72 | SF3B4 | −1.66 |
| AGR2 | −1.97 | SDF2L1 | −1.82 | KIAA0746 | −1.72 | KHDRBS1 | −1.66 |
| SLC7A5 | −1.94 | RPH3AL | −1.82 | LOC115648 | −1.72 | EGFR | −1.66 |
| NSF | −1.94 | OGDH | −1.82 | TIA1 | −1.72 | FRMD5 | −1.65 |
| BCL2L1 | −1.94 | CDYL | −1.81 | FLJ10120 | −1.71 | ZNF252 | −1.65 |
| KIAA1267 | −1.93 | RHOQ | −1.81 | DUSP5 | −1.71 | FNBP1 | −1.65 |
| NT5C2 | −1.93 | ITGB4 | −1.81 | RNF12 | −1.71 | TNKS2 | −1.65 |
| C9orf3 | −1.65 | C14orf118 | −1.61 | | | | |
| AOF1 | −1.65 | PIAS1 | −1.61 | | | | |
| PDP2 | −1.65 | PXN | −1.61 | | | | |
| MLLT10 | −1.65 | C14orf118 | −1.61 | | | | |
| WIRE | −1.65 | PIAS1 | −1.61 | | | | |
| ATXN1 | −1.65 | FLJ43663 | −1.65 | | | | |
| WARS | −1.65 | SOS2 | −1.61 | | | | |
| RAB5B | −1.64 | FLJ43663 | −1.60 | | | | |
| SQLE | −1.64 | HCRP1 | −1.60 | | | | |
| SCNN1A | −1.64 | LOC646916 | −1.60 | | | | |
| C14orf78 | −1.64 | NUP43 | −1.60 | | | | |
| SHMT2 | −1.63 | PEBP1 | −1.60 | | | | |
| PSCD3 | −1.63 | FLJ23556 | −1.60 | | | | |
| LOC643998 | −1.63 | NRP1 | −1.60 | | | | |
| PHGDH | −1.63 | JUP | −1.60 | | | | |
| HEXA | −1.63 | | | | | | |
| CDRT4 | −1.63 | | | | | | |
| ACTN4 | −1.63 | | | | | | |
| C6orf155 | −1.63 | | | | | | |
| EXT1 | −1.63 | | | | | | |
| JDP2 | −1.63 | | | | | | |
| LSS | −1.63 | | | | | | |
| PITPNC1 | −1.63 | | | | | | |
| C20orf18 | −1.63 | | | | | | |
| CLDN7 | −1.63 | | | | | | |
| NPC1 | −1.62 | | | | | | |
| IDH1 | −1.62 | | | | | | |
| THBD | −1.62 | | | | | | |
| GSTM4 | −1.62 | | | | | | |
| ATP5C1 | −1.62 | | | | | | |
| PMM1 | −1.62 | | | | | | |
| C9orf5 | −1.62 | | | | | | |
| COL8A2 | −1.62 | | | | | | |
| CST1 | −1.62 | | | | | | |
| MAGI1 | −1.62 | | | | | | |
| G6PD | −1.62 | | | | | | |
| FOSL1 | −1.61 | | | | | | |
| RASD1 | −1.61 | | | | | | |
| PITX1 | −1.61 | | | | | | |
| P2RY2 | −1.61 | | | | | | |
| HYOU1 | −1.61 | | | | | | |
| CSF2RA | −1.61 | | | | | | |

TABLE 4-continued

Fold reduction by miR-126 in LM2 cells

| Gene Name | Fold | Gene Name | Fold | Gene Name | Fold | Gene Name | Fold |
|---|---|---|---|---|---|---|---|
| SLC16A4 | −1.61 | | | | | | |
| SQLE | −1.61 | | | | | | |
| EFHD2 | −1.61 | | | | | | |
| ABCB9 | −1.61 | | | | | | |
| SYDE1 | −1.61 | | | | | | |
| MAGI1 | −1.61 | | | | | | |
| SLC7A11 | −1.61 | | | | | | |
| HSPA5 | −1.61 | | | | | | |

Thus, the binding protein IGF-binding protein 2, the receptor kinase MERTK, the phosphatidylinositol transfer protein PITPNC1, and the hydroxymethyltranferase enzyme SHMT2 comprise a set of direct targets of miR-126 in human breast cancer.

EXAMPLE 6

IGFBP2, PITPNC1, and MERTK Promote Endothelial Recruitment and Metastasis

Figure 4A:
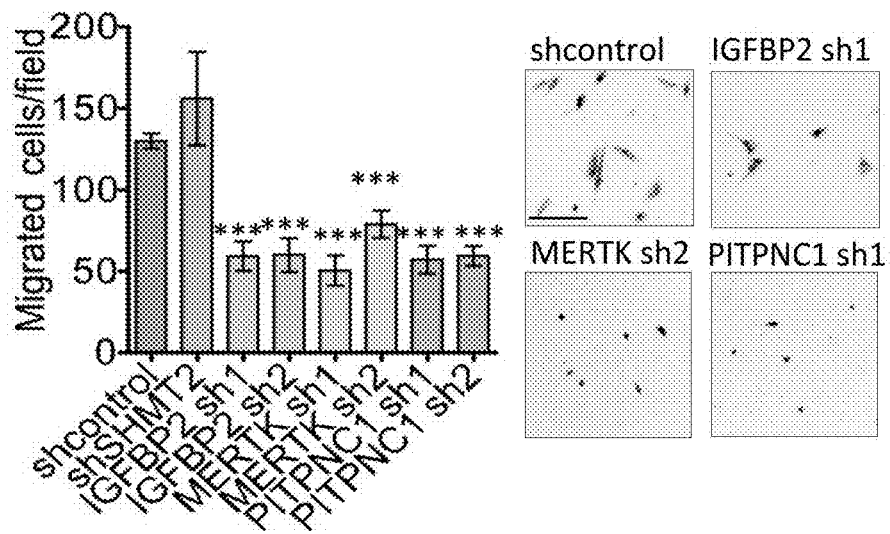
FIGS. 4a-4e are a set of diagrams and photographs showing that IGFBP2, PITPNC1 and MERTK promoted metastatic colonization and angiogenesis.
Figure 14:
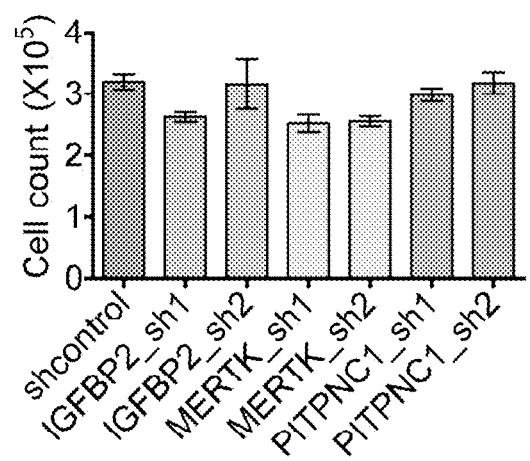
FIG. 14 is a diagram showing proliferation analysis of miR-126 target genes. $2.5\times10^4$ LM2 cells expressing a control hairpin or short hairpins targeting IGFBP2, PITPNC1 or MERTK were seeded in triplicate and viable cells were counted at 5 days after seeding. n=3; error bars represent s.e.m.

In this example, assays were carried out to examine if any of the miR-126 target genes regulate the recruitment of endothelial cells by cancer cells. Of these four genes, knockdown of IGFBP2, MERTK, or PITPNC1 using independent short hairpins significantly suppressed the ability of metastatic LM2 cells to recruit endothelial cells (FIG. 4a and FIG. 13). Importantly, knockdown of these genes did not result in a significant decrease in cell proliferation (FIG. 14).

Given the robust effects of the miR-126 target genes on endothelial recruitment, it was examined whether the expression levels of these genes individually correlate with metastatic propensity of human cancers. The expression levels of each of these genes were thus analyzed through qPCR in an entirely independent set of 96 human breast cancers for which cDNAs were available.

Figure 4B:
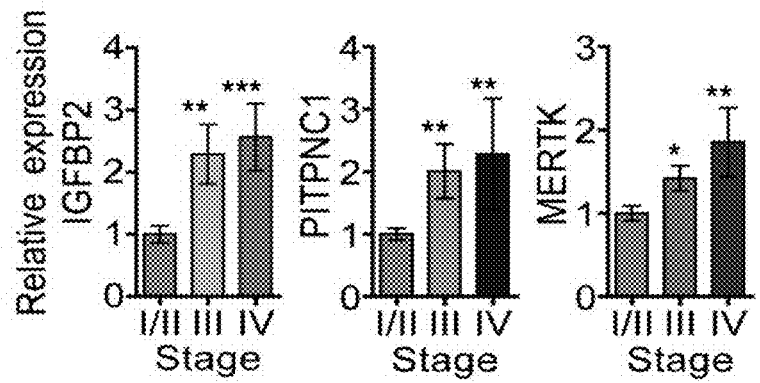

Patients with stage III and stage IV breast cancers display local metastatic dissemination and distal metastases, respectively, and collectively comprise those that develop distal relapse at much higher rates than stage I and II patients. Interestingly, expression levels of IGFBP2 (P<0.0003), MERTK (P<0.002), and PITPNC1 (P<0.004) were individually significantly increased in primary cancers of stage III and IV patients relative to stage I and II patients (FIG. 4b). Given their requirement for endothelial recruitment by metastatic cells, as well as their direct targeting by miR-126, it was sought to determine if any of the miR-126 target genes are required for metastatic colonization.

Figure 4C:
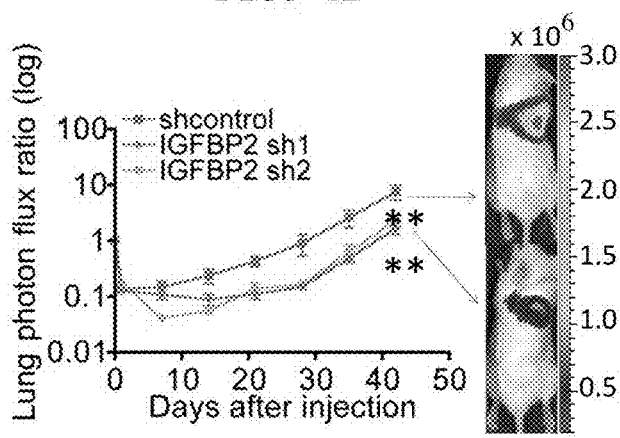
Figure 4D:
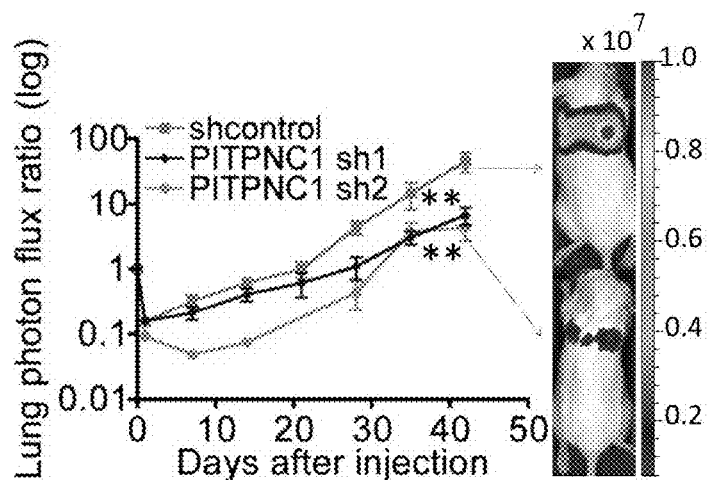
Figure 4E:
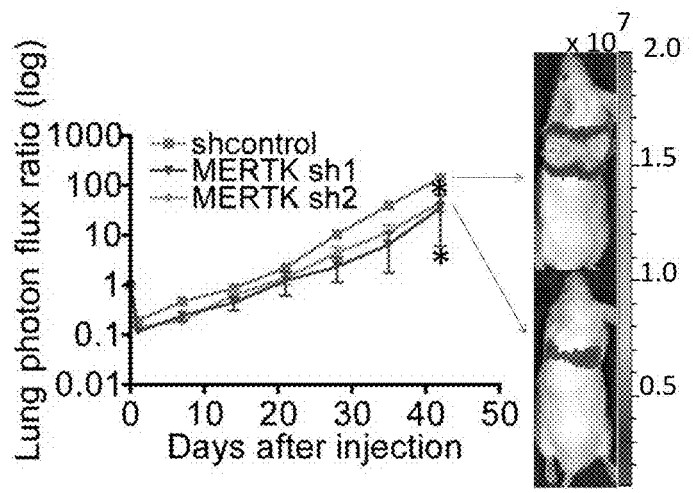

It was found that, importantly, knockdown of IGFBP2 using independent short hairpins significantly suppressed metastatic colonization to the lung (sh$_1$: 10-fold; sh$_2$: 6.25 fold; FIG. 4c). In addition, knockdown of PITPNC1 and MERTK also strongly inhibited metastatic colonization (PITPNC1sh$_1$: 7.69-fold; PITPNC1sh$_2$: 4.55-fold, FIG. 4d; MERTKsh$_1$: 3.91-fold; MERTK1sh$_2$: 3.08-fold, FIG. 4e). shRNA sequences used are listed in Table 5 below.

These findings revealed that the miR-126 direct target genes IGFBP2, PITPNC1 and MERTK are each individually required for endothelial recruitment and metastatic colonization and individually correlate in expression with human metastatic progression.

TABLE 5 shRNA sequences

| Gene | Sequence |
|---|---|
| IGFBP2_sh1 | CCGGCCAGTTCTGACACACGTATTTCTCG AGAAATACGTGTGTCAGAACTGGTTTTT (SEQ ID NO: 1) |
| IGFBP2_sh2 | CCGGCAGGTTGCAGACAATGGCGATCTCG AGATCGCCATTGTCTGCAACCTGTTTTT (SEQ ID NO: 2) |
| MERTK_sh1 | CCGGGCTTCTGGTCTTGATGTATTTCTCG AGAAATACATCAAGACCAGAAGCTTTTT (SEQ ID NO: 3) |
| MERTK_sh2 | CCGGCCTGCATACTTACTTACTTTACTCG AGTAAAGTAAGTAAGTATGCAGGTTTTT (SEQ ID NO: 4) |
| PITPNC1_sh1 | CCGGCGGGTGTATCTCAACAGCAAACTCG AGTTTGCTGTTGAGATACACCCGTTTTG (SEQ ID NO: 5) |
| PITPNC1_sh2 | CCGGCAATGGATGAAGTCCGAGAATCTCG AGATTCTCGGACTTCATCCATTGTTTTG (SEQ ID NO: 6) |
| shSHMT2 | CCGGCCGGAGAGTTGTGGACTTTATCTCG AGATAAAGTCCACAACTCTCCGGTTTTG (SEQ ID NO: 7) |
| shcontrol | CCGGCAACAAGATGAAGAGCACCAACTC- GAGTTGGTGCTCTTCATCTTGTTGTTTTT (SEQ ID NO: 8) |

EXAMPLE 7

IGFBP2 Mediates Recruitment Through IGF1/IGF1R Activation of Endothelial Cells Of the miR-126 targets, IGFBP2 is a secreted factor and, as such, poised to mediate inter-cellular communication between metastatic cancer cells and endothelial cells. Thus, it was examined if metastatic cells secrete increased levels of IGFBP2. It was found that, indeed, ELISA analysis revealed metastatic LM2 cells to secrete 2.1-fold higher levels of this factor than the poorly metastatic MDA-231 parental line (FIG. 5a).

Members of the IGFBP family exert their effects by interacting with various insulin-like growth factors (IGF's) and modulate their binding to IGF receptors (Baxter, R. C., Horm Res 42 (4-5), 140 (1994) and Jones, J. I. et al. Endocr Rev 16 (1), 3 (1995). To determine if metastatic endothelial recruitment is mediated through secreted IGFBP2, IGFBP2 binding to the IGF's was inhibited by means of incubation with neutralizing IGFBP2 antibody.

It was found that antibody-mediated inhibition of IGFBP2 in a trans-well recruitment assay significantly inhibited metastatic cell endothelial recruitment to levels comparable to that obtained with miR-126 over-expression (FIG. 5b) and also prevented miR-126 dependent recruitment (FIG. 5b). Thus, this effect was specific to the miR-126/IGFBP2 pathway, as inhibition of endothelial recruitment by IGFBP2 antibody was occluded upon miR-126 over-expression (FIG. 5b). Antibody-mediated inhibition of IGFBP2 also suppressed endothelial recruitment by the CNLM1A derivative of the independent CN34 malignant line and resulted in a statistically significant reduction in miR-126-dependent endothelial recruitment (FIG. 5c). These findings revealed secreted IGFBP2 to be an inter-cellular signalling mediator for miR-126-dependent endothelial recruitment by metastatic cells.

IGFBP2 was known to bind both IGF1 and IGF2 in the extracellular space and modulate their signaling activity (Jones, J. I. et al. *Endocr Rev* 16 (1), 3 (1995); Arai, T., et al. *Endocrinology* 137 (11), 4571 (1996); Rajaram, S., et al. *Endocr Rev* 18 (6), 801 (1997); and Hoflich, A. et al., *FEBS Lett* 434 (3), 329 (1998)). To determine which IGF mediates miR-126-dependent endothelial recruitment, cells were treated with blocking antibodies against IGF1, IGF2, or with immunoglobulin control. Antibody-mediated inhibition of IGF1, but not IGF2, significantly reduced endothelial recruitment resulting from miR-126 knockdown (FIG. 5d).

Next, it was sought to determine the receptor through which the miR-126-dependent endothelial recruitment is being mediated Inhibition of the IGF type-1 receptor (IGF1R) by incubation with IGF1R blocking antibody significantly reduced endothelial recruitment resulting from miR-126 knockdown, while IGF2R neutralization had no effect (FIG. 5e). These findings demonstrated that the miR-126/IGFBP2/IGF1 pathway activates IGF1R on endothelial cells.

To be certain that the miR-126-dependent recruitment was mediated through IGF1R on endothelial cells—rather than on cancer cells—HUVEC endothelial or cancer cells were pre-incubated with the IGF1R antibody prior to the endothelial recruitment assay. This revealed that only IGF1R antibody pre-incubation of endothelial cells inhibited miR-126 mediated endothelial recruitment as there was no effect on recruitment upon pre-incubation with the cancer cells (FIG. 5f).

Figure 15:
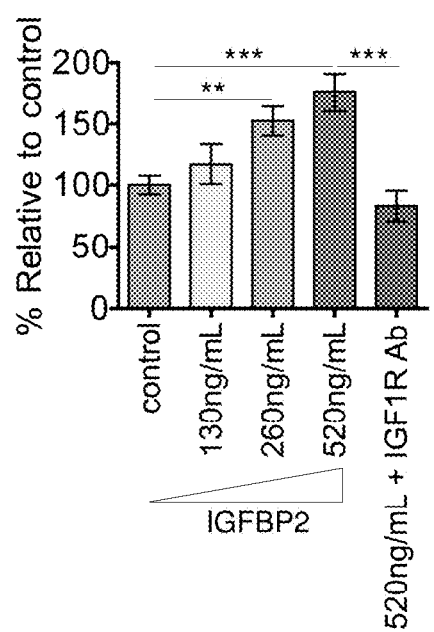
FIG. 15 is a diagram showing that IGFBP2 promoted HUVEC migration. HUVEC cells were stimulated with the given amounts of recombinant human IGFBP2 protein and anti-IGF1R Ab (10 µg/ml) for 40 min, trypsinized and $5\times10^4$ cells were seeded into a porous transwell insert. The cells were allowed to migrate for 24 hours before the number of cells that migrated across the membrane was quantified. n=6; error bars represent s.e.m.; p-values were obtained using student's t-test.

The above findings are consistent with metastatic endothelial recruitment resulting from the secretion of the miR-126 target gene IGFBP2, which binds IGF1 in the extracellular space and enhances IGF1-dependent activation of the IGF1 receptor on endothelial cells. Enhanced IGF1R activation on endothelial cells in turn stimulates endothelial migration towards metastatic breast cancer cells. Consistent with this model, recombinant IGFBP2 protein was sufficient, in a dose-dependent way, to promote endothelial chemotaxis (FIG. 5g) and migration (FIG. 15) in an IGF1R dependent manner.

EXAMPLE 8

MERTK Mediates Recruitment Through GAS6

In this example, assays were carried out to investigate the mechanisms by which the other miR-126 target genes PITPNC1 and MERTK mediate endothelial recruitment.

Figure 6A:
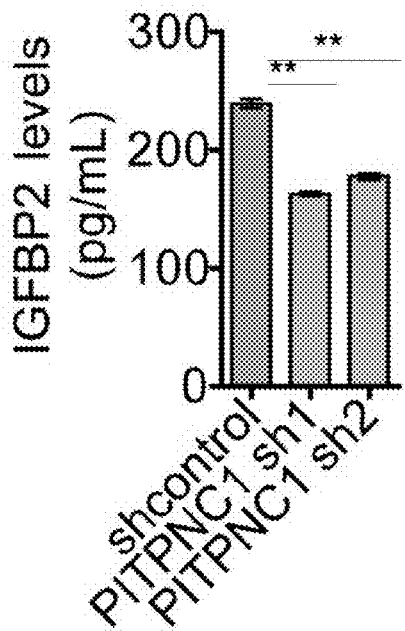
FIGS. 6a-6e are diagrams and photographs showing that MERTK mediated recruitment through GAS6.

Given the identification of IGFBP2 as a secreted miR-126-dependent factor that mediates this phenotype, the role PITPNC1 or MERTK in the regulation of the secretion of this factor from cancer cells was investigated. It was found that knockdown of PITPNC1 using independent hairpins reduced IGFBP2 secretion from breast cancer cells (FIG. 6a)—consistent with PITPNC1 regulation of endothelial recruitment being in part mediated through positive regulation of IGFBP2 secretion. Knockdown of MERTK, however, did not lead to decreased IGFBP2 secretion, suggesting an IGFBP2 independent pathway by which this miR-126 target gene mediates recruitment.

Figure 6B:
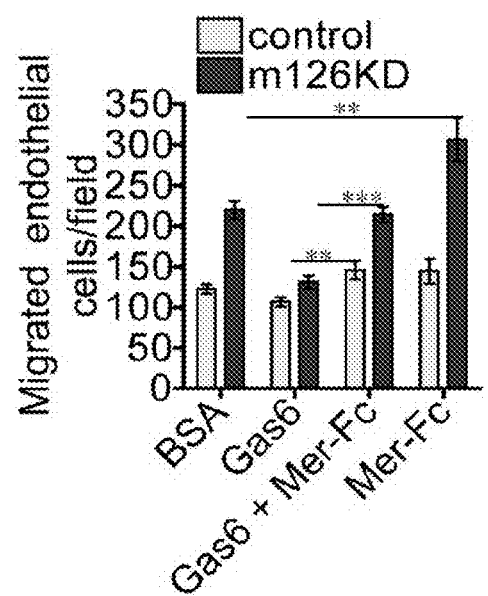
Figure 16:
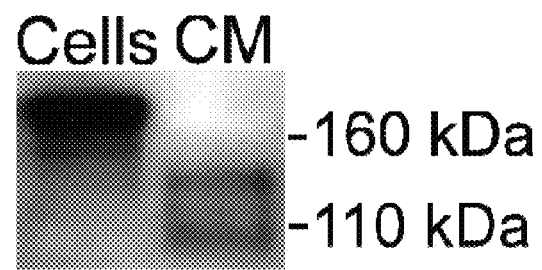
FIG. 16 is a photograph of Western blot analysis of MERTK in MDA-MB-231 cellular lysate and conditioned media, showing that ectodomain of MERTK was cleaved and secreted by MDA-MB-231 cells.

To determine the mechanism by which the MERTK receptor mediates recruitment, assays were carried out to test the impact of its soluble ligand GAS6 on cancer-mediated endothelial recruitment. Adding recombinant GAS6 to the co-culture system—at a physiological concentration found in human serum (Balogh, I. et al., *Arterioscler Thromb Vasc Biol* 25 (6), 1280 (2005)—potently reduced miR-126 dependent recruitment (FIG. 6b), suggesting that GAS6 acts as an inhibitor of endothelial recruitment. MERTK receptor exists in both membrane bound and soluble forms, where the extracellular domain has been cleaved and thus generally is believed to act as a decoy receptor to negatively regulate MERTK receptor activation on cells expressing it (Sather, S. et al., *Blood* (3), 1026 (2007). Soluble MERTK was detected in conditioned media of MDA-MB-231 cells (FIG. 16). Without being bound by theory, soluble MERTK released from cancer cells may promote endothelial recruitment through binding and inhibition of GAS6. Consistent with this, the addition of recombinant soluble form of the MERTK extracellular domain (MerFc) suppressed exogenous as well as serum GAS6-mediated inhibition of endothelial recruitment by cancer cells (FIG. 6b). Importantly, this effect was miR-126 dependent (FIG. 6b). These findings suggest that secreted MERTK from metastatic cells acts as a decoy receptor for GAS6, thereby reducing the suppressive effects of GAS6 on endothelial cell recruitment. Listed below are amino acids sequences of three GAS6 isoforms.

Isoform 1
MAPSLSPGPAALRRAPQLLLLLLAAECALAALLPAREATQFLRPRQRR

AFQVFEEAKQGHLERECVEELCSREEAREVFENDPETDYFYPRYLDCI

NKYGSPYTKNSGFATCVQNLPDQCTPNPCDRKGTQACQDLMGNFFCLC

KAGWGGRLCDKDVNECSQENGGCLQICHNKPGSFHCSCHSGFELSSDG

RTCQDIDECADSEACGEARCKNLPGSYSCLCDEGFAYSSQEKACRDVD

ECLQGRCEQVCVNSPGSYTCHCDGRGGLKLSQDMDTCEDILPCVPFSV

AKSVKSLYLGRMFSGTPVIRLRFKRLQPTRLVAEFDFRTFDPEGILLF

AGGHQDSTWIVLALRAGRLELQLRYNGVGRVTSSGPVINHGMWQTISV

EELARNLVIKVNRDAVMKIAVAGDLFQPERGLYHLNLTVGGIPFHEKD

LVQPINPRLDGCMRSWNWLNGEDTTIQETVKVNTRMQCFSVTERGSFY

PGSGFAFYSLDYMRTPLDVGTESTWEVEVVAHIRPAADTGVLFALWAP

DLRAVPLSVALVDYHSTKKLKKQLVVLAVEHTALALMEIKVCDGQEHV

VTVSLRDGEATLEVDGTRGQSEVSAAQLQERLAVLERHLRSPVLTFAG

GLPDVPVTSAPVTAFYRGCMTLEVNRRLLDLDEAAYKHSDITAHSCPP

VEPAAA

Isoform 2
MDTCEDILPCVPFSVAKSVKSLYLGRMFSGTPVIRLRFKRLQPTRLVA

EFDFRTFDPEGILLFAGGHQDSTWIVLALRAGRLELQLRYNGVGRVTS

```
-continued
SGPVINHGMWQTISVEELARNLVIKVNRDAVMKIAVAGDLFQPERGLY

HLNLTVGGIPFHEKDLVQPINPRLDGCMRSWNWLNGEDTTIQETVKVN

TRMQCFSVTERGSFYPGSGFAFYSLDYMRTPLDVGTESTWEVEVVAHI

RPAADTGVLFALWAPDLRAVPLSVALVDYHSTKKLKKQLVVLAVEHTA

LALMEIKVCDGQEHVVTVSLRDGEATLEVDGTRGQSEVSAAQLQERLA

VLERHLRSPVLTFAGGLPDVPVTSAPVTAFYRGCMTLEVNRRLLDLDE

AAYKHSDITAHSCPPVEPAAA

Isoform 3
MFSGTPVIRLRFKRLQPTRLVAEFDFRTFDPEGILLFAGGHQDSTWIV

LALRAGRLELQLRYNGVGRVTSSGPVINHGMWQTISVEELARNLVIKV

NRDAVMKIAVAGDLFQPERGLYHLNLTVGGIPFHEKDLVQPINPRLDG

CMRSWNWLNGEDTTIQETVKVNTRMQCFSVTERGSFYPGSGFAFYSLD

YMRTPLDVGTESTWEVEVVAHIRPAADTGVLFALWAPDLRAVPLSVAL

VDYHSTKKLKKQLVVLAVEHTALALMEIKVCDGQEHVVTVSLRDGEAT

LEVDGTRGQSEVSAAQLQERLAVLERHLRSPVLTFAGGLPDVPVTSAP

VTAFYRGCMTLEVNRRLLDLDEAAYKHSDITAHSCPPVEPAAA
```

Figure 6C:
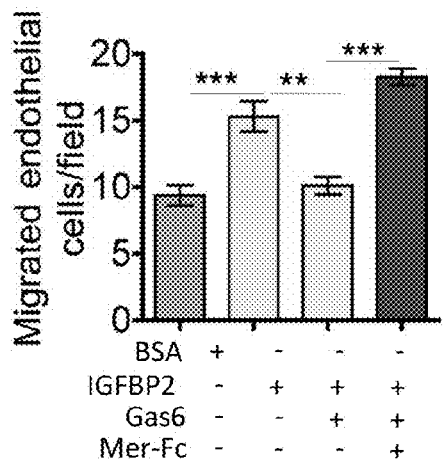

To determine whether recombinant forms of IGFBP2 and MERTK, which are expressed by metastatic cells, and GAS6, which is present in human serum, are sufficient to regulate endothelial chemotaxis, trans-well chemotactic assays were performed for quantifying the chemotactic migration of endothelial cells towards these factors. Recombinant GAS6 at low, physiological doses inhibited endothelial chemotaxis towards recombinant IGFBP2 (FIG. 6c). Importantly, recombinant soluble MERTK ectodomain abrogated the GAS6 suppressive effect on endothelial chemotaxis (FIG. 6c). Pre-incubation of endothelial cells with GAS6 did not affect endothelial migration, suggesting that GAS6 inhibits chemotactic migration. These findings reveal that IGFBP2 mediates a positive migratory and chemotactic signal to endothelial cells through the IGF type-1 receptor, while soluble MERTK receptor antagonizes an inhibitory chemotactic signal mediated by GAS6.

Figure 6D:
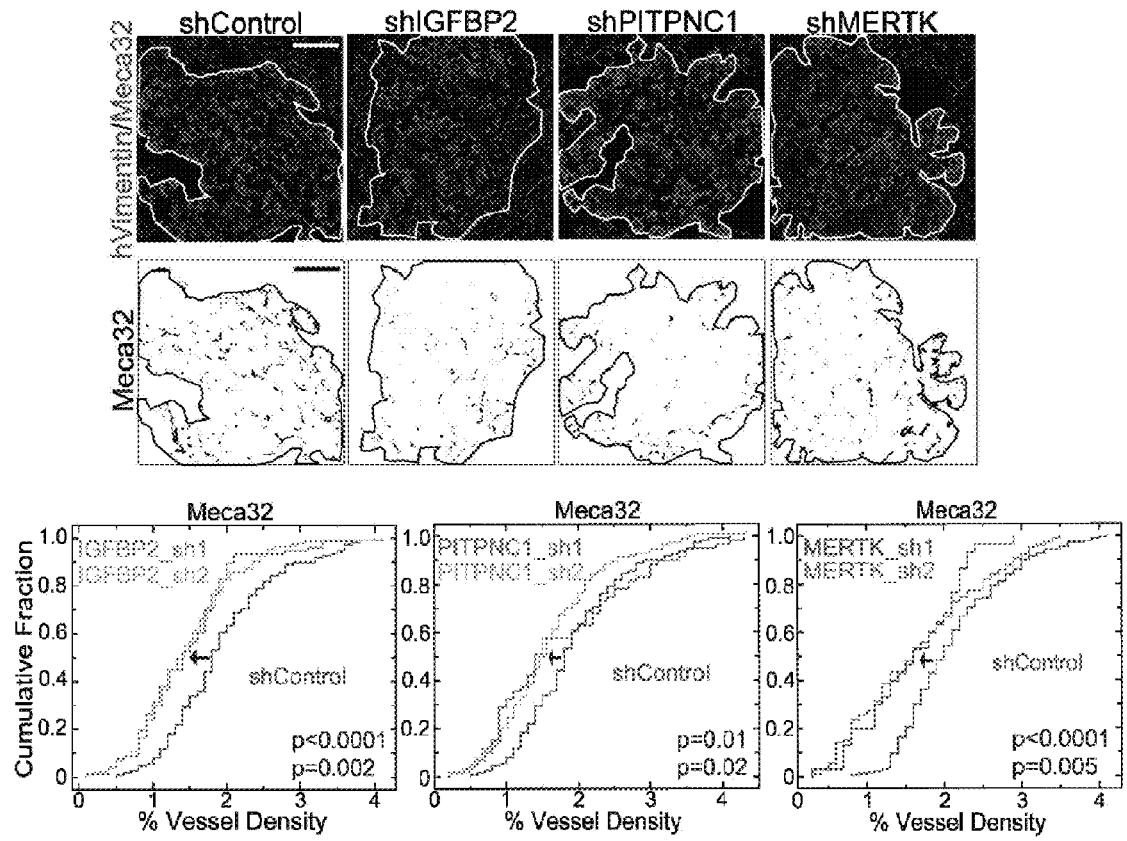
Figure 17:
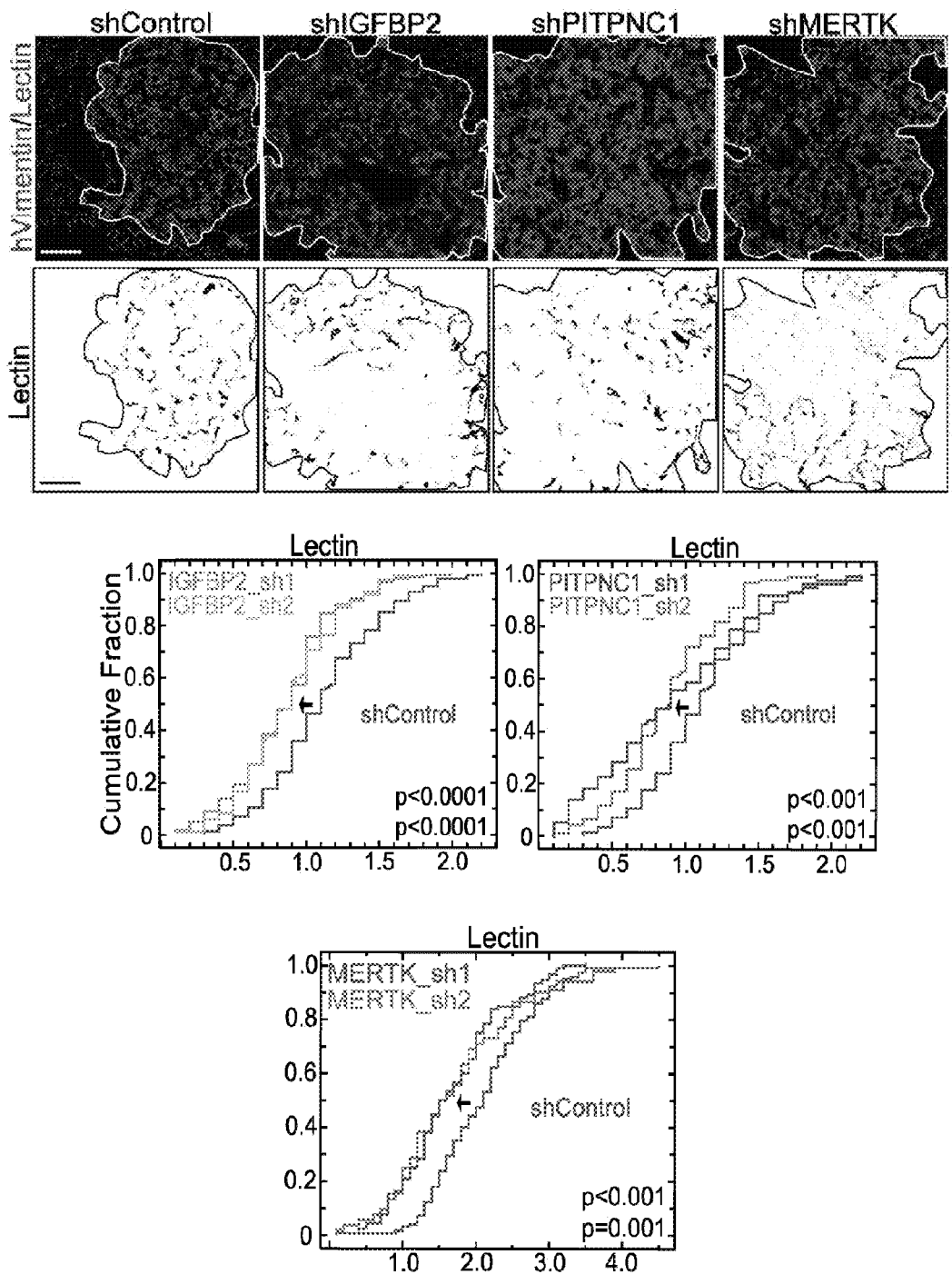
FIG. 17 is a set of photographs and diagrams showing that GFBP2, PITPNC1 and MERTK promoted metastatic angiogenesis. Lung sections were histologically double-stained for human vimentin and intravenously injected lectin. Nodule borders were demarcated based on vimentin staining and lectin staining inside metastatic nodules. ImageJ was used to determine the area positive for lectin staining within each nodule. % vessel density represents the area covered by lectin staining per area of a given nodule. The distribution of % vessel density between the injected LM2 cells expressing the control hairpin or short hairpins targeting IGFBP2, PITPNC1 or MERTK are shown in a cumulative fraction plot. n=5. P-value based on the Kolmogorov-Smirnov test.

Given the roles of IGFPB2, PITPNC1, and MERTK in endothelial recruitment in vitro and metastatic colonization in vivo, assays were carried out to examine if these genes regulate in vivo endothelial recruitment. To this end, MECA-32 staining was performed on lungs from mice injected with control and knockdown breast cancer cells to quantify endothelial recruitment in vivo as measured by metastatic vessel density. Inhibiting of IGFPB2, PITPNC1, and MERTK individually using independent short hairpins significantly reduced metastatic endothelial density (FIG. 6d; P<0.0001 and P=0.002 for shIGFBP2, P=0.01 and P=0.02 for shPITPNC1, and P<0.0001 and P=0.005 for shMERTK). Additionally, lectin perfusion and cytochemistry revealed a significant reduction in functional metastatic vessel content as well (FIG. 17). Thus, the miR-126 target genes IGFBP2, PITPNC1 and MERTK are individually required for metastatic endothelial recruitment in vivo.

Figure 6E:
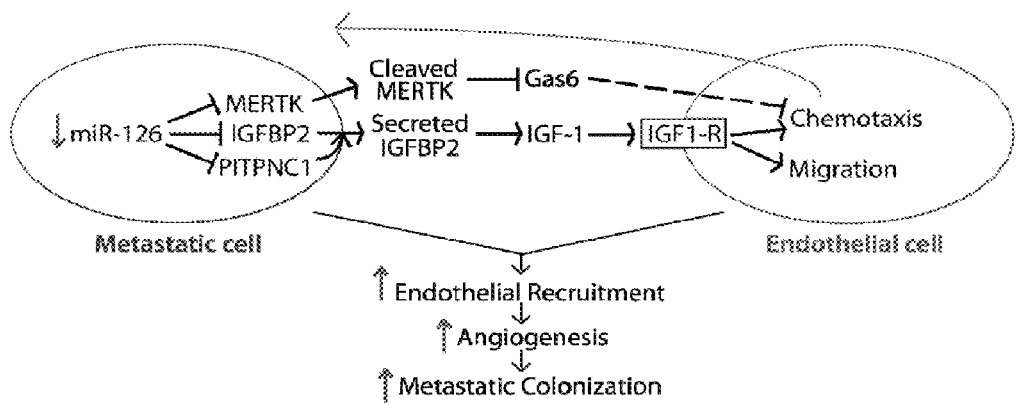

The above findings, comprising both cancer cell mediated endothelial recruitment and recombinant protein-mediated recruitment assays in vitro as well as in vivo analyses, demonstrated that cancer-expressed IGFBP2 and MERTK are necessary and sufficient for mediating endothelial recruitment and relay parallel pathways emanating from metastatic cancer cells (FIG. 6e).

EXAMPLE 9 miRNA Regulon that Mediates Metastatic Angiogenesis

The above-described findings revealed that a miRNA expressed in cancer cells can non-cell-autonomously regulate the complex process of metastatic endothelial recruitment and vascular perfusion through the coordinate regulation of IGFBP2, MERTK, and PITPNC1—a novel set of angiogenesis and metastasis genes.

It was found that the increased expression of these metastatic angiogenesis genes endows highly metastatic breast cancer cells with enhanced endothelial recruitment capacity relative to poorly metastatic cells. Metastatic cells overexpressing these genes are able to more readily establish blood vessels needed for effective colonization. Although the requirement for all of these three genes in metastatic endothelial recruitment was demonstrated, one of them, i.e., secreted IGFBP2, is a trans-cellular mediator of this phenotype.

Additionally, it was discovered the IGF1 signaling pathway—modulated by IGFBP2 secreted from cancer cells and culminating in IGF1R activation on endothelial cells—as a mediator of metastatic-cell endothelial recruitment and have identified miR-126 in cancer cells as a regulator of this pathway. Although roles of IGF1 and IGF2 in organismal and cellular growth have been reported (Laviola, L., et al. Curr Pharm Des 13 (7), 663 (2007) and Varela-Nieto, I., et al. Curr Pharm Des 13 (7), 687 (2007).), the ubiquitous expression of these growth factors and their receptors in various tissues and their requirements for normal physiology limit their therapeutic application (Varela-Nieto, I., et al. Curr Pharm Des 13 (7), 687 (2007)).

IGFBP2 is one of 16 members of the IGFBP family; see Schmid, C., Cell Biol Int 19 (5), 445 (1995); Hwa, V., et al. Endocr Rev 20 (6), 761 (1999); and Firth, S. M. et al. Endocr Rev 23 (6), 824 (2002). Identification of IGFBP2 as a promoter of metastasis, its over-expression in metastatic human breast cancer, and the robust effect of its antibody-mediated inhibition on endothelial recruitment by metastatic cells provides a specific handle for therapeutic targeting of the IGF pathway in breast cancer progression and cancer angiogenesis.

While IGFBP2 was identified as a positive regulator of endothelial recruitment through its activation of a positive regulator of this process (IGF1), MERTK was also discovered as a promoter of recruitment through its inhibition of a negative regulator of endothelial chemotaxis (GAS6). Thus a single miRNA can control a complex phenotype by modulating both positive and negative regulators of a phenomenon.

Subsequent to its identification as a metastasis suppressor miRNA, miR-126, which is developmentally expressed in endothelial cells, was genetically targeted in mice. It was found that miR-126 deletion led to partial embryonic lethality, loss of vascular integrity, and hemorrhage (Wang, S. et al., Dev Cell 15 (2), 261 (2008).). Endothelial-expressed miR-126 was thus found to be a promoter of normal developmental angiogenesis in mouse and zebrafish systems (Nicoli, S. et al., Nature 464 (7292), 1196 (2010) and Fish, J. E. et al., Dev Cell 15 (2), 272 (2008).)

Figure 18:
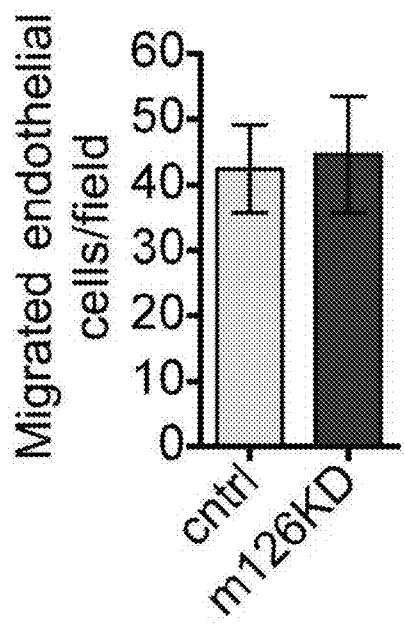
FIG. 18 is a diagram showing that endogenous miR-126 expression in HUVEC cells did not suppress recruitment of other HUVEC cells. An antagomiR targeting miR-126 or a control antagomiR were transfected into HUVEC cells before being subjected to the HUVEC recruitment assay. Images of the basal side of the inserts were obtained and cells counted using ImageJ software. n=4; error bars represent s.e.m.
Figure 19:
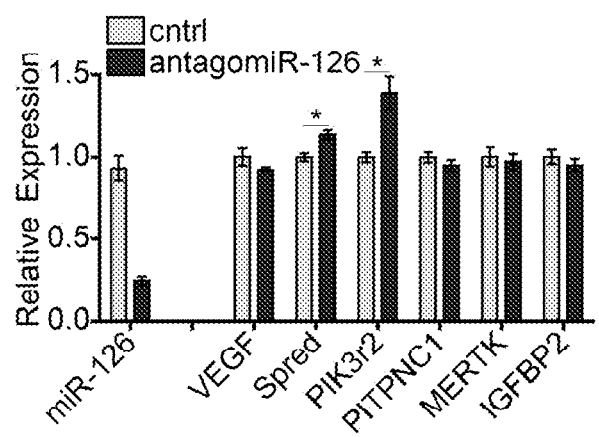
FIG. 19 is a diagram showing expression of potential miR-126 targets in HUVEC cells with suppressed miR-126 levels. An antagomiR targeting miR-126 or a control antagomiR were transfected into HUVEC cells and the relative expression of potential targets in transfected cells were quantified using qPCR. Error bars represent s.e.m., p-values obtained using student's t-test.

In view of its role as an angiogenesis promoter, it was unexpected that miR-126 also suppressed angiogenesis in, e.g., breast cancer, as disclosed herein. It was unexpected that miR-126 could act in at least two different ways. On one hand, it acts in a cell-type specific fashion to suppress pathologic angiogenesis as disclosed in this application. As disclosed in this application, miR-126 suppressed pathologic endothelial migration to metastases. On the other hand, while in development miR-126 expression maintains vessel integrity. Indeed, endothelial miR-126 was shown to regulate developmental angiogenesis through targeting of Spred-1 and PIK3R2, genes that were not significantly regulated by miR-126 in breast cancer cells (Wang, S. et al., *Dev Cell* 15 (2), 261 (2008) and Fish, J. E. et al., Dev Cell 15 (2), 272 (2008).). See Table 6. Conversely, it was found that miR-126 inhibition in endothelial cells does not enhance endothelial recruitment by endothelial cells (FIG. 18) as it does in breast cancer cells. Consistent with this, miR-126 inhibition in endothelial cells did not alter the expression of PITPNC1, MERTK, or IGFBP2, while it did increase the expression of established endothelial miR-126 targets SPRED1 and PIK3R2 (FIG. 19).

TABLE 6

| Gene Name | LM2 | LM2 miR-126 OE | Fold |
|---|---|---|---|
| SPRED1 | 979 | 851 | −1.1030 |
| PIK3R2 | 2188 | 1513 | −1.2634 |

EXAMPLE 10

Identifying Genes or Non-Coding RNAs that Regulate Metastatic Cancer Colonization of any Body Tissue This example describes two approaches for identifying a gene or a non-coding RNA that regulates metastatic cancer colonization of a body tissue
1. Lenti-miR Approach
Transduction of Lenti-miR Library into Cells and Injection into Animals
The lenti-miR library (SYSTEM BIOSCIENCES, Cat # PMIRHPLVAHT-1) was used in this approach. This library consists of a pool of lentivirus containing precursor microRNAs representative of the entire human genome. Parental populations of the SW620 and LS174T cell-lines ($2\times10^5$ cells) were transduced with the library at a multiplicity of infection (MOI) of 1 to obtain a heterogeneous pool of parental cells with individual cells over-expressing different microRNA. Each microRNA precursor was represented at approximately 50× after transduction. Four days after transduction, a half-portion of the transduced cells were set aside and genomic DNA extracted using Qiagen DNeasy kit. This was the reference pool of genomic DNA prior to the selective pressure of liver colonization. The remaining half population was injected into the livers of NOD/SCID mice. 3-5 weeks after injection, genomic DNA was extracted from the tumors that formed in the livers. Transductions and injections were performed in replicates for both cell-lines.
Identification of microRNAs Modulating Liver Colonization
Lenti-miR derived microRNA precursors were recovered from genomic DNA by PCR amplification in the linear range using library-specific, T7 promoter-containing primers (forward primer: 5'-GAAATTAATACGACTCACTATAGGGC-CTGGAGACGCCATCCAC GCTG-3'; reverse primer: 5': GATGTGCGCTCTGCCCACTGAC-3') on the reference genomic DNA and tumor genomic DNA. Four PCR reactions using 400 ng of genomic DNA as template were performed and pooled per sample to ensure adequate representation of transduced precursor microRNAs.

The resulting PCR amplicons were a composite of different precursor microRNAs with T7 promoter sequences and were used as templates for in vitro transcription to obtain a biotinylated precursor library. The biotinylated library obtained from the reference pool and tumors were labeled with Cy3 and Cy5 respectively and hybridized to a microarray designed to detect the microRNA sequences (Genosensor). A dye-swap experiment was performed to control for dye-bias.

The ratio of the abundance of each microRNA precursor between the reference pool and after selective pressure during liver colonization was calculated after normalization of microarray signal. microRNAs that became over-represented in the tumor population compared to the reference pool were considered as promoters and microRNAs that were under-represented, suppressors of liver colonization.
2. Lentiplex Approach
Transduction of Lentiplex Library into Cells and Injection into Animals
The lentiplex whole-genome shRNA library (SIGMA-ALDRICH, Cat # SHPH01) was used in this approach. This library is a pooled library of lentivirus containing approximately 150,000 shRNAs targeting the whole human genome, with each gene being targeted by 3-5 independent shRNAs.
Parental populations of the cell-lines SW620, LS174T and WiDR ($2\times10^6$ cells) were transduced with the library at a MOI of 1, resulting in a pool of heterogeneous population, with individual cells expressing a single shRNA. Each shRNA was transduced at approximately 100× representation. 48 hrs after transduction; the transduced cells were selected with puromycin for 48 hrs to remove untransduced cells. After antibiotic selection, the remaining cells were allowed to recover for a week prior to subsequent experiments. A half-portion of the selected cells were set aside and genomic DNA extracted. This was the reference pool of genomic DNA prior to the selective pressure of liver colonization. The remaining half population was injected into the livers of NOD/SCID mice. 3-5 weeks after injection, genomic DNA was extracted from the tumors that formed in the livers. Transductions and injections were performed in replicates for all three cell-lines.
Identification of Novel Genes Modulating Liver Colonization Through Whole Genome Pooled shRNA Screen
To recover a complex pool of shRNA library sequences from the genomic DNA, a PCR approach followed by Solexa deep sequencing of PCR amplicons were used. An initial PCR amplification was performed on 500 ng of genomic DNA using primers (forward primer: 5'-TGGAC-TATCATATGCTTACCGTAACT-3'; reverse primer: 5'-AAAGAGGAT CTCTGTCCCTGT-3') specific for the virus vector, followed by primers with sequences required for Solexa deep sequencing (forward primer: 5'-AATGA-TACGGCGACCACCGAG ATCTACACTCTTTCCCTA-CACGACGCTCTTCCGATCTGTATTCTTGGCTT-TATATATCT TGTGGAAAGGAC-3'; reverse primer: 5'-CAAGCAGAAGACGGCATACG AGCTCTTC-CGATCTGGATGAATACTGCCATTTGTCTCGAG-GTCGA-3') to obtain amplicons containing the shRNA sequences. Ten PCR reactions equivalent to 5 ug of genomic DNA were performed for each set of genomic DNA and the products pooled for sequencing to ensure adequate representation of shRNAs.

The pooled amplicons represent a composite of genome-wide shRNA sequences and deep sequencing was performed to determine the representation of each shRNA species in reference pool compared to the pool amplified from tumors. The count for each shRNA species was normalized against the total number of sequences obtained and their gene targets identified by matching to a database provided by Sigma. Gene targets whose shRNAs which became over-represented in the tumor pool are considered suppressors of liver colonization and vice versa. To account for non-specific effects of shRNA-silencing, only gene targets hit identified by three or more independent shRNA "hits" were considered as putative suppressors or promoters.

EXAMPLE 11

Figure 20:
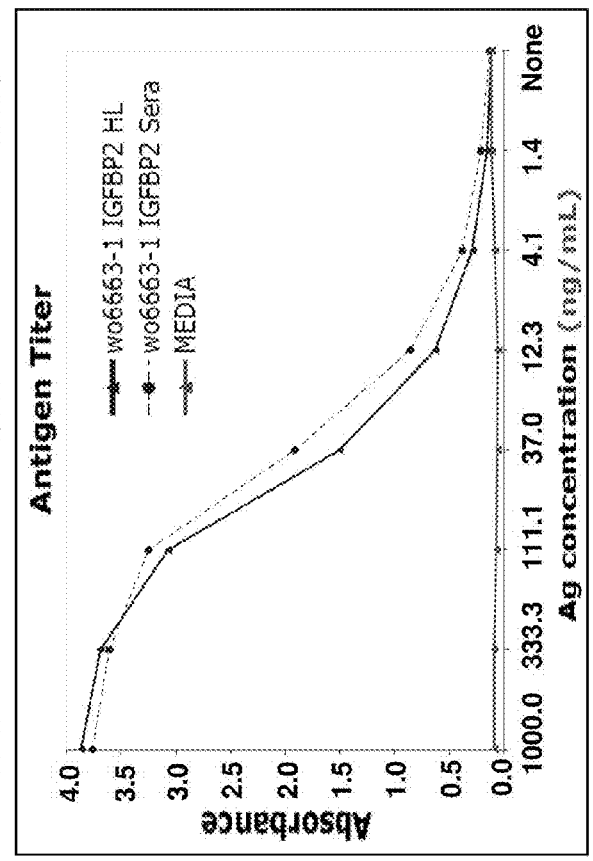
FIG. 20 is a set of diagrams showing data from antibody-capture ELISA assays used to characterize binding properties of IGFBP2 neutralizing antibodies. The figure shows that supernatant from one of the hybridoma libraries (wo6663-1) generated from animals inoculated with recombinant IGFBP2 total peptide, contains antibodies that bind to IGFBP2 with high affinity.
Figure 21:
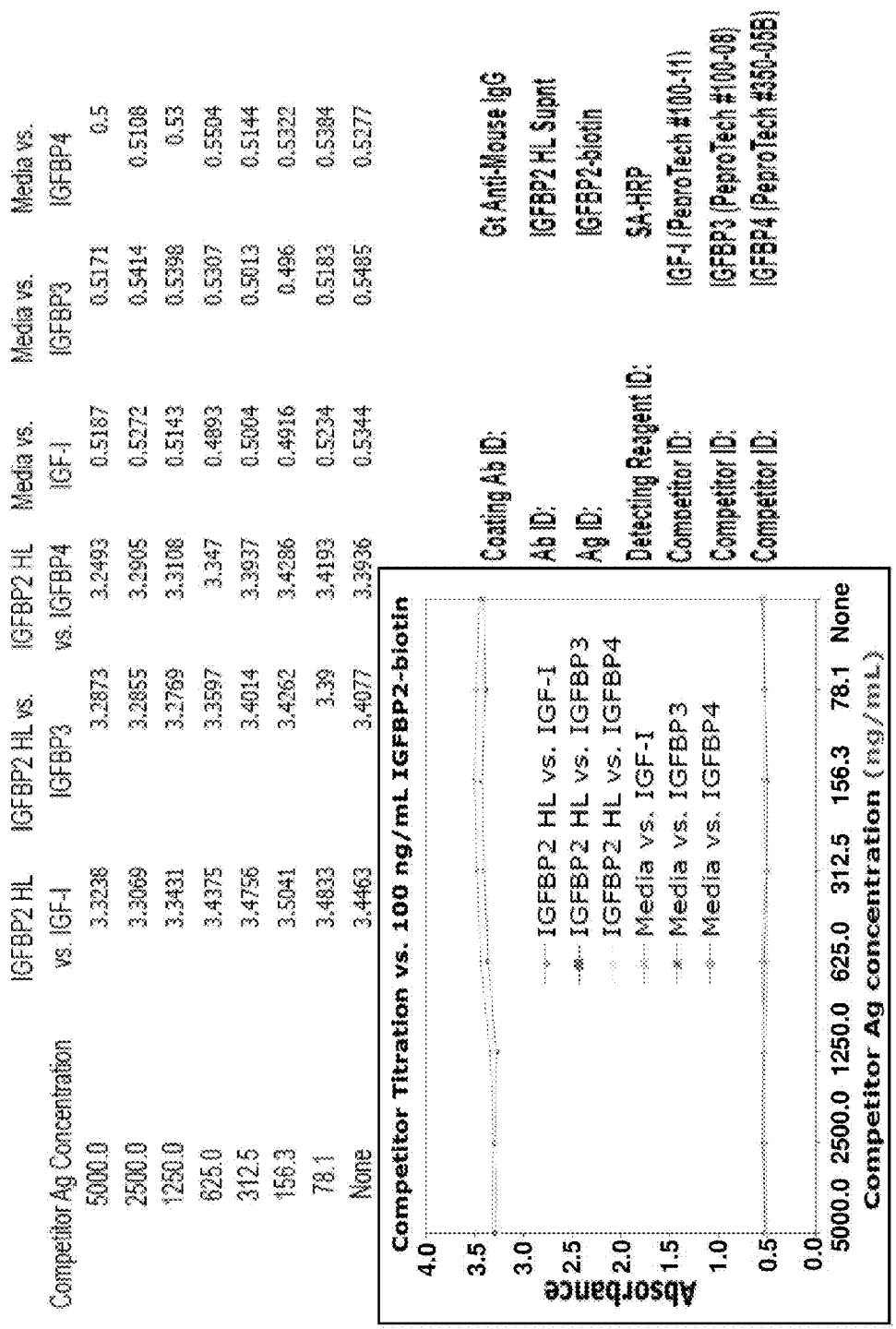
FIG. 21 is a set of diagrams showing data from antibody capture ELISA assays used to characterize binding properties of IGFBP2 neutralizing antibodies. The figure shows that supernatant from hybridoma wo6663-1 contains antibodies that bind to IGFBP2 to neutralize IGF1 binding to IGFBP2. Also note that the antibodies from the hybridoma wo6663-1 bind specifically to IGFBP2, and do not bind other IGFBP family members (IGFBP3, IGFBP4).
Figure 22:
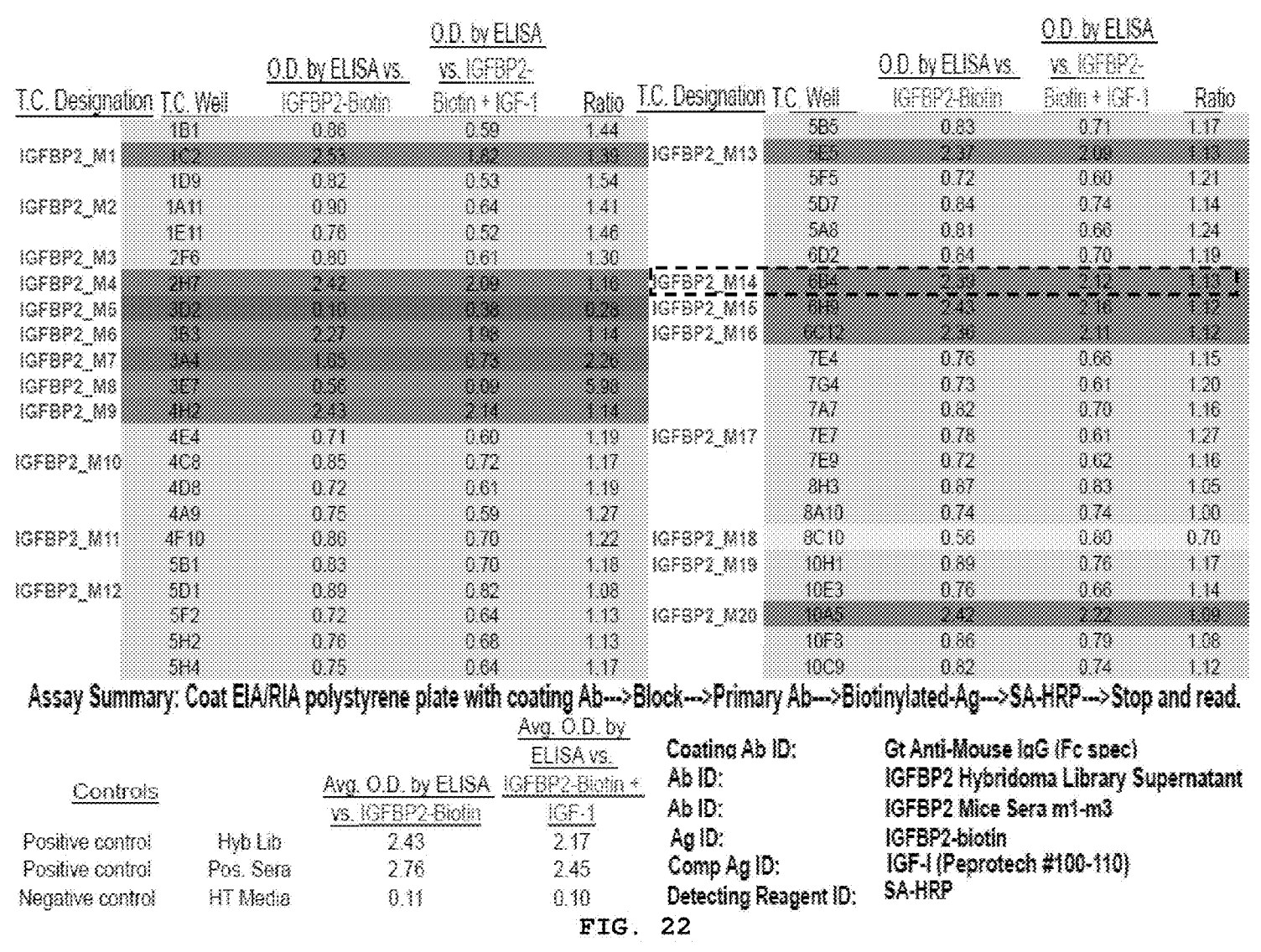
Figure 23:
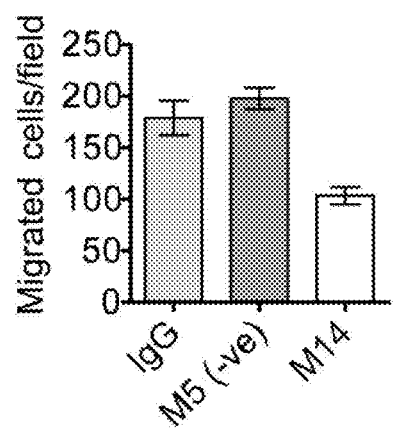
FIG. 23 is a diagram showing that a composition containing physiological concentrations of the monoclonal antibody M14 is capable of inhibiting endothelial recruitment by metastatic breast cancer cells. As in experiments described above, a trans-well migration assay was used to quantify endothelial recruitment by metastatic cells. Highly metastatic LM2 human breast cancer cells were placed in the bottom of a Boyden chamber, where their ability to recruit HUVECS through a porous trans-well insert could be assayed. The addition of a small physiologic concentration of M14 to the transwell was able to significantly inhibit the recruitment and migration (migrated cells per field) of HUVEC cells (50% reduction in migrated cells) versus the negative controls (IgG and M5 antibodies). Error bars represent s.e.m.

Monoclonal Antibody that Neutralizes IGFBP2 Function Inhibited Endothelial Recruitment by Metastatic Human Breast Cancer Cells This example demonstrates a monoclonal antibody that inhibits endothelial recruitment by metastatic breast cancer cells by binding to IGFBP2 and inhibiting the interaction (binding) of IGF1 to IGFBP2. By blocking IGF1 binding to IGFBP2, this monoclonal antibody is capable of inhibiting endothelial recruitment by metastatic human breast cancer cells. The methods used to generate neutralizing antibodies to IGFBP2 are those commonly known in the art.
In short, mice were immunized with recombinant IGFBP2 total peptide to generate a polyclonal antibody response. Next, hybridomas libraries were generated by fusion of B cells isolated from the immunimized mice to myeloma cell lines. Supernatant from these hybridomas were then isolated in order to screen and identify those hybridoma cells generating antibodies that bind IGFBP2 with high affinity, using antibody capture competitive ELISA assays (FIG. 20). Once identified, hybridomas generating antibodies with high affinity to IGFBP2 were screened in order to identify those that generate antibodies capable of inhibiting IGFBP2 from binding IGF1, using antibody capture competitive ELISA assays (FIG. 21). Hybridoma library wo6663-1 contained antibodies that bound to IGFBP2 to neutralize IGF1 binding, without binding to other IGFBP family members IGFBP3 and IGFBP4 (FIGS. 20 and 21). To isolate single clones (monoclonal) hybridoma cells, seperation and screening was performed on hybridoma library wo6663-1. 2000 single hybridoma clones (monoclonal) were screened from this library to identify those that generated monoclonal antibodies that bound to IGFBP2 with high affinity to neutralize IGF1 binding. The table in FIG. 22 lists antibody-capture ELISA competitor assay data of several monoclonal antibodies isolated from the above screen, many that had affinity to IGFBP2 and were capable of inhibiting IGF1 binding to IGFBP2 (FIG. 22), including the monoclonal antibody IGFBP2_14 (M14) (dashed box in FIG. 22). These IGFBP2 neutralizing monoclonal antibodies were then screened to identify those capable of inhibiting endothelial recruitment by metastatic cells using trans-well endothelial migration assays. The monoclonal antibody IGFBP2_M14 (M14) inhibited endothelial recruitment by human metastatic breast cancer cells:

To identify monoclonal antibodies that could inhibit endothelial recruitment, the IGFBP2 neutralizing monoclonal antibodies generated in the above screen were tested in an in vitro endothelial recruitment assay using transwells. Highly metastatic LM2 human breast cancer cells were placed in the bottom of a Boyden chamber, where their ability to recruit HUVECS through a porous trans-well insert could be assayed. Small physiologic concentration of IGFBP2 neutralizing antibodies (including M1, M4, M6, M9, M13, M14, M15, and M16 (from FIG. 22)) were added to the transwells individually in physiologic concentrations. Of all antibodies tested, M14 (dashed box in FIG. 22) was able to significantly inhibit the recruitment (migrated cells/field) of HUVEC cells (50% reduction in migrated cells) versus the negative controls antibodies IgG and M5 (FIG. 23). This demonstrates the ability of the monoclonal antibody M14 to inhibit human endothelial cell recruitment by human metastatic cancer cells (FIG. 23).

To further characterize M14, the heavy chain and light chain variable regions of the antibody were sequenced. The amino acid sequence of both the heavy chain and light chain variable regions of M14 are presented in Table 7.

TABLE 7

| | |
|---|---|
| M14 heavy chain variable region amino acid sequence | QVQLEQSGGGLVQPGGSLKLSCGASGF TFSDYYMYWIRQTPEKRLEWVAYISNG GGITYYPDTVKGRFTISRDNAKNTLYL QMSRLKSEDTAVYYCVRRSDGSWFVYW GQGTLVTVSA (SEQ ID NO: 9) |
| M14 light chain variable region amino acid sequence | DIVITQSPSSLAVSVGEKVTLSCKSSQ SLLYSSNQKNCLAWYQQKPGQSPKLLI YWASTRESGVPDRFTGSGSGTDFTLTI SSVKAEDLAVYYCQQYYSYLTFGAGTK LELKRADAAPTVS (SEQ ID NO: 10) |

EXAMPLE 12

Monoclonal Antibody M14 Inhibited Tumor Progression of Human Breast Cancer In Vivo This example demonstrates that the IGFBP2 neutralizing antibody M14 is capable of inhibiting tumor progression and tumor metastasis in vivo in a mouse model of human breast cancer.

Figure 24:
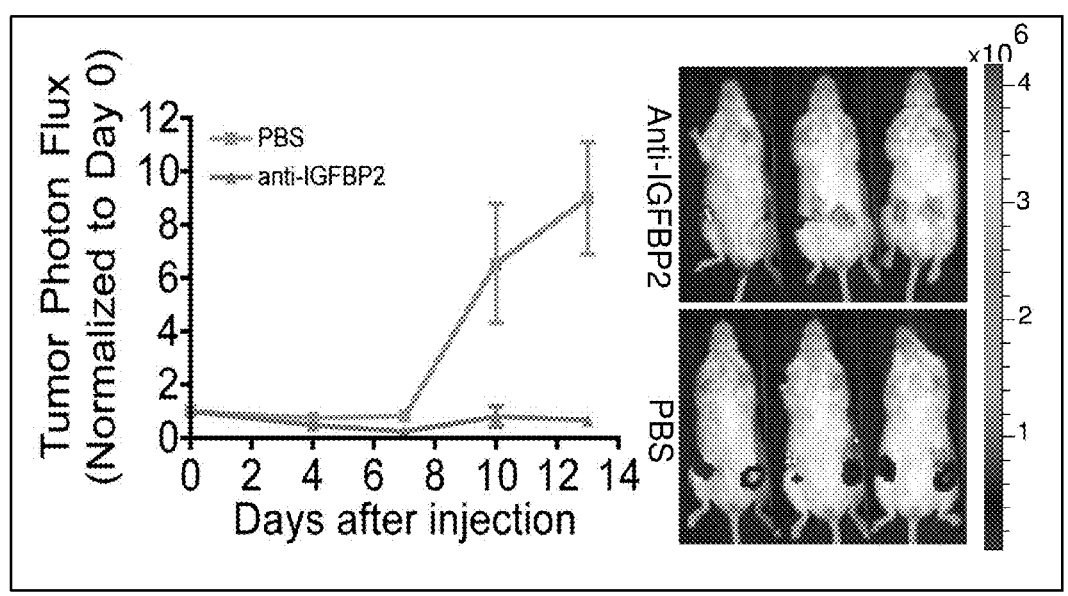
FIG. 24 is a diagram showing that a composition containing physiological concentrations of the monoclonal antibody M14 is capable of inhibiting breast cancer tumor progression in vivo in a mouse model. Bioluminescence imaging of mammary tumor growth by 2000 MDA-MB-231 human breast cancer cells in animals treated with either PBS or monoclonal antibody M14. At day 14, tumor progression was significantly inhibited by treatment with M14 (7 to 11 fold reduction in tumor progression) compared with the PBS treated mice. The signal is normalized to signal from Day 0. Significance is based on a two sided student T-test.

To test whether monoclonal antibody M14 was able to reduce tumor burden and inhibit tumor progression in vivo, 2000 luciferase expressing MDA-MB-231 human breast cancer cells were mixed in a 1:1 ratio with growth factor reduced matrigel and injected bilaterally in the mammary fat pads of NOD-SCID mice. Immediately after injection, luciferin was injected and the cancer cell bioluminescence signal was quantified to establish a Day 0 baseline signal of tumor burden. The mice were then separated randomly into two groups: a control group which were treated with PBS alone, and an M14 group treated with M14 monoclonal antibody. Intraperitoneal injections of PBS and M14 antibody (250 micrograms) were given immediately on Day 0 to mice in each group respectively, and then subsequently, injections were given biweekly. Tumor burden in both the M14 treated and PBS treated control mice were followed twice a week by bioluminensence from the luciferase reporter. At day 14, tumor progression was significantly inhibited by treatment with M14 (7 to 11 fold reduction in tumor progression) compared with the PBS treated mice (FIG. 24).

The foregoing example and description of the preferred embodiments should be taken as illustrating, rather than as limiting the present invention as defined by the claims. All publications cited herein are hereby incorporated by reference in their entirety. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

What is claimed is:

1. A method for quantifying an RNA-encoding nucleic acid in a sample, comprising,
   a) introducing a retrovirus having a polynucleotide encoding an shRNA, RNAi, microRNA, or non-coding RNA molecule into a population of starting cancer cells to generate a population of engineered cancer cells;
   b) transplanting said population of engineered cancer cells into a tissue of the body of an animal;
   c) maintaining the animal for a period of time to allow the transplanted engineered cancer cells to form a tumor;
   d) isolating from the tumor cells to obtain a population of isolated cancer cells; and
   e) assessing the quantity of a nucleic acid encoding the shRNA, RNAi, microRNA, or non-coding RNA molecule in the population of isolated cancer cells
   wherein the assessing step is performed using microarray analysis, DNA sequencing technology, deep sequencing technology, cloning analysis, PCR analysis, Southern analysis or Northern analysis.

2. The method of claim 1, wherein the population of starting cancer cells is obtained according to a method for generating a population of mammalian cancer cells with increased metastatic tissue colonization potential, comprising performing serial rounds of transplantation, isolation, and repeat transplantation of a population of labeled or unlabeled cancer cells into a living tissue.

3. The method of claim 1, wherein
   the introducing step comprises introducing to the population of starting cancer cells a second retrovirus having a second polynucleotide encoding an second shRNA, RNAi, microRNA, or non-coding RNA molecule, and
   the assessing step comprise assessing the quantity of a second nucleic acid encoding the second shRNA, RNAi, microRNA, or non-coding RNA molecule in the population of isolated cancer cells,
   wherein the assessing step is performed using microarray analysis, DNA sequencing technology, deep sequencing technology, cloning analysis, PCR analysis, Southern analysis or Northern analysis
   wherein a decrease in the quantity of said second nucleic acid in the population of isolated cells relative to its quantity prior to transplantation indicates that the target gene of said second shRNA, RNAi, microRNA, or non-coding RNA molecule represents a gene required for metastatic colonization of said tissue.

4. The method of claim 1, wherein the nucleic acid is genomic DNA.

5. The method of claim 4, wherein the genomic DNA is derived from the retrovirus.

6. The method of claim 1, wherein the starting cancer cells have increased metastatic tissue colonization potential.

7. The method of claim 6, wherein the starting cancer cells are generated by a process comprising performing serial rounds of transplantation, isolation, and repeat transplantation of a population of labeled or unlabeled cancer cells into a living tissue.

* * * * *

SEQUENCE LISTING

<160> NUMBER OF SEQ ID NOS: 140

<210> SEQ ID NO 1
<211> LENGTH: 57
<212> TYPE: DNA
<213> ORGANISM: Homo sapiens

<400> SEQUENCE: 1
ccggccagtt ctgacacacg tatttctcga gaaatacgtg tgtcagaact ggttttt      57

<210> SEQ ID NO 2
<211> LENGTH: 57
<212> TYPE: DNA
<213> ORGANISM: Homo sapiens

<400> SEQUENCE: 2
ccggcaggtt gcagacaatg gcgatctcga gatcgccatt gtctgcaacc tgttttt      57

<210> SEQ ID NO 3
<211> LENGTH: 57
<212> TYPE: DNA
<213> ORGANISM: Homo sapiens

<400> SEQUENCE: 3
ccgggcttct ggtcttgatg tatttctcga gaaatacatc aagaccagaa gctttt       57

<210> SEQ ID NO 4
<211> LENGTH: 57
<212> TYPE: DNA
<213> ORGANISM: Homo sapiens

<400> SEQUENCE: 4
ccggcctgca tacttactta ctttactcga gtaaagtaag taagtatgca ggttttt      57

<210> SEQ ID NO 5
<211> LENGTH: 58
<212> TYPE: DNA
<213> ORGANISM: Homo sapiens

<400> SEQUENCE: 5
ccggcgggtg tatctcaaca gcaaactcga gtttgctgtt gagatacacc cgtttttg     58

<210> SEQ ID NO 6
<211> LENGTH: 58
<212> TYPE: DNA
<213> ORGANISM: Homo sapiens

<400> SEQUENCE: 6
ccggcaatgg atgaagtccg agaatctcga gattctcgga cttcatccat tgtttttg     58

<210> SEQ ID NO 7
<211> LENGTH: 58
<212> TYPE: DNA
<213> ORGANISM: Homo sapiens

<400> SEQUENCE: 7
ccggccggag agttgtggac tttatctcga gataaagtcc acaactctcc ggtttttg     58

<210> SEQ ID NO 8
<211> LENGTH: 57
<212> TYPE: DNA
<213> ORGANISM: Homo sapiens

<400> SEQUENCE: 8
ccggcaacaa gatgaagagc accaactcga gttggtgctc ttcatcttgt tgttttt        57

<210> SEQ ID NO 9
<211> LENGTH: 118
<212> TYPE: PRT
<213> ORGANISM: Artificial
<220> FEATURE:
<223> OTHER INFORMATION: monoclonal antibody IGFBP2 M14 heavy chain
      variable region amino acid sequence

<400> SEQUENCE: 9

Gln Val Gln Leu Glu Gln Ser Gly Gly Gly Leu Val Gln Pro Gly Gly
1               5                   10                  15

Ser Leu Lys Leu Ser Cys Gly Ala Ser Gly Phe Thr Phe Ser Asp Tyr
            20                  25                  30

Tyr Met Tyr Trp Ile Arg Gln Thr Pro Glu Lys Arg Leu Glu Trp Val
        35                  40                  45

Ala Tyr Ile Ser Asn Gly Gly Ile Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Val Tyr Tyr Cys
                85                  90                  95

Val Arg Arg Ser Asp Gly Ser Trp Phe Val Tyr Trp Gly Gln Gly Thr
            100                 105                 110

Leu Val Thr Val Ser Ala
        115

<210> SEQ ID NO 10
<211> LENGTH: 121
<212> TYPE: PRT
<213> ORGANISM: Artificial
<220> FEATURE:
<223> OTHER INFORMATION: monoclonal antibody IGFBP2 M14 light chain
      variable region amino acid sequence

<400> SEQUENCE: 10

Asp Ile Val Ile Thr Gln Ser Pro Ser Ser Leu Ala Val Ser Val Gly
1               5                   10                  15

Glu Lys Val Thr Leu Ser Cys Lys Ser Ser Gln Ser Leu Leu Tyr Ser
            20                  25                  30

Ser Asn Gln Lys Asn Cys Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Leu Thr Phe Gly Ala Gly Thr Lys Leu Glu Leu Lys
            100                 105                 110

Arg Ala Asp Ala Ala Pro Thr Val Ser
        115                 120

<210> SEQ ID NO 11
<211> LENGTH: 328
<212> TYPE: PRT
<213> ORGANISM: Homo sapiens

<400> SEQUENCE: 11

```
Met Leu Pro Arg Val Gly Cys Pro Ala Leu Pro Leu Pro Pro Pro
1               5                   10                  15

Leu Leu Pro Leu Leu Pro Leu Leu Leu Leu Leu Gly Ala Ser Gly
                20                  25                  30

Gly Gly Gly Gly Ala Arg Ala Glu Val Leu Phe Arg Cys Pro Cys
            35                  40                  45

Thr Pro Glu Arg Leu Ala Ala Cys Gly Pro Pro Val Ala Pro Pro
        50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
                100                 105                 110

Arg Cys Tyr Pro His Pro Gly Ser Glu Leu Pro Leu Gln Ala Leu Val
            115                 120                 125

Met Gly Glu Gly Thr Cys Glu Lys Arg Arg Asp Ala Glu Tyr Gly Ala
130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
            195                 200                 205

Gly Lys His His Leu Gly Leu Glu Glu Pro Lys Lys Leu Arg Pro Pro
210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
            275                 280                 285

Val Asn Pro Asn Thr Gly Lys Leu Ile Gln Gly Ala Pro Thr Ile Arg
            290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325
```

<210> SEQ ID NO 12
<211> LENGTH: 158
<212> TYPE: PRT
<213> ORGANISM: Homo sapiens

<400> SEQUENCE: 12

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30
```

```
Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
 50                  55                  60

Val Cys Gly Asp Arg Gly Phe Tyr Phe Asn Lys Pro Thr Gly Tyr Gly
 65                  70                  75                  80

Ser Ser Ser Arg Arg Ala Pro Gln Thr Gly Ile Val Asp Glu Cys Cys
                 85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Tyr Gln Pro Pro Ser Thr Asn Lys Asn Thr
        130                 135                 140

Lys Ser Gln Arg Arg Lys Gly Ser Thr Phe Glu Glu Arg Lys
145                 150                 155
```

<210> SEQ ID NO 13
<211> LENGTH: 137
<212> TYPE: PRT
<213> ORGANISM: Homo sapiens

<400> SEQUENCE: 13

```
Met Ile Thr Pro Thr Val Lys Met His Thr Met Ser Ser Ser His Leu
  1               5                  10                  15

Phe Tyr Leu Ala Leu Cys Leu Leu Thr Phe Thr Ser Ser Ala Thr Ala
             20                  25                  30

Gly Pro Glu Thr Leu Cys Gly Ala Glu Leu Val Asp Ala Leu Gln Phe
            35                  40                  45

Val Cys Gly Asp Arg Gly Phe Tyr Phe Asn Lys Pro Thr Gly Tyr Gly
 50                  55                  60

Ser Ser Ser Arg Arg Ala Pro Gln Thr Gly Ile Val Asp Glu Cys Cys
 65                  70                  75                  80

Phe Arg Ser Cys Asp Leu Arg Arg Leu Glu Met Tyr Cys Ala Pro Leu
                 85                  90                  95

Lys Pro Ala Lys Ser Ala Arg Ser Val Arg Ala Gln Arg His Thr Asp
            100                 105                 110

Met Pro Lys Thr Gln Lys Glu Val His Leu Lys Asn Ala Ser Arg Gly
            115                 120                 125

Ser Ala Gly Asn Lys Asn Tyr Arg Met
        130                 135
```

<210> SEQ ID NO 14
<211> LENGTH: 195
<212> TYPE: PRT
<213> ORGANISM: Homo sapiens

<400> SEQUENCE: 14

```
Met Gly Lys Ile Ser Ser Leu Pro Thr Gln Leu Phe Lys Cys Cys Phe
  1               5                  10                  15

Cys Asp Phe Leu Lys Val Lys Met His Thr Met Ser Ser Ser His Leu
             20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
 50                  55                  60
```

```
Val Cys Gly Asp Arg Gly Phe Tyr Phe Asn Lys Pro Thr Gly Tyr Gly
 65                  70                  75                  80

Ser Ser Ser Arg Arg Ala Pro Gln Thr Gly Ile Val Asp Glu Cys Cys
                 85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys
                165                 170                 175

Glu Gln Arg Arg Glu Ile Gly Ser Arg Asn Ala Glu Cys Arg Gly Lys
            180                 185                 190

Lys Gly Lys
        195

<210> SEQ ID NO 15
<211> LENGTH: 153
<212> TYPE: PRT
<213> ORGANISM: Homo sapiens

<400> SEQUENCE: 15

Met Gly Lys Ile Ser Ser Leu Pro Thr Gln Leu Phe Lys Cys Cys Phe
 1               5                  10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
 65                  70                  75                  80

Ser Ser Ser Arg Arg Ala Pro Gln Thr Gly Ile Val Asp Glu Cys Cys
                 85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 16
<211> LENGTH: 1367
<212> TYPE: PRT
<213> ORGANISM: Homo sapiens

<400> SEQUENCE: 16

Met Lys Ser Gly Ser Gly Gly Gly Ser Pro Thr Ser Leu Trp Gly Leu
 1               5                  10                  15

Leu Phe Leu Ser Ala Ala Leu Ser Leu Trp Pro Thr Ser Gly Glu Ile
                20                  25                  30
```

-continued

```
Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
 50              55                      60

Ser Lys Ala Glu Asp Tyr Arg Ser Tyr Arg Phe Pro Lys Leu Thr Val
 65                  70                  75                  80

Ile Thr Glu Tyr Leu Leu Leu Phe Arg Val Ala Gly Leu Glu Ser Leu
                 85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
                115                 120                 125

Gly Leu Tyr Asn Leu Arg Asn Ile Thr Arg Gly Ala Ile Arg Ile Glu
        130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
                180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
        290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
                340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
        435                 440                 445
```

-continued

```
Ala Phe Asn Pro Lys Leu Cys Val Ser Glu Ile Tyr Arg Met Glu Glu
    450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
            500                 505                 510
Arg Pro Pro Asp Tyr Arg Asp Leu Ile Ser Phe Thr Val Tyr Tyr Lys
        515                 520                 525
Glu Ala Pro Phe Lys Asn Val Thr Glu Tyr Asp Gly Gln Asp Ala Cys
    530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
        595                 600                 605
Ser Val Pro Ser Ile Pro Leu Asp Val Leu Ser Ala Ser Asn Ser Ser
    610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Glu Val Thr Glu Asn Pro Lys
        675                 680                 685
Thr Glu Val Cys Gly Gly Glu Lys Gly Pro Cys Cys Ala Cys Pro Lys
    690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
        755                 760                 765
Glu Glu Leu Glu Thr Glu Tyr Pro Phe Phe Glu Ser Arg Val Asp Asn
    770                 775                 780
Lys Glu Arg Thr Val Ile Ser Asn Leu Arg Pro Phe Thr Leu Tyr Arg
785                 790                 795                 800
Ile Asp Ile His Ser Cys Asn His Glu Ala Glu Lys Leu Gly Cys Ser
                805                 810                 815
Ala Ser Asn Phe Val Phe Ala Arg Thr Met Pro Ala Glu Gly Ala Asp
            820                 825                 830
Asp Ile Pro Gly Pro Val Thr Trp Glu Pro Arg Pro Glu Asn Ser Ile
        835                 840                 845
Phe Leu Lys Trp Pro Glu Pro Glu Asn Pro Asn Gly Leu Ile Leu Met
    850                 855                 860
Tyr Glu Ile Lys Tyr Gly Ser Gln Val Glu Asp Gln Arg Glu Cys Val
```

```
              865                 870                 875                 880
        Ser Arg Gln Glu Tyr Arg Lys Tyr Gly Gly Ala Lys Leu Asn Arg Leu
                        885                 890                 895
        Asn Pro Gly Asn Tyr Thr Ala Arg Ile Gln Ala Thr Ser Leu Ser Gly
                        900                 905                 910
        Asn Gly Ser Trp Thr Asp Pro Val Phe Phe Tyr Val Gln Ala Lys Thr
                        915                 920                 925
        Gly Tyr Glu Asn Phe Ile His Leu Ile Ile Ala Leu Pro Val Ala Val
                        930                 935                 940
        Leu Leu Ile Val Gly Gly Leu Val Ile Met Leu Tyr Val Phe His Arg
        945                 950                 955                 960
        Lys Arg Asn Asn Ser Arg Leu Gly Asn Gly Val Leu Tyr Ala Ser Val
                        965                 970                 975
        Asn Pro Glu Tyr Phe Ser Ala Ala Asp Val Tyr Val Pro Asp Glu Trp
                        980                 985                 990
        Glu Val Ala Arg Glu Lys Ile Thr Met Ser Arg Glu Leu Gly Gln Gly
                        995                 1000                1005
        Ser Phe Gly Met Val Tyr Glu Gly Val Ala Lys Gly Val Val Lys
        1010                1015                1020
        Asp Glu Pro Glu Thr Arg Val Ala Ile Lys Thr Val Asn Glu Ala
        1025                1030                1035
        Ala Ser Met Arg Glu Arg Ile Glu Phe Leu Asn Glu Ala Ser Val
        1040                1045                1050
        Met Lys Glu Phe Asn Cys His His Val Val Arg Leu Leu Gly Val
        1055                1060                1065
        Val Ser Gln Gly Gln Pro Thr Leu Val Ile Met Glu Leu Met Thr
        1070                1075                1080
        Arg Gly Asp Leu Lys Ser Tyr Leu Arg Ser Leu Arg Pro Glu Met
        1085                1090                1095
        Glu Asn Asn Pro Val Leu Ala Pro Pro Ser Leu Ser Lys Met Ile
        1100                1105                1110
        Gln Met Ala Gly Glu Ile Ala Asp Gly Met Ala Tyr Leu Asn Ala
        1115                1120                1125
        Asn Lys Phe Val His Arg Asp Leu Ala Ala Arg Asn Cys Met Val
        1130                1135                1140
        Ala Glu Asp Phe Thr Val Lys Ile Gly Asp Phe Gly Met Thr Arg
        1145                1150                1155
        Asp Ile Tyr Glu Thr Asp Tyr Tyr Arg Lys Gly Gly Lys Gly Leu
        1160                1165                1170
        Leu Pro Val Arg Trp Met Ser Pro Glu Ser Leu Lys Asp Gly Val
        1175                1180                1185
        Phe Thr Thr Tyr Ser Asp Val Trp Ser Phe Gly Val Val Leu Trp
        1190                1195                1200
        Glu Ile Ala Thr Leu Ala Glu Gln Pro Tyr Gln Gly Leu Ser Asn
        1205                1210                1215
        Glu Gln Val Leu Arg Phe Val Met Glu Gly Gly Leu Leu Asp Lys
        1220                1225                1230
        Pro Asp Asn Cys Pro Asp Met Leu Phe Glu Leu Met Arg Met Cys
        1235                1240                1245
        Trp Gln Tyr Asn Pro Lys Met Arg Pro Ser Phe Leu Glu Ile Ile
        1250                1255                1260
        Ser Ser Ile Lys Glu Glu Met Glu Pro Gly Phe Arg Glu Val Ser
        1265                1270                1275
```

```
Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 17
<211> LENGTH: 999
<212> TYPE: PRT
<213> ORGANISM: Homo sapiens

<400> SEQUENCE: 17

Met Gly Pro Ala Pro Leu Pro Leu Leu Gly Leu Phe Leu Pro Ala
1               5                   10                  15

Leu Trp Arg Arg Ala Ile Thr Glu Ala Arg Glu Glu Ala Lys Pro Tyr
                20                  25                  30

Pro Leu Phe Pro Gly Pro Phe Pro Gly Ser Leu Gln Thr Asp His Thr
                35                  40                  45

Pro Leu Leu Ser Leu Pro His Ala Ser Gly Tyr Gln Pro Ala Leu Met
50                  55                  60

Phe Ser Pro Thr Gln Pro Gly Arg Pro His Thr Gly Asn Val Ala Ile
65                  70                  75                  80

Pro Gln Val Thr Ser Val Glu Ser Lys Pro Leu Pro Pro Leu Ala Phe
                85                  90                  95

Lys His Thr Val Gly His Ile Ile Leu Ser Glu His Lys Gly Val Lys
                100                 105                 110

Phe Asn Cys Ser Ile Ser Val Pro Asn Ile Tyr Gln Asp Thr Thr Ile
                115                 120                 125

Ser Trp Trp Lys Asp Gly Lys Glu Leu Leu Gly Ala His His Ala Ile
    130                 135                 140

Thr Gln Phe Tyr Pro Asp Asp Glu Val Thr Ala Ile Ile Ala Ser Phe
145                 150                 155                 160

Ser Ile Thr Ser Val Gln Arg Ser Asp Asn Gly Ser Tyr Ile Cys Lys
                165                 170                 175

Met Lys Ile Asn Asn Glu Glu Ile Val Ser Asp Pro Ile Tyr Ile Glu
                180                 185                 190

Val Gln Gly Leu Pro His Phe Thr Lys Gln Pro Glu Ser Met Asn Val
        195                 200                 205

Thr Arg Asn Thr Ala Phe Asn Leu Thr Cys Gln Ala Val Gly Pro Pro
    210                 215                 220

Glu Pro Val Asn Ile Phe Trp Val Gln Asn Ser Ser Arg Val Asn Glu
225                 230                 235                 240

Gln Pro Glu Lys Ser Pro Ser Val Leu Thr Val Pro Gly Leu Thr Glu
                245                 250                 255

Met Ala Val Phe Ser Cys Glu Ala His Asn Asp Lys Gly Leu Thr Val
                260                 265                 270

Ser Lys Gly Val Gln Ile Asn Ile Lys Ala Ile Pro Ser Pro Pro Thr
```

```
            275                 280                 285
Glu Val Ser Ile Arg Asn Ser Thr Ala His Ser Ile Leu Ile Ser Trp
290                 295                 300

Val Pro Gly Phe Asp Gly Tyr Ser Pro Phe Arg Asn Cys Ser Ile Gln
305                 310                 315                 320

Val Lys Glu Ala Asp Pro Leu Ser Asn Gly Ser Val Met Ile Phe Asn
                325                 330                 335

Thr Ser Ala Leu Pro His Leu Tyr Gln Ile Lys Gln Leu Gln Ala Leu
                340                 345                 350

Ala Asn Tyr Ser Ile Gly Val Ser Cys Met Asn Glu Ile Gly Trp Ser
                355                 360                 365

Ala Val Ser Pro Trp Ile Leu Ala Ser Thr Thr Glu Gly Ala Pro Ser
                370                 375                 380

Val Ala Pro Leu Asn Val Thr Val Phe Leu Asn Glu Ser Ser Asp Asn
385                 390                 395                 400

Val Asp Ile Arg Trp Met Lys Pro Pro Thr Lys Gln Gln Asp Gly Glu
                405                 410                 415

Leu Val Gly Tyr Arg Ile Ser His Val Trp Gln Ser Ala Gly Ile Ser
                420                 425                 430

Lys Glu Leu Leu Glu Glu Val Gly Gln Asn Gly Ser Arg Ala Arg Ile
                435                 440                 445

Ser Val Gln Val His Asn Ala Thr Cys Thr Val Arg Ile Ala Ala Val
450                 455                 460

Thr Arg Gly Gly Val Gly Pro Phe Ser Asp Pro Val Lys Ile Phe Ile
465                 470                 475                 480

Pro Ala His Gly Trp Val Asp Tyr Ala Pro Ser Ser Thr Pro Ala Pro
                485                 490                 495

Gly Asn Ala Asp Pro Val Leu Ile Ile Phe Gly Cys Phe Cys Gly Phe
                500                 505                 510

Ile Leu Ile Gly Leu Ile Leu Tyr Ile Ser Leu Ala Ile Arg Lys Arg
                515                 520                 525

Val Gln Glu Thr Lys Phe Gly Asn Ala Phe Thr Glu Glu Asp Ser Glu
530                 535                 540

Leu Val Val Asn Tyr Ile Ala Lys Lys Ser Phe Cys Arg Arg Ala Ile
545                 550                 555                 560

Glu Leu Thr Leu His Ser Leu Gly Val Ser Glu Glu Leu Gln Asn Lys
                565                 570                 575

Leu Glu Asp Val Val Ile Asp Arg Asn Leu Leu Ile Leu Gly Lys Ile
                580                 585                 590

Leu Gly Glu Gly Glu Phe Gly Ser Val Met Glu Gly Asn Leu Lys Gln
                595                 600                 605

Glu Asp Gly Thr Ser Leu Lys Val Ala Val Lys Thr Met Lys Leu Asp
                610                 615                 620

Asn Ser Ser Gln Arg Glu Ile Glu Glu Phe Leu Ser Glu Ala Ala Cys
625                 630                 635                 640

Met Lys Asp Phe Ser His Pro Asn Val Ile Arg Leu Leu Gly Val Cys
                645                 650                 655

Ile Glu Met Ser Ser Gln Gly Ile Pro Lys Pro Met Val Ile Leu Pro
                660                 665                 670

Phe Met Lys Tyr Gly Asp Leu His Thr Tyr Leu Leu Tyr Ser Arg Leu
                675                 680                 685

Glu Thr Gly Pro Lys His Ile Pro Leu Gln Thr Leu Leu Lys Phe Met
                690                 695                 700
```

```
Val Asp Ile Ala Leu Gly Met Glu Tyr Leu Ser Asn Arg Asn Phe Leu
705                 710                 715                 720

His Arg Asp Leu Ala Ala Arg Asn Cys Met Leu Arg Asp Met Thr
            725                 730                 735

Val Cys Val Ala Asp Phe Gly Leu Ser Lys Lys Ile Tyr Ser Gly Asp
        740                 745                 750

Tyr Tyr Arg Gln Gly Arg Ile Ala Lys Met Pro Val Lys Trp Ile Ala
            755                 760                 765

Ile Glu Ser Leu Ala Asp Arg Val Tyr Thr Ser Lys Ser Asp Val Trp
770                 775                 780

Ala Phe Gly Val Thr Met Trp Glu Ile Ala Thr Arg Gly Met Thr Pro
785                 790                 795                 800

Tyr Pro Gly Val Gln Asn His Glu Met Tyr Asp Tyr Leu Leu His Gly
                805                 810                 815

His Arg Leu Lys Gln Pro Glu Asp Cys Leu Asp Glu Leu Tyr Glu Ile
            820                 825                 830

Met Tyr Ser Cys Trp Arg Thr Asp Pro Leu Asp Arg Pro Thr Phe Ser
        835                 840                 845

Val Leu Arg Leu Gln Leu Glu Lys Leu Leu Glu Ser Leu Pro Asp Val
    850                 855                 860

Arg Asn Gln Ala Asp Val Ile Tyr Val Asn Thr Gln Leu Leu Glu Ser
865                 870                 875                 880

Ser Glu Gly Leu Ala Gln Gly Ser Thr Leu Ala Pro Leu Asp Leu Asn
                885                 890                 895

Ile Asp Pro Asp Ser Ile Ile Ala Ser Cys Thr Pro Arg Ala Ala Ile
            900                 905                 910

Ser Val Val Thr Ala Glu Val His Asp Ser Lys Pro His Glu Gly Arg
        915                 920                 925

Tyr Ile Leu Asn Gly Gly Ser Glu Glu Trp Glu Asp Leu Thr Ser Ala
    930                 935                 940

Pro Ser Ala Ala Val Thr Ala Glu Lys Asn Ser Val Leu Pro Gly Glu
945                 950                 955                 960

Arg Leu Val Arg Asn Gly Val Ser Trp Ser His Ser Ser Met Leu Pro
                965                 970                 975

Leu Gly Ser Ser Leu Pro Asp Glu Leu Leu Phe Ala Asp Asp Ser Ser
            980                 985                 990

Glu Gly Ser Glu Val Leu Met
        995

<210> SEQ ID NO 18
<211> LENGTH: 332
<212> TYPE: PRT
<213> ORGANISM: Homo sapiens

<400> SEQUENCE: 18

Met Leu Leu Lys Glu Tyr Arg Ile Cys Met Pro Leu Thr Val Asp Glu
1               5                   10                  15

Tyr Lys Ile Gly Gln Leu Tyr Met Ile Ser Lys His Ser His Glu Gln
            20                  25                  30

Ser Asp Arg Gly Glu Gly Val Glu Val Gln Asn Glu Pro Phe Glu
        35                  40                  45

Asp Pro His His Gly Asn Gly Gln Phe Thr Glu Lys Arg Val Tyr Leu
    50                  55                  60

Asn Ser Lys Leu Pro Ser Trp Ala Arg Ala Val Val Pro Lys Ile Phe
```

```
              65                  70                  75                  80
Tyr Val Thr Glu Lys Ala Trp Asn Tyr Tyr Pro Tyr Thr Ile Thr Glu
                        85                  90                  95

Tyr Thr Cys Ser Phe Leu Pro Lys Phe Ser Ile His Ile Glu Thr Lys
                100                 105                 110

Tyr Glu Asp Asn Lys Gly Ser Asn Asp Thr Ile Phe Asp Asn Glu Ala
                115                 120                 125

Lys Asp Val Glu Arg Val Cys Phe Ile Asp Ile Ala Cys Asp Glu
            130                 135                 140

Ile Pro Glu Arg Tyr Tyr Lys Glu Ser Glu Asp Pro Lys His Phe Lys
145                 150                 155                 160

Ser Glu Lys Thr Gly Arg Gly Gln Leu Arg Glu Gly Trp Arg Asp Ser
                165                 170                 175

His Gln Pro Ile Met Cys Ser Tyr Lys Leu Val Thr Val Lys Phe Glu
                180                 185                 190

Val Trp Gly Leu Gln Thr Arg Val Glu Gln Phe Val His Lys Val Val
                195                 200                 205

Arg Asp Ile Leu Leu Ile Gly His Arg Gln Ala Phe Ala Trp Val Asp
            210                 215                 220

Glu Trp Tyr Asp Met Thr Met Asp Glu Val Arg Glu Phe Glu Arg Ala
225                 230                 235                 240

Thr Gln Glu Ala Thr Asn Lys Lys Ile Gly Ile Phe Pro Pro Ala Ile
                245                 250                 255

Ser Ile Ser Ser Ile Pro Leu Leu Pro Ser Ser Val Arg Ser Ala Pro
                260                 265                 270

Ser Ser Ala Pro Ser Thr Pro Leu Ser Thr Asp Ala Pro Glu Phe Leu
            275                 280                 285

Ser Val Pro Lys Asp Arg Pro Arg Lys Lys Ser Ala Pro Glu Thr Leu
                290                 295                 300

Thr Leu Pro Asp Pro Glu Lys Lys Ala Thr Leu Asn Leu Pro Gly Met
305                 310                 315                 320

His Ser Ser Asp Lys Pro Cys Arg Pro Lys Ser Glu
                325                 330

<210> SEQ ID NO 19
<211> LENGTH: 268
<212> TYPE: PRT
<213> ORGANISM: Homo sapiens

<400> SEQUENCE: 19

Met Leu Leu Lys Glu Tyr Arg Ile Cys Met Pro Leu Thr Val Asp Glu
1               5                   10                  15

Tyr Lys Ile Gly Gln Leu Tyr Met Ile Ser Lys His Ser His Glu Gln
            20                  25                  30

Ser Asp Arg Gly Glu Gly Val Glu Val Val Gln Asn Glu Pro Phe Glu
        35                  40                  45

Asp Pro His His Gly Asn Gly Gln Phe Thr Glu Lys Arg Val Tyr Leu
    50                  55                  60

Asn Ser Lys Leu Pro Ser Trp Ala Arg Ala Val Val Pro Lys Ile Phe
65                  70                  75                  80

Tyr Val Thr Glu Lys Ala Trp Asn Tyr Tyr Pro Tyr Thr Ile Thr Glu
                85                  90                  95

Tyr Thr Cys Ser Phe Leu Pro Lys Phe Ser Ile His Ile Glu Thr Lys
                100                 105                 110
```

```
Tyr Glu Asp Asn Lys Gly Ser Asn Asp Thr Ile Phe Asp Asn Glu Ala
            115                 120                 125

Lys Asp Val Glu Arg Glu Val Cys Phe Ile Asp Ile Ala Cys Asp Glu
130                 135                 140

Ile Pro Glu Arg Tyr Tyr Lys Glu Ser Glu Asp Pro Lys His Phe Lys
145                 150                 155                 160

Ser Glu Lys Thr Gly Arg Gly Gln Leu Arg Glu Gly Trp Arg Asp Ser
                165                 170                 175

His Gln Pro Ile Met Cys Ser Tyr Lys Leu Val Thr Val Lys Phe Glu
            180                 185                 190

Val Trp Gly Leu Gln Thr Arg Val Glu Gln Phe Val His Lys Val Val
        195                 200                 205

Arg Asp Ile Leu Leu Ile Gly His Arg Gln Ala Phe Ala Trp Val Asp
    210                 215                 220

Glu Trp Tyr Asp Met Thr Met Asp Asp Val Arg Glu Tyr Glu Lys Asn
225                 230                 235                 240

Met His Glu Gln Thr Asn Ile Lys Val Cys Asn Gln His Ser Ser Pro
                245                 250                 255

Val Asp Asp Ile Glu Ser His Ala Gln Thr Ser Thr
            260                 265

<210> SEQ ID NO 20
<211> LENGTH: 766
<212> TYPE: PRT
<213> ORGANISM: Homo sapiens

<400> SEQUENCE: 20

Met Arg Leu Trp Lys Ala Val Val Thr Leu Ala Phe Met Ser Val
1               5                   10                  15

Asp Ile Cys Val Thr Thr Ala Ile Tyr Val Phe Ser His Leu Asp Arg
                20                  25                  30

Ser Leu Leu Glu Asp Ile Arg His Phe Asn Ile Phe Asp Ser Val Leu
            35                  40                  45

Asp Leu Trp Ala Ala Cys Leu Tyr Arg Ser Cys Leu Leu Leu Gly Ala
        50                  55                  60

Thr Ile Gly Val Ala Lys Asn Ser Ala Leu Gly Pro Arg Arg Leu Arg
65                  70                  75                  80

Ala Ser Trp Leu Val Ile Thr Leu Val Cys Leu Phe Val Gly Ile Tyr
                85                  90                  95

Ala Met Val Lys Leu Leu Leu Phe Ser Glu Val Arg Arg Pro Ile Arg
            100                 105                 110

Asp Pro Trp Phe Trp Ala Leu Phe Val Trp Thr Tyr Ile Ser Leu Gly
        115                 120                 125

Ala Ser Phe Leu Leu Trp Trp Leu Leu Ser Thr Val Arg Pro Gly Thr
    130                 135                 140

Gln Ala Leu Glu Pro Gly Ala Ala Thr Glu Ala Glu Gly Phe Pro Gly
145                 150                 155                 160

Ser Gly Arg Pro Pro Pro Glu Gln Ala Ser Gly Ala Thr Leu Gln Lys
                165                 170                 175

Leu Leu Ser Tyr Thr Lys Pro Asp Val Ala Phe Leu Val Ala Ala Ser
            180                 185                 190

Phe Phe Leu Ile Val Ala Ala Leu Gly Glu Thr Phe Leu Pro Tyr Tyr
        195                 200                 205

Thr Gly Arg Ala Ile Asp Gly Ile Val Ile Gln Lys Ser Met Asp Gln
    210                 215                 220
```

-continued

```
Phe Ser Thr Ala Val Val Ile Val Cys Leu Leu Ala Ile Gly Ser Ser
225                 230                 235                 240

Phe Ala Ala Gly Ile Arg Gly Gly Ile Phe Thr Leu Ile Phe Ala Arg
            245                 250                 255

Leu Asn Ile Arg Leu Arg Asn Cys Leu Phe Arg Ser Leu Val Ser Gln
            260                 265                 270

Glu Thr Ser Phe Phe Asp Glu Asn Arg Thr Gly Asp Leu Ile Ser Arg
            275                 280                 285

Leu Thr Ser Asp Thr Thr Met Val Ser Asp Leu Val Ser Gln Asn Ile
290                 295                 300

Asn Val Phe Leu Arg Asn Thr Val Lys Val Thr Gly Val Val Val Phe
305                 310                 315                 320

Met Phe Ser Leu Ser Trp Gln Leu Ser Leu Val Thr Phe Met Gly Phe
            325                 330                 335

Pro Ile Ile Met Met Val Ser Asn Ile Tyr Gly Lys Tyr Tyr Lys Arg
            340                 345                 350

Leu Ser Lys Glu Val Gln Asn Ala Leu Ala Arg Ala Ser Asn Thr Ala
            355                 360                 365

Glu Glu Thr Ile Ser Ala Met Lys Thr Val Arg Ser Phe Ala Asn Glu
370                 375                 380

Glu Glu Glu Ala Glu Val Tyr Leu Arg Lys Leu Gln Gln Val Tyr Lys
385                 390                 395                 400

Leu Asn Arg Lys Glu Ala Ala Tyr Met Tyr Tyr Val Trp Gly Ser
            405                 410                 415

Gly Leu Thr Leu Leu Val Val Gln Val Ser Ile Leu Tyr Gly Gly
            420                 425                 430

His Leu Val Ile Ser Gly Gln Met Thr Ser Gly Asn Leu Ile Ala Phe
            435                 440                 445

Ile Ile Tyr Glu Phe Val Leu Gly Asp Cys Met Glu Ser Val Gly Ser
            450                 455                 460

Val Tyr Ser Gly Leu Met Gln Gly Val Gly Ala Ala Glu Lys Val Phe
465                 470                 475                 480

Glu Phe Ile Asp Arg Gln Pro Thr Met Val His Asp Gly Ser Leu Ala
            485                 490                 495

Pro Asp His Leu Glu Gly Arg Val Asp Phe Glu Asn Val Thr Phe Thr
            500                 505                 510

Tyr Arg Thr Arg Pro His Thr Gln Val Leu Gln Asn Val Ser Phe Ser
            515                 520                 525

Leu Ser Pro Gly Lys Val Thr Ala Leu Val Gly Pro Ser Gly Ser Gly
530                 535                 540

Lys Ser Ser Cys Val Asn Ile Leu Glu Asn Phe Tyr Pro Leu Glu Gly
545                 550                 555                 560

Gly Arg Val Leu Leu Asp Gly Lys Pro Ile Ser Ala Tyr Asp His Lys
            565                 570                 575

Tyr Leu His Arg Val Ile Ser Leu Val Ser Gln Glu Pro Val Leu Phe
            580                 585                 590

Ala Arg Ser Ile Thr Asp Asn Ile Ser Tyr Gly Leu Pro Thr Val Pro
            595                 600                 605

Phe Glu Met Val Val Glu Ala Ala Gln Lys Ala Asn Ala His Gly Phe
610                 615                 620

Ile Met Glu Leu Gln Asp Gly Tyr Ser Thr Glu Thr Gly Glu Lys Gly
625                 630                 635                 640
```

```
Ala Gln Leu Ser Gly Gly Gln Lys Gln Arg Val Ala Met Ala Arg Ala
                645                 650                 655

Leu Val Arg Asn Pro Pro Val Leu Ile Leu Asp Glu Ala Thr Ser Ala
            660                 665                 670

Leu Asp Ala Glu Ser Glu Tyr Leu Ile Gln Gln Ala Ile His Gly Asn
        675                 680                 685

Leu Gln Lys His Thr Val Leu Ile Ile Ala His Arg Leu Ser Thr Val
    690                 695                 700

Glu His Ala His Leu Ile Val Val Leu Asp Lys Gly Arg Val Val Gln
705                 710                 715                 720

Gln Gly Thr His Gln Gln Leu Leu Ala Gln Gly Gly Leu Tyr Ala Lys
                725                 730                 735

Leu Val Gln Arg Gln Met Leu Gly Leu Gln Pro Ala Ala Asp Phe Thr
            740                 745                 750

Ala Gly His Asn Glu Pro Val Ala Asn Gly Ser His Lys Ala
        755                 760                 765

<210> SEQ ID NO 21
<211> LENGTH: 370
<212> TYPE: PRT
<213> ORGANISM: Homo sapiens

<400> SEQUENCE: 21

Met Asp Ala Pro Arg Gln Val Val Asn Phe Gly Pro Gly Pro Ala Lys
1               5                   10                  15

Leu Pro His Ser Val Leu Leu Glu Ile Gln Lys Glu Leu Leu Asp Tyr
            20                  25                  30

Lys Gly Val Gly Ile Ser Val Leu Glu Met Ser His Arg Ser Ser Asp
        35                  40                  45

Phe Ala Lys Ile Ile Asn Asn Thr Glu Asn Leu Val Arg Glu Leu Leu
    50                  55                  60

Ala Val Pro Asp Asn Tyr Lys Val Ile Phe Leu Gln Gly Gly Gly Cys
65                  70                  75                  80

Gly Gln Phe Ser Ala Val Pro Leu Asn Leu Ile Gly Leu Lys Ala Gly
                85                  90                  95

Arg Cys Ala Asp Tyr Val Val Thr Gly Ala Trp Ser Ala Lys Ala Ala
            100                 105                 110

Glu Glu Ala Lys Lys Phe Gly Thr Ile Asn Ile Val His Pro Lys Leu
        115                 120                 125

Gly Ser Tyr Thr Lys Ile Pro Asp Pro Ser Thr Trp Asn Leu Asn Pro
    130                 135                 140

Asp Ala Ser Tyr Val Tyr Tyr Cys Ala Asn Glu Thr Val His Gly Val
145                 150                 155                 160

Glu Phe Asp Phe Ile Pro Asp Val Lys Gly Ala Val Leu Val Cys Asp
                165                 170                 175

Met Ser Ser Asn Phe Leu Ser Lys Pro Val Asp Val Ser Lys Phe Gly
            180                 185                 190

Val Ile Phe Ala Gly Ala Gln Lys Asn Val Gly Ser Ala Gly Val Thr
        195                 200                 205

Val Val Ile Val Arg Asp Asp Leu Leu Gly Phe Ala Leu Arg Glu Cys
    210                 215                 220

Pro Ser Val Leu Glu Tyr Lys Val Gln Ala Gly Asn Ser Ser Leu Tyr
225                 230                 235                 240

Asn Thr Pro Pro Cys Phe Ser Ile Tyr Val Met Gly Leu Val Leu Glu
                245                 250                 255
```

Trp Ile Lys Asn Asn Gly Gly Ala Ala Ala Met Glu Lys Leu Ser Ser
            260                 265                 270

Ile Lys Ser Gln Thr Ile Tyr Glu Ile Ile Asp Asn Ser Gln Gly Phe
            275                 280                 285

Tyr Val Cys Pro Val Glu Pro Gln Asn Arg Ser Lys Met Asn Ile Pro
            290                 295                 300

Phe Arg Ile Gly Asn Ala Lys Gly Asp Asp Ala Leu Glu Lys Arg Phe
305                 310                 315                 320

Leu Asp Lys Ala Leu Glu Leu Asn Met Leu Ser Leu Lys Gly His Arg
                325                 330                 335

Ser Val Gly Gly Ile Arg Ala Ser Leu Tyr Asn Ala Val Thr Ile Glu
                340                 345                 350

Asp Val Gln Lys Leu Ala Ala Phe Met Lys Lys Phe Leu Glu Met His
                355                 360                 365

Gln Leu
    370

<210> SEQ ID NO 22
<211> LENGTH: 324
<212> TYPE: PRT
<213> ORGANISM: Homo sapiens

<400> SEQUENCE: 22

Met Asp Ala Pro Arg Gln Val Val Asn Phe Gly Pro Gly Pro Ala Lys
1               5                   10                  15

Leu Pro His Ser Val Leu Leu Glu Ile Gln Lys Glu Leu Leu Asp Tyr
            20                  25                  30

Lys Gly Val Gly Ile Ser Val Leu Glu Met Ser His Arg Ser Ser Asp
            35                  40                  45

Phe Ala Lys Ile Ile Asn Asn Thr Glu Asn Leu Val Arg Glu Leu Leu
    50                  55                  60

Ala Val Pro Asp Asn Tyr Lys Val Ile Phe Leu Gln Gly Gly Gly Cys
65                  70                  75                  80

Gly Gln Phe Ser Ala Val Pro Leu Asn Leu Ile Gly Leu Lys Ala Gly
                85                  90                  95

Arg Cys Ala Asp Tyr Val Val Thr Gly Ala Trp Ser Ala Lys Ala Ala
                100                 105                 110

Glu Glu Ala Lys Lys Phe Gly Thr Ile Asn Ile Val His Pro Lys Leu
            115                 120                 125

Gly Ser Tyr Thr Lys Ile Pro Asp Pro Ser Thr Trp Asn Leu Asn Pro
            130                 135                 140

Asp Ala Ser Tyr Val Tyr Tyr Cys Ala Asn Glu Thr Val His Gly Val
145                 150                 155                 160

Glu Phe Asp Phe Ile Pro Asp Val Lys Gly Ala Val Leu Val Cys Asp
                165                 170                 175

Met Ser Ser Asn Phe Leu Ser Lys Pro Val Asp Val Ser Lys Phe Gly
                180                 185                 190

Val Ile Phe Ala Gly Ala Gln Lys Asn Val Gly Ser Ala Gly Val Thr
            195                 200                 205

Val Val Ile Val Arg Asp Asp Leu Leu Gly Phe Ala Leu Arg Glu Cys
            210                 215                 220

Pro Ser Val Leu Glu Tyr Lys Val Gln Ala Gly Asn Ser Ser Leu Tyr
225                 230                 235                 240

Asn Thr Pro Pro Cys Phe Ser Ile Tyr Val Met Gly Leu Val Leu Glu

-continued

```
                245                 250                 255
Trp Ile Lys Asn Asn Gly Gly Ala Ala Ala Met Glu Lys Leu Ser Ser
            260                 265                 270

Ile Lys Ser Gln Thr Ile Tyr Glu Ile Ile Asp Asn Ser Gln Gly Phe
        275                 280                 285

Tyr Val Ser Val Gly Gly Ile Arg Ala Ser Leu Tyr Asn Ala Val Thr
    290                 295                 300

Ile Glu Asp Val Gln Lys Leu Ala Ala Phe Met Lys Lys Phe Leu Glu
305                 310                 315                 320

Met His Gln Leu
```

<210> SEQ ID NO 23
<211> LENGTH: 843
<212> TYPE: PRT
<213> ORGANISM: Homo sapiens

<400> SEQUENCE: 23

```
Met Ala Lys Pro Leu Thr Asp Ser Glu Lys Arg Lys Gln Ile Ser Val
1               5                   10                  15

Arg Gly Leu Ala Gly Leu Gly Asp Val Ala Glu Val Arg Lys Ser Phe
            20                  25                  30

Asn Arg His Leu His Phe Thr Leu Val Lys Asp Arg Asn Val Ala Thr
        35                  40                  45

Pro Arg Asp Tyr Phe Phe Ala Leu Ala His Thr Val Arg Asp His Leu
    50                  55                  60

Val Gly Arg Trp Ile Arg Thr Gln Gln His Tyr Tyr Glu Arg Asp Pro
65                  70                  75                  80

Lys Arg Ile Tyr Tyr Leu Ser Leu Glu Phe Tyr Met Gly Arg Thr Leu
                85                  90                  95

Gln Asn Thr Met Val Asn Leu Gly Leu Gln Asn Ala Cys Asp Glu Ala
            100                 105                 110

Ile Tyr Gln Leu Gly Leu Asp Leu Glu Glu Leu Glu Glu Ile Glu Glu
        115                 120                 125

Asp Ala Gly Leu Gly Asn Gly Gly Leu Gly Arg Leu Ala Ala Cys Phe
    130                 135                 140

Leu Asp Ser Met Ala Thr Leu Gly Leu Ala Ala Tyr Gly Tyr Gly Ile
145                 150                 155                 160

Arg Tyr Glu Phe Gly Ile Phe Asn Gln Lys Ile Val Asn Gly Trp Gln
                165                 170                 175

Val Glu Glu Ala Asp Asp Trp Leu Arg Tyr Gly Asn Pro Trp Glu Lys
            180                 185                 190

Ala Arg Pro Glu Tyr Met Leu Pro Val His Phe Tyr Gly Arg Val Glu
        195                 200                 205

His Thr Pro Asp Gly Val Lys Trp Leu Asp Thr Gln Val Val Leu Ala
    210                 215                 220

Met Pro Tyr Asp Thr Pro Val Pro Gly Tyr Lys Asn Asn Thr Val Asn
225                 230                 235                 240

Thr Met Arg Leu Trp Ser Ala Lys Ala Pro Asn Asp Phe Lys Leu Gln
                245                 250                 255

Asp Phe Asn Val Gly Asp Tyr Ile Glu Ala Val Leu Asp Arg Asn Leu
            260                 265                 270

Ala Glu Asn Ile Ser Arg Val Leu Tyr Pro Asn Asp Asn Phe Phe Glu
        275                 280                 285

Gly Lys Glu Leu Arg Leu Lys Gln Glu Tyr Phe Val Val Ala Ala Thr
```

-continued

```
                290                 295                 300
Leu Gln Asp Ile Ile Arg Arg Phe Lys Ser Ser Lys Phe Gly Cys Arg
305                 310                 315                 320

Asp Pro Val Arg Thr Cys Phe Glu Thr Phe Pro Asp Lys Val Ala Ile
                325                 330                 335

Gln Leu Asn Asp Thr His Pro Ala Leu Ser Ile Pro Glu Leu Met Arg
                340                 345                 350

Ile Leu Val Asp Val Glu Lys Val Asp Trp Asp Lys Ala Trp Glu Ile
                355                 360                 365

Thr Lys Lys Thr Cys Ala Tyr Thr Asn His Thr Val Leu Pro Glu Ala
                370                 375                 380

Leu Glu Arg Trp Pro Val Ser Met Phe Glu Lys Leu Leu Pro Arg His
385                 390                 395                 400

Leu Glu Ile Ile Tyr Ala Ile Asn Gln Arg His Leu Asp His Val Ala
                405                 410                 415

Ala Leu Phe Pro Gly Asp Val Asp Arg Leu Arg Arg Met Ser Val Ile
                420                 425                 430

Glu Glu Gly Asp Cys Lys Arg Ile Asn Met Ala His Leu Cys Val Ile
                435                 440                 445

Gly Ser His Ala Val Asn Gly Val Ala Arg Ile His Ser Glu Ile Val
                450                 455                 460

Lys Gln Ser Val Phe Lys Asp Phe Tyr Glu Leu Glu Pro Glu Lys Phe
465                 470                 475                 480

Gln Asn Lys Thr Asn Gly Ile Thr Pro Arg Arg Trp Leu Leu Leu Cys
                485                 490                 495

Asn Pro Gly Leu Ala Asp Thr Ile Val Glu Lys Ile Gly Glu Glu Phe
                500                 505                 510

Leu Thr Asp Leu Ser Gln Leu Lys Lys Leu Leu Pro Leu Val Ser Asp
                515                 520                 525

Glu Val Phe Ile Arg Asp Val Ala Lys Val Lys Gln Glu Asn Lys Leu
                530                 535                 540

Lys Phe Ser Ala Phe Leu Glu Lys Glu Tyr Lys Val Lys Ile Asn Pro
545                 550                 555                 560

Ser Ser Met Phe Asp Val His Val Lys Arg Ile His Glu Tyr Lys Arg
                565                 570                 575

Gln Leu Leu Asn Cys Leu His Val Thr Leu Tyr Asn Arg Ile Lys
                580                 585                 590

Arg Asp Pro Ala Lys Ala Phe Val Pro Arg Thr Val Met Ile Gly Gly
                595                 600                 605

Lys Ala Ala Pro Gly Tyr His Met Ala Lys Leu Ile Ile Lys Leu Val
610                 615                 620

Thr Ser Ile Gly Asp Val Val Asn His Asp Pro Val Val Gly Asp Arg
625                 630                 635                 640

Leu Lys Val Ile Phe Leu Glu Asn Tyr Arg Val Ser Leu Ala Glu Lys
                645                 650                 655

Val Ile Pro Ala Ala Asp Leu Ser Gln Gln Ile Ser Thr Ala Gly Thr
                660                 665                 670

Glu Ala Ser Gly Thr Gly Asn Met Lys Phe Met Leu Asn Gly Ala Leu
                675                 680                 685

Thr Ile Gly Thr Met Asp Gly Ala Asn Val Glu Met Ala Glu Glu Ala
                690                 695                 700

Gly Ala Glu Asn Leu Phe Ile Phe Gly Leu Arg Val Glu Asp Val Glu
705                 710                 715                 720
```

```
Ala Leu Asp Arg Lys Gly Tyr Asn Ala Arg Glu Tyr Asp His Leu
                725                 730                 735

Pro Glu Leu Lys Gln Ala Val Asp Gln Ile Ser Ser Gly Phe Phe Ser
            740                 745                 750

Pro Lys Glu Pro Asp Cys Phe Lys Asp Ile Val Asn Met Leu Met His
            755                 760                 765

His Asp Arg Phe Lys Val Phe Ala Asp Tyr Glu Ala Tyr Met Gln Cys
    770                 775                 780

Gln Ala Gln Val Asp Gln Leu Tyr Arg Asn Pro Lys Glu Trp Thr Lys
785                 790                 795                 800

Lys Val Ile Arg Asn Ile Ala Cys Ser Gly Lys Phe Ser Ser Asp Arg
                805                 810                 815

Thr Ile Thr Glu Tyr Ala Arg Glu Ile Trp Gly Val Glu Pro Ser Asp
            820                 825                 830

Leu Gln Ile Pro Pro Asn Ile Pro Arg Asp
            835                 840

<210> SEQ ID NO 24
<211> LENGTH: 504
<212> TYPE: PRT
<213> ORGANISM: Homo sapiens

<400> SEQUENCE: 24

Met Leu Tyr Phe Ser Leu Phe Trp Ala Ala Arg Pro Leu Gln Arg Cys
1               5                   10                  15

Gly Gln Leu Val Arg Met Ala Ile Arg Ala Gln His Ser Asn Ala Ala
            20                  25                  30

Gln Thr Gln Thr Gly Glu Ala Asn Arg Gly Trp Thr Gly Gln Glu Ser
        35                  40                  45

Leu Ser Asp Ser Asp Pro Glu Met Trp Glu Leu Leu Gln Arg Glu Lys
    50                  55                  60

Asp Arg Gln Cys Arg Gly Leu Glu Leu Ile Ala Ser Glu Asn Phe Cys
65                  70                  75                  80

Ser Arg Ala Ala Leu Glu Ala Leu Gly Ser Cys Leu Asn Asn Lys Tyr
                85                  90                  95

Ser Glu Gly Tyr Pro Gly Lys Arg Tyr Tyr Gly Gly Ala Glu Val Val
            100                 105                 110

Asp Glu Ile Glu Leu Leu Cys Gln Arg Arg Ala Leu Glu Ala Phe Asp
        115                 120                 125

Leu Asp Pro Ala Gln Trp Gly Val Asn Val Gln Pro Tyr Ser Gly Ser
    130                 135                 140

Pro Ala Asn Leu Ala Val Tyr Thr Ala Leu Leu Gln Pro His Asp Arg
145                 150                 155                 160

Ile Met Gly Leu Asp Leu Pro Asp Gly Gly His Leu Thr His Gly Tyr
                165                 170                 175

Met Ser Asp Val Lys Arg Ile Ser Ala Thr Ser Ile Phe Phe Glu Ser
            180                 185                 190

Met Pro Tyr Lys Leu Asn Pro Lys Thr Gly Leu Ile Asp Tyr Asn Gln
        195                 200                 205

Leu Ala Leu Thr Ala Arg Leu Phe Arg Pro Arg Leu Ile Ile Ala Gly
    210                 215                 220

Thr Ser Ala Tyr Ala Arg Leu Ile Asp Tyr Ala Arg Met Arg Glu Val
225                 230                 235                 240

Cys Asp Glu Val Lys Ala His Leu Leu Ala Asp Met Ala His Ile Ser
```

```
              245                 250                 255
Gly Leu Val Ala Ala Lys Val Ile Pro Ser Pro Phe Lys His Ala Asp
            260                 265                 270
Ile Val Thr Thr Thr His Lys Thr Leu Arg Gly Ala Arg Ser Gly
            275                 280             285
Leu Ile Phe Tyr Arg Lys Gly Val Lys Ala Val Asp Pro Lys Thr Gly
290                 295                 300
Arg Glu Ile Pro Tyr Thr Phe Glu Asp Arg Ile Asn Phe Ala Val Phe
305                 310                 315                 320
Pro Ser Leu Gln Gly Gly Pro His Asn His Ala Ile Ala Ala Val Ala
                325                 330                 335
Val Ala Leu Lys Gln Ala Cys Thr Pro Met Phe Arg Glu Tyr Ser Leu
            340                 345                 350
Gln Val Leu Lys Asn Ala Arg Ala Met Ala Asp Ala Leu Leu Glu Arg
            355                 360                 365
Gly Tyr Ser Leu Val Ser Gly Thr Asp Asn His Leu Val Leu Val
        370                 375                 380
Asp Leu Arg Pro Lys Gly Leu Asp Gly Ala Arg Ala Glu Arg Val Leu
385                 390                 395                 400
Glu Leu Val Ser Ile Thr Ala Asn Lys Asn Thr Cys Pro Gly Asp Arg
                405                 410                 415
Ser Ala Ile Thr Pro Gly Gly Leu Arg Leu Gly Ala Pro Ala Leu Thr
            420                 425                 430
Ser Arg Gln Phe Arg Glu Asp Phe Arg Arg Val Val Asp Phe Ile
            435                 440                 445
Asp Glu Gly Val Asn Ile Gly Leu Glu Val Lys Ser Lys Thr Ala Lys
            450                 455                 460
Leu Gln Asp Phe Lys Ser Phe Leu Leu Lys Asp Ser Glu Thr Ser Gln
465                 470                 475                 480
Arg Leu Ala Asn Leu Arg Gln Arg Val Glu Gln Phe Ala Arg Ala Phe
                485                 490                 495
Pro Met Pro Gly Phe Asp Glu His
                500

<210> SEQ ID NO 25
<211> LENGTH: 494
<212> TYPE: PRT
<213> ORGANISM: Homo sapiens

<400> SEQUENCE: 25

Met Leu Tyr Phe Ser Leu Phe Trp Ala Ala Arg Pro Leu Gln Arg Cys
1               5                   10                  15
Gly Gln Leu Val Arg Met Ala Ile Arg Ala Gln His Ser Asn Ala Ala
            20                  25                  30
Gln Thr Gln Thr Gly Glu Ala Asn Arg Gly Trp Thr Gly Gln Glu Ser
        35                  40                  45
Leu Ser Asp Ser Asp Pro Glu Met Trp Glu Leu Leu Gln Arg Glu Lys
    50                  55                  60
Asp Arg Gln Cys Arg Gly Leu Glu Leu Ile Ala Ser Glu Asn Phe Cys
65                  70                  75                  80
Ser Arg Ala Ala Leu Glu Ala Leu Gly Ser Cys Leu Asn Asn Lys Tyr
                85                  90                  95
Ser Glu Gly Tyr Pro Gly Lys Arg Tyr Tyr Gly Gly Ala Glu Val Val
            100                 105                 110
```

Asp Glu Ile Glu Leu Leu Cys Gln Arg Arg Ala Leu Glu Ala Phe Asp
            115                 120                 125

Leu Asp Pro Ala Gln Trp Gly Val Asn Val Gln Pro Tyr Ser Gly Ser
130                 135                 140

Pro Ala Asn Leu Ala Val Tyr Thr Ala Leu Leu Gln Pro His Asp Arg
145                 150                 155                 160

Ile Met Gly Leu Asp Leu Pro Asp Gly Gly His Leu Thr His Gly Tyr
                165                 170                 175

Met Ser Asp Val Lys Arg Ile Ser Ala Thr Ser Ile Phe Phe Glu Ser
            180                 185                 190

Met Pro Tyr Lys Leu Asn Leu Ala Leu Thr Ala Arg Leu Phe Arg Pro
        195                 200                 205

Arg Leu Ile Ile Ala Gly Thr Ser Ala Tyr Ala Arg Leu Ile Asp Tyr
    210                 215                 220

Ala Arg Met Arg Glu Val Cys Asp Glu Val Lys Ala His Leu Leu Ala
225                 230                 235                 240

Asp Met Ala His Ile Ser Gly Leu Val Ala Ala Lys Val Ile Pro Ser
                245                 250                 255

Pro Phe Lys His Ala Asp Ile Val Thr Thr Thr Thr His Lys Thr Leu
            260                 265                 270

Arg Gly Ala Arg Ser Gly Leu Ile Phe Tyr Arg Lys Gly Val Lys Ala
        275                 280                 285

Val Asp Pro Lys Thr Gly Arg Glu Ile Pro Tyr Thr Phe Glu Asp Arg
    290                 295                 300

Ile Asn Phe Ala Val Phe Pro Ser Leu Gln Gly Gly Pro His Asn His
305                 310                 315                 320

Ala Ile Ala Ala Val Ala Val Ala Leu Lys Gln Ala Cys Thr Pro Met
                325                 330                 335

Phe Arg Glu Tyr Ser Leu Gln Val Leu Lys Asn Ala Arg Ala Met Ala
            340                 345                 350

Asp Ala Leu Leu Glu Arg Gly Tyr Ser Leu Val Ser Gly Gly Thr Asp
        355                 360                 365

Asn His Leu Val Leu Val Asp Leu Arg Pro Lys Gly Leu Asp Gly Ala
    370                 375                 380

Arg Ala Glu Arg Val Leu Glu Leu Val Ser Ile Thr Ala Asn Lys Asn
385                 390                 395                 400

Thr Cys Pro Gly Asp Arg Ser Ala Ile Thr Pro Gly Gly Leu Arg Leu
                405                 410                 415

Gly Ala Pro Ala Leu Thr Ser Arg Gln Phe Arg Glu Asp Phe Arg
            420                 425                 430

Arg Val Val Asp Phe Ile Asp Glu Gly Val Asn Ile Gly Leu Glu Val
        435                 440                 445

Lys Ser Lys Thr Ala Lys Leu Gln Asp Phe Lys Ser Phe Leu Leu Lys
    450                 455                 460

Asp Ser Glu Thr Ser Gln Arg Leu Ala Asn Leu Arg Gln Arg Val Glu
465                 470                 475                 480

Gln Phe Ala Arg Ala Phe Pro Met Pro Gly Phe Asp Glu His
                485                 490

<210> SEQ ID NO 26
<211> LENGTH: 483
<212> TYPE: PRT
<213> ORGANISM: Homo sapiens

<400> SEQUENCE: 26

-continued

```
Met Ala Ile Arg Ala Gln His Ser Asn Ala Gln Thr Gln Thr Gly
1               5                   10                  15

Glu Ala Asn Arg Gly Trp Thr Gly Gln Glu Ser Leu Ser Asp Ser Asp
            20                  25                  30

Pro Glu Met Trp Glu Leu Leu Gln Arg Glu Lys Asp Arg Gln Cys Arg
        35                  40                  45

Gly Leu Glu Leu Ile Ala Ser Glu Asn Phe Cys Ser Arg Ala Ala Leu
    50                  55                  60

Glu Ala Leu Gly Ser Cys Leu Asn Asn Lys Tyr Ser Glu Gly Tyr Pro
65                  70                  75                  80

Gly Lys Arg Tyr Tyr Gly Gly Ala Glu Val Val Asp Glu Ile Glu Leu
                85                  90                  95

Leu Cys Gln Arg Arg Ala Leu Glu Ala Phe Asp Leu Asp Pro Ala Gln
            100                 105                 110

Trp Gly Val Asn Val Gln Pro Tyr Ser Gly Ser Pro Ala Asn Leu Ala
        115                 120                 125

Val Tyr Thr Ala Leu Leu Gln Pro His Asp Arg Ile Met Gly Leu Asp
    130                 135                 140

Leu Pro Asp Gly His Leu Thr His Gly Tyr Met Ser Asp Val Lys
145                 150                 155                 160

Arg Ile Ser Ala Thr Ser Ile Phe Phe Glu Ser Met Pro Tyr Lys Leu
                165                 170                 175

Asn Pro Lys Thr Gly Leu Ile Asp Tyr Asn Gln Leu Ala Leu Thr Ala
            180                 185                 190

Arg Leu Phe Arg Pro Arg Leu Ile Ile Ala Gly Thr Ser Ala Tyr Ala
        195                 200                 205

Arg Leu Ile Asp Tyr Ala Arg Met Arg Glu Val Cys Asp Glu Val Lys
    210                 215                 220

Ala His Leu Leu Ala Asp Met Ala His Ile Ser Gly Leu Val Ala Ala
225                 230                 235                 240

Lys Val Ile Pro Ser Pro Phe Lys His Ala Asp Ile Val Thr Thr Thr
                245                 250                 255

Thr His Lys Thr Leu Arg Gly Ala Arg Ser Gly Leu Ile Phe Tyr Arg
            260                 265                 270

Lys Gly Val Lys Ala Val Asp Pro Lys Thr Gly Arg Glu Ile Pro Tyr
        275                 280                 285

Thr Phe Glu Asp Arg Ile Asn Phe Ala Val Phe Pro Ser Leu Gln Gly
    290                 295                 300

Gly Pro His Asn His Ala Ile Ala Ala Val Ala Val Ala Leu Lys Gln
305                 310                 315                 320

Ala Cys Thr Pro Met Phe Arg Glu Tyr Ser Leu Gln Val Leu Lys Asn
                325                 330                 335

Ala Arg Ala Met Ala Asp Ala Leu Leu Glu Arg Gly Tyr Ser Leu Val
            340                 345                 350

Ser Gly Gly Thr Asp Asn His Leu Val Leu Val Asp Leu Arg Pro Lys
        355                 360                 365

Gly Leu Asp Gly Ala Arg Ala Glu Arg Val Leu Glu Leu Val Ser Ile
    370                 375                 380

Thr Ala Asn Lys Asn Thr Cys Pro Gly Asp Arg Ser Ala Ile Thr Pro
385                 390                 395                 400

Gly Gly Leu Arg Leu Gly Ala Pro Ala Leu Thr Ser Arg Gln Phe Arg
                405                 410                 415
```

```
Glu Asp Asp Phe Arg Arg Val Val Asp Phe Ile Asp Glu Gly Val Asn
            420                 425                 430

Ile Gly Leu Glu Val Lys Ser Lys Thr Ala Lys Leu Gln Asp Phe Lys
        435                 440                 445

Ser Phe Leu Leu Lys Asp Ser Glu Thr Ser Gln Arg Leu Ala Asn Leu
450                 455                 460

Arg Gln Arg Val Glu Gln Phe Ala Arg Ala Phe Pro Met Pro Gly Phe
465                 470                 475                 480

Asp Glu His

<210> SEQ ID NO 27
<211> LENGTH: 457
<212> TYPE: PRT
<213> ORGANISM: Homo sapiens

<400> SEQUENCE: 27

Met Arg Pro Pro Ser Pro Leu Pro Ala Arg Trp Leu Cys Val Leu Ala
1               5                   10                  15

Gly Ala Leu Ala Trp Ala Leu Gly Pro Ala Gly Gly Gln Ala Ala Arg
            20                  25                  30

Leu Gln Glu Glu Cys Asp Tyr Val Gln Met Ile Glu Val Gln His Lys
        35                  40                  45

Gln Cys Leu Glu Glu Ala Gln Leu Glu Asn Glu Thr Ile Gly Cys Ser
    50                  55                  60

Lys Met Trp Asp Asn Leu Thr Cys Trp Pro Ala Thr Pro Arg Gly Gln
65                  70                  75                  80

Val Val Val Leu Ala Cys Pro Leu Ile Phe Lys Leu Phe Ser Ser Ile
                85                  90                  95

Gln Gly Arg Asn Val Ser Arg Ser Cys Thr Asp Glu Gly Trp Thr His
            100                 105                 110

Leu Glu Pro Gly Pro Tyr Pro Ile Ala Cys Gly Leu Asp Asp Lys Ala
        115                 120                 125

Ala Ser Leu Asp Glu Gln Gln Thr Met Phe Tyr Gly Ser Val Lys Thr
    130                 135                 140

Gly Tyr Thr Ile Gly Tyr Gly Leu Ser Leu Ala Thr Leu Leu Val Ala
145                 150                 155                 160

Thr Ala Ile Leu Ser Leu Phe Arg Lys Leu His Cys Thr Arg Asn Tyr
                165                 170                 175

Ile His Met His Leu Phe Ile Ser Phe Ile Leu Arg Ala Ala Ala Val
            180                 185                 190

Phe Ile Lys Asp Leu Ala Leu Phe Asp Ser Gly Glu Ser Asp Gln Cys
        195                 200                 205

Ser Glu Gly Ser Val Gly Cys Lys Ala Ala Met Val Phe Phe Gln Tyr
    210                 215                 220

Cys Val Met Ala Asn Phe Phe Trp Leu Leu Val Glu Gly Leu Tyr Leu
225                 230                 235                 240

Tyr Thr Leu Leu Ala Val Ser Phe Phe Ser Glu Arg Lys Tyr Phe Trp
                245                 250                 255

Gly Tyr Ile Leu Ile Gly Trp Gly Val Pro Ser Thr Phe Thr Met Val
            260                 265                 270

Trp Thr Ile Ala Arg Ile His Phe Glu Asp Tyr Gly Cys Trp Asp Thr
        275                 280                 285

Ile Asn Ser Ser Leu Trp Trp Ile Ile Lys Gly Pro Ile Leu Thr Ser
    290                 295                 300
```

Ile Leu Val Asn Phe Ile Leu Phe Ile Cys Ile Arg Ile Leu Leu
305                 310                 315                 320

Gln Lys Leu Arg Pro Pro Asp Ile Arg Lys Ser Asp Ser Ser Pro Tyr
            325                 330                 335

Ser Arg Leu Ala Arg Ser Thr Leu Leu Leu Ile Pro Leu Phe Gly Val
            340                 345                 350

His Tyr Ile Met Phe Ala Phe Phe Pro Asp Asn Phe Lys Pro Glu Val
            355                 360                 365

Lys Met Val Phe Glu Leu Val Val Gly Ser Phe Gln Gly Phe Val Val
            370                 375                 380

Ala Ile Leu Tyr Cys Phe Leu Asn Gly Glu Val Gln Ala Glu Leu Arg
385                 390                 395                 400

Arg Lys Trp Arg Arg Trp His Leu Gln Gly Val Leu Gly Trp Asn Pro
                405                 410                 415

Lys Tyr Arg His Pro Ser Gly Gly Ser Asn Gly Ala Thr Cys Ser Thr
                420                 425                 430

Gln Val Ser Met Leu Thr Arg Val Ser Pro Gly Ala Arg Arg Ser Ser
            435                 440                 445

Ser Phe Gln Ala Glu Val Ser Leu Val
    450                 455

<210> SEQ ID NO 28
<211> LENGTH: 20
<212> TYPE: DNA
<213> ORGANISM: Artificial
<220> FEATURE:
<223> OTHER INFORMATION: ABCB9 Forward Primer

<400> SEQUENCE: 28
gaccttcacc taccgcactc                                          20

<210> SEQ ID NO 29
<211> LENGTH: 20
<212> TYPE: DNA
<213> ORGANISM: Artificial
<220> FEATURE:
<223> OTHER INFORMATION: ABCB9 Reverse Primer

<400> SEQUENCE: 29
cacaggagct cttcccactg                                          20

<210> SEQ ID NO 30
<211> LENGTH: 18
<212> TYPE: DNA
<213> ORGANISM: Artificial
<220> FEATURE:
<223> OTHER INFORMATION: BEX2 forward primer

<400> SEQUENCE: 30
gccccgaaag taggaagc                                            18

<210> SEQ ID NO 31
<211> LENGTH: 21
<212> TYPE: DNA
<213> ORGANISM: Artificial
<220> FEATURE:
<223> OTHER INFORMATION: BEX2 reverse primer

<400> SEQUENCE: 31
ctccattact cctgggccta t                                        21

```
<210> SEQ ID NO 32
<211> LENGTH: 20
<212> TYPE: DNA
<213> ORGANISM: Artificial
<220> FEATURE:
<223> OTHER INFORMATION: BGLAP forward primer

<400> SEQUENCE: 32
ggcgctacct gtatcaatgg                                                   20

<210> SEQ ID NO 33
<211> LENGTH: 20
<212> TYPE: DNA
<213> ORGANISM: Artificial
<220> FEATURE:
<223> OTHER INFORMATION: BGLAP reverse primer

<400> SEQUENCE: 33
tcagccaact cgtcacagtc                                                   20

<210> SEQ ID NO 34
<211> LENGTH: 21
<212> TYPE: DNA
<213> ORGANISM: Artificial
<220> FEATURE:
<223> OTHER INFORMATION: CA12 forward primer

<400> SEQUENCE: 34
ccaaggctac aatctgtctg c                                                 21

<210> SEQ ID NO 35
<211> LENGTH: 19
<212> TYPE: DNA
<213> ORGANISM: Artificial
<220> FEATURE:
<223> OTHER INFORMATION: CA12 reverse primer

<400> SEQUENCE: 35
gggcaggttc agcttcact                                                    19

<210> SEQ ID NO 36
<211> LENGTH: 18
<212> TYPE: DNA
<213> ORGANISM: Artificial
<220> FEATURE:
<223> OTHER INFORMATION: GDF15 forward primer

<400> SEQUENCE: 36
ccggatactc acgccaga                                                     18

<210> SEQ ID NO 37
<211> LENGTH: 20
<212> TYPE: DNA
<213> ORGANISM: Artificial
<220> FEATURE:
<223> OTHER INFORMATION: GDF15 reverse primer

<400> SEQUENCE: 37
agagatacgc aggtgcaggt                                                   20

<210> SEQ ID NO 38
<211> LENGTH: 19
<212> TYPE: DNA
<213> ORGANISM: Artificial
<220> FEATURE:
<223> OTHER INFORMATION: GEM forward primer
```

```
<400> SEQUENCE: 38
gacagcatgg acagcgact                                          19

<210> SEQ ID NO 39
<211> LENGTH: 20
<212> TYPE: DNA
<213> ORGANISM: Artificial
<220> FEATURE:
<223> OTHER INFORMATION: GEM reverse primer

<400> SEQUENCE: 39
aaccatcagg gttcgttcat                                         20

<210> SEQ ID NO 40
<211> LENGTH: 18
<212> TYPE: DNA
<213> ORGANISM: Artificial
<220> FEATURE:
<223> OTHER INFORMATION: IGFBP2 forward primer

<400> SEQUENCE: 40
ccaagaagct gcgaccac                                           18

<210> SEQ ID NO 41
<211> LENGTH: 20
<212> TYPE: DNA
<213> ORGANISM: Artificial
<220> FEATURE:
<223> OTHER INFORMATION: IGFBP2 reverse primer

<400> SEQUENCE: 41
gggatgtgca gggagtagag                                         20

<210> SEQ ID NO 42
<211> LENGTH: 19
<212> TYPE: DNA
<213> ORGANISM: Artificial
<220> FEATURE:
<223> OTHER INFORMATION: ITGB4 forward primer

<400> SEQUENCE: 42
tcagcctctc tgggacctt                                          19

<210> SEQ ID NO 43
<211> LENGTH: 20
<212> TYPE: DNA
<213> ORGANISM: Artificial
<220> FEATURE:
<223> OTHER INFORMATION: ITGB4 reverse primer

<400> SEQUENCE: 43
tatccacacg gacacactcc                                         20

<210> SEQ ID NO 44
<211> LENGTH: 21
<212> TYPE: DNA
<213> ORGANISM: Artificial
<220> FEATURE:
<223> OTHER INFORMATION: KIAA0746 forward primer

<400> SEQUENCE: 44
gttgtctgtg cagatgtacg c                                       21

<210> SEQ ID NO 45
<211> LENGTH: 20
```

```
<212> TYPE: DNA
<213> ORGANISM: Artificial
<220> FEATURE:
<223> OTHER INFORMATION: KIAA0746 reverse primer

<400> SEQUENCE: 45
tagcagggcc aggttaaaaa                                            20

<210> SEQ ID NO 46
<211> LENGTH: 18
<212> TYPE: DNA
<213> ORGANISM: Artificial
<220> FEATURE:
<223> OTHER INFORMATION: KLF4 forward primer

<400> SEQUENCE: 46
gccgctccat taccaaga                                              18

<210> SEQ ID NO 47
<211> LENGTH: 19
<212> TYPE: DNA
<213> ORGANISM: Artificial
<220> FEATURE:
<223> OTHER INFORMATION: KLF4 reverse primer

<400> SEQUENCE: 47
tcttcccctc tttggcttg                                             19

<210> SEQ ID NO 48
<211> LENGTH: 20
<212> TYPE: DNA
<213> ORGANISM: Artificial
<220> FEATURE:
<223> OTHER INFORMATION: MARS forward primer

<400> SEQUENCE: 48
aacaacctgg gcaacttcat                                            20

<210> SEQ ID NO 49
<211> LENGTH: 20
<212> TYPE: DNA
<213> ORGANISM: Artificial
<220> FEATURE:
<223> OTHER INFORMATION: MARS reverse primer

<400> SEQUENCE: 49
accatctcag gcacatagcc                                            20

<210> SEQ ID NO 50
<211> LENGTH: 17
<212> TYPE: DNA
<213> ORGANISM: Artificial
<220> FEATURE:
<223> OTHER INFORMATION: MERTK forward primer

<400> SEQUENCE: 50
ggagacagga ccaaagc                                               17

<210> SEQ ID NO 51
<211> LENGTH: 20
<212> TYPE: DNA
<213> ORGANISM: Artificial
<220> FEATURE:
<223> OTHER INFORMATION: MERTK reverse primer

<400> SEQUENCE: 51
```
gggcaatatc caccatgaac                                              20

<210> SEQ ID NO 52
<211> LENGTH: 20
<212> TYPE: DNA
<213> ORGANISM: Artificial
<220> FEATURE:
<223> OTHER INFORMATION: PADI4 forward primer

<400> SEQUENCE: 52
aagtgcaagc tgaccatctg                                              20

<210> SEQ ID NO 53
<211> LENGTH: 19
<212> TYPE: DNA
<213> ORGANISM: Artificial
<220> FEATURE:
<223> OTHER INFORMATION: PADI4 reverse primer

<400> SEQUENCE: 53
gccgatctcc atttcatcc                                               19

<210> SEQ ID NO 54
<211> LENGTH: 20
<212> TYPE: DNA
<213> ORGANISM: Artificial
<220> FEATURE:
<223> OTHER INFORMATION: PHGDH forward primer

<400> SEQUENCE: 54
tggtggaaaa gcagaacctt                                              20

<210> SEQ ID NO 55
<211> LENGTH: 22
<212> TYPE: DNA
<213> ORGANISM: Artificial
<220> FEATURE:
<223> OTHER INFORMATION: PHGDH reverse primer

<400> SEQUENCE: 55
aacaataagg ccttcacagt cc                                           22

<210> SEQ ID NO 56
<211> LENGTH: 23
<212> TYPE: DNA
<213> ORGANISM: Artificial
<220> FEATURE:
<223> OTHER INFORMATION: PITPNC1 forward primer

<400> SEQUENCE: 56
gcgctactac aaagaatctg agg                                          23

<210> SEQ ID NO 57
<211> LENGTH: 22
<212> TYPE: DNA
<213> ORGANISM: Artificial
<220> FEATURE:
<223> OTHER INFORMATION: PITPNC1 reverse primer

<400> SEQUENCE: 57
gagcacatga taggctgatg ac                                           22

<210> SEQ ID NO 58
<211> LENGTH: 19
<212> TYPE: DNA
<213> ORGANISM: Artificial

```
<220> FEATURE:
<223> OTHER INFORMATION: PSAT1 forward primer

<400> SEQUENCE: 58
tcttgtgcgg gaattgcta                                                    19

<210> SEQ ID NO 59
<211> LENGTH: 20
<212> TYPE: DNA
<213> ORGANISM: Artificial
<220> FEATURE:
<223> OTHER INFORMATION: PSAT1 reverse primer

<400> SEQUENCE: 59
aaggggacag cactgaactg                                                   20

<210> SEQ ID NO 60
<211> LENGTH: 20
<212> TYPE: DNA
<213> ORGANISM: Artificial
<220> FEATURE:
<223> OTHER INFORMATION: PYGB forward primer

<400> SEQUENCE: 60
tccagggtcc tgtatccaaa                                                   20

<210> SEQ ID NO 61
<211> LENGTH: 21
<212> TYPE: DNA
<213> ORGANISM: Artificial
<220> FEATURE:
<223> OTHER INFORMATION: PYGB reverse primer

<400> SEQUENCE: 61
ccacgaagta ctcctgcttc a                                                 21

<210> SEQ ID NO 62
<211> LENGTH: 24
<212> TYPE: DNA
<213> ORGANISM: Artificial
<220> FEATURE:
<223> OTHER INFORMATION: RGC32 forward primer

<400> SEQUENCE: 62
tgctgatctt gacaaaactt tagc                                              24

<210> SEQ ID NO 63
<211> LENGTH: 20
<212> TYPE: DNA
<213> ORGANISM: Artificial
<220> FEATURE:
<223> OTHER INFORMATION: RGC32 reverse primer

<400> SEQUENCE: 63
gcaggtcctc ggaactttct                                                   20

<210> SEQ ID NO 64
<211> LENGTH: 20
<212> TYPE: DNA
<213> ORGANISM: Artificial
<220> FEATURE:
<223> OTHER INFORMATION: SHMT2 forward primer

<400> SEQUENCE: 64
gagggagaag gacaggcagt                                                   20
```

<210> SEQ ID NO 65
<211> LENGTH: 20
<212> TYPE: DNA
<213> ORGANISM: Artificial
<220> FEATURE:
<223> OTHER INFORMATION: SHMT2 reverse primer

<400> SEQUENCE: 65
ctcggctgca gaagttctct                                              20

<210> SEQ ID NO 66
<211> LENGTH: 19
<212> TYPE: DNA
<213> ORGANISM: Artificial
<220> FEATURE:
<223> OTHER INFORMATION: SMAD4 forward primer

<400> SEQUENCE: 66
tggcccagga tcagtaggt                                               19

<210> SEQ ID NO 67
<211> LENGTH: 20
<212> TYPE: DNA
<213> ORGANISM: Artificial
<220> FEATURE:
<223> OTHER INFORMATION: SMAD4 reverse primer

<400> SEQUENCE: 67
catcaacacc aattccagca                                              20

<210> SEQ ID NO 68
<211> LENGTH: 19
<212> TYPE: DNA
<213> ORGANISM: Artificial
<220> FEATURE:
<223> OTHER INFORMATION: THBD forward primer

<400> SEQUENCE: 68
aattgggagc ttgggaatg                                               19

<210> SEQ ID NO 69
<211> LENGTH: 22
<212> TYPE: DNA
<213> ORGANISM: Artificial
<220> FEATURE:
<223> OTHER INFORMATION: THBD reverse primer

<400> SEQUENCE: 69
tgaggacctg attaaggcta gg                                           22

<210> SEQ ID NO 70
<211> LENGTH: 27
<212> TYPE: DNA
<213> ORGANISM: Artificial
<220> FEATURE:
<223> OTHER INFORMATION: TNFSF4 forward primer

<400> SEQUENCE: 70
gtatcctcga attcaaagta tcaaagt                                      27

<210> SEQ ID NO 71
<211> LENGTH: 21
<212> TYPE: DNA
<213> ORGANISM: Artificial
<220> FEATURE:
<223> OTHER INFORMATION: TNFSF4 reverse primer

```
<400> SEQUENCE: 71
ctgagttgtt ctgcaccttc a                                              21

<210> SEQ ID NO 72
<211> LENGTH: 20
<212> TYPE: DNA
<213> ORGANISM: Artificial
<220> FEATURE:
<223> OTHER INFORMATION: VIPR1 forward primer

<400> SEQUENCE: 72
ctgtcccctc atcttcaagc                                                20

<210> SEQ ID NO 73
<211> LENGTH: 18
<212> TYPE: DNA
<213> ORGANISM: Artificial
<220> FEATURE:
<223> OTHER INFORMATION: VIPR1 reverse primer

<400> SEQUENCE: 73
cagctgcggc ttacattg                                                  18

<210> SEQ ID NO 74
<211> LENGTH: 2301
<212> TYPE: DNA
<213> ORGANISM: Homo sapiens

<400> SEQUENCE: 74
atgcggctgt ggaaggcggt ggtggtgact ttggccttca tgagtgtgga catctgcgtg    60
accacggcca tctatgtctt cagccacctg gaccgcagcc tcctggagga catccgccac   120
ttcaacatct ttgactcggt gctggatctc tgggcagcct gcctgtaccg cagctgcctg   180
ctgctgggag ccaccattgg tgtggccaag aacagtgcgc tggggccccg gcggctgcgg   240
gcctcgtggc tggtcatcac cctcgtgtgc ctcttcgtgg gcatctatgc catggtgaag   300
ctgctgctct tctcagaggt gcgcaggccc atccgggacc cctggttttg ggccctgttc   360
gtgtggacgt acatttcact cggcgcatcc ttcctgctct ggtggctgct gtccaccgtg   420
cggccaggca cccaggccct ggagccaggg gcggccaccg aggctgaggg cttccctggg   480
agcggccggc caccgcccga gcaggcgtct ggggccacgt gcagaagct gctctcctac   540 accaagcccg acgtggcctt cctcgtggcc gcctccttct tcctcatcgt ggcagctctg   600
ggagagacct tcctgcccta ctacacgggc gcgccattg atggcatcgt catccagaaa   660
agcatggatc agttcagcac ggctgtcgtc atcgtgtgcc tgctggccat tggcagctca   720
tttgccgcag gtattcgggg cggcatttt accctcatat tgccagact gaacattcgc   780 cttcgaaact gtctcttccg ctcactggtg tcccaggaga caagcttctt tgatgagaac   840
cgcacagggg acctcatctc ccgcctgacc tcgacacca ccatggtcag cgacctggtc   900
tcccagaaca tcaatgtctt cctgcggaac acagtcaagg tcacgggcgt ggtggtcttc   960
atgttcagcc tctcatggca gctctccttg gtcaccttca tgggcttccc catcatcatg  1020
atggtgtcca acatctacgg caagtactac aagaggctct ccaaagaggt ccagaatgcc  1080
ctggccagag cgagcaacac ggcggaggag accatcagtg ccatgaagac tgtccggagc  1140
ttcgccaatg aggaggagga ggcagaggtg taccctgcga agctgcagca ggtgtacaag  1200
ctgaacagga aggaggcagc tgcctacatg tactacgtct ggggcagcgg gctcacactg  1260
```

-continued

| | |
|---|---|
| ctggtggtcc aggtcagcat cctctactac gggggccacc ttgtcatctc aggccagatg | 1320 |
| accagcggca acctcatcgc cttcatcatc tacgagtttg tcctgggaga ttgtatggag | 1380 |
| tccgtgggct ccgtctacag tggcctgatg cagggagtgg gggctgctga aaggtgttc | 1440 |
| gagttcatcg accggcagcc gaccatggtg cacgatggca gcttggcccc cgaccacctg | 1500 |
| gagggccggg tggactttga aatgtgacc ttcacctacc gcactcggcc ccacacccag | 1560 |
| gtcctgcaga tgtctccttt cagcctgtcc cccggcaagg tgacggccct ggtggggccc | 1620 |
| tcgggcagtg ggaagagctc ctgtgtcaac atcctggaga acttctaccc cctggagggg | 1680 |
| ggccgggtgc tgctggacgg caagcccatc agcgcctacg accacaagta cttgcaccgt | 1740 |
| gtgatctccc tggtgagcca ggagcccgtg ctgttcgccc gctccatcac ggataacatc | 1800 |
| tcctacggcc tgcccactgt gccttcgag atggtggtgg aggccgcaca aaggccaat | 1860 |
| gcccacggct tcatcatgga actccaggac ggctacagca cagagacagg ggagaagggc | 1920 |
| gcccagctgt caggtggcca gaagcagcgg gtggccatgg cccgggctct ggtgcggaac | 1980 |
| cccccagtcc tcatcctgga tgaagccacc agcgctttgg atgccgagag cgagtatctg | 2040 |
| atccagcagg ccatccatgg caacctgcag aagcacacgg tactcatcat cgcgcaccgg | 2100 |
| ctgagcaccg tggagcacgc gcacctcatt gtggtgctgg acaagggccg cgtagtgcag | 2160 |
| cagggcaccc accagcagct gctggcccag ggcggcctct acgccaagct ggtgcagcgg | 2220 |
| cagatgctgg ggcttcagcc cgccgcagac ttcacagctg ccacaacga gcctgtagcc | 2280 |
| aacggcagtc acaaggcctg a | 2301 |

<210> SEQ ID NO 75
<211> LENGTH: 919
<212> TYPE: DNA
<213> ORGANISM: Homo sapiens

<400> SEQUENCE: 75

| | |
|---|---|
| tgggggccc ctgcttctcc cggtggggca gaggacccgg tgcctgcctg gcagatgtgc | 60 |
| ccacggaggc ccccagctgc cctccgagcc caggcctgca gcactgaaag acgacctgcc | 120 |
| atgtcccatg gatcaccgct tcctgcatct tgccccctggt ccctgcccca ttcccagggc | 180 |
| actccttacc cctgctgccc tgagccaacg ccttcacgga cctccctagc ctcctaagca | 240 |
| aaggtagagc tgccttttta aacctaggtc ttaccagggt ttttactgtt tggtttgagg | 300 |
| caccccagtc aactcctaga tttcaaaaac ctttttctaa ttgggagtaa tggcgggcac | 360 |
| tttcaccaag atgttctaga aacttctgag ccaggagtga atggcccttc cttagtagcc | 420 |
| tgggggatgt ccagagacta ggcctctccc ctttaccct ccagagaagg ggcttccctg | 480 |
| tcccggaggg agacacgggg aacgggattt tccgtctctc cctcttgcca gctctgtgag | 540 |
| tctggccagg gcgggtaggg agcgtggagg gcatctgtct gccatcgccc gctgccaatc | 600 |
| taagccagtc tcactgtgaa ccacacgaaa cctcaactgg gggagtgagg ggctggccag | 660 |
| gtctggaggg gcctcagggg tgcccccagc ccggcaccca gcgctttcgc ccctcgtcca | 720 |
| cccaccctg gctggcagcc tccctcccca cacccgcccc tgtgctctgc tgtctggagg | 780 |
| ccacgtggat gttcatgaga tgcattctct tctgtctttg gtggatggga tggtggcaaa | 840 |
| gcccaggatc tggctttgcc agaggttgca acatgttgag agaacccggt caataaagtg | 900 |
| tactacctct taccccctaa | 919 |

<210> SEQ ID NO 76
<211> LENGTH: 978

```
<212> TYPE: DNA
<213> ORGANISM: Homo sapiens

<400> SEQUENCE: 76
atgctgccga gagtgggctg ccccgcgctg ccgctgccgc cgccgccgct gctgccgctg      60
ctgctgctgc tactgggcgc gagtggcggc ggcggcgggg cgcgcgcgga ggtgctgttc     120
cgctgcccgc cctgcacacc cgagcgcctg gccgcctgcg ggccccccgcc ggttgcgccg    180
cccgccgcgg tggccgcagt ggccggaggc cccgcatgc catgcgcgga gctcgtccgg      240
gagccgggct gcggctgctg ctcggtgtgc gcccggctgg agggcgaggc gtgcggcgtc     300
tacaccccgc gctgcggcca ggggctgcgc tgctatcccc acccgggctc cgagctgccc    360
ctgcaggcgc tggtcatggg cgagggcact tgtgagaagc gccgggacgc cgagtatggc     420
gccagcccga agcaggttgc agacaatggc gatgaccact cagaaggagg cctggtggag    480
aaccacgtgg acagcaccat gaacatgttg ggcgggggag gcagtgctgg ccggaagccc     540
ctcaagtcgg gtatgaagga gctggccgtg ttccgggaga aggtcactga gcagcaccgg    600
cagatgggca agggtggcaa gcatcacctt ggcctggagg agcccaagaa gctgcgacca     660
ccccctgcca ggactccctg ccaacaggaa ctggaccagg tcctggagcg gatctccacc    720
atgcgccttc cggatgagcg gggccctctg gagcacctct actccctgca catccccaac     780
tgtgacaagc atggcctgta caacctcaaa cagtgcaaga tgtctctgaa cgggcagcgt    840
ggggagtgct ggtgtgtgaa ccccaacacc gggaagctga tccagggagc ccccaccatc     900
cgggggggacc ccgagtgtca tctcttctac aatgagcagc aggaggctcg cggggtgcac    960
acccagcgga tgcagtag                                                   978

<210> SEQ ID NO 77
<211> LENGTH: 331
<212> TYPE: DNA
<213> ORGANISM: Homo sapiens

<400> SEQUENCE: 77
accgcagcca gccggtgcct ggcgcccctg cccccgccc ctctccaaac accggcagaa       60
aacggagagt gcttgggtgg tgggtgctgg aggattttcc agttctgaca cacgtattta     120
tatttggaaa gagaccagca ccgagctcgg cacctccccg gcctctctct tcccagctgc     180
agatgccaca cctgctcctt cttgctttcc ccggggagg aaggggggttg tggtcgggga     240
gctggggtac aggtttgggg aggggaagga gaaatttttta ttttttgaacc cctgtgtccc   300
ttttgcataa gattaaagga aggaaaagta a                                    331

<210> SEQ ID NO 78
<211> LENGTH: 3000
<212> TYPE: DNA
<213> ORGANISM: Homo sapiens

<400> SEQUENCE: 78
atggggccgg ccccgctgcc gctgctgctg ggcctcttcc tccccgcgct ctggcgtaga      60
gctatcactg aggcaaggga agaagccaag ccttacccgc tattcccggg accttttcca    120
gggagcctgc aaactgacca cacaccgctg ttatcccttc ctcacgccag tgggtaccag     180
cctgccttga tgttttcacc aacccagcct ggaagaccac atacaggaaa cgtagccatt    240
ccccaggtga cctctgtcga atcaaagccc ctaccgcctc ttgccttcaa acacacagtt     300
ggacacataa tactttctga acataaaggt gtcaaattta attgctcaat cagtgtacct    360
```

```
aatatatacc aggacaccac aatttcttgg tggaaagatg ggaaggaatt gcttggggca    420
catcatgcaa ttacacagtt ttatccagat gatgaagtta cagcaataat cgcttccttc    480
agcataacca gtgtgcagcg ttcagacaat gggtcgtata tctgtaagat gaaaataaac    540
aatgaagaga tcgtgtctga tcccatctac atcgaagtac aaggacttcc tcactttact    600
aagcagcctg agagcatgaa tgtcaccaga acacagcct tcaacctcac ctgtcaggct    660
gtgggcccgc ctgagcccgt caacattttc tgggttcaaa acagtagccg tgttaacgaa    720
cagcctgaaa atccccctc cgtgctaact gttccaggcc tgacggagat ggcggtcttc    780
agttgtgagg cccacaatga caaagggctg accgtgtcca agggagtgca gatcaacatc    840
aaagcaattc cctccccacc aactgaagtc agcatccgta acagcactgc acacagcatt    900
ctgatctcct gggttcctgg ttttgatgga tactccccgt tcaggaattg cagcattcag    960
gtcaaggaag ctgatccgct gagtaatggc tcagtcatga ttttttaacac ctctgcctta    1020 ccacatctgt accaaatcaa gcagctgcaa gccctggcta attacagcat tggtgtttcc    1080
tgcatgaatg aaataggctg gtctgcagtg agcccttgga ttctagccag cacgactgaa    1140
ggagccccat cagtagcacc tttaaatgtc actgtgtttc tgaatgaatc tagtgataat    1200
gtggacatca gatggatgaa gcctccgact aagcagcagg atggagaact ggtgggctac    1260
cggatatccc acgtgtggca gagtgcaggg atttccaaag agctcttgga ggaagttggc    1320
cagaatggca gccgagctcg gatctctgtt caagtccaca atgctacgtg cacagtgagg    1380
attgcagccg tcaccagagg gggagttggg cccttcagtg atccagtgaa aatatttatc    1440
cctgcacacg gttgggtaga ttatgccccc tcttcaactc cggcgcctgg caacgcagat    1500
cctgtgctca tcatctttgg ctgcttttgt ggatttattt tgattgggtt gatttttatac    1560 atctccttgg ccatcagaaa aagagtccag gagacaaagt ttgggaatgc attcacagag    1620
gaggattctg aattagtggt gaattatata gcaaagaaat ccttctgtcg gcgagccatt    1680
gaacttacct tacatagctt gggagtcagt gaggaactac aaaataaact agaagatgtt    1740
gtgattgaca ggaatcttct aattcttgga aaaattctgg gtgaaggaga gtttgggtct    1800
gtaatggaag gaaatcttaa gcaggaagat gggacctctc tgaaagtggc agtgaagacc    1860
atgaagttgg acaactcttc acagcgggag atcgaggagt ttctcagtga ggcagcgtgc    1920
atgaaagact tcagccaccc aaatgtcatt cgacttctag gtgtgtgtat agaaatgagc    1980
tctcaaggca tcccaaagcc catggtaatt ttacccttca tgaaatacgg ggacctgcat    2040
acttacttac tttattcccg attggagaca ggaccaaagc atattcctct gcagacacta    2100
ttgaagttca tggtggatat tgccctggga atggagtatc tgagcaacag gaattttctt    2160
catcgagatt tagctgctcg aaactgcatg ttgcagatg acatgactgt ctgtgttgcg    2220
gacttcggcc tctctaagaa gatttacagt ggcgattatt accgccaagg ccgcattgct    2280
aagatgcctg ttaaatggat cgccatagaa agtcttgcag accgagtcta cacaagtaaa    2340
agtgatgtgt gggcatttgg cgtgaccatg tgggaaatag ctacgcgggg aatgactccc    2400
tatcctgggg tccagaacca tgagatgtat gactatcttc tccatggcca caggttgaag    2460
cagcccgaag actgcctgga tgaactgtat gaaataatgt actcttgctg gagaaccgat    2520
cccttagacc gccccacctt ttcagtattg aggctgcagc tagaaaaact cttagaaagt    2580
ttgcctgacg ttcggaacca agcagacgtt atttacgtca atacacagtt gctggagagc    2640
tctgagggcc tggcccaggg ctccacccctt gctccactgg acttgaacat cgaccctgac    2700
tctataattg cctcctgcac tccccgcgct gccatcagtg tggtcacagc agaagttcat    2760
```

-continued

```
gacagcaaac ctcatgaagg acggtacatc ctgaatgggg gcagtgagga atgggaagat    2820
ctgacttctg cccccctctgc tgcagtcaca gctgaaaaga acagtgtttt accgggggag   2880
agacttgtta ggaatggggt ctcctggtcc cattcgagca tgctgcccctt gggaagctca   2940
ttgcccgatg aacttttgtt tgctgacgac tcctcagaag gctcagaagt cctgatgtga   3000
```

<210> SEQ ID NO 79
<211> LENGTH: 504
<212> TYPE: DNA
<213> ORGANISM: Homo sapiens

<400> SEQUENCE: 79

```
ggagaggtgc ggggagacat tccaaaaatc aagccaattc ttctgctgta ggagaatcca     60
attgtacctg atgttttttgg tatttgtctt ccttaccaag tgaactccat ggccccaaag    120
caccagatga atgttgttaa gtaagctgtc attaaaaata cataatatat atttatttaa    180
agagaaaaaa tatgtgtata tcatggaaaa agacaaggat attttaataa aacattactt    240
atttcatttc acttatcttg catatcttaa aattaagctt cagctgctcc ttgatattaa    300
catttgtaca gagttgaagt tgttttttca agttcttttc ttttttcatga ctattaaatg    360
taaaaatatt tgtaaaatga aatgccatat ttgacttggc ttctggtctt gatgtatttg    420
ataagaatga ttcattcaat gtttaaagtt gtataactga ttaattttct gatatggctt    480
cctaataaaa tatgaataag gaag                                           504
```

<210> SEQ ID NO 80
<211> LENGTH: 999
<212> TYPE: DNA
<213> ORGANISM: Homo sapiens

<400> SEQUENCE: 80

```
atgctgctga aagagtaccg gatctgcatg ccgctcaccg tagacgagta caaaattgga     60
cagctgtaca tgatcagcaa acacagccat gaacagagtg accggggaga aggggtggag    120
gtcgtccaga atgagccctt tgaggaccct caccatggca atgggcagtt caccgagaag    180
cgggtgtatc tcaacagcaa actgcctagt tgggctagag ctgttgtccc caaaatattt    240
tatgtgacag agaaggcttg gaactattat ccctacacaa ttacagaata cacatgttcc    300
tttctgccga aattctccat tcatatagaa accaagtatg aggacaacaa aggaagcaat    360
gacaccattt tcgacaatga agccaaagac gtggagagag aagtttgctt tattgatatt    420
gcctgcgatg aaattccaga gcgctactac aaagaatctg aggatcctaa gcacttcaag    480
tcagagaaga caggacgggg acagttgagg gaaggctgga gagatagtca tcagcctatc    540
atgtgctcct acaagctggt gactgtgaag tttgaggtct gggggcttca gaccagagtg    600
gaacaatttg tacacaaggt ggtccgagac attctgctga ttggacatag acaggctttt    660
gcatgggttg atgagtggta tgacatgaca atggatgaag tccagaaatt tgaacgagcc    720
actcaggaag ccaccaacaa gaaaatcggc attttccac ctgcaatttc tatctccagc    780
atcccctgc tgccttcttc cgtccgcagt gcgccttcta gtgctccatc cacccctctc    840
tccacagacg cacccgaatt tctgtccgtt cccaaagatc ggccccggaa aaagtctgcc    900
ccagaaactc tcacacttcc agaccctgag aaaaagcca ccctgaattt acccggcatg    960
cactcttcag ataagccatg tcggcccaaa tctgagtaa                           999
```

<210> SEQ ID NO 81

<211> LENGTH: 807
<212> TYPE: DNA
<213> ORGANISM: Homo sapiens

<400> SEQUENCE: 81

```
atgctgctga aagagtaccg gatctgcatg ccgctcaccg tagacgagta caaaattgga      60
cagctgtaca tgatcagcaa acacagccat gaacagagtg accggggaga aggggtggag     120
gtcgtccaga tgagcccttt tgaggaccct caccatggca atgggcagtt caccgagaag     180
cgggtgtatc tcaacagcaa actgcctagt tgggctagag ctgttgtccc caaatatttt     240
tatgtgacag agaaggcttg gaactattat ccctacacaa ttacagaata cacatgttcc     300
tttctgccga aattctccat tcatatagaa accaagtatg aggacaacaa aggaagcaat     360
gacaccattt tcgacaatga agccaaagac gtggagagag aagtttgctt tattgatatt     420
gcctgcgatg aaattccaga gcgctactac aaagaatctg ggatcctaa gcacttcaag     480
tcagagaaga caggacgggg acagttgagg aaggctgga gagatagtca tcagcctatc     540
atgtgctcct acaagctggt gactgtgaag tttgaggtct gggggcttca gaccagagtg     600
gaacaatttg tacacaaggt ggtccgagac attctgctga ttggacatag acaggctttt     660
gcatgggttg atgagtggta tgatatgaca atggatgatg ttcgggaata cgagaaaaac     720
atgcatgaac aaaccaacat aaaagtttgc aatcagcatt cctcccctgt ggatgacata     780
gagagtcatg cccaaacaag tacatga                                         807
```

<210> SEQ ID NO 82
<211> LENGTH: 954
<212> TYPE: DNA
<213> ORGANISM: Homo sapiens

<400> SEQUENCE: 82

```
caatggatga agtccgagaa tttgaacgag ccactcagga agccaccaac aagaaaatcg      60
gcatttccc acctgcaatt tctatctcca gcatcccct gctgccttct tccgtccgca     120
gtgcgccttc tagtgctcca tccaccccctc tctccacaga cgcacccgaa tttctgtccg     180
ttcccaaaga tcggccccgg aaaaagtctg ccccagaaac tctcacactt ccagaccctg     240
agaaaaaagc caccctgaat ttacccggca tgcactcttc agataagcca tgtcggccca     300
aatctgagta actttatata aatatctcat gggggtttat attttcattt gttgttgttg     360
tttttttta agaatcttct gatagagaaa aagactgctt tgtcactcaa acatgttcct     420
tcgacccttc agtgtgcatg tgactcagta acttcacata gaatatgatt ccctaagtat     480
gctacacagc atcatattag atgtaagatg taagacttgc aaaggacaga aggaatcttc     540
tgtaaccaca tagctgtatg ccagagagga agccttgtta ttgggcattt gatgaggttt     600
ggcatggact tcaaggataa atgaatgaaa actttgcacc acttttgtta caaggtacgg     660
tagaaaatag tgaagtcagt ttcctctcat caaatctaaa attctccaaa atactctcag     720
gcataacata cttagctgtt aaattttgaa ctgctaatta ctaatacttg aataccaata     780
gttactgaga ttcctatttt gtggttagtc tgactcagga tttggagcct aattaactct     840
aaacttttga aaattttaat catcaagcta tagaggctcc aagtgcaatt aataataact     900
catttatacc ttccacagaa tttaataaag attctacttg tttctgtctt ttaa            954
```

<210> SEQ ID NO 83
<211> LENGTH: 1113
<212> TYPE: DNA
<213> ORGANISM: Homo sapiens

<400> SEQUENCE: 83

```
atggacgccc ccaggcaggt ggtcaacttt gggcctggtc ccgccaagct gccgcactca      60
gtgttgttag agatacaaaa ggaattatta gactacaaag gagttggcat tagtgttctt     120
gaaatgagtc acaggtcatc agattttgcc aagattatta acaatacaga gaatcttgtg     180
cgggaattgc tagctgttcc agacaactat aaggtgattt ttctgcaagg aggtgggtgc     240
ggccagttca gtgctgtccc cttaaacctc attggcttga agcaggaag gtgtgctgac     300
tatgtggtga caggagcttg gtcagctaag gccgcagaag aagccaagaa gtttgggact     360
ataaatatcg ttcaccctaa acttgggagt tatacaaaaa ttccagatcc aagcacctgg     420
aacctcaacc cagatgcctc ctacgtgtat tattgcgcaa atgagacggt gcatggtgtg     480
gagtttgact ttatacccga tgtcaaggga gcagtactgg tttgtgacat gtcctcaaac     540
ttcctgtcca agccagtgga tgtttccaag tttggtgtga tttttgctgg tgcccagaag     600
aatgttggct ctgctggggt caccgtggtg attgtccgtg atgacctgct ggggtttgcc     660
ctccgagagt gcccctcggt cctggaatac aaggtgcagg ctggaaacag ctccttgtac     720
aacacgcctc catgtttcag catctacgtc atgggcttgg ttctggagtg gattaaaaac     780
aatggaggtg ccgcggccat ggagaagctt agctccatca atctcaaac aatttatgag     840
attattgata ttctcaagg attctacgtt tgtccagtgg agcccaaaa tagaagcaag     900
atgaatattc cattccgcat tggcaatgcc aaaggagatg atgctttaga aaaagatttt    960
cttgataaag ctcttgaact caatatgttg tccttgaaag gcataggtc tgtgggaggc    1020
atccgggcct ctctgtataa tgctgtcaca attgaagacg ttcagaagct ggccgccttc    1080
atgaaaaaat ttttggagat gcatcagcta tga                                 1113
```

<210> SEQ ID NO 84
<211> LENGTH: 1007
<212> TYPE: DNA
<213> ORGANISM: Homo sapiens

<400> SEQUENCE: 84

```
acacatccta accaggatat actctgttct tgaacaacat acaaagttta aagtaacttg      60
gggatggcta caaaaagtta acacagtatt tttctcaaat gaacatgttt attgcagatt     120
cttctttttt gaaagaacaa cagcaaaaca tccacaactc tgtaaagctg gtgggaccta     180
atgtcaccttt aattctgact tgaactggaa gcattttaag aaatcttgtt gcttttctaa     240
caaattcccg cgtattttgc ctttgctgct acttttccta gttagatttc aaacttgcct     300
gtggacttaa taatgcaagt tgcgattaat tatttctgga gtcatgggaa cacacagcac     360
agagggtagg ggggccctct agtgctgaa tctacacatc tgtggggtct cctgggttca     420
gcggctgttg attcaaggtc aacattgacc attggaggag tggtttaaga gtgccaggcg     480
aagggcaaac tgtagatcga tctttatgct gttattacag gagaagtgac atacttttata     540
tatgtttata ttagcaaggt ctgttttttaa taccatatac tttatatttc tatacatttta     600
tatttctaat aatacagtta tcactgatat atgtagacac ttttagaatt tattaaatcc     660
ttgaccttgt gcattatagc attccattag caagagttgt accccctccc cagtcttcgc     720
cttcctctttt ttaagctgtt ttatgaaaaa gacctagaag ttcttgattc attttttacca     780
ttctttccat aggtagaaga gaaagttgat tggttggttg ttttttcaatt atgccattaa     840
actaaacatt tctgttaaat taccctatcc tttgttctct actgttttct ttgtaatgta     900
```

| | |
|---|---|
| tgactacgag agtgatactt tgctgaaaag tctttcccct attgtttatc tattgtcagt | 960 |
| attttatgtt gaatatgtaa agaacattaa agtcctaaaa catctaa | 1007 |

<210> SEQ ID NO 85
<211> LENGTH: 2532
<212> TYPE: DNA
<213> ORGANISM: Homo sapiens

<400> SEQUENCE: 85

| | |
|---|---|
| atggcgaagc cgctgacgga cagcgagaag cggaagcaga tcagcgtgcg cggcctggcg | 60 |
| gggctaggcg acgtggccga ggtgcggaag agcttcaacc ggcacttgca cttcacgctg | 120 |
| gtcaaggacc gcaatgtggc cacgccccgc gactacttct tcgcgctggc gcacacggtg | 180 |
| cgcgaccacc tcgtgggccg ctggatccgc acgcagcagc actactacga gcgcgacccc | 240 |
| aagcgcattt attatctttc cctggaattc tacatgggtc gcacgctgca gaacacgatg | 300 |
| gtgaacctgg gccttcagaa tgcctgcgat gaagccatct atcagttggg gttagacttg | 360 |
| gaggaactcg aggagataga agaagatgct ggccttggga tggaggcct ggggaggctg | 420 |
| gcagcgtgtt tccttgactc aatggctacc ttgggcctgg cagcatacgg ctatggaatc | 480 |
| cgctatgaat ttgggatttt taaccagaag attgtcaatg ctggcaggt agaggaggcc | 540 |
| gatgactggc tgcgctacgg caaccctgg gagaaagcgc ggcctgagta tatgcttccc | 600 |
| gtgcacttct acggacgcgt ggagcacacc cccgacggcg tgaagtggct ggacacacag | 660 |
| gtggtgctgg ccatgcccta cgacacccca gtgcccggct acaagaacaa caccgtcaac | 720 |
| accatgcggc tgtggtccgc caaggctccc aacgacttca gctgcagga cttcaacgtg | 780 |
| ggagactaca tcgaggcggt cctggaccgg aacttggctg agaacatctc cagggtcctg | 840 |
| tatccaaatg ataacttctt tgaggggaag gagctgcggc tgaagcagga gtacttcgtg | 900 |
| gtggccgcca cgctccagga catcatccgc cgcttcaagt cgtccaagtt cggctgccgg | 960 |
| gaccctgtga aacctgttt cgagacgttc ccagacaagg tggccatcca gctgaacgac | 1020 |
| acccaccccg ccctctccat ccctgagctc atgcggatcc tggtggacgt ggagaaggtg | 1080 |
| gactgggaca aggcctggga aatcacgaag aagacctgtg catacaccaa ccacactgtg | 1140 |
| ctgcctgagg ccttggagcg ctggcccgtg tccatgtttg agaagctgct gccgcggcac | 1200 |
| ctggagataa tctatgccat caaccagcgg cacctggacc acgtgccgc gctgtttccc | 1260 |
| ggcgatgtgg accgctgcg caggatgtct gtgatcgagg aggggactg caagcggatc | 1320 |
| aacatggccc acctgtgtgt gattgggtcc catgctgtca atggtgtggc gaggatccac | 1380 |
| tcggagatcg tgaaacagtc ggtctttaag gattttatg aactggagcc agagaagttc | 1440 |
| cagaataaga ccaatggcat caccccccgc cggtggctgc tgctgtgcaa cccggggctg | 1500 |
| gccgatacca tcgtggagaa aattggggag gagttcctga ctgacctgag ccagctgaag | 1560 |
| aagctgctgc cgctggtcag tgacgaggtg ttcatcaggg acgtggccaa ggtcaaacag | 1620 |
| gagaacaagc tcaagttctc ggccttcctg agaaggagt acaaggtgaa gatcaacccc | 1680 |
| tcctccatgt tcgatgtgca tgtgaagagg atccacgagt acaagcggca gctgctcaac | 1740 |
| tgcctgcacg tcgtcaccct gtacaatcga atcaagagag acccggccaa ggcttttgtg | 1800 |
| cccaggactg ttatgattgg gggcaaggca gcgcccggtt accacatggc caagctgatc | 1860 |
| atcaagttgg tcacctccat cggcgacgtc gtcaatcatg acccagttgt gggtgacagg | 1920 |
| ttgaaagtga tcttcctgga gaactaccgt gtgtccttgg ctgagaaagt gatcccggcc | 1980 |
| gctgatctgt cgcagcagat ctccactgca ggcaccgagg cctcaggcac aggcaacatg | 2040 |

```
aagttcatgc tcaacggggc cctcaccatc ggcaccatgg acggcgccaa cgtggagatg      2100
gccgaggagg ccggggccga gaacctcttc atcttcggcc tgcgggtgga ggatgtcgag      2160
gccttggacc ggaaagggta caatgccagg gagtactacg accacctgcc cgagctgaag      2220
caggccgtgg accagatcag cagtggcttt ttttctccca aggagccaga ctgcttcaag      2280
gacatcgtga acatgctgat gcaccatgac aggttcaagg tgtttgcaga ctatgaagcc      2340
tacatgcagt gccaggcaca ggtggaccag ctgtaccgga accccaagga gtggaccaag      2400
aaggtcatca ggaacatcgc ctgctcgggc aagttctcca gtgaccggac catcacggag      2460
tatgcacggg agatctgggg tgtggagccc tccgacctgc agatcccgcc ccccaacatc      2520
ccccgggact ag                                                         2532

<210> SEQ ID NO 86
<211> LENGTH: 1490
<212> TYPE: DNA
<213> ORGANISM: Homo sapiens

<400> SEQUENCE: 86
gcacaccctg ccttggcggg accagcgggc atttgttttc ttgctgactt tgcacctcct        60
ttttccccca aacactttgc cagccactgg tggtccctgc ttttctgagt accatgtttc       120
caggaggggc catggggtc agggtggttt tgagagagca gggtaaggaa ggaatgtgct       180
agaagtgctc ctagtttctt gtaaaggaag ccagagttga cagtacaaag ggtcgtggcc       240
agccctgcag cttcagcacc tgccccaccc agagtgggag tcaggtggag ccacctgctg       300
ggctccccca gaactttgca cacatcttgc tatgtattag ccgatgtctt tagtgttgag       360
cctctggatt ctggggtctg ggccagtggc catagtgaag cctgggaatg agtgttactg       420
cagcatctgg gctgccagcc acaggaagg gccaagcccc atgtagcccc agtcatcctg       480
cccagccctg cctcctggcc atgccggag gggtcggatc ctctaggcat cgccttcaca       540
gccccctgcc ccctgccctc tgtcctggct ctgcacctgg tatatgggtc atggacccag       600
atggggcttt ccctttgtag ccatccaatg ggcattgtgt gggtgcttgg aacccgggat       660
gactgagggg gacactggag tgggtgcttg tgtctgctgt ctcagaggcc ttggtcagga       720
tgaagttggc tgacacagct tagcttggtt ttgcttattc aaaagagaaa ataactacac       780
atggaaatga aactagctga agccttttct tgttttagca actgaaaatt gtacttggtc       840 actttgtgc ttgaggaggc ccattttctg cctggcaggg ggcaggtctg tgccctcccg       900
ctgactcctg ctgtgtcctg aggtgcattt cctgttgtac acacaagggc caggctccat       960
tctccctccc tttccaccag tgccacagcc tcgtctggaa aaaggaccag gggtcccgga      1020
ggaacccatt tgtgctctgc ttggacagca ggcctggcac tggaggtgg gggtgagccc      1080 ctcacagcct tgcccctccc caaggctggc aacctgcctc ccattgccca agagagaggg      1140
cagggaacag gctactgtcc ttccctgtgg aattgccgag aaatctagca ccttgcatgc      1200
tggatctggg ctgcggggag gctctttttc tccctggcct ccagtgccca ccaggaggat      1260
ctgcgcacgg tgcacagccc accagagcac tacagccttt tattgagtgg ggcaagtgct      1320
gggctgtggt cgtgccctga cagcatcttc cccaggcagc ggctctgtgg aggaggccat      1380
actcccctag ttggccactg ggccaccac cctgaccacc actgtgcccc tcattgttac      1440
tgccttgtga gataaaaact gattaaacct ttgtggctgt ggttggctga                1490

<210> SEQ ID NO 87
```

```
<211> LENGTH: 1515
<212> TYPE: DNA
<213> ORGANISM: Homo sapiens

<400> SEQUENCE: 87
atgctgtact tctctttgtt ttgggcggct cggcctctgc agagatgtgg gcagctggtc      60
aggatggcca ttcgggctca gcacagcaac gcagcccaga ctcagactgg ggaagcaaac     120
aggggctgga caggccagga gagcctgtcg gacagtgatc ctgagatgtg ggagttgctg     180
cagagggaga aggacaggca gtgtcgtggc ctggagctca ttgcctcaga gaacttctgc     240
agccgagctg cgctggaggc cctggggtcc tgtctgaaca caagtactc ggagggttat      300 cctggcaaga gatactatgg gggagcagag gtggtggatg aaattgagct gctgtgccag     360
cgccgggcct tggaagcctt tgacctggat cctgcacagt ggggagtcaa tgtccagccc     420
tactccgggt ccccagccaa cctggccgtc tacacagccc ttctgcaacc tcacgaccgg     480
atcatggggc tggacctgcc cgatgggggc catctcaccc acggctacat gtctgacgtc     540
aagcggatat cagccacgtc catcttcttc gagtctatgc cctataagct caaccccaaa     600
actggcctca ttgactacaa ccagctggca ctgactgctc gacttttccg gccacggctc     660
atcatagctg gcaccagcgc ctatgctcgc ctcattgact acgcccgcat gagagaggtg     720
tgtgatgaag tcaaagcaca cctgctggca gacatggccc acatcagtgg cctggtggct     780
gccaaggtga ttccctcgcc tttcaagcac gcggacatcg tcaccaccac tactcacaag     840
actcttcgag gggccaggtc agggctcatc ttctaccgga aaggggtgaa ggctgtggac     900
cccaagactg gccgggagat cccttacaca tttgaggacc gaatcaactt tgccgtgttc     960
ccatccctgc agggggggccc ccacaatcat gccattgctg cagtagctgt ggccctaaag    1020
caggcctgca cccccatgtt ccgggagtac tccctgcagg ttctgaagaa tgctcgggcc    1080
atggcagatg ccctgctaga gcgaggctac tcactggtat caggtggtac tgacaaccac    1140
ctggtgctgg tggacctgcg gcccaagggc ctggatggag ctcggctgga gcgggtgcta    1200
gagcttgtat ccatcactgc caacaagaac acctgtcctg agaccgaag tgccatcaca    1260 ccgggcggcc tgcggcttgg ggccccagcc ttaacttctc gacagttccg tgaggatgac    1320
ttccggagag ttgtggactt tatagatgaa ggggtcaaca ttggcttaga ggtgaagagc    1380
aagactgcca agctccagga tttcaaatcc ttcctgctta aggactcaga acaagtcag     1440 cgtctggcca acctcaggca acgggtggag cagtttgcca gggccttccc catgcctggt    1500
tttgatgagc attga                                                    1515

<210> SEQ ID NO 88
<211> LENGTH: 570
<212> TYPE: DNA
<213> ORGANISM: Homo sapiens

<400> SEQUENCE: 88
aggcacctgg gaaatgaggc ccacagactc aaagttactc tccttccccc tacctgggcc      60
agtgaaatag aaagcctttc tattttttgg tgcgggaggg aagacctctc acttagggca     120
agagccaggt atagtctccc ttcccagaat ttgtaactga agatctttt tctttttcct      180 ttttttggta acaagactta aaggagggc ccaggcactt tctgtttgaa ccctgtcat       240 gatcacagtg tcagagacgc gtcctctttc ttggggaagt tgaggagtgc ccttcagagc     300
cagtagcagg caggggtggg taggcaccct ccttcctgtt tttatctaat aaaatgctaa     360
cctgccctga gtttccatta ctgtgggtgg ggttcccctg ggccaaacag tgatttgtct     420
```

```
ccctcaatgt gtacaccgct ccgctcccac caccgctacc acaaggaccc ccggggctgc    480
agcctcctct ttctgtctct gatcagagcc gacaccagac gtgattagca ggcgcagcaa    540
attcaatttg ttaaatgaaa ttgtattttg                                     570
```

<210> SEQ ID NO 89
<211> LENGTH: 1374
<212> TYPE: DNA
<213> ORGANISM: Homo sapiens

<400> SEQUENCE: 89

```
atgcgcccgc caagtccgct gcccgcccgc tggctatgcg tgctggcagg cgccctcgcc     60
tgggcccttg ggccggcggg cggccaggcg ccaggctgc aggaggagtg tgactatgtg    120
cagatgatcg aggtgcagca caagcagtgc ctggaggagg cccagctgga gaatgagaca    180
ataggctgca gcaagatgtg ggacaacctc acctgctggc cagccacccc tcggggccag    240
gtagttgtct tggcctgtcc cctcatcttc aagctcttct cctccattca aggccgcaat    300
gtaagccgca gctgcaccga cgaaggctgg acgcacctgg agcctggccc gtaccccatt    360
gcctgtggtt tggatgacaa ggcagcgagt ttggatgagc agcagaccat gttctacggt    420
tctgtgaaga ccggctacac cattggctac ggcctgtccc tcgccaccct tctggtcgcc    480
acagctatcc tgagcctgtt caggaagctc cactgcacgc ggaactacat ccacatgcac    540
ctcttcatat ccttcatcct gagggctgcc gctgtcttca tcaaagactt ggccctcttc    600
gacagcgggg agtcggacca gtgctccgag ggctcggtgg gctgtaaggc agccatggtc    660
tttttccaat attgtgtcat ggctaacttc ttctggctgc tggtggaggg cctctacctg    720
tacaccctgc ttgccgtctc cttcttctct gagcggaagt acttctgggg gtacatactc    780
atcggctggg gggtacccag cacattcacc atggtgtgga ccatcgccag gatccatttt    840
gaggattatg ggtgctggga caccatcaac tcctcactgt ggtggatcat aaagggcccc    900
atcctcacct ccatcttggt aaacttcatc ctgtttattt gcatcatccg aatcctgctt    960
cagaaactgc ggcccccaga tatcaggaag agtgacagca gtccatactc aaggctagcc   1020
aggtccacac tcctgctgat cccctgtttt ggagtacact acatcatgtt cgccttcttt   1080
ccggacaatt ttaagcctga agtgaagatg gtctttgagc tcgtcgtggg gtctttccag   1140
ggttttgtgg tggctatcct ctactgcttc ctcaatggtg aggtgcaggc ggagctgagg   1200
cggaagtggc ggcgctggca cctgcagggc gtcctgggct ggaacccaa ataccggcac   1260 ccgtcgggag gcagcaacgg cgccacgtgc agcacgcagg tttccatgct gacccgcgtc   1320
agcccaggtg cccgccgctc ctccagcttc aagccgaag tctccctggt ctga          1374
```

<210> SEQ ID NO 90
<211> LENGTH: 1287
<212> TYPE: DNA
<213> ORGANISM: Homo sapiens

<400> SEQUENCE: 90

```
ccaccaggat cccaggggcc caaggcggcc cctcccgccc cttcccactc acccggcag     60 acgccgggga cagaggcctg cccgggcgcg ccagccccg ccctgggct cggaggctgc    120 ccccggcccc ctggtctctg gtccggacac tcctagagaa cgcagcccta gagcctgcct    180
ggagcgtttc tagcaagtga gagagatggg agctcctctc ctggaggatt gcaggtggaa    240
ctcagtcatt agactcctcc tccaaaggcc ccctacgcca atcaagggca aaaagtctac    300
```

| | |
|---|---|
| atactttcat cctgactctg cccctgctg gctcttctgc ccaattggag gaaagcaacc | 360 |
| ggtggatcct caaacaacac tggtgtgacc tgagggcaga aaggttctgc ccgggaaggt | 420 |
| caccagcacc aacaccacgg tagtgcctga aatttcacca ttgctgtcaa gttcctttgg | 480 |
| gttaagcatt accactcagg catttgactg aagatgcagc tcactaccct attctctctt | 540 |
| tacgcttagt tatcagctttt ttaaagtggg ttattctgga gtttttgttt ggagagcaca | 600 |
| cctatcttag tggttcccca ccgaagtgga ctggcccctg ggtcagtctg gtgggaggac | 660 |
| ggtgcaaccc aaggactgag ggactctgaa gcctctggga aatgagaagg cagccaccag | 720 |
| cgaatgctag gtctcggact aagcctacct gctctccaag tctcagtggc ttcatctgtc | 780 |
| aagtgggatc tgtcacacca gccatactta tctctctgtg ctgtggaagc aacaggaatc | 840 |
| aagagctgcc ctccttgtcc acccaccat gtgccaactg ttgtaactag gctcagagat | 900 |
| gtgcacccat gggctctgac agaaagcaga tacctcaccc tgctacacat acaggatttg | 960 |
| aactcagatc tgtctgatag gaatgtgaaa gcacggactc ttactgctaa cttttgtgta | 1020 |
| tcgtaaccag ccagatcctc ttggttattt gtttaccact tgtattatta atgccattat | 1080 |
| ccctgaatcc cccttgccac cccaccctcc ctggagtgtg gctgaggagg cctccatctc | 1140 |
| atgtatcatc tggataggag cctgctggtc acagcctcct ctgtctgccc ttcaccccag | 1200 |
| tggccactca gcttcctacc cacacctctg ccagaagatc ccctcaggac tgcaacaggc | 1260 |
| ttgtgcaaca taaatgttg gcttgga | 1287 |

<210> SEQ ID NO 91
<211> LENGTH: 32
<212> TYPE: DNA
<213> ORGANISM: Artificial
<220> FEATURE:
<223> OTHER INFORMATION: ABCB9 3'UTR cloning forward primer

<400> SEQUENCE: 91
ccggccctcg agtgggggc ccctgcttct cc    32

<210> SEQ ID NO 92
<211> LENGTH: 34
<212> TYPE: DNA
<213> ORGANISM: Artificial
<220> FEATURE:
<223> OTHER INFORMATION: ABCB9 3'UTR cloning reverse primer

<400> SEQUENCE: 92
ccggccgcgg ccgcttaggg gtaagaggta gtac    34

<210> SEQ ID NO 93
<211> LENGTH: 32
<212> TYPE: DNA
<213> ORGANISM: Artificial
<220> FEATURE:
<223> OTHER INFORMATION: ABCB9 CDS forward primer

<400> SEQUENCE: 93
ccggccctcg agatgcggct gtggaaggcg gt    32

<210> SEQ ID NO 94
<211> LENGTH: 34
<212> TYPE: DNA
<213> ORGANISM: Artificial
<220> FEATURE:
<223> OTHER INFORMATION: ABCB9 CDS reverse primer

<400> SEQUENCE: 94

-continued ccggccgcgg ccgctcaggc cttgtgactg ccgt                               34

<210> SEQ ID NO 95
<211> LENGTH: 32
<212> TYPE: DNA
<213> ORGANISM: Artificial
<220> FEATURE:
<223> OTHER INFORMATION: IGFBP2 3'UTR forward primer

<400> SEQUENCE: 95
ccggccctcg agaccgcagc cagccggtgc ct                                 32

<210> SEQ ID NO 96
<211> LENGTH: 34
<212> TYPE: DNA
<213> ORGANISM: Artificial
<220> FEATURE:
<223> OTHER INFORMATION: IGFBP2 3'UTR reverse primer

<400> SEQUENCE: 96
ccggccgcgg ccgcttactt ttccttcctt taat                               34

<210> SEQ ID NO 97
<211> LENGTH: 32
<212> TYPE: DNA
<213> ORGANISM: Artificial
<220> FEATURE:
<223> OTHER INFORMATION: IGFBP2 CDS forward primer

<400> SEQUENCE: 97
ccggccctcg agatgctgcc gagagtgggc tg                                 32

<210> SEQ ID NO 98
<211> LENGTH: 34
<212> TYPE: DNA
<213> ORGANISM: Artificial
<220> FEATURE:
<223> OTHER INFORMATION: IGFBP2 CDS reverse primer

<400> SEQUENCE: 98
ccggccgcgg ccgcctactg catccgctgg gtgt                               34

<210> SEQ ID NO 99
<211> LENGTH: 32
<212> TYPE: DNA
<213> ORGANISM: Artificial
<220> FEATURE:
<223> OTHER INFORMATION: MERTK 3'UTR forward primer

<400> SEQUENCE: 99
ccggccctcg agggagaggt gcggggagac at                                 32

<210> SEQ ID NO 100
<211> LENGTH: 34
<212> TYPE: DNA
<213> ORGANISM: Artificial
<220> FEATURE:
<223> OTHER INFORMATION: MERTK 3'UTR reverse primer

<400> SEQUENCE: 100
ccggccgcgg ccgccttcct tattcatatt ttat                               34

<210> SEQ ID NO 101
<211> LENGTH: 32
<212> TYPE: DNA

<213> ORGANISM: Artificial
<220> FEATURE:
<223> OTHER INFORMATION: MERTK CDS forward primer

<400> SEQUENCE: 101
ccggccctcg agatggggcc ggccccgctg cc                           32

<210> SEQ ID NO 102
<211> LENGTH: 34
<212> TYPE: DNA
<213> ORGANISM: Artificial
<220> FEATURE:
<223> OTHER INFORMATION: MERTK CDS reverse primer

<400> SEQUENCE: 102
ccggccgcgg ccgctcacat caggacttct gagc                         34

<210> SEQ ID NO 103
<211> LENGTH: 32
<212> TYPE: DNA
<213> ORGANISM: Artificial
<220> FEATURE:
<223> OTHER INFORMATION: PITPNC1 3'UTR forward primer

<400> SEQUENCE: 103
ccggccctcg agcaatggat gaagtccgag aa                           32

<210> SEQ ID NO 104
<211> LENGTH: 34
<212> TYPE: DNA
<213> ORGANISM: Artificial
<220> FEATURE:
<223> OTHER INFORMATION: PITPNC1 3'UTR reverse primer

<400> SEQUENCE: 104
ccggccgcgg ccgcttaaaa gacagaaaca agta                         34

<210> SEQ ID NO 105
<211> LENGTH: 32
<212> TYPE: DNA
<213> ORGANISM: Artificial
<220> FEATURE:
<223> OTHER INFORMATION: PITPNC1 CDS forward primer

<400> SEQUENCE: 105
ccggccctcg agatgctgct gaaagagtac cg                           32

<210> SEQ ID NO 106
<211> LENGTH: 34
<212> TYPE: DNA
<213> ORGANISM: Artificial
<220> FEATURE:
<223> OTHER INFORMATION: PITPNC1 CDS reverse primer

<400> SEQUENCE: 106
ccggccgcgg ccgctcatgt acttgtttgg gcat                         34

<210> SEQ ID NO 107
<211> LENGTH: 32
<212> TYPE: DNA
<213> ORGANISM: Artificial
<220> FEATURE:
<223> OTHER INFORMATION: PSAT1 3'UTR forward primer

<400> SEQUENCE: 107
ccggccctcg agacacatcc taaccaggat at                           32

```
<210> SEQ ID NO 108
<211> LENGTH: 34
<212> TYPE: DNA
<213> ORGANISM: Artificial
<220> FEATURE:
<223> OTHER INFORMATION: PSAT1 3'UTR reverse primer

<400> SEQUENCE: 108
ccggccgcgg ccgcttagat gttttaggac ttta                               34

<210> SEQ ID NO 109
<211> LENGTH: 34
<212> TYPE: DNA
<213> ORGANISM: Artificial
<220> FEATURE:
<223> OTHER INFORMATION: PSAT1 CDS forward primer

<400> SEQUENCE: 109
ccggccgcgg ccgctcatag ctgatgcatc tcca                               34

<210> SEQ ID NO 110
<211> LENGTH: 32
<212> TYPE: DNA
<213> ORGANISM: Artificial
<220> FEATURE:
<223> OTHER INFORMATION: PSAT1 CDS reverse primer

<400> SEQUENCE: 110
ccggccctcg agatggacgc ccccaggcag gt                                 32

<210> SEQ ID NO 111
<211> LENGTH: 32
<212> TYPE: DNA
<213> ORGANISM: Artificial
<220> FEATURE:
<223> OTHER INFORMATION: PYGB 3'UTR forward primer

<400> SEQUENCE: 111
ccggccctcg aggcacaccc tgccttggcg gg                                 32

<210> SEQ ID NO 112
<211> LENGTH: 34
<212> TYPE: DNA
<213> ORGANISM: Artificial
<220> FEATURE:
<223> OTHER INFORMATION: PYGB 3'UTR reverse primer

<400> SEQUENCE: 112
ccggccgcgg ccgctcagcc aaccacagcc acaa                               34

<210> SEQ ID NO 113
<211> LENGTH: 34
<212> TYPE: DNA
<213> ORGANISM: Artificial
<220> FEATURE:
<223> OTHER INFORMATION: PYGB CDS forward primer

<400> SEQUENCE: 113
ccggccgttt aaacatggcg aagccgctga cgga                               34

<210> SEQ ID NO 114
<211> LENGTH: 34
<212> TYPE: DNA
<213> ORGANISM: Artificial
<220> FEATURE:
```

<223> OTHER INFORMATION: PYGB CDS reverse primer

<400> SEQUENCE: 114
ccggccgcgg ccgcctagtc ccggggatg ttgg            34

<210> SEQ ID NO 115
<211> LENGTH: 32
<212> TYPE: DNA
<213> ORGANISM: Artificial
<220> FEATURE:
<223> OTHER INFORMATION: SHMT2 3'UTR forward primer

<400> SEQUENCE: 115
ccggccctcg agaggcacct gggaaatgag gc              32

<210> SEQ ID NO 116
<211> LENGTH: 34
<212> TYPE: DNA
<213> ORGANISM: Artificial
<220> FEATURE:
<223> OTHER INFORMATION: SHMT2 3'UTR reverse primer

<400> SEQUENCE: 116
ccggccgcgg ccgccaaaat acaatttcat ttaa            34

<210> SEQ ID NO 117
<211> LENGTH: 32
<212> TYPE: DNA
<213> ORGANISM: Artificial
<220> FEATURE:
<223> OTHER INFORMATION: SHMT2 CDS forward primer

<400> SEQUENCE: 117
ccggccctcg agatgctgta cttctctttg tt              32

<210> SEQ ID NO 118
<211> LENGTH: 34
<212> TYPE: DNA
<213> ORGANISM: Artificial
<220> FEATURE:
<223> OTHER INFORMATION: SHMT2 CDS reverse primer

<400> SEQUENCE: 118
ccggccgcgg ccgctcaatg ctcatcaaaa ccag            34

<210> SEQ ID NO 119
<211> LENGTH: 34
<212> TYPE: DNA
<213> ORGANISM: Artificial
<220> FEATURE:
<223> OTHER INFORMATION: VIPR CDS forward primer

<400> SEQUENCE: 119
ccggccgttt aaactcagac cagggagact tcgg            34

<210> SEQ ID NO 120
<211> LENGTH: 32
<212> TYPE: DNA
<213> ORGANISM: Artificial
<220> FEATURE:
<223> OTHER INFORMATION: VIPR CDS reverse primer

<400> SEQUENCE: 120
ccggccctcg agatgcgccc gccaagtccg ct              32

```
<210> SEQ ID NO 121
<211> LENGTH: 32
<212> TYPE: DNA
<213> ORGANISM: Artificial
<220> FEATURE:
<223> OTHER INFORMATION: VIPR1 3'UTR forward primer

<400> SEQUENCE: 121
ccggccctcg agccaccagg atcccagggg cc                                    32

<210> SEQ ID NO 122
<211> LENGTH: 34
<212> TYPE: DNA
<213> ORGANISM: Artificial
<220> FEATURE:
<223> OTHER INFORMATION: VIPR1 3'UTR reverse primer

<400> SEQUENCE: 122
ccggccgcgg ccgctccaag ccaacattta ttgt                                  34

<210> SEQ ID NO 123
<211> LENGTH: 15
<212> TYPE: DNA
<213> ORGANISM: Artificial
<220> FEATURE:
<223> OTHER INFORMATION: Complementary miR-126 sequence

<400> SEQUENCE: 123
ttactcacgg tacga                                                       15

<210> SEQ ID NO 124
<211> LENGTH: 53
<212> TYPE: DNA
<213> ORGANISM: Artificial
<220> FEATURE:
<223> OTHER INFORMATION: IGFBP2 3'UTR Mutagenesis forward primer

<400> SEQUENCE: 124 aaggggggttg tggtcgggga gctggcacac aggtttgggg aggggaagaa gaa            53

<210> SEQ ID NO 125
<211> LENGTH: 53
<212> TYPE: DNA
<213> ORGANISM: Artificial
<220> FEATURE:
<223> OTHER INFORMATION: MERTK 3'UTR Mutagenesis forward primer

<400> SEQUENCE: 125
attctaggcg atcgctcgag ggagacacgc ggggagacat tccaaaaatc aag             53

<210> SEQ ID NO 126
<211> LENGTH: 53
<212> TYPE: DNA
<213> ORGANISM: Artificial
<220> FEATURE:
<223> OTHER INFORMATION: PITPNC1 CDS Mutagenesis forward primer

<400> SEQUENCE: 126
tatgacaatg gatgatgttc gggaagtaga gaaaaacatg catgaacaaa cca             53

<210> SEQ ID NO 127
<211> LENGTH: 53
<212> TYPE: DNA
<213> ORGANISM: Artificial
<220> FEATURE:
<223> OTHER INFORMATION: SHMT2 CDS Mutagenesis forward primer
```

-continued

<400> SEQUENCE: 127
gcgaggctac tcactggtat caggtcacac tgacaaccac ctggtgctgg tgg                53

<210> SEQ ID NO 128
<211> LENGTH: 53
<212> TYPE: DNA
<213> ORGANISM: Artificial
<220> FEATURE:
<223> OTHER INFORMATION: IGFBP2 3'UTR Mutagenesis reverse primer

<400> SEQUENCE: 128
ttctcttccc cctccccaaa cctgtgtgcc agctccccga ccacaacccc ctt                53

<210> SEQ ID NO 129
<211> LENGTH: 53
<212> TYPE: DNA
<213> ORGANISM: Artificial
<220> FEATURE:
<223> OTHER INFORMATION: MERTK 3'UTR Mutagenesis reverse primer

<400> SEQUENCE: 129
cttgattttt ggaatgtctc cccgcgtgtc tccctcgagc gatcgcctag aat                53

<210> SEQ ID NO 130
<211> LENGTH: 53
<212> TYPE: DNA
<213> ORGANISM: Artificial
<220> FEATURE:
<223> OTHER INFORMATION: PITPNC1 CDS Mutagenesis reverse primer

<400> SEQUENCE: 130
tggtttgttc atgcatgttt ttctctactt cccgaacatc atccattgtc ata                53

<210> SEQ ID NO 131
<211> LENGTH: 53
<212> TYPE: DNA
<213> ORGANISM: Artificial
<220> FEATURE:
<223> OTHER INFORMATION: SHMT2 CDS Mutagenesis reverse primer

<400> SEQUENCE: 131
ccaccagcac caggtggttg tcagtgtgac ctgataccag tgagtagcct cgc                53

<210> SEQ ID NO 132
<211> LENGTH: 678
<212> TYPE: PRT
<213> ORGANISM: Homo sapiens

<400> SEQUENCE: 132

Met Ala Pro Ser Leu Ser Pro Gly Pro Ala Ala Leu Arg Arg Ala Pro
1               5                   10                  15

Gln Leu Leu Leu Leu Leu Ala Ala Glu Cys Ala Leu Ala Ala Leu
            20                  25                  30

Leu Pro Ala Arg Glu Ala Thr Gln Phe Leu Arg Pro Arg Gln Arg Arg
        35                  40                  45

Ala Phe Gln Val Phe Glu Glu Ala Lys Gln Gly His Leu Glu Arg Glu
    50                  55                  60

Cys Val Glu Glu Leu Cys Ser Arg Glu Glu Ala Arg Glu Val Phe Glu
65                  70                  75                  80

Asn Asp Pro Glu Thr Asp Tyr Phe Tyr Pro Arg Tyr Leu Asp Cys Ile
                85                  90                  95

Asn Lys Tyr Gly Ser Pro Tyr Thr Lys Asn Ser Gly Phe Ala Thr Cys

```
                100             105             110
Val Gln Asn Leu Pro Asp Gln Cys Thr Pro Asn Pro Cys Asp Arg Lys
            115                 120                 125

Gly Thr Gln Ala Cys Gln Asp Leu Met Gly Asn Phe Phe Cys Leu Cys
    130                 135                 140

Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
        195                 200                 205

Glu Ala Arg Cys Lys Asn Leu Pro Gly Ser Tyr Ser Cys Leu Cys Asp
    210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Gly Leu Lys Leu Ser Gln
            260                 265                 270

Asp Met Asp Thr Cys Glu Asp Ile Leu Pro Cys Val Pro Phe Ser Val
        275                 280                 285

Ala Lys Ser Val Lys Ser Leu Tyr Leu Gly Arg Met Phe Ser Gly Thr
    290                 295                 300

Pro Val Ile Arg Leu Arg Phe Lys Arg Leu Gln Pro Thr Arg Leu Val
305                 310                 315                 320

Ala Glu Phe Asp Phe Arg Thr Phe Asp Pro Glu Gly Ile Leu Leu Phe
                325                 330                 335

Ala Gly Gly His Gln Asp Ser Thr Trp Ile Val Leu Ala Leu Arg Ala
            340                 345                 350

Gly Arg Leu Glu Leu Gln Leu Arg Tyr Asn Gly Val Gly Arg Val Thr
        355                 360                 365

Ser Ser Gly Pro Val Ile Asn His Gly Met Trp Gln Thr Ile Ser Val
    370                 375                 380

Glu Glu Leu Ala Arg Asn Leu Val Ile Lys Val Asn Arg Asp Ala Val
385                 390                 395                 400

Met Lys Ile Ala Val Ala Gly Asp Leu Phe Gln Pro Glu Arg Gly Leu
                405                 410                 415

Tyr His Leu Asn Leu Thr Val Gly Gly Ile Pro Phe His Glu Lys Asp
            420                 425                 430

Leu Val Gln Pro Ile Asn Pro Arg Leu Asp Gly Cys Met Arg Ser Trp
        435                 440                 445

Asn Trp Leu Asn Gly Glu Asp Thr Thr Ile Gln Glu Thr Val Lys Val
    450                 455                 460

Asn Thr Arg Met Gln Cys Phe Ser Val Thr Glu Arg Gly Ser Phe Tyr
465                 470                 475                 480

Pro Gly Ser Gly Phe Ala Phe Tyr Ser Leu Asp Tyr Met Arg Thr Pro
                485                 490                 495

Leu Asp Val Gly Thr Glu Ser Thr Trp Glu Val Glu Val Ala His
            500                 505                 510

Ile Arg Pro Ala Ala Asp Thr Gly Val Leu Phe Ala Leu Trp Ala Pro
        515                 520                 525
```

```
Asp Leu Arg Ala Val Pro Leu Ser Val Ala Leu Val Asp Tyr His Ser
            530                 535                 540

Thr Lys Lys Leu Lys Lys Gln Leu Val Val Leu Ala Val Glu His Thr
545                 550                 555                 560

Ala Leu Ala Leu Met Glu Ile Lys Val Cys Asp Gly Gln Glu His Val
                565                 570                 575

Val Thr Val Ser Leu Arg Asp Gly Glu Ala Thr Leu Glu Val Asp Gly
            580                 585                 590

Thr Arg Gly Gln Ser Glu Val Ser Ala Ala Gln Leu Gln Glu Arg Leu
        595                 600                 605

Ala Val Leu Glu Arg His Leu Arg Ser Pro Val Leu Thr Phe Ala Gly
    610                 615                 620

Gly Leu Pro Asp Val Pro Val Thr Ser Ala Pro Val Thr Ala Phe Tyr
625                 630                 635                 640

Arg Gly Cys Met Thr Leu Glu Val Asn Arg Arg Leu Leu Asp Leu Asp
                645                 650                 655

Glu Ala Ala Tyr Lys His Ser Asp Ile Thr Ala His Ser Cys Pro Pro
                660                 665                 670

Val Glu Pro Ala Ala Ala
            675

<210> SEQ ID NO 133
<211> LENGTH: 405
<212> TYPE: PRT
<213> ORGANISM: Homo sapiens

<400> SEQUENCE: 133

Met Asp Thr Cys Glu Asp Ile Leu Pro Cys Val Pro Phe Ser Val Ala
1               5                   10                  15

Lys Ser Val Lys Ser Leu Tyr Leu Gly Arg Met Phe Ser Gly Thr Pro
            20                  25                  30

Val Ile Arg Leu Arg Phe Lys Arg Leu Gln Pro Thr Arg Leu Val Ala
        35                  40                  45

Glu Phe Asp Phe Arg Thr Phe Asp Pro Glu Gly Ile Leu Leu Phe Ala
    50                  55                  60

Gly Gly His Gln Asp Ser Thr Trp Ile Val Leu Ala Leu Arg Ala Gly
65                  70                  75                  80

Arg Leu Glu Leu Gln Leu Arg Tyr Asn Gly Val Gly Arg Val Thr Ser
                85                  90                  95

Ser Gly Pro Val Ile Asn His Gly Met Trp Gln Thr Ile Ser Val Glu
            100                 105                 110

Glu Leu Ala Arg Asn Leu Val Ile Lys Val Asn Arg Asp Ala Val Met
        115                 120                 125

Lys Ile Ala Val Ala Gly Asp Leu Phe Gln Pro Glu Arg Gly Leu Tyr
    130                 135                 140

His Leu Asn Leu Thr Val Gly Gly Ile Pro Phe His Glu Lys Asp Leu
145                 150                 155                 160

Val Gln Pro Ile Asn Pro Arg Leu Asp Gly Cys Met Arg Ser Trp Asn
                165                 170                 175

Trp Leu Asn Gly Glu Asp Thr Thr Ile Gln Glu Thr Val Lys Val Asn
            180                 185                 190

Thr Arg Met Gln Cys Phe Ser Val Thr Glu Arg Gly Ser Phe Tyr Pro
        195                 200                 205

Gly Ser Gly Phe Ala Phe Tyr Ser Leu Asp Tyr Met Arg Thr Pro Leu
```

```
                    210                 215                 220
Asp Val Gly Thr Glu Ser Thr Trp Glu Val Glu Val Ala His Ile
225                 230                 235                 240

Arg Pro Ala Ala Asp Thr Gly Val Leu Phe Ala Leu Trp Ala Pro Asp
                    245                 250                 255

Leu Arg Ala Val Pro Leu Ser Val Ala Leu Val Asp Tyr His Ser Thr
                    260                 265                 270

Lys Lys Leu Lys Lys Gln Leu Val Val Leu Ala Val Glu His Thr Ala
275                 280                 285

Leu Ala Leu Met Glu Ile Lys Val Cys Asp Gly Gln Glu His Val Val
            290                 295                 300

Thr Val Ser Leu Arg Asp Gly Glu Ala Thr Leu Glu Val Asp Gly Thr
305                 310                 315                 320

Arg Gly Gln Ser Glu Val Ser Ala Ala Gln Leu Gln Arg Leu Ala
                    325                 330                 335

Val Leu Glu Arg His Leu Arg Ser Pro Val Leu Thr Phe Ala Gly Gly
                340                 345                 350

Leu Pro Asp Val Pro Val Thr Ser Ala Pro Val Thr Ala Phe Tyr Arg
            355                 360                 365

Gly Cys Met Thr Leu Glu Val Asn Arg Arg Leu Leu Asp Leu Asp Glu
            370                 375                 380

Ala Ala Tyr Lys His Ser Asp Ile Thr Ala His Ser Cys Pro Pro Val
385                 390                 395                 400

Glu Pro Ala Ala Ala
                405

<210> SEQ ID NO 134
<211> LENGTH: 379
<212> TYPE: PRT
<213> ORGANISM: Homo sapiens

<400> SEQUENCE: 134

Met Phe Ser Gly Thr Pro Val Ile Arg Leu Arg Phe Lys Arg Leu Gln
1               5                   10                  15

Pro Thr Arg Leu Val Ala Glu Phe Asp Phe Arg Thr Phe Asp Pro Glu
            20                  25                  30

Gly Ile Leu Leu Phe Ala Gly Gly His Gln Asp Ser Thr Trp Ile Val
        35                  40                  45

Leu Ala Leu Arg Ala Gly Arg Leu Glu Leu Gln Leu Arg Tyr Asn Gly
    50                  55                  60

Val Gly Arg Val Thr Ser Ser Gly Pro Val Ile Asn His Gly Met Trp
65                  70                  75                  80

Gln Thr Ile Ser Val Glu Glu Leu Ala Arg Asn Leu Val Ile Lys Val
                85                  90                  95

Asn Arg Asp Ala Val Met Lys Ile Ala Val Ala Gly Asp Leu Phe Gln
            100                 105                 110

Pro Glu Arg Gly Leu Tyr His Leu Asn Leu Thr Val Gly Gly Ile Pro
        115                 120                 125

Phe His Glu Lys Asp Leu Val Gln Pro Ile Asn Pro Arg Leu Asp Gly
    130                 135                 140

Cys Met Arg Ser Trp Asn Trp Leu Asn Gly Glu Asp Thr Thr Ile Gln
145                 150                 155                 160

Glu Thr Val Lys Val Asn Thr Arg Met Gln Cys Phe Ser Val Thr Glu
                165                 170                 175
```

Arg Gly Ser Phe Tyr Pro Gly Ser Gly Phe Ala Phe Tyr Ser Leu Asp
            180                 185                 190

Tyr Met Arg Thr Pro Leu Asp Val Gly Thr Glu Ser Thr Trp Glu Val
        195                 200                 205

Glu Val Val Ala His Ile Arg Pro Ala Ala Asp Thr Gly Val Leu Phe
    210                 215                 220

Ala Leu Trp Ala Pro Asp Leu Arg Ala Val Pro Leu Ser Val Ala Leu
225                 230                 235                 240

Val Asp Tyr His Ser Thr Lys Lys Leu Lys Lys Gln Leu Val Val Leu
                245                 250                 255

Ala Val Glu His Thr Ala Leu Ala Leu Met Glu Ile Lys Val Cys Asp
            260                 265                 270

Gly Gln Glu His Val Val Thr Val Ser Leu Arg Asp Gly Glu Ala Thr
        275                 280                 285

Leu Glu Val Asp Gly Thr Arg Gly Gln Ser Glu Val Ser Ala Ala Gln
    290                 295                 300

Leu Gln Glu Arg Leu Ala Val Leu Glu Arg His Leu Arg Ser Pro Val
305                 310                 315                 320

Leu Thr Phe Ala Gly Gly Leu Pro Asp Val Pro Val Thr Ser Ala Pro
                325                 330                 335

Val Thr Ala Phe Tyr Arg Gly Cys Met Thr Leu Glu Val Asn Arg Arg
            340                 345                 350

Leu Leu Asp Leu Asp Glu Ala Ala Tyr Lys His Ser Asp Ile Thr Ala
        355                 360                 365

His Ser Cys Pro Pro Val Glu Pro Ala Ala Ala
    370                 375

<210> SEQ ID NO 135
<211> LENGTH: 47
<212> TYPE: DNA
<213> ORGANISM: Artificial
<220> FEATURE:
<223> OTHER INFORMATION: T7 promoter-containing forward primer

<400> SEQUENCE: 135
gaaattaata cgactcacta tagggcctgg agacgccatc cacgctg                47

<210> SEQ ID NO 136
<211> LENGTH: 22
<212> TYPE: DNA
<213> ORGANISM: Artificial
<220> FEATURE:
<223> OTHER INFORMATION: T7 promoter-containing reverse primer

<400> SEQUENCE: 136
gatgtgcgct ctgcccactg ac                                           22

<210> SEQ ID NO 137
<211> LENGTH: 26
<212> TYPE: DNA
<213> ORGANISM: Artificial
<220> FEATURE:
<223> OTHER INFORMATION: Synthetic primer

<400> SEQUENCE: 137
tggactatca tatgcttacc gtaact                                       26

<210> SEQ ID NO 138
<211> LENGTH: 21
<212> TYPE: DNA

```
<213> ORGANISM: Artificial
<220> FEATURE:
<223> OTHER INFORMATION: Synthetic primer

<400> SEQUENCE: 138
aaagaggatc tctgtccctg t                                                       21

<210> SEQ ID NO 139
<211> LENGTH: 92
<212> TYPE: DNA
<213> ORGANISM: Artificial
<220> FEATURE:
<223> OTHER INFORMATION: Synthetic primer

<400> SEQUENCE: 139
aatgatacgg cgaccaccga gatctacact ctttccctac acgacgctct tccgatctgt             60
attcttggct ttatatatct tgtggaaagg ac                                           92

<210> SEQ ID NO 140
<211> LENGTH: 65
<212> TYPE: DNA
<213> ORGANISM: Artificial
<220> FEATURE:
<223> OTHER INFORMATION: Synthetic primer

<400> SEQUENCE: 140
caagcagaag acggcatacg agctcttccg atctggatga atactgccat ttgtctcgag             60
gtcga                                                                         65
```